United States Patent
Raymond et al.

(10) Patent No.: US 7,999,010 B2
(45) Date of Patent: *Aug. 16, 2011

(54) INDENE DERIVATIVES AS PHARMACEUTICAL AGENTS

(75) Inventors: Jeffery R. Raymond, Vancouver (CA); Kang Han, Vancouver (CA); Yuanlin Zhou, Richmond (CA); Yuehua He, Surrey (CA); Bradley Noren, Delta (CA); James Gee Ken Yee, Vancouver (CA)

(73) Assignee: Aquinox Pharmaceuticals Inc., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/710,909

(22) Filed: Feb. 23, 2010

(65) Prior Publication Data

US 2011/0009439 A1    Jan. 13, 2011

Related U.S. Application Data

(60) Continuation of application No. 12/564,747, filed on Sep. 22, 2009, which is a division of application No. 10/825,084, filed on Apr. 15, 2004, now Pat. No. 7,601,874.

(60) Provisional application No. 60/463,216, filed on Apr. 15, 2003.

(51) Int. Cl.
*A61K 31/045* (2006.01)
*C07C 211/00* (2006.01)

(52) U.S. Cl. ........ 514/727; 514/825; 514/826; 514/863; 564/454

(58) Field of Classification Search .......... 564/454; 514/727, 825, 826, 863
See application file for complete search history.

(56) References Cited

U.S. PATENT DOCUMENTS

| | | | |
|---|---|---|---|
| 3,682,983 A | 8/1972 | Prezewowsky et al. | ... 260/397.3 |
| 3,869,467 A | 3/1975 | Guthrie et al. | ............ 260/307 D |
| 3,962,275 A | 6/1976 | Guthrie et al. | ............ 260/310 C |
| 5,686,621 A | 11/1997 | Clark et al. | .................... 548/129 |
| 6,046,185 A | 4/2000 | Burgoyne et al. | ............. 514/178 |
| 2001/0010293 A1 | 8/2001 | Ishida et al. | .................... 208/19 |

FOREIGN PATENT DOCUMENTS

| | | |
|---|---|---|
| DE | 1 084 718 | 7/1960 |
| JP | 1-290624 A | 11/1989 |
| JP | 5-221901 | 8/1993 |
| JP | 5-221924 A | 8/1993 |
| WO | WO 93/13124 A1 | 7/1993 |
| WO | WO 94/14833 A2 | 7/1994 |
| WO | WO 96/11939 A1 | 4/1996 |
| WO | WO 2004/092100 A1 | 10/2004 |

OTHER PUBLICATIONS

Ahmad and Khan, "The Baeyer-Villiger Oxidation of 5α-Cholestane-3,6-Dione," *Acta Chim. Acad. Sci. Hung.* 106(2): 111-113, 1981.

Buckingham et al., "6-Phenylazocholestane derivatives: Reassignment of the Structures of Products from Phenylhydrazine and Ozonised Cholesterol Derivatives," *J. Chem. Soc.(C)* 18: 1703-1706, 1967.

Clinton et al., "Steroidal[3,2-c]pyrazoles. II. Androstanes, 19-Norandrostanes and their Unsaturated Analogs," *Journal of the American Chemical Society* 83: 1478-1491, Mar. 20, 1961.

Cookson et al., "Photochemical Rearrangement of α-Hydroxy-ketones to Lactones," *J. Chem. Soc.* (C): 2494-2500, 1968.

Dauben and Brookhart, "Stereocontrolled Synthesis of Steroidal Side Chains," *J. Am. Chem. Soc.* 103: 237-238, 1981.

Gumulka et al, "Oxidative Cleavage of the Double Bond of 7-Dehydrocholesterol Acetate Peroxide," *Polish Journal of Chemistry* 57(4/5/6): 403-411, 1983.

Hara, "Azasteroid. IV. Synthesis of B-Azacholane Derivative," Chemical Abstracts Online, Accession No. 1959:17427, 1959. See also *Yakugaku Zasshi* 78(9): 1030-1033, Sep. 1958.

Kaspar and Witzel, "Steroid Binding to the Cytosolic Estrogen Receptor From Rat Uterus. Influence of the Orientation of Substituents in the 17-Position of the 8β- and 8α-Series," *J. steroid Biochem.* 23(3): 259-265, 1985.

Lettré and Werner, "Polyols from steroids and steroid derivatives. IV. 7,8-Seco-derivatives of cholestanols," Chemical Abstracts Online, Accession No. 1967:46521, 1967. See Also *Justus Liebigs Annalen Der Chemie* 697: 217-221, 1966.

Madaio et al., "Minor 5,6-Secosterols From the Marine Sponge *Hippospongia communis*. Isolation and Synthesis of (7Z,22E,24R)-24-Methyl-5,6-Secocholesta-7,22-Diene-3β,5β,6-Triol," *Journal of Natural Products* 53(3): 565-572, May-Jun. 1990.

Manson et al., "Steroidal Heterocycles. VII. Androstano[2,3-d]isoxazoles and Related Compounds," *J. Med. Chem.* 6(1): 1-9, Jan. 18, 1963.

Mincione and Bovicelli, Synthesis via Organoiron Complexes of 9-(4-Keto-1-Methylcyclohex-2-enyl)-8-Keto-des-AB-Ergost-22,23-ene; A Useful Chiral Intermediate in Steroid Synthesis, *Heterocycles* 23(7): 1607-1610, 1985.

Reichstein and Meystre, "Über Bestandteile der Nebennierenrinde und verwandte Stoffe—Allo-pregnan-diol-(3, 17)-Derivate der 17(β)-Reihe. Weiterer Beweis für die Zugehörigkeit der Substanzen P und K zur 17(β)-Reihe," *Helv. Chim. Acta* 22(111): 728-741, 1939.

(Continued)

*Primary Examiner* — Barbara P Badio
(74) *Attorney, Agent, or Firm* — Seed IP Law Group PLLC

(57) ABSTRACT

Compounds of formula (Ia):

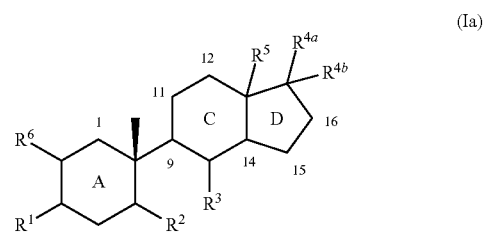

wherein $R^1$, $R^2$, $R^3$, $R^{4a}$, $R^{4b}$, $R^5$ and $R^6$ are defined herein, as well as other indene derivatives are disclosed herein. Pharmaceutical compositions containing the compounds and methods of using the compounds are also disclosed.

22 Claims, No Drawings

OTHER PUBLICATIONS

Rodewald and Piotrowski, "Secosteroids. I. Synthesis of vic-Diols in B-Secocholestane Group," *Journal Prakt. Chem.* 330(5): 775-881, 1988.

Rodewald and Wielogórski, "Selective Esterification of Hydroxyl Groups in Methyl Ester of 3β,8α-Dihydroxy-7,8-Secocholestan-7-oic Acid," *Roczniki Chemii Ann. Soc. Chim. Polonorum* 51(4): 809-814, 1977.

Speckamp et al., "6-Thiasteroids A Novel Stereoselective Preparation of 6-Heterosteroids," *Tetrahedron Letters* 38: 3405-3408, 1974.

Suginome and Yamada, "Photoinduced Transformations. 77. A Four-Step Substitution of a Carbonyl Group of Steroidal Ketones by an Oxygen Atom. A New Method for the Synthesis of Cyclic Ethers," *Journal of Organic Chemistry* 50(14): 2489-2494, 1985.

Westmijze et al., "Ag(I)-Assisted Hydrolysis of Mestranol Methanesulfonate Into Epimestranol," *Tetrahedron Letters* 21: 2665-2666, Apr. 15, 1980.

Chemical Abstracts Database, Accession No. 120:77523, Aug. 1993.

Chemical Abstracts Database, Accession No. 112:211000, Nov. 1989.

Chemical Abstracts Database, Accession No. 101:192278, 1983.

Chemical Abstracts Database, Accession No. 82:73301, 1974.

Beilstein Database, Beilstein Registry No. 3061562, 1968.

Beilstein Database, Beilstein Registry No. 3102039, 1967.

Hara, "Azasteroid. IV. Synthesis of B-Azacholane Derivative," *Yakugaku Zasshi* 78: 1030-1033, Sep. 1958.

Lettré and Wener, "Mehrwertige Alkohole aus Sterinen und Sterinderivaten. IV. 7.8-*seco*-Derivate des Cholestanols," *Justus Liebigs Annalen Der Chemie* 697: 217-221, 1966.

INDENE DERIVATIVES AS PHARMACEUTICAL AGENTS

CROSS-REFERENCE TO RELATED APPLICATIONS

This application is a continuation of U.S. patent application Ser. No. 12/564,747, filed Sep. 22, 2009 (now pending); which is a divisional of U.S. patent application Ser. No. 10/825,084, filed Apr. 15, 2004 (now U.S. Pat. No. 7,601, 874); which application claims the benefit of U.S. Provisional Patent Application No. 60/463,216, filed Apr. 15, 2003. These applications are incorporated herein by reference in their entirety.

BACKGROUND OF THE INVENTION

1. Field of the Invention

This invention is directed to indene derivatives, methods of using the derivatives and pharmaceutical compositions containing same.

2. Description of the Related Art

The normal inflammatory response is an essential localized host response to invading microorganisms or tissue injury which involves cells of the immune system. The inflammatory response allows the body to specifically recognize and eliminate an invading organism and/or repair tissue injury. The classic signs of inflammation include redness (erythema), swelling (edema), pain and increased heat production (pyrema) at the site of injury. Many of the acute changes at the site of inflammation are either directly or indirectly attributable to the massive influx of leukocytes (e.g., neutrophils, eosinophils, lymphocytes, monocytes) which is intrinsic to this response. Leukocytic infiltration and accumulation in tissue results in their activation and subsequent release of inflammatory mediators such as $LTB_4$, prostaglandins, TNF-$\alpha$, IL-1$\beta$, IL-8, IL-5, IL-6, histamine, proteases and reactive oxygen species for example.

Normal inflammation is a highly regulated process that is tightly controlled at several levels for each of the cell types involved in the response. For example, expression of the pro-inflammatory cytokine TNF-$\alpha$ is controlled at the level of gene expression, translation, post-translational modification, and release of the mature form from the cell membrane. Pro-inflammatory responses are normally countered by endogenous anti-inflammatory mechanisms such as generation of IL-10 or IL-4. A characteristic of a normal inflammatory response is that it is temporary in nature and is followed by a resolution phase which brings the state of the tissue back to its prior condition. The resolution phase is thought to involve up-regulation of anti-inflammatory mechanisms, such as IL-10, as well as down-regulation of the pro-inflammatory processes.

Inflammatory disease occurs when an inflammatory response is initiated that is inappropriate and/or does not resolve in the normal manner, but rather persists and results in a chronic inflammatory state. Disease may also involve a perturbation of the cellular immune response that results in recognition of host proteins (antigens) as foreign. Here, the inflammatory response becomes misdirected at host tissues with effector cells targeting specific organs or tissues often resulting in irreversible damage. The self-recognition aspect of auto-immune disease is often reflected by the clonal expansion of T-cell subsets characterized by a particular T-cell receptor (TCR) subtype in the disease state. Often inflammatory disease is also characterized by an imbalance in the levels of T-helper (Th) subsets (i.e., Th1 cells vs. Th2 cells). Inflammatory disease may be systemic (e.g. lupus) or localized to particular tissues or organs (e.g. asthma), and exerts an enormous personal and economic burden on society. Examples of some of the most common and problematic inflammatory diseases are asthma, multiple sclerosis, rheumatoid arthritis, inflammatory bowel disease, psoriasis, and atopic dermatitis.

Therapeutic strategies aimed at curing inflammatory diseases usually fall into one of two categories: (a) down-modulation of processes that are up-regulated in the disease state or (b) up-regulation of anti-inflammatory pathways in the affected cells or tissues. Most regimes currently employed in the clinic fall into the first category. Some examples of which are corticosteroids and non-steroidal anti-inflammatory drugs (NSAIDs).

Many of the tissue, cellular and biochemical processes which are perturbed in inflammatory disease have been elucidated and this has allowed the development of experimental models or assays to mimic the disease state. These assays and models enable screening and selection of compounds with a reasonable probability of therapeutic efficacy in the relevant inflammatory disease. Despite the use of these models, effective drugs have not been discovered for many inflammatory diseases. There is a significant need for therapeutic agents that effectively arrest or reverse disease progression for disease states or pathologies such as asthma, chronic obstructive pulmonary disease, multiple sclerosis, psoriasis, and inflammatory bowel disease.

BRIEF SUMMARY OF THE INVENTION

The compounds of the present invention are useful as anti-inflammatory agents.

Accordingly, in one aspect the invention provides compounds of formula (I):

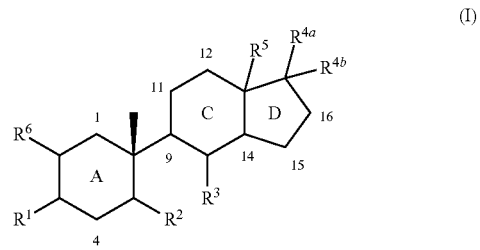

wherein:

the A, C or D ring is independently fully saturated, partially saturated or fully unsaturated;

C1, C4, C11, C12, C15 and C16 are each independently substituted with two of the following, which are independently selected: hydrogen, alkyl, —$R^8$—$OR^7$, or —$R^8$—$N(R^7)_2$, provided that C4 is not substituted by two methyl groups;

C9 and C14 are each independently substituted with hydrogen, alkyl, —$R^8$—$OR^7$, or —$R^8$—$N(R^7)_2$;

$R^1$ is —$OR^7$ or —$N(R^7)_2$;

$R^2$ and $R^3$ are each independently selected from the group consisting of —$R^8$—$OR^7$, —$R^8$—$OC(O)R^9$, —$R^{10}$—$N(R^7)_2$, —$R^{10}$—$N(R^9)C(O)R^9$, —$R^{10}$—$N(R^9)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, $-R^8-OR^7$ or $-R^8-N(R^7)_2$;

each $R^7$ is independently selected from the group consisting of hydrogen, $-R^{10}-OR^9$, $-R^{10}-N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain;

as a single stereoisomer, a mixture of stereoisomers, or as a racemic mixture of stereoisomers;

or a pharmaceutically acceptable salt, solvate or prodrug thereof, in isolation or in a mixture.

In another aspect, the invention provides compounds of formula (II):

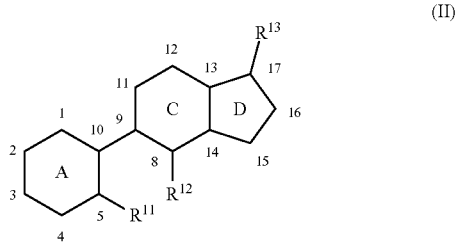

(II)

wherein:

the A, C or D ring is independently fully saturated, partially saturated or fully unsaturated;

C1, C2, C4, C11, C12, C15 and C16 are each independently substituted with:

(a) one of the following: $=O$, $=C(R^{14})_2$, $=C=C(R^{14})_2$, $-[C(R^{14})_2]_n-$ (where n is 2 to 6) and $-O-[C(R^{14})_2]_m-O-$ (where m is 1 to 6); or (b) two of the following, which are independently selected: $-R^{14}$, $-OR^{15}$ and $-N(R^{16})_2$;

C3 is substituted with two of the following, independently selected: $-R^{14}$, $-OR^{15}$ and $-N(R^{16})_2$;

C5, C8, C9, C10, C13, C14 and C17 are each independently optionally substituted with one of the following: $-R^{14}$, $-OR^{15}$ and $-N(R^{16})_2$;

$R^{11}$ and $R^{12}$ are each independently selected from the group consisting of hydrogen, halo, $=O$, $-OR^{15}$, $-N(R^{16})_2$ and a $C_{1-30}$ organic moiety;

$R^{13}$ is $-R^{14}$, $-OR^{15}$, $-N(R^{16})_2$, $=C(R^{14})_2$, $=C=C(R^{14})_2$, $-[C(R^{14})_2]_n-$ (where n is 2 to 5) or $-O-[C(R^{14})_2]_m-O-$ (where m is 1 to 5);

each $R^{14}$ is independently selected from hydrogen, halo and $C_{1-30}$ organic moiety where two geminal $R^{14}$ groups may together form a ring with the carbon to which they are attached;

each $R^{15}$ is independently selected from the group consisting of hydrogen, an oxygen protecting group such that $-OR^{15}$ is a protected hydroxy group, a leaving group initiator such that $-OR^{15}$ is a leaving group and a $C_{1-30}$ organic moiety that may optionally contain at least one heteroatom selected from the group consisting of boron, halogen, nitrogen, oxygen, phosphorus, silicon and sulfur, where vicinal $-OR^{15}$ groups together with the carbons to which they are attached may form a cyclic structure that protects vicinal hydroxy groups and where geminal $-OR^{15}$ groups together with the carbon to which they are attached, may form a cyclic structure that protects a carbonyl group;

each $R^{16}$ is independently selected from the group consisting of hydrogen, $-OR^{17}$, oxygen (so as to form a nitro or an oxime group), and a $C_{1-30}$ organic moiety that may optionally contain at least one heteroatom selected from the group consisting of boron, halogen, nitrogen, oxygen, phosphorus, silicon and sulfur; or two $R^{16}$ groups, together with the nitrogen to which they are attached, form a heterocyclic ring; and each $R^{17}$ is independently selected from hydrogen and a $C_{1-30}$ hydrocarbyl;

as a single stereoisomer, a mixture of stereoisomers, or as a racemic mixture of stereoisomers;

or a pharmaceutically acceptable salt, solvate or prodrug thereof, in isolation or in a mixture;

provided, however, that (1). C4 can not be substituted with two methyl groups (2) $R^{13}$ can not be $=O$ or 6-methylhept-2-yl;

(3) when C17 is substituted with hydrogen, $R^{13}$ can not be $-OH$ or $-OC(O)R$ where R is methyl, ethyl, phenyl or cyclohexyl;

(4) when C1, C2, C4, C11, C12, C15 and C16 are each substituted with two hydrogens, C3 is substituted with hydrogen and hydroxy, C8, C9, C14 and C17 are each substituted with hydrogen, C10 and C13 are each substituted with methyl, $R^{11}$ is $=O$, and $R^{12}$ is $-CH_2C(O)H$, $R^{13}$ can not be $-C(CH_3)HCH_2CH_2C(O)OCH_3$ or $-C(CH_3)HCH_2CH_2C(CH_2CH_3)HC(CH_3)_2H$;

(5) when C1, C2, C4, C11, C12, and C15 are each substituted with two hydrogens, C16 is substituted with hydrogen and hydroxy, C8, C9, C14 and C17 are each substituted with hydrogen, C10 and C13 are each substituted with methyl, C3 is substituted with hydrogen and hydroxy, $R^{11}$ is $=O$, and $R^{12}$ is $-CH_2C(O)OH$ or $-CH_2C(O)OCH_3$, $R^{13}$ can not be $-C(CH_3)HNHCH_2CH_2N(CH_3)_2$, $-C(CH_3)HCH_2CH_2C(CH_2CH_3)HC(CH_3)_2H$, or $-C(CH_3)H-R$ (where R is 5-methylpiperidin-2-yl);

(6) when C1, C2, C11, C12, C15 and C16 are each substituted with two hydrogens, C3 is substituted with hydrogen and hydroxy, C4 is substituted with two hydrogens or C4 is double bonded to C3, C8, C9, C14 and C17 are each substituted with hydrogen, C10 and C13 are each substituted with methyl, $R^{11}$ is $=O$, and $R^{12}$ is $-CH_2CN$, $R^{13}$ can not be $-C(O)OCH_3$;

(7) when C1, C2, C4, C11, C12, C15 and C16 are each substituted with two hydrogens, C3 is substituted with hydrogen and hydroxy, C9, C14 and C17 are each substituted with hydrogen, C10 and C13 are each substituted with methyl, $R^{11}$ is $=O$, and $R^{12}$ is $=CHC(O)H$, $R^{13}$ can not be $-C(CH_3)HCHCHC(CH_3)HC(CH_3)_2H$;

(8) when C1, C2, C4, C11, C12, C15 and C16 are each substituted with two hydrogens, C3 is substituted with hydrogen and hydroxy, C8, C9, C14 and C17 are each substituted with hydrogen, C10 and C13 are each substituted with methyl, $R^{11}$ is $=O$, and $R^{12}$ is $-CH_2CH_3$, $R^{13}$ can not be $-C(CH_3)HOC(O)CH_3$;

(9) when C1, C2, C4, C11, C12, C15 and C16 are each substituted with two hydrogens, C3 is substituted with hydrogen and hydroxy, C5, C9, C14 and C17 are each substituted with hydrogen, C10 and C13 are each substituted with methyl, $R^{11}$ is hydroxy, and $R^{12}$ is =CHCH$_2$OH, $R^{13}$ can not be —C(CH$_3$)HCH$_2$CH$_2$C(CH$_2$CH$_3$)HC(CH$_3$)$_2$H, or —C(CH$_3$)HCHCHC(CH$_3$)HC(CH$_3$)$_2$H, —C(CH$_3$)HCH$_2$CH$_2$C(CH$_2$)C(CH$_3$)$_2$H, or —C(CH$_3$)HCHC[CH$_2$C(CH$_3$)$_2$H]H;

(10) when C1, C2, C4, C11, C12, and C15 are each substituted with two hydrogens, C3 is substituted with hydrogen and hydroxy, C5, C8, C9, C14 and C17 are each substituted with hydrogen, C10 and C13 are each substituted with methyl, C16 is substituted with two hydrogens or with one hydrogen and hydroxy, $R^{11}$ is hydroxy, and $R^{12}$ is —CH$_2$CH$_2$OH, $R^{13}$ can not be —C(CH$_3$)HCH$_2$CH$_2$C(CH$_2$CH$_3$)HC(CH$_3$)$_2$H, —C(CH$_3$)HCH$_2$OH, —CH$_2$OH, or —C(CH$_3$)H—R (where R is 5-methylpiperidin-2-yl);

(11) when C1, C2, C4, C11, C12, C15 and C16 are each substituted with two hydrogens, C3 is substituted with hydrogen and hydroxy, C5, C8, C9, C14 and C17 are each substituted with hydrogen, C10 and C13 are each substituted with methyl, $R^{11}$ is hydroxy, and $R^{12}$ is —CH$_2$CH$_3$, $R^{13}$ can not be —C(CH$_3$)HCH$_2$C(CH$_3$)HC(CH$_3$)$_2$H or —C(OH)HCH$_3$;

(12) when C1, C2, C4, C11, C12, C15 and C16 are each substituted with two hydrogens, C3 is substituted with hydrogen and hydroxy, C5, C8, C9, C14 and C17 are each substituted with hydrogen, C10 and C13 are each substituted with methyl, $R^{11}$ is hydroxy, and $R^{12}$ is —CHCH$_2$, $R^{13}$ can not be —C(OH)HCH$_3$;

(13) when C1, C4, C11, C12, C15 and C16 are each substituted with two hydrogens, C2 is substituted with hydrogen and hydroxy, C3 is substituted with hydrogen and hydroxy, C5, C8, C9, C14 and C17 are each substituted with hydrogen, C10 and C13 are each substituted with methyl, $R^{11}$ is —C(O)OH, and $R^{13}$ is —C(CH$_3$)HC(OH)HC(OH)HC(CH$_2$CH$_3$)HC(CH$_3$)$_2$H, $R^{12}$ can not be —CH$_2$SH or —CH$_2$SSCH$_2$R (where R is hydrogen or a $C_{1-30}$ organic moiety);

(14) when C1, C4, C11, C12, C15 and C16 are each substituted with two hydrogens, C2 is substituted with two hydrogens or with hydrogen and hydroxy, C3 is substituted with hydrogen and hydroxy, C5, C8, C9, C14 and C17 are each substituted with hydrogen, C10 and C13 are each substituted with methyl, $R^{11}$ is —C(O)OH or —CH$_2$OH, and $R^{12}$ is —CH$_2$OH, $R^{13}$ can not be —CH$_2$OH, —C(CH$_3$)HC(OH)HC(OH)HC(CH$_3$)HC(CH$_3$)$_2$H or —C(CH$_3$)HC(OH)HC(OH)HC(CH$_2$CH$_3$)HC(CH$_3$)$_2$H;

(15) when C1, C2, C11, C12 and C15 are each substituted with two hydrogens, C3 is substituted with hydrogen and hydroxy, C4 is substituted with hydrogen and methyl or with two hydrogens, C5 and C9 are each substituted with hydrogen, C8 and C14 are each substituted with hydrogen or each are substituted with methyl, C10 and C13 are each substituted with methyl, C16 is substituted with hydrogen and —OC(O)CH$_3$, $R^{11}$ is —C(O)H, and $R^{12}$ is —C(O)H, $R^{13}$ can not be =C[C(O)OH]CH$_2$CH$_2$CHC(CH$_3$)$_2$ or —C(CH$_3$)HCH$_2$CH$_2$C(O)OCH$_3$;

(16) when C1, C2, C4, C11, C15 and C16 are each substituted with two hydrogens, C3 is substituted with hydrogen and hydroxy, C5, C8, C9, C14 and C17 are each substituted with hydrogen, C10 and C13 are each substituted with methyl, C12 is substituted with hydrogen and hydroxy, $R^{11}$ is —CH$_2$C(O)OH or —CH$_2$C(O)OCH$_3$, and $R^{12}$ is —NH$_2$ or —N(CH$_3$)$_3$, $R^{13}$ can not be —C(CH$_3$)HCH$_2$CH$_2$C(O)OCH$_3$ or —C(CH$_3$)HCH$_2$CH$_2$C(O)OH;

(17) when C1, C2, C4, C11, C12, C15 and C16 are each substituted with two hydrogens, C3 is substituted with hydrogen and hydroxy, C5, C8, C9, C14 and C17 are each substituted with hydrogen, C10 and C13 are each substituted with methyl, $R^{11}$ is —NH$_2$ or —N(CH$_3$)$_2$, and $R^{12}$ is —CH$_2$C(O)OH or —CH$_2$C(O)OCH$_3$, $R^{13}$ can not be —C(CH$_3$)HCH$_2$CH$_2$C(O)OCH$_3$ or —C(CH$_3$)HCH$_2$CH$_2$C(O)OH;

(18) when C1, C2, C4, C11, C12, C15 and C16 are each substituted with two hydrogens, C3 is substituted with hydrogen and hydroxy, C8, C9, C14 and C17 are each substituted with hydrogen, C10 and C13 are each substituted with methyl, $R^{11}$ is =NNHC(NH)NH$_2$, and $R^{12}$ is —CH$_2$CH$_2$C(O)OH, $R^{13}$ can not be —C(CH$_3$)NNHC(NH)NH$_2$);

(19a) when C1, C2, C4, C11 and C12 are each substituted with two hydrogens, C3 is substituted with =O, C8, C14 and C17 are each substituted with hydrogen, C9 is substituted with hydrogen or hydroxy, C10 and C13 are each substituted with methyl, C15 is substituted with two hydrogens or C15 is substituted with hydrogen and double bonded to C16, C16 is substituted with hydrogen or hydroxy and is double bonded to C15 or C16 is substituted with =CH$_2$OH, $R^{11}$ is =O, and $R^{12}$ is =CHC(O)OH, $R^{13}$ can not be —C(CH$_3$)HC(O)CH$_2$C(CH$_3$)HC(CH$_3$)$_2$H;

(19b) when C1, C2, C4, C11 and C12 are each substituted with two hydrogens, C3 is substituted with =O, C8 and C14 are double bonded to each other, C9 is substituted with hydroxy, C10 and C13 are each substituted with methyl, C15 is substituted with hydrogen and double bonded to C16, C16 is substituted with methoxy and double bonded to C15, C17 is substituted with hydrogen, $R^{11}$ is =O, and $R^{12}$ is —CH$_2$C(O)OCH$_3$, $R^{13}$ can not be —C(CH$_3$)HC(O)CH$_2$C(CH$_3$)HC(CH$_3$)$_2$H;

(20) when C1, C2, C4, C11, C12, C15 and C16 are each substituted with two hydrogens, C3 is substituted with =O, C8, C9, C14 and C17 are each substituted with hydrogen, C10 and C13 are each substituted with methyl, $R^{11}$ is =O, and $R^{12}$ is —CH$_2$CN, $R^{13}$ can not be —C(O)NHR (where R is 5-trifluoromethyl-2-t-butylphenyl) or —C(O)OCH$_3$;

(21) when C1, C2, C4, C11, C12, C15 and C16 are each substituted with two hydrogens, C3 is substituted with =O, C8, C9, C14 and C17 are each substituted with hydrogen, C10 is substituted with methyl or —CH$_2$OC(O)H, C13 is substituted with methyl, $R^{11}$ is =O, and $R^{12}$ is —CH$_2$CH$_3$ or —CH$_2$I, $R^{13}$ can not be —C(O)CH$_3$;

(22) when C1, C2, C4, C11, C12, C15 and C16 are each substituted with two hydrogens, C3 is substituted with =O, C5, C8, C9, C14 and C17 are each substituted with hydrogen, C10 and C13 are each substituted with methyl, $R^{11}$ is —C(O)OH, and $R^{12}$ is —C(O)OH, $R^{13}$ can not be —C(CH$_3$)HCH$_2$C(O)OH or —C(CH$_3$)HCH$_2$CH$_3$;

(23) when C1, C2, C4, C11, C12, C15 and C16 are each substituted with two hydrogens, C3 is substituted with =O, C5, C9, C14 and C17 are each substituted with hydrogen, C10 and C13 are each substituted with methyl, $R^{11}$ is —CN, and $R^{12}$ is =O, $R^{13}$ can not be —C(CH$_3$)HCHCHC(CH$_3$)HC(CH$_3$)$_2$H;

(24) when C1, C2, C4, C12 and C15 are each substituted with two hydrogens, C3 is substituted with hydrogen and —OC(O)CH$_3$, C8, C9, and C14 are each substituted with hydrogen, C11 is substituted with two hydrogens, hydrogen and hydroxy, or hydrogen and —OC(O)CH$_3$, C16 is substituted with two hydrogens or =CH$_2$, C17 is substituted with hydrogen, hydroxy or —OC(O)CH$_3$, C10 and C13 are each substituted with methyl, $R^{11}$ is =O, and $R^{12}$ is —CH$_2$C(O)OH, $R^{13}$ can not be —CH$_3$, —CH$_2$CH$_3$, —C(O)CH$_3$, cyclopentanone, —C(CH$_3$)HOC(O)R (where R is phenyl), —C(CH$_3$)HCH$_2$CH$_2$C(O)OCH$_3$, —C(O)CH$_2$OC(O)CH$_3$ or —C(CH$_3$)HCH$_2$CH$_2$C(CH$_2$CH$_3$)HC(CH$_3$)$_2$H;

(25) when C1, C2, C4, C11, C12 and C16 are each substituted with two hydrogens, C3 is substituted with hydrogen and —OC(O)CH$_3$, C8 and C9 are each substituted with hydrogen, C10 and C13 are each substituted with methyl, C14 is substituted with methyl or —OC(O)CH$_3$, C15 is substituted with two hydrogens or =O, C17 is substituted with hydrogen or —OC(O)CH$_3$, R$^{11}$ is =O, and R$^{12}$ is —CH$_2$C(O)H, R$^{13}$ can not be —C(O)OCH$_3$, —C(O)CH$_3$ or —CH$_3$;

(26) when C1, C2, C4, C11, C12, and C15 are each substituted with two hydrogens, C3 is substituted with hydrogen and —OC(O)CH$_3$, C8, C9, and C14 are each substituted with hydrogen, C10 and C13 are each substituted with methyl, C16 is substituted with two hydrogens or forms a double bond with C17, R$^{11}$ is =O, and R$^{12}$ is —CH$_2$CN, R$^{13}$ can not be —C(O)CH$_3$;

(27) when C1, C2, C4, C11, C12, C15 and C16 are each substituted with two hydrogens, C3 is substituted with hydrogen and —OC(O)CH$_3$, C8, C9, C14 and C17 are each substituted with hydrogen, C10 is substituted with hydrogen or —CH$_2$C(O)OH, C13 is substituted with methyl, R$^{11}$ is =O, and R$^{12}$ is —CH$_2$I or —CH$_2$C(O)OCH$_3$, R$^{13}$ can not be —C(O)CH$_3$;

(28) when C1, C2, C4, C11, C12, C15 and C16 are each substituted with two hydrogens, C3 is substituted with hydrogen and —OC(O)CH$_3$, C8, C9, C14 and C17 are each substituted with hydrogen, C10 is substituted with hydrogen or —CH$_2$C(O)OH, C13 is substituted with methyl, R$^{11}$ is =O, and R$^{12}$ is —CH$_2$I, —CHCH$_2$, —CCH, —C(O)OCH$_3$ or —CH$_2$OCH$_3$, R$^{13}$ can not be —C(CH$_3$)HOC(O)CH$_3$

(29) when C1, C2, C4, C11, C12, C15 and C16 are each substituted with two hydrogens, C3 is substituted with hydrogen and —OC(O)CH$_3$, C8, C9, C14 and C17 are each substituted with hydrogen, C10 and C13 are each substituted with methyl, R$^{11}$ is =O, and R$^{12}$ is —CH$_2$NCO, —CH$_2$C(O)N$_3$ or —C(O)OH, R$^{13}$ can not be —C(CH$_3$)HCH$_2$CH$_2$C(CH$_2$CH$_3$)HC(CH$_3$)$_2$H;

(30) when C1, C2, C4, C11, C12, C15 and C16 are each substituted with two hydrogens, C3 is substituted with hydrogen and —OC(O)CH$_3$, C8, C9, and C14 are each substituted with hydrogen, C10 and C13 are each substituted with methyl, C17 is substituted with —OC(O)CH$_3$, R$^{11}$ is =O, and R$^{12}$ is —CH$_2$CHNNHR (where R is 2,4-dinitrophenyl), R$^{13}$ can not be —CH$_3$;

(31) when C1, C4, C11, C12, C15 and C16 are each substituted with two hydrogens, C2 is substituted with hydrogen and —OC(O)CH$_3$, C3 is substituted with hydrogen and —OC(O)CH$_3$, C5, C8, C9, C14 and C17 are each substituted with hydrogen, C10 and C13 are each substituted with methyl, R$^{11}$ is —C(O)OH, and R$^{12}$ is —C(O)H, R$^{13}$ can not be —C(CH$_3$)HCH$_2$CH$_2$OH$_2$CH$_3$;

(32) when C1, C4, C11, C12, C15 and C16 are each substituted with two hydrogens, C2 is substituted with hydrogen and —OC(O)CH$_3$, O3 is substituted with hydrogen and —OC(O)CH$_3$, C5, C8, C9, C14 and C17 are each substituted with hydrogen, C10 and C13 are each substituted with methyl, R$^{11}$ is —C(O)OH or —C(O)OCH$_3$, and R$^{12}$ is —C(O)H, —CH$_2$SSCH$_2$R (where R is hydrogen or a C$_{1-30}$ organic moiety), —CH$_2$OS(O)$_2$CH$_3$, or —CH$_2$OH, R$^{13}$ can not be —C(CH$_3$)HC[OC(O)CH$_3$]HC[OC(O)CH$_3$]HC(CH$_2$CH$_3$)HC(CH$_3$)$_2$H;

(33) when C1, C2, C4, C11, C12, C15 and C16 are each substituted with two hydrogens, C3 is substituted with hydrogen and —OC(O)CH$_3$, C5, C8, C9, C14 and C17 are each substituted with hydrogen, C10 and C13 are each substituted with methyl, R$^{11}$ is —C(O)OH, and R$^{12}$ is —C(O)OH, R$^{13}$ can not be —C(CH$_3$)HCH$_2$CH$_2$C(O)OH;

(34) when C1, C2, C11, C12, C15 and C16 are each substituted with two hydrogens, C3 is substituted with hydrogen and —OC(O)CH$_3$, C4 is substituted with hydrogen and methyl, C5, C9, C14 and C17 are each substituted with hydrogen, C10 and C13 are each substituted with methyl, R$^{11}$ is —CH$_2$C(O)H, and R$^{12}$ is =O, R$^{13}$ can not be —C(CH$_3$)HCH$_2$CH$_2$C(O)C(CH$_3$)$_2$H;

(35) when C1, C2, C4, C11, C12, C15 and C16 are each substituted with two hydrogens, C3 is substituted with hydrogen and —OC(O)CH$_3$, C5, C8, C9, C14 and C17 are each substituted with hydrogen, C10 and C13 are each substituted with methyl, and R$^{11}$ and R$^{12}$ are both —CHNOCH$_3$ or —CHNOCH$_2$CH$_3$, R$^{13}$ can not be —C(CH$_3$)HCH$_2$CH$_2$C(O)OCH$_3$;

(36) when C1, C2, C4, C11, C12 and C15 are each substituted with two hydrogens, C3 is substituted with hydrogen and —OC(O)CH$_3$, C5, C8, C9, C14 and C17 are each substituted with hydrogen, C10 and C13 are each substituted with methyl, C16 is substituted with hydrogen and —OC(O)CH$_3$, R$^{11}$ is —OC(O)CH$_3$, and R$^{12}$ is —CH$_2$CH$_2$OC(O)CH$_3$, R$^{13}$ can not be —C(CH$_3$)HR (where R is 5-methyl-1-acetylpiperidin-2-yl);

(37) when C1, C2, C4, C11, C12, C15 and C16 are each substituted with two hydrogens, C3 is substituted with hydrogen and triisopropylsilyloxy, C8, C9, C14 and C17 are each substituted with hydrogen, C10 and C13 are each substituted with methyl, R$^{11}$ is =O, and R$^{12}$ is —CH$_2$C(O)OH, —CH$_2$C(O)H, —CH$_2$CH$_2$N$_3$, —CH$_2$CH$_2$OH, —CH$_2$CH$_2$OS(O)$_2$CH$_3$ or —CH$_2$C(O)N$_3$, R$^{13}$ can not be —C(O)N(CH$_2$CH$_3$)$_2$;

(38) when C1, C2, C4, C11, C12, C15 and C16 are each substituted with two hydrogens, C3 is substituted with hydrogen and triisopropylsilyloxy, C8, C9, C14 and C17 are each substituted with hydrogen, C10 and C13 are each substituted with methyl, R$^{11}$ is =O, and R$^{12}$ is —CH$_2$C(O)OH, —CH$_2$C(O)H or —CH$_2$C(O)Cl, R$^{13}$ can not be —C(O)OCH$_3$;

(39) when C1, C2, C4, C11, C12, C15 and C16 are each substituted with two hydrogens, C3 is substituted with hydrogen and triisopropylsilyloxy, C5, C8, C9, C14 and C17 are each substituted with hydrogen, C10 and C13 are each substituted with methyl, and R$^{11}$ and R$^{12}$ are both —CHNOCH$_3$, R$^{13}$ can not be —C(CH$_3$)HCH$_2$CH$_2$C(O)OCH$_3$;

(40) when C1, C2, C4, C11, C12, C15 and C16 are each substituted with two hydrogens, C3 is substituted hydrogen and —OC(O)R (where R is 4-nitrophenyl or 3,5-dinitrophenyl), C5, C8, C9, C14 and C17 are each substituted with hydrogen, C10 and C13 are each substituted with methyl, R$^{11}$ is —OH, and R$^{12}$ is —CH$_2$CH$_2$OC(O)R (where R is 4-nitrophenyl or 3,5-dinitrophenyl), R$^{13}$ can not be —C(CH$_3$)HCH$_2$OC(O)R (where R is 4-nitrophenyl or 3,5-dinitrophenyl) or —C(CH$_3$)HCH$_2$CH$_2$C(CH$_2$CH$_3$)HC(CH$_3$)$_2$H;

(41) when C1, C2, C4, C11, C12, C15 and C16 are each substituted with two hydrogens, C3 is substituted with hydrogen and —OCH$_2$OCH$_3$, C5, C9, C14 and C17 are each substituted with hydrogen, C10 and C13 are each substituted with methyl, R$^{11}$ is —CN, and R$^{12}$ is —OH or =O, R$^{13}$ can not be —C(CH$_3$)HCHCHC(CH$_3$)HC(CH$_3$)$_2$H;

(42) when C1, C2, C4, C11, C12, C15 and C16 are each substituted with two hydrogens, C3 is substituted with hydrogen and —OCH$_2$CH$_2$CH$_3$, C8, C9, C14 and C17 are each substituted with hydrogen, C10 and C13 are each substituted with methyl, R$^{11}$ is =O, and R$^{12}$ is —CH$_2$C(O)OH, R$^{13}$ can not be —OCH$_2$CH$_2$CH$_3$;

(43) when C1, C2, C4, C11, C12, C15 and C16 are each substituted with two hydrogens, C3 is substituted with =NNHR (where is R is 2,4-dinitrophenyl), C5, C8, C9, C14 and C17 are each substituted with hydrogen, C10 and C13 are each substituted with methyl, and $R^{11}$ and $R^{12}$ are both —C(O)OH, $R^{13}$ can not be —C(CH$_3$)HCH$_2$CH$_2$C(O)OH;

(44) when C1, C2, C4, C11, C12, C15 and C16 are each substituted with two hydrogens, C3 is substituted with hydrogen and —OCH$_2$R (where R is phenyl), C5, C9, C14 and C17 are each substituted with hydrogen, C10 and C13 are each substituted with methyl, $R^{11}$ is —CH$_2$C(O)H, and $R^{12}$ is =O, $R^{13}$ can not be —C(CH$_3$)HCH$_2$CH$_2$C(CH$_3$)HC(CH$_3$)$_2$H;

(45) when C1, C2, C4, C11, C12, C15 and C16 are each substituted with two hydrogens, C3 is substituted with hydrogen and —CH$_3$, C8, C9, C14 and C17 are each substituted with hydrogen, C10 and C13 are each substituted with methyl, $R^{11}$ is =O, and $R^{12}$ is —C(O)OH, $R^{13}$ can not be —OC(CH$_3$)$_3$; and

(46) when C1, C2, C4, C11, C12, C15 and C16 are each substituted with two hydrogens, C3 is substituted with hydrogen and —OC(CH$_3$)$_3$, C5, C8, C9, C14 and C17 are each substituted with hydrogen, C10 and C13 are each substituted with methyl, $R^{11}$ is hydroxy, and $R^{12}$ is —CH$_2$OH, $R^{13}$ can not be —OC(CH$_3$)$_3$.

In another aspect, the invention provides pharmaceutical compositions comprising a pharmaceutically acceptable excipient and a compound of formula (I) or a compound of formula (II), as described above.

In another aspect, the invention provides a method of treating an inflammatory condition or disease in a mammal, which method comprises administering to the mammal in need thereof a therapeutically effective amount of a compound of formula (I) or a compound of formula (II), as described above.

DETAILED DESCRIPTION OF THE INVENTION

The present invention provides pharmaceutical compositions and methods useful in the treatment and/or prevention of various disease conditions. For example, in one aspect, the present invention provides a method of treating inflammation in a mammal, preferably a human. The method includes administering to a mammal in need thereof a therapeutically effective amount of a compound of the invention or a pharmaceutically acceptable salt thereof, or an effective amount of a pharmaceutical composition containing a compound of the invention or a pharmaceutically acceptable salt thereof.

Before describing the invention in further detail, certain definitions as used herein are provided with the following definitions, and certain conventions used herein are also set forth.

Definition Of Terms

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to seven carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like.

"Alkenyl" refers to a straight or branched hydrocarbon chain radical group consisting solely of carbon and hydrogen atoms, containing at least one double bond, having from two to seven carbon atoms, and which is attached to the rest of the molecule by a single bond, e.g., ethenyl, prop-1-enyl, but-1-enyl, pent-1-enyl, penta-1,4-dienyl, and the like.

"Alkynyl" refers to a straight or branched hydrocarbon chain radical group consisting solely of carbon and hydrogen atoms, containing at least one triple bond, having from two to seven carbon atoms, and which is attached to the rest of the molecule by a single bond, e.g., ethynyl, prop-2-ynyl, but-2-ynyl, pent-2-ynyl, penta-1,4-diynyl, and the like.

"Aryl" refers to refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, —$R^8$—$OR^7$, —$R^8$—N($R^7$)$_2$, —$R^8$—C(O)$R^7$, —$R^8$—C(O)O$R^7$, —$R^8$—C(O)N($R^7$)$_2$, —$R^8$—N($R^9$)C(O)O$R^9$, —$R^8$—N($R^9$)C(O)$R^9$, —$R^8$—N($R^9$)(S(O)$_t R^9$) (where t is 1 to 2), —$R^8$—S(O)$_p$O$R^9$ (where p is 1 to 2), —$R^8$—S(O)$_t R^9$ (where t is 0 to 2), and —$R^8$—S(O)$_p$N($R^9$)$_2$ (where p is 1 to 2) where each $R^7$, $R^8$ and $R^9$ is as defined above in the Summary of the Invention.

"Aralkyl" refers to a radical of the formula —$R_a R_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aralkenyl" refers to a radical of the formula —$R_c R_b$ where $R_c$ is an alkenyl radical as defined above and $R_b$ is one or more aryl radicals as defined above, which may be optionally substituted as described above.

"Alkylene" and "alkylene chain" refer to a straight or branched divalent hydrocarbon chain, linking the rest of the molecule to a radical group, consisting solely of carbon and hydrogen, containing no unsaturation and having from one to seven carbon atoms, e.g., methylene, ethylene, propylene, n-butylene, and the like. The alkylene chain may be attached to the rest of the molecule and to the radical group can be through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to seven carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through any two carbons within the chain.

"Alkylidene" refers to a straight or branched hydrocarbon radical group consisting solely of carbon and hydrogen, containing at least one double bond, having from one to seven carbon atoms, and that is attached to the rest of the molecule through a double bond, e.g., methylene, ethylidene, propylidene, n-butylidene, and the like.

"Cycloalkyl" refers to a stable monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, $-R^8-OR^7$, $-R^8-N(R^7)_2$, $-R^8-C(O)R^7$, $-R^8-C(O)OR^7$, $-R^8-C(O)N(R^7)_2$, $-R^8-N(R^9)C(O)OR^9$, $-R^8-N(R^9)C(O)R^9$, $-R^8-N(R^9)(S(O)_tR^9)$ (where t is 1 to 2), $-R^8-S(O)_pOR^9$ (where p is 1 to 2), $-R^8-S(O)_tR^9$ (where t is 0 to 2), and $-R^8-S(O)_pN(R^9)_2$ (where p is 1 to 2) where each $R^7$, $R^8$ and $R^9$ is as defined above in the Summary of the Invention.

"Cycloalkylalkyl" refers to a radical of the formula $-R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

"Haloalkylidene" refers to an alkylidene radical, as defined above, that is substituted by one or more halo radicals, as defined above, e.g., difluoromethylene, dichloromethylene, and the like.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, $-R^8-OR^7$, $-R^8-N(R^7)_2$, $-R^8-C(O)R^7$, $-R^8-C(O)OR^7$, $-R^8-C(O)N(R^7)_2$, $-R^8-N(R^9)C(O)OR^9$, $-R^8-N(R^9)C(O)R^9$, $-R^8-N(R^9)(S(O)_tR^9)$ (where t is 1 to 2), $-R^8-S(O)_pOR^9$ (where p is 1 to 2), $-R^8-S(O)_tR^9$ (where t is 0 to 2), and $-R^8-S(O)_pN(R^9)_2$ (where p is 1 to 2) where each $R^7$, $R^8$ and $R^9$ is as defined above in the Summary of the Invention.

"Heterocyclylalkyl" refers to a radical of the formula $-R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

"Heteroaryl" refers to a 3- to 18-membered aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, $-R^8-OR^7$, $-R^8-N(R^7)_2$, $-R^8-C(O)R^7$, $-R^8-C(O)OR^7$, $-R^8-C(O)N(R^7)_2$, $-R^8-N(R^9)C(O)OR^9$, $-R^8-N(R^9)C(O)R^9$, $-R^8-N(R^9)(S(O)_tR^9)$ (where t is 1 to 2), $-R^8-S(O)_pOR^9$ (where p is 1 to 2), $-R^8-S(O)_tR^9$ (where t is 0 to 2), and $-R^8-S(O)_pN(R^9)_2$ (where p is 1 to 2) where each $R^7$, $R^8$ and $R^9$ is as defined above in the Summary of the Invention.

"Heteroarylalkyl" refers to a radical of the formula $-R_aR_f$ where $R_a$ is an alkyl radical as defined above and $R_f$ is a heteroaryl radical as defined above. The heteroaryl radical may be optionally substituted as defined above.

"Heteroarylalkenyl" refers to a radical of the formula $-R_bR_f$ where $R_b$ is an alkenyl radical as defined above and $R_f$ is a heteroaryl radical as defined above. The heteroaryl radical may be optionally substituted as defined above.

As used herein, compounds which are "commercially available" may be obtained from standard commercial sources including Acros Organics (Pittsburgh Pa.), Aldrich Chemical (Milwaukee Wis.; including Sigma Chemical and Fluka), American Tissue Culture Collection (ATCC, Rockville, Md.), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), EM Industries, Inc. (Hawthorne, N.Y.; World Wide Web), Fisher Scientific Co. (Pittsburgh Pa.), Fisher Scientific Co. (Hampton, N.H.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.; www.lancaster.co.uk), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Praxair (Vancouver, B.C.), Riedel de Haen AG (Hannover, Germany), Spectrum Quality Product, Inc. (New Brunswick, N.J.), Steraloids Inc. (Newport, R.I.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present invention is P. H. Stahl & C. G. Wermuth "Handbook of Pharmaceutical Salts", Verlag Helvetica Chimica Acta, Zurich, 2002.

As used herein, the term $C_{1-30}$ organic moiety refers to a stable arrangement of atoms composed of at least one and not more than about the maximum carbon number set forth in the range, typically not more than about 30 carbon atoms, and any number of non-carbon atoms.

The $C_{1-30}$ organic moiety may be a saturated or unsaturated hydrocarbyl radical. A saturated hydrocarbyl radical is defined according to the present invention as any radical composed exclusively of carbon and hydrogen, where single bonds are exclusively used to join carbon atoms together. Thus, any stable arrangement of carbon and hydrogen atoms, having at least one carbon atom, is included within the scope of a saturated hydrocarbon radical according to the invention. Some specific terminology that may be used to refer to specific carbon atom arrangements will be discussed below.

The carbon atoms may form an alkyl group as defined herein. The carbon atoms may form a cycloalkyl group as defined herein. Additional groups within the scope of "cycloalkyl" as defined herein are polycycloalkyl groups, defined below.

A polycycloalkyl group is an arrangement of carbon atoms wherein at least one carbon atom is a part of at least two separately identifiable rings. The polycycloalkyl group may contain bridging between two carbon atoms, where bicyclo [1.1.0]butyl, bicyclo[3.2.1]octyl, bicyclo[5.2.0]nonyl, tricycl $[2.2.1.0^1]$heptyl, norbornyl and pinanyl are representative examples. The polycycloalkyl group may contain one or more fused ring systems, where decalinyl (radical from decalin) and perhydroanthracenyl are representative examples. The polycycloalkyl group may contain a spiro union, in which a single atom is the only common member of two rings. Spiro [3.4]octyl, spiro[3.3]heptyl and spiro[4.5]decyl are representative examples.

In addition, the saturated hydrocarbyl radical can be composed of any combination of two or more of the above, i.e., any combination of alkyl and cycloalkyl groups. Thus, the $C_{1-30}$ organic moiety may be an alkyl group (e.g., methyl) with a cycloalkyl (e.g., cyclohexyl) substituent, so that $C_{1-30}$ organic moiety is a cyclohexylmethyl group. As another example, the $C_{1-30}$ organic moiety may be a cycloalkyl group (e.g., cyclooctyl) having two alkyl substituents (e.g., a methyl and ethyl substituent), so that the $C_{1-30}$ organic moiety is a methylethylcyclooctyl group. As a final example, the $C_{1-30}$ organic moiety may be a cycloalkyl group with an alkyl substituent, where the alkyl substituent is substituted with a polycycloalkyl substituent.

As indicated above, the $C_{1-30}$ organic moiety may be an unsaturated hydrocarbyl radical. Such an $C_{1-30}$ organic moiety is defined as having a carbon arrangement as set forth above for saturated hydrocarbyl radicals, with the additional feature that at least one bond between any two carbon atoms is other than a single bond. An alkyl group containing at least one single double bond is referred to herein as an alkenyl group. An alkyl group containing at least one triple bond is referred herein to as an alkynyl group.

Likewise, the cycloalkyl group may have one or more double or triple bonds, and be included within the scope of an unsaturated hydrocarbyl radical according to the invention. Cycloalkenyl and cycloalkynyl are general names given to groups having a single carbon-based ring with a single double and triple bond in the ring, respectively. Cycloalkadienyl groups are cycloalkyl groups with two double bonds contained in the ring structure. The double bond may be exocyclic to the ring, e.g., a carbon atom of the ring may have a $=CH_2$ group (i.e., a methylidene group) or higher homologue bonded to it.

A ring may be unsaturated to the extent of being aromatic, and still be included within the scope of an unsaturated hydrocarbyl radical. Thus, an aryl group as defined herein is included within the scope of such hydrocarbyl groups. As any combination of the above is also included within the scope of an unsaturated hydrocarbyl radical, aralkyl ($C_{1-30}$ organic moiety is an alkyl group with at least one aryl substituent, e.g., benzyl) and alkylaryl ($C_{1-30}$ organic moiety is an aryl ring with at least one alkyl substituent, e.g., tolyl) groups are included within the scope of $C_{1-30}$ organic moiety. $C_6$ aryls are a preferred component of organic moieties of the invention.

Also included within the scope of an $C_{1-30}$ organic moiety are those organic moieties that contain one or more heteroatoms. Heteroatoms according to the invention are any atom other than carbon and hydrogen. A preferred class of heteroatoms are naturally occurring atoms (other than carbon and hydrogen). Another preferred class are non-metallic (other than carbon and hydrogen). Another preferred class consists of boron, nitrogen, oxygen, phosphorous, sulfur, selenium and halogen (i.e., fluorine, chlorine, bromine and iodine, with fluorine and chlorine being preferred). Another preferred class consists of nitrogen, oxygen, sulfur and halogen. Another preferred class consists of nitrogen, oxygen and sulfur. Oxygen is a preferred heteroatom. Nitrogen is a preferred heteroatom.

For example, the $C_{1-30}$ organic moiety may be a hydrocarbyl radical as defined above, with at least one substituent containing at least one heteroatom. In other words, the $C_{1-30}$ organic moiety may be a hydrocarbyl radical as defined above, wherein at least one hydrogen atom is replaced with a heteroatom. For example, if the heteroatom is oxygen, the substituent may be a carbonyl group, i.e., two hydrogens on a single carbon atom are replaced by an oxygen, to form either a ketone or aldehyde group. Alternatively, one hydrogen may be replaced by an oxygen atom, in the form of an hydroxy, alkoxy, aryloxy, aralkyloxy, alkylaryloxy (where alkoxy, aryloxy, aralkyloxy, alkylaryloxy may be collectively referred to as hydrocarbyloxy), heteroaryloxy, —OC(O)R, ketal, acetal, hemiketal, hemiacetal, epoxy and —OSO$_3$M. The heteroatom may be a halogen. The heteroatom may be a nitrogen, where the nitrogen forms part of an amino (—NH$_2$, —NHR, —N(R)$_2$), alkylamido, arylamido, arylalkylamido, alkylarylamido, nitro, —N(R)SO$_3$M or aminocarbonylamide group. The heteroatom may be a sulfur, where the sulfur forms part of a thiol, thiocarbonyl, —SO$_3$M, sulfonyl, sulfonamide or sulfonhydrazide group. The heteroatom may be part of a carbon-containing substituent such as formyl, cyano, —C(O)OH, —C(O)OR, —C(O)OM, —C(O)R, —C(O)N(R)$_2$, carbamate, carbohydrazide and carbohydroxamic acid.

In the above exemplary heteroatom-containing substituents, R represents the remainder of the $C_{1-30}$ organic moiety and M represents proton or a metal ion. Preferred metal ions, in combination with a counterion, form physiologically tolerated salts. A preferred metal from which a metal ion may be formed include an alkali metal [for example, lithium (Li), sodium (Na), potassium (K), rubidium (Rb) and cesium (Cs)] an alkaline earth metal (for example, magnesium (Mg), calcium (Ca) and strontium (Sr)], or manganese (Mn), iron (Fe), zinc (Zn) or silver (Ag). An alkali metal or an alkaline earth metal are preferred M groups. Sodium, potassium, magnesium and calcium are preferred M groups. Sodium and potassium are preferred M groups.

Another class of $C_{1-30}$ organic moieties according to the invention are hydrocarbyl radicals as defined above, wherein at least one heteroatom is substituted for a carbon atom in the hydrocarbyl. One example of such organic moieties is the heterocyclyls defined herein. Another example of such organic moieties have a heteroatom bridging (a) the radical to which the organic moiety is bonded and (b) the remainder of the organic moiety. Examples include alkoxy, aryloxy, aralkoxy and alkylaryloxy radicals, which may collectively be referred to herein as hydrocarbyloxy radicals or moieties. Thus, —OR is an exemplary $C_{1-30}$ organic moiety of the invention (where R is the remainder of the $C_{1-30}$ organic moiety). Another example is —NHR (where R is the remainder of the $C_{1-30}$ organic moiety). Other examples include —R$^8$—OR$^7$ and —R$^8$—N(R$^7$)$_2$ where R$^7$ and R$^8$ are as defined above in the Summary of the Invention and R$^{10}$ is a bond or a straight or branched alkylene or alkenylene chain.

While the $C_{1-30}$ organic moiety may have up to about 30 carbon atoms, preferred organic moieties of the invention have fewer than 30 carbon atoms, for example, up to about 25 carbon atoms, more preferably up to about 20 carbon atoms. The organic moiety may have up to about 15 carbon atoms, or up to about 12 or 10 carbon atoms. A preferred category of organic moieties has up to about 8 or 6 carbon atoms.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention.

Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Oxygen protecting group" refers to a radical which protects and maintains a hydroxy group during subsequent chemical reactions. Such groups include, but are not limited to, trialkylsilyl or diarylalkylsilyl (e.g., t-butyldimethylsilyl, t-butyldiphenylsilyl or trimethylsilyl), tetrahydropyranyl, benzyl, and the like. Protecting groups may be added or removed in accordance with standard techniques, which are well-known to those skilled in the art and as described herein. The use of protecting groups, particularly oxygen protecting groups, is described in detail in Green, T. W. and P. G. M. Wutz, Protective Groups in Organic Synthesis (1991), 2nd Ed., Wiley-Interscience.

"Leaving group initiator" refers to a radical which, together with the oxygen to which is it attached, forms a leaving group which is easily removed from the rest of the molecule upon attack by the appropriate nucleophile. The hydroxy radical is not a good leaving group and must therefore be converted to a group that does leave. One way is to protonate the hydroxy radical (to form a more acidic leaving group). Another is to convert the hydroxy to a reactive ester, most commonly, to a sulfonic ester. The sulfonic ester groups tosylate, brosylate, nosylate and mesylate are frequently used. Other leaving groups include oxonium ions, alkyl perchorates, ammonioalkanesulfonate esters, alkyl fluorosulfonates and the fluorinated compounds triflates and nonaflates.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a mammal, preferably a human, is sufficient to effect treatment, as defined below, of inflammatory disease in the mammal. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

Compounds of the invention have a central nucleus of three rings, designated herein as A, C, and D as shown below:

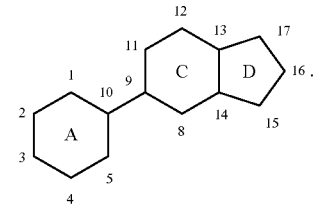

The carbons of the central nucleus are numbered as set forth above. For purposes herein, the carbon at position 1 of the central nucleus is indicated herein as C1, and so forth.

In the compounds of the invention, unless otherwise indicated, each of rings A, C, and D is independently fully saturated, partially saturated or fully unsaturated. That is, hydrogens attached to any of the carbons at positions 1-5 and 8-17 may be omitted so as to allow unsaturation within the A, C and/or D rings. For example, when carbons at numerals 5, 8, 9, 10, 13 and 14 are indicated as being substituted with one hydrogen, and it is also indicated that each of rings A, C and D is independently fully saturated, partially saturated or fully unsaturated, then any one or more of the hydrogens attached to carbons at numerals 5, 8, 9 and 14 may be omitted in order to allow unsaturation at the carbon atom.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein for the compounds of the invention is a modified form of the I.U.P.A.C. nomenclature system wherein the compounds are named herein as derivatives of the indene moiety. The locant numbering of the various substituents off the indene ring in the names of the compounds of the invention is based on the standard locant numbering system for indene rings. In addition, the configuration of the substituents are indicated in the names of the compounds by an "α" if the substituent is below the plane of the indene ring and by a "β" is the substituent is above the plane of the indene ring. For example, a compound of formula (Ia) (showing the numbering of the carbons:

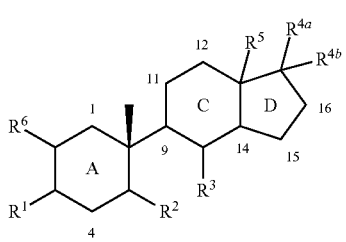

(Ia)

where C1, C4, C11, C12, C15 and C16 are each independently substituted with two hydrogens; C9 and C14 are each independently substituted with hydrogen; $R^1$ is β-hydroxy; $R^2$ is β-(2-hydroxyethyl); $R^3$ is α-hydroxy; $R^{4a}$ and $R^{4b}$ together form methylene; $R^5$ is β-methyl; and $R^6$ is hydrogen, i.e., a compound of the following formula:

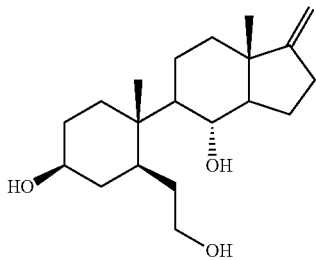

is named herein as 5-(1β-methyl-4β-hydroxy-2β-(2-hydroxyethyl)cyclohexyl)-4α-hydroxy-7αβ-methyl-1-methyleneoctahydroindene.

The compounds of the invention may, and typically do, exist as solids, including crystalline solids which can be crystallized from common solvents such as ethanol, N,N-dimethylformamide, water, or the like or mixtures thereof. The crystallization process may, depending on the crystallization conditions, provide various polymorphic structures. Typically, a more thermodynamically stable polymorph is advantageous to the commercial scale manufacture of a steroid compound of the invention, and is a preferred form of the compound.

Often, crystallizations produce a solvate of the compound of the invention. As used herein, the term "solvate" refers to an aggregate that comprises one or more compounds of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or solvent or a mixture of water and solvent.

As used herein, a "pharmaceutically acceptable solvate" refers to a solvate that retains the biological effectiveness and properties of the biologically active compounds of the invention. Examples of pharmaceutically acceptable solvates include, but are not limited to, water, isopropanol, ethanol, methanol, DMSO, EtOAc, acetic acid, and ethanolamine. It should be appreciated by those skilled in the art that solvated forms are equivalent to unsolvated forms and are intended to be encompassed within the scope of the present invention. Sykes, P. A., *Guidebook to Mechanism in Organic Chemistry*, 6th Ed (1986, John Wiley & Sons, N.Y.) is an exemplary reference that describe solvates.

B. Pharmaceutical Compositions

The present invention provides a pharmaceutical or veterinary composition (hereinafter, collectively referred to as a pharmaceutical composition) containing a compound of the invention as described above, in admixture with a pharmaceutically acceptable carrier. The invention further provides a composition, preferably a pharmaceutical composition, containing an effective amount of a compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, ocular, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of the invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes an (where "a" and "an" refers here, and throughout this specification, as one or more) active compound of the invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form.

Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1% and about 80% of the weight of the composition. Preferred oral compositions contain between about 4% and about 50% of the active compound of the invention. Preferred compositions and preparations according to the present invention are prepared so that a parenteral dosage unit contains between 0.01% to 2% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of formula the invention of from about 0.01% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active component(s) and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation (including asthma, allergy, rheumatoid arthritis, multiple sclerosis, etc.), autoimmune diseases (including diabetes and lupus erythematosus), and proliferative disorders (cancers).

The pharmaceutical compositions may be prepared by methodology well known in the pharmaceutical art.

A composition intended to be administered by injection can be prepared by combining the compound of the invention with water so as to form a solution. A surfactant may be added to facilitate the formation of a homogeneous solution or suspension. Surfactants are compounds that non-covalently interact with the compound of the invention so as to facilitate dissolution or homogeneous suspension of the active compound in the aqueous delivery system.

C. Methods of Use

The compounds of the invention, or pharmaceutical compositions comprising one of more of these compounds and a pharmaceutically acceptable carrier, diluent or excipient, may be used in a method for treating or preventing an inflammatory condition or disease in a patient, where the method comprises administering to the patient in need thereof an amount of a compound or composition according to the present invention, where the amount is effective to treat or prevent the inflammatory condition or disease of the patient.

The inflammatory condition or disease may involve acute or chronic inflammation of bone and/or cartilage of joints; the inflammatory condition or disease may be an arthritis selected from rheumatoid arthritis, gouty arthritis or juvenile rheumatoid arthritis; the inflammatory condition may be an autoimmune condition or disease; the inflammatory condition or disease may involve central nervous system inflammation (e.g., wherein the central nervous system disease is multiple sclerosis, or wherein the central nervous system disease is Alzheimer's); the inflammatory condition or disease may be lupus erythematosus disease; the inflammatory condition or disease may be an inflammatory bowel disease (e.g., Crohn's disease or ulcerative colitis); the inflammatory condition or disease may be an inflammatory cutaneous disease (e.g., psoriasis or dermatitis); the inflammatory condition or disease may be graft vs host disease; the inflammatory condition or disease may be vascular (e.g., vasculitis); the inflammatory condition or disease may be an atherosclerotic disease; the inflammatory condition or disease may involve respiratory inflammation (e.g., wherein the respiratory disease is asthma, or wherein the respiratory disease is chronic obstructive pulmonary disease; or wherein the respiratory disease is emphysema); the inflammatory condition or disease may be pulmonary sarcadosis; the inflammatory condition or disease may be ocular inflammation or allergy; the inflammatory condition or disease may be allergic rhinitis; the condition or disease may be associated with leukocyte infiltration; the condition or disease may be associated with edema; the condition or disease may be associated with ischemia reperfusion injury; the condition or disease may be associated with elevated levels of inflammatory cytokines (e.g., wherein the inflammatory cytokine is IL-1, or wherein the inflammatory cytokine is IL-2, or wherein the inflammatory cytokine is IL-3, or wherein the inflammatory cytokine is interleukin (IL)-4, or wherein the inflammatory cytokine is IL-5, or wherein the inflammatory cytokine is IL-6, or wherein the inflammatory cytokine is IL-8, or wherein the inflammatory cytokine is IL-9, or wherein the inflammatory cytokine is IL-10, or wherein the inflammatory cytokine is IL-12, or wherein the inflammatory cytokine is IL-13, or wherein the inflammatory cytokine is IL-18, or wherein the inflammatory cytokine is TNF-α, or wherein the inflammatory cytokine is TGF-β, or wherein the inflammatory cytokine is GM-CSF, or wherein the inflammatory cytokine is IFN-γ, or wherein the inflammatory cytokine is LTB4, or wherein the inflammatory cytokine is a member of the cysteinyl leukotriene family, or wherein the inflammatory cytokine is regulated on activation normal T cell expressed and secreted (RANTES), or wherein the inflammatory cytokine is eotaxin-1, 2, or 3, or wherein the inflammatory cytokine is macrophage inflammatory protein (MIP)-1α, or wherein the inflammatory cytokine is monocyte chemoattractant protein-1, 2, 3, or 4); the condition or disease may be associated with altered levels of inflammatory adhesion molecules (e.g., wherein the adhesion molecule is an immunoglobulin such as vascular cell adhesion molecule (VCAM-1 or 2) or intercellular adhesion molecule (ICAM-1 or 2); wherein the adhesion molecule is an integrin such as very late antigen-4 (VLA-4) or Mac-1, wherein the adhesion molecule is a selectin such as e-selectin).

Furthermore, the present invention provides a method for treating or preventing a disease or condition in a patient, where the disease or condition is associated with pathological conditions that involve leukocyte infiltration, the method comprising administering to a patient in need thereof an amount of a compound or a composition of the present invention, wherein the amount is effective to treat or prevent a disease or condition associated with pathological conditions that involve leukocyte infiltration.

Furthermore, the present invention provides a method of treating or preventing arthritis in a patient, comprising administering to a patient in need thereof an amount of a compound or composition of the present invention, where the amount is effective to treat or prevent arthritis in the patient.

Furthermore, the present invention provides a method of treating or preventing inflammatory bowel disease in a patient, comprising administering to a patient in need thereof an amount of a compound or composition of the present invention, where the amount is effective to treat or prevent inflammatory bowel disease in the patient.

Furthermore, the present invention provides a method of treating or preventing inflammatory bowel disease in a patient, comprising administering to a patient in need thereof an amount of a compound or composition of the present invention, where the amount is effective to treat or prevent psoriasis in the patient.

Furthermore, the present invention provides a method of treating or preventing atherosclerosis in a patient, comprising administering to a patient in need thereof an amount of a compound or composition of the present invention, where the amount is effective to treat or prevent atherosclerosis in the patient.

In a method of the present invention, a compound of the invention, or a pharmaceutical composition comprising one or more compounds of the invention and a pharmaceutically acceptable carrier, diluent or excipient, may, although need not, achieve one or more of the following desired results in the subject to whom has been administered a compound of the invention as defined above, or a composition containing one of these compounds and a pharmaceutically acceptable carrier, diluent or excipient:

1. Inhibition of leukocyte infiltration (e.g., neutrophils, macrophages, etc.)
2. Inhibition of leukocyte activation
3. Alteration of lymphocyte ratio (e.g., TH1 vs TH2 cells)
4. Inhibition of leukocyte chemotaxis;
5. Inhibition of TNF-α production and/or release;
6. Inhibition of chemokine production and/or release (e.g., eotaxin, etc.);
7. Inhibition of adhesion molecule production, release and/or function (e.g. VCAM, VLA-4, etc.);
8. Inhibition of edema;
9. Inhibition of interleukin cytokine production and/or release (e.g., IL-1, IL-2, IL-3, IL-4, IL-5, IL6, IL-8, IL-9, IL10, IL-12, IL-13, IL-18);
10. Inhibition of inflammatory mediator release (e.g., leukotrienes, tryptase, adenosine etc.);
11. Inhibition of parameters of arthritis;
12. Inhibition of parameters of inflammatory bowel disease;
13. Inhibition of parameters of psoriasis;
14. Inhibition of parameters of atherosclerosis.

The compounds of the invention disclosed herein or pharmaceutical or compositions comprising one of more of these compounds and a pharmaceutically acceptable carrier, diluent or excipient, may be used in a method for treating or preventing a proliferative disorder in a patient, where the method comprises administering to the patient in need thereof an amount of a compound or composition according to the present invention, where the amount is effective to treat or prevent the proliferative disorder of the patient. As used herein, proliferative disorders includes, without limitation, all leukemias and solid tumors that are susceptible to undergoing differentiation or apoptosis upon interruption of their cell cycle.

Thus, the inventive method may be used to treat inflammation, including both acute and chronic inflammation, as well as certain proliferative disorders (cancers). As used herein, inflammation includes, without limitation, arthritis (where this term encompasses over 100 kinds of diseases, including rheumatoid arthritis, psoriatic arthritis, ankylosing spondylitis, osteoarthritis, gout, and synovitis), inflammations of the brain (including multiple sclerosis, Alzheimer's, AIDS dementia, stroke, encephalitis, trauma, and Creutzfeld-Jakob disease), inflammatory bowel disease (including Crohn's disease and ulcerative colitis), irritable bowel syndrome, ischemia-reperfusion injury including myocardial infarction, sarcoidosis, psoriasis, tissue/organ transplant, graft vs host disease, systemic lupus erythematosus, Type I juvenile diabetes, vasculitis, artherosclerosis, cardiomyopathy, autoimmune myocarditis, atopic dermatitis, asthma, allergy, allergic rhinitis, and chronic obstructive pulmonary disease (including emphysema and bronchitis).

The inventive method provides for administering a therapeutically effective amount of a compound of the invention, including salts, compositions etc. thereof. As used herein, the actual amount encompassed by the term "therapeutically effective amount" will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors that those skilled in the medical arts will recognize.

A therapeutically effective amount of a compound or pharmaceutical composition of the present invention will be sufficient to treat inflammation or proliferative diseases in a warm-blooded animal, such as a human. Methods of administering therapeutically effective amounts of anti-inflammatory agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices.

The dosage amount and frequency are selected to create a therapeutically effective level of the agent without harmful effects. It will generally range from a dosage of about 0.001 to 100 mg/Kg/day, and typically from about 0.01 to 10 mg/Kg/day where administered orally or intravenously. Also, the dosage range will be typically from about 0.0001 to 10 mg/Kg/day where administered intranasally or by inhalation.

D. Preferred Embodiments of the Invention

Of the compounds of formula (I) set forth above in the Summary of the Invention, a preferred group of compounds are those compounds of formula (Ia):

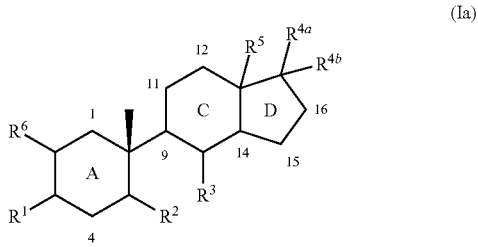

(Ia)

wherein:
the A, C or D ring is independently fully saturated or partially saturated;

C1, C4, C11, C12, C15 and C16 are each independently substituted with two hydrogens;

C9 and C14 are each independently substituted with hydrogen;

$R^1$ is —$OR^7$ or —$N(R^7)_2$;

$R^2$ and $R^3$ are each independently selected from the group consisting of —$R^8$—$OR^7$, —$R^8$—$OC(O)R^9$, —$R^{10}$—$N(R^7)_2$, —$R^{10}$—$(N(R^9)C(O)R^9$, —$R^{10}$—$N(R^9)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of this group of compounds, one preferred subgroup of compounds is the subgroup wherein:

$R^1$ is —$OR^7$;

$R^2$ and $R^3$ are each independently selected from the group consisting of —$R^8$—$OR^7$, —$R^8$—$OC(O)R^9$, —$R^{10}$—$N(R^7)_2$, —$R^{10}$—$N(R^9)C(O)R^9$, —$R^{10}$—$N(R)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of this subgroup of compounds, one preferred class of compounds is that class wherein:

$R^1$ is —$OR^7$;

$R^2$ is —$R^8$—$OR^7$;

$R^3$ is selected from the group consisting of —$R^8$—$OR^7$, —$R^8$—$OC(O)R^9$, —$R^{10}$—$N(R^7)_2$, —$R^{10}$—$N(R^9)C(O)R^9$, $N(R^9)C(O)R^9$, —$R^{10}$—$N(R^9)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of this class of compounds, one preferred subclass of compounds is that subclass wherein:

$R^1$ is —$OR^7$;

$R^2$ is —$R^8$—$OR^7$;

$R^3$ is —$R^8$—$OR^7$;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl;

$R^6$ is hydrogen;

each $R^7$ is independently selected from the group consisting of hydrogen, alkyl, substituted aryl or optionally substituted aralkyl; and each $R^8$ is independently selected from the group consisting of a direct bond, a straight or branched alkylene chain, and a straight or branched alkenylene chain.

Of this class of compounds, another preferred subclass of compounds is that subclass wherein:

$R^1$ is —$OR^7$;

$R^2$ is —$R^8$—$OR^7$;

$R^3$ is —$R^{10}$—$N(R^7)_2$;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of the preferred subgroup described above, another preferred class of compounds is that class wherein:

$R^1$ is —$OR^7$;

$R^2$ is —$R^{10}$—$N(R^7)_2$;

$R^3$ is selected from the group consisting of —$R^8$—$OR^7$, —$R^8$—$OC(O)R^9$, —$R^{10}$—$N(R^7)_2$, —$R^{10}$—$N(R^9)C(O)R^9$, —$R^{10}$—$N(R^9)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, $N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of this preferred class of compounds, one preferred subclass of compounds is that subclass wherein:

$R^1$ is —$OR^7$;

$R^2$ is —$R^{10}$—$N(R^7)_2$;

$R^3$ is —$R^8$—$OR^7$;

$R^{4a}$ and $R^{4b}$ are each independently selected from hydrogen, alkyl, alkenyl or alkynyl;

or $R^{4a}$ is hydrogen, alkyl, alkenyl or alkynyl and $R^{4b}$ is a direct bond to the carbon at C16;

or $R^{4a}$ and $R^{4b}$ together form alkylidene or haloalkylidene;

$R^5$ is alkyl or $R^5$ is a direct bond to the carbon at C14;

$R^6$ is hydrogen, —$R^8$—$OR^7$ or —$R^8$—$N(R^7)_2$;

each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of this preferred class of compounds, another preferred subclass of compounds is that subclass wherein:

$R^1$ is —$OR^7$;
$R^2$ is —$R^{10}$—$N(R^7)_2$;
$R^3$ is —$R^{10}$—$N(R^7)_2$;
$R^{4a}$ and $R^{4b}$ are each independently selected from hydrogen, alkyl, alkenyl or alkynyl;
or $R^{4a}$ is hydrogen, alkyl, alkenyl or alkynyl and $R^{4b}$ is a direct bond to the carbon at C16;
or $R^{4a}$ and $R^{4b}$ together form alkylidene or haloalkylidene;
$R^5$ is alkyl or $R^5$ is a direct bond to the carbon at C14;
$R^6$ is hydrogen, —$R^8$—$OR^7$ or —$R^8$—$N(R)_2$;
each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of the group of compound first described above, another preferred subgroup of compounds is that subgroup wherein:

$R^1$ is —$N(R^7)_2$;
$R^2$ and $R^3$ are each independently selected from the group consisting of —$R^8$—$OR^7$, —$R^8$—$OC(O)R^9$, —$R^{10}$—$N(R^7)_2$, —$R^{10}$—$N(R^9)C(O)R^9$, —$R^{10}$—$N(R^9)S(O)_tR^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;
$R^{4a}$ and $R^{4b}$ are each independently selected from hydrogen, alkyl, alkenyl or alkynyl;
or $R^{4a}$ is hydrogen, alkyl, alkenyl or alkynyl and $R^{4b}$ is a direct bond to the carbon at C16;
or $R^{4a}$ and $R^{4b}$ together form alkylidene or haloalkylidene;
$R^5$ is alkyl or $R^5$ is a direct bond to the carbon at C14;
$R^6$ is hydrogen, —$R^8$—$OR^7$ or —$R^8$—$N(R)_2$;
each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of the preferred class of compounds first described above, another preferred subclass of compounds is that subclass wherein:

$R^1$ is —$OR^7$;
$R^2$ is —$R^8$—$OR^7$;
$R^3$ is —$R^{10}$—$N(R^9)C(O)R^9$, —$R^{10}$—$N(R^9)S(O)_tR^9$ (where t is 1 or 2) or —$R^{10}$—$N(R^9)C(NR^9)N(R^9)_2$;
$R^{4a}$ and $R^{4b}$ are each independently selected from hydrogen, alkyl, alkenyl or alkynyl;
or $R^{4a}$ is hydrogen, alkyl, alkenyl or alkynyl and $R^{4b}$ is a direct bond to the carbon at C16;
or $R^{4a}$ and $R^{4b}$ together form alkylidene or haloalkylidene;
$R^5$ is alkyl or $R^5$ is a direct bond to the carbon at C14;
$R^6$ is hydrogen, —$R^8$—$OR^7$ or —$R^8$—$N(R^7)_2$;
each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of the preferred subgroup of compounds first described above, another preferred class of compounds is that class wherein:

$R^1$ is —$OR^7$;
$R^2$ is selected from the group consisting of —$R^8$—$OC(O)R^9$, —$R^{10}$—$N(R^9)C(O)R^9$, —$R^{10}$—$N(R)S(O)R^9$ (where t is 1 or 2), —$R^{10}$—$N(R^9)C(NR^9)N(R^9)_2$, alkyl, alkenyl, optionally substituted aralkyl, optionally substituted aralkenyl, optionally substituted heterocyclylalkyl, optionally substituted heteroarylalkyl, optionally substituted heteroarylalkenyl, and optionally substituted heteroarylalkenyl;
$R^3$ is —$R^8$—$OR^7$ or —$R^8$—$OC(O)R^9$;
$R^{4a}$ and $R^{4b}$ are each independently selected from hydrogen, alkyl, alkenyl or alkynyl;
or $R^{4a}$ is hydrogen, alkyl, alkenyl or alkynyl and $R^{4b}$ is a direct bond to the carbon at C16;
or $R^{4a}$ and $R^{4b}$ together form alkylidene or haloalkylidene;
$R^5$ is alkyl or $R^5$ is a direct bond to the carbon at C14;
$R^6$ is hydrogen, —$R^8$—$OR^7$ or —$R^8$—$N(R)_2$;
each $R^7$ is independently selected from the group consisting of hydrogen, —$R^{10}$—$OR^9$, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;

each $R^8$ is independently selected from the group consisting of a direct bond, a straight or branched alkylene chain, and a straight or branched alkenylene chain; and each $R^9$ is independently selected from the group consisting of hydrogen, alkyl, aryl and aralkyl;

each $R^{10}$ is independently selected from the group consisting of a straight or branched alkylene and a straight or branched alkenylene chain.

Of the preferred class of compounds first described above, another subclass of compounds is that subclass wherein:

$R^1$ is —$OR^7$;
$R^2$ is —$R^8$—$OR^7$;
$R^3$ is heterocyclylalkyl, optionally substituted heteroarylalkyl, optionally substituted heteroarylalkenyl or optionally substituted heteroarylalkenyl;
$R^{4a}$ and $R^{4b}$ are each independently selected from hydrogen, alkyl, alkenyl or alkynyl;
or $R^{4a}$ is hydrogen, alkyl, alkenyl or alkynyl and $R^{4b}$ is a direct bond to the carbon at C16;
or $R^{4a}$ and $R^{4b}$ together form alkylidene or haloalkylidene;
$R^5$ is alkyl or $R^5$ is a direct bond to the carbon at C14;
$R^6$ is hydrogen, —$R^8$—$OR^7$ or —$R^8$—$N(R^7)_2$;
each $R^7$ is independently selected from the group consisting of hydrogen, —$R^{10}$—$N(R^9)_2$, alkyl, optionally substituted cycloalkyl, optionally substituted cycloalkylalkyl, optionally substituted aryl, optionally substituted aralkyl, optionally substituted heterocyclylalkyl, optionally substituted heteroaryl and optionally substituted heteroarylalkyl;
each $R^8$ is independently selected from the group consisting of a direct bond, a straight or branched alkylene chain, and a straight or branched alkenylene chain; and
each $R^9$ is independently selected from the group consisting of hydrogen, alkyl, aryl and aralkyl;
each $R^{10}$ is independently selected from the group consisting of a straight or branched alkylene and a straight or branched alkenylene chain.

Of the preferred groups of compounds set forth above, the most preferred compounds of the invention are those compounds which are disclosed below in the "Synthesis Examples". Of the preferred groups of compounds set forth above, the most preferred $R^1$, $R^2$, $R^3$, $R^{4a}$, $R^{4b}$, $R^5$, $R^6$, $R^7$, $R^8$, $R^9$ and $R^{10}$ selections may be discerned from the compounds which are disclosed below in the "Synthesis Examples". For example, the most preferred selection for $R^{4a}$ and $R^{4b}$ is when they together form a methylene or an ethylidene group. For example, a preferred selection for $R^1$ is —$R^8$—$OR^7$ where $R^8$ is a direct bond and $R^7$ is hydrogen. For example, a preferred selection for $R^5$ is methyl. For example, a preferred selection for $R^6$ is hydrogen. Similar preferred embodiments are readily discernible by the following disclosure and the attached claims.

Of the methods of treating an inflammatory condition or disease in a mammal by administering a compound of the invention, as set forth above in the Summary of the Invention, a preferred method administers a compound of formula (Ia). In addition, a preferred method is one wherein the inflammatory condition or disease is selected from the following:

arthritis (including rheumatoid arthritis, psoriatic arthritis, ankylosing spondylitis, osteoarthritis, gout, and synovitis), inflammations of the brain (including multiple sclerosis, Alzheimer's, AIDS dementia, stroke, encephalitis, trauma, and Creutzfeld-Jakob disease), inflammatory bowel disease (including Crohn's disease and ulcerative colitis), irritable bowel syndrome, ischemia-reperfusion injury (including myocardial infarction), sarcoidosis, psoriasis, tissue/organ transplant, graft vs host disease, systemic lupus erythematosus, Type I juvenile diabetes, vasculitis, artherosclerosis, cardiomyopathy, autoimmune myocarditis, atopic dermatitis, asthma, allergy, allergic rhinitis, and chronic obstructive pulmonary disease (including emphysema and bronchitis).

E. Preparation of the Compounds of the Invention

The compounds of the invention can be prepared by methods employing steps known to those skilled in the art or analogous to those steps. General methods for the reactions on steroids can be found in "Steroid Reactions", C. Djerassi, Ed. Holden Day, San Francisco, Calif., 1963 and references cited therein. General synthetic methods can be found in "Comprehensive Organic Transformations", R. C. Larock, VCH Publishers, New York, N.Y., 1989 and references cited therein. Additional literature references useful for the synthesis of compounds of the invention are as follows: T. Reichstein; C. H. Meystre, *Helv. Chim. Acta,* 1932, 22, 728; H. Westmijze; H. Kleyn; P. Vermeer; L. A. van Dijck, *Tet. Lett.* 1980, 21, 2665; K. Prezewowsky; R Wiechert, U.S. Pat. No. 3,682,983; P. Kaspar; H. Witzel, *J. Steroid Biochem.* 1985, 23, 259; W. G. Dauben; T. Brookhart, *J. Am. Chem. Soc.* 1981, 103, 237; A. J. Manson et al., *J. Med. Chem.* 1963, 6, 1; R. O. Clinton et al, *J. Am. Chem. Soc.* 1961, 83, 1478; M. S. Ahmad; L. A. Khan, *Acta. Chim. Acad. Sci. Hung.* 1981, 106, 111.

In particular, compounds of the invention may be prepared by the following Schemes or by the Reaction Schemes disclosed in the following Synthesis Examples. It is understood that other compounds of the invention may be prepared in a similar manner as described below or by methods known to one of ordinary skill in the art. It is also understood that although the following Synthesis Examples may be directed to the preparation of a specific substituent on a particular carbon in the compounds, one of ordinary skill in the art would be able to prepare similar substituents on other carbons of the compounds based on the teachings provided herein and in view of what is commonly known in the art.

Referring to the following Scheme A, ketones of compound 1, or compounds analogous thereto, can be alkylated with a variety of alkylating groups to give compounds of the invention having but not limited to alkyl, cycloalkyl, aryl and heteroaryl substitution. Alkylation of the 17-ketone 1 with the anion of acetylene generates the 17α-ethynyl-17β-hydroxyl intermediate 2. Reversal of the stereochemistry of the C17 substituents may be carried out by first forming the methylsulfonate followed by treatment with silver (I) nitrate in tetrahydrofuran (THF) and water. Dehydration of compound 2 using POCl$_3$ in 2,4-lutidine gives compound 3. Treatment with tetrabutylammonium fluoride removes the tert-butyldimethylsilyl groups to give compound 4.

SCHEME A

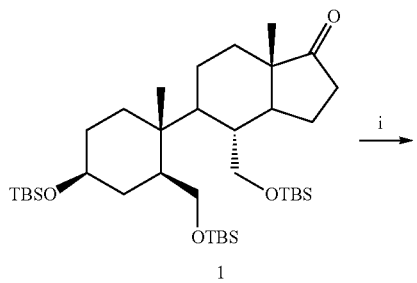

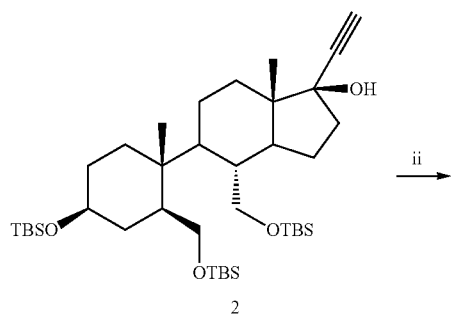

2

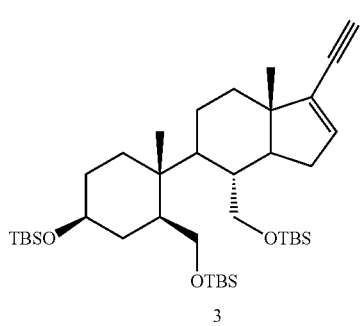

3

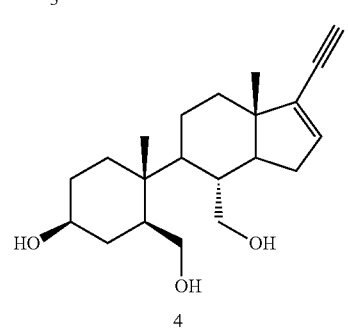

4 i) KCCH; ii) POCl₃, 2,4-lutidine; iii) Bu₄NF.

Referring to the following Scheme B, compounds of the invention having an allene functionality may be prepared from intermediates analogous to compound 2. Exemplary is the reaction of compound 2 with LiAlH₄ and AlCl₃ in THF to give the allene 5. Treatment with tetrabutylammonium fluoride removes the tert-butyldimethylsilyl groups to give compound 6.

SCHEME B

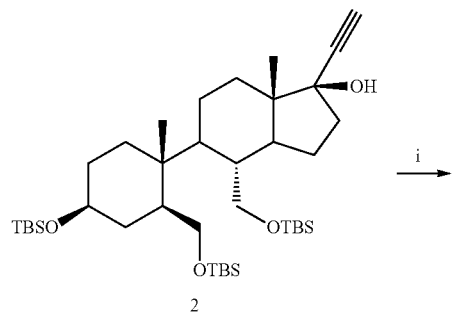

2

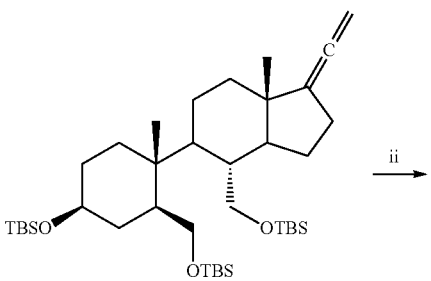

5

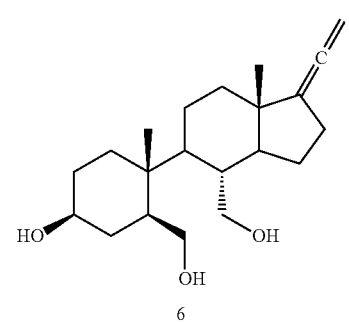

6 i) LiAlH₄, AlCl₃, THF; ii) Bu₄NF.

Referring to the following Scheme C, compounds of the invention having an alkynyl functionality may be prepared from allene intermediates. Exemplary is the treatment of compound 5 with n-BuLi in THF giving the 17β-ethynyl compound 7. Treatment with tetrabutylammonium fluoride removes the tert-butyldimethylsilyl groups to give compound 8.

SCHEME C

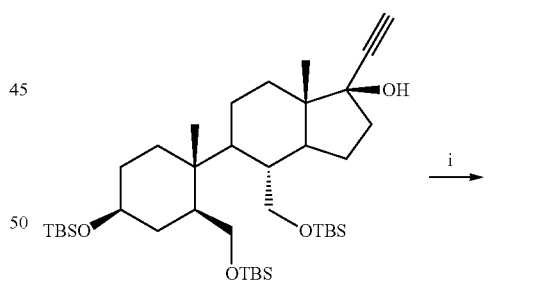

2

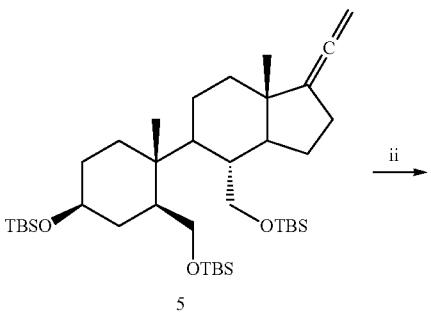

5

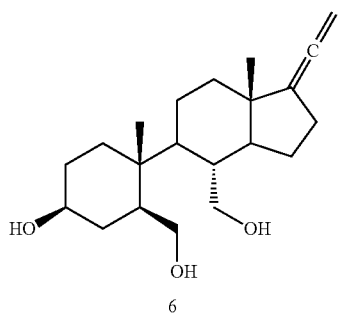

i) n-BuLi, THF; ii) Bu₄NF.

Referring to the following Scheme D, compounds of the invention having alkenyl functionality may be prepared from alkyne intermediates. Exemplary is the controlled hydrogenation of compound 7 using Pd—CaCO₃ as catalyst to give the alkene 9. Treatment with tetrabutylammonium fluoride removes the tert-butyldimethylsilyl groups to give compound 10.

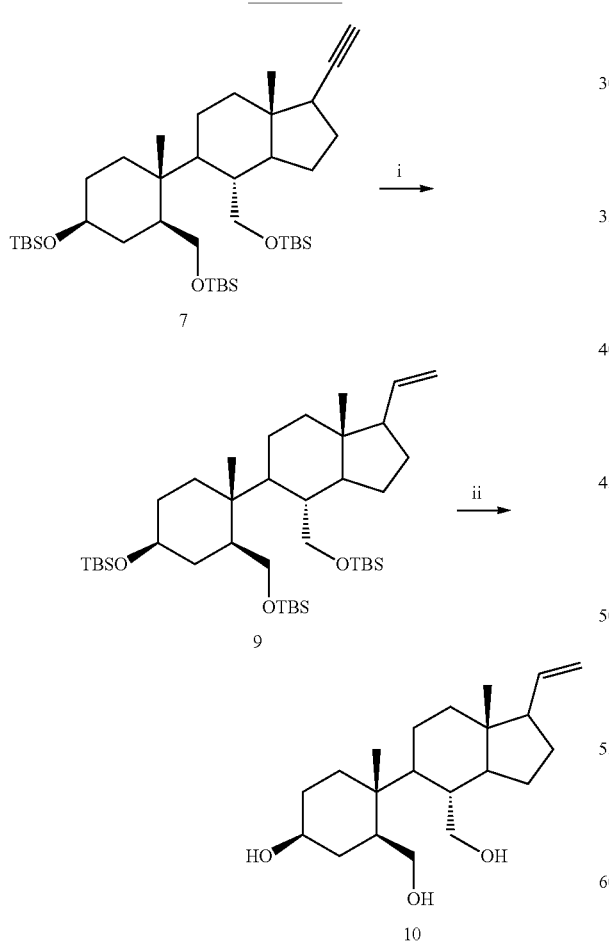

i) H₂, Pd-CaCO₃; ii) Bu₄NF.

Compound 1 can be used in a multitude of olefination reactions, including Wittig-type reactions to provide compounds of the invention having an exocyclic olefin. For example, as illustrated in the following Scheme E, compound 1 may be treated with ethyltriphenylphosphonium bromide and potassium tert-butoxide to provide compound 11 having $R_1$=methyl and $R_2$=hydrogen. Treatment with tetrabutylammonium fluoride removes the tert-butyldimethylsilyl groups to give compound 12.

In analogy to the synthesis shown in the following Scheme E, ketones such as compound 1 may be reacted with other Wittig-type reagents such as, but not limited to, methyl-, propyl-, butyl-, pentyl- or hexyltriphenyl-phosphonium bromide to give compounds of the invention analogous to compound 12 having $R_2$=hydrogen and $R_1$=hydrogen, ethyl, propyl, butyl or pentyl.

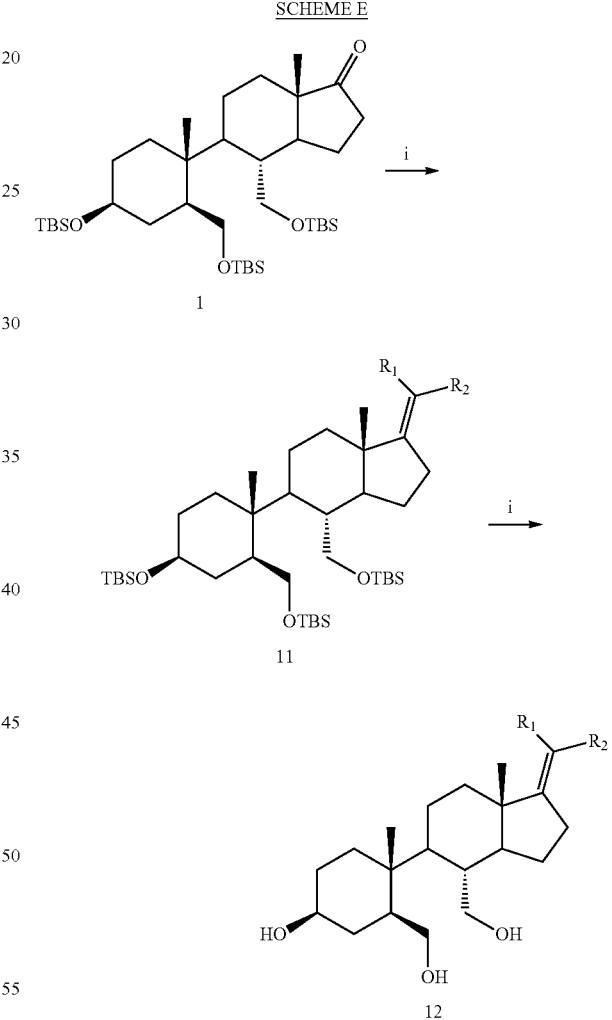

i) EtPPh₃Br, KOᵗBu, Toluene; ii) Bu₄NF.

Compounds of the invention can contain exocyclic double bonds of E and/or Z geometry. For example, as illustrated in the following Scheme F, the Z-olefin 11 in cyclohexane may be treated with UV light in the presence of diphenyl disulfide resulting in isomerization to the E-olefin 13. Treatment with tetrabutylammonium fluoride removes the tert-butyldimethylsilyl groups to give compound 14.

SCHEME F

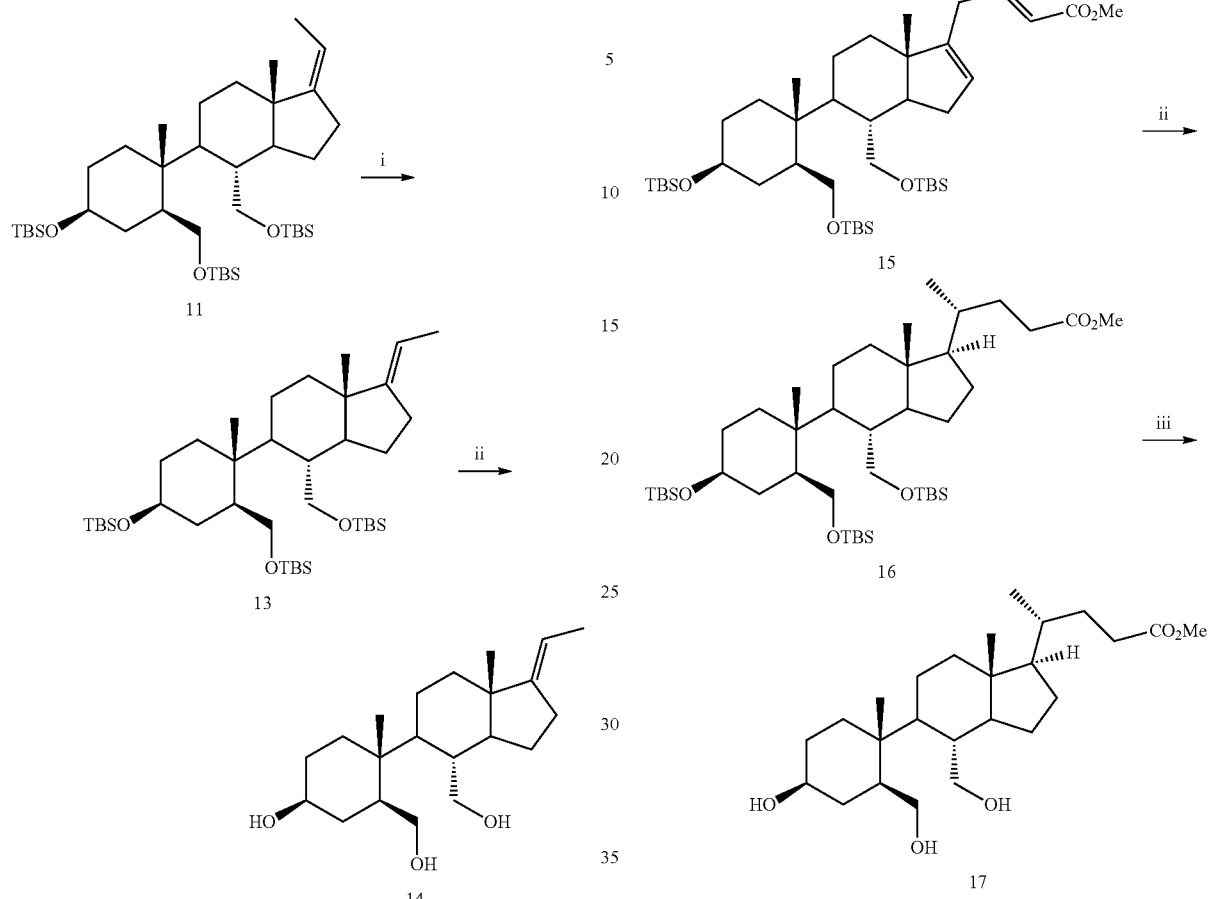

i) (PhS)₂, hυ, cyclohexane; ii) Bu₄NF.

i) HCCCO₂Me, Et₂AlCl; ii) H₂, Pt; iii) Bu₄NF.

A multitude of compounds of the invention having functionalized sidechains can be prepared using methods such as Lewis acid promoted couplings to aldehydes and Michael acceptors. For example, as illustrated in the following Scheme G, compound 11 may be reacted with methyl propiolate in the presence of diethylaluminum chloride to give compound 15. The double bonds may be hydrogenated using a catalyst such as platinum to give compound 16. Treatment with tetrabutylammonium fluoride removes the tert-butyldimethylsilyl groups to give compound 17.

SCHEME G

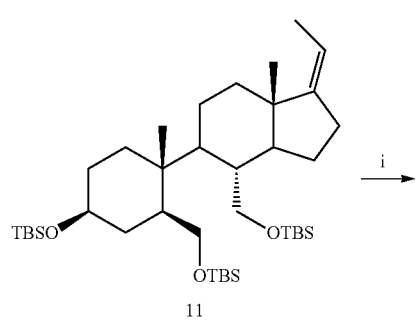

The following specific examples are provided as a guide to assist in the practice of the invention, and are not intended as a limitation on the scope of the invention.

Unless otherwise stated, flash chromatography and column chromatography used in the following examples may be accomplished using Merck silica gel 60 (230-400 mesh). Flash chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 23. Column chromatography refers to the process whereby the flow rate of eluent through a packing material is determined by gravity. In all cases flash chromatography and radial chromatography may be used interchangeably. Radial chromatography may be performed using silica gel on a Chromatotron Model # 7924T (Harrison Research, Palo Alto, Calif.). Unless otherwise stated, quoted $R_f$ values are obtained by thin layer chromatography using Silica Gel 60 $F_{254}$ (Merck KGaA, 64271, Darmstadt, Germany). Brine refers to a saturated solution of sodium chloride.

Also, unless otherwise stated, chemical reactants and reagents were obtained from standard chemical supply houses, such as Aldrich (Milwaukee, Wis.; www.aldrich.sial-.com); EM Industries, Inc. (Hawthorne, N.Y.); Fisher Scientific Co. (Hampton, N.H.); and Lancaster Synthesis, Inc. (Windham, N.H.). Gases were obtained from Praxair (Vancouver, B.C.). Cell lines, unless otherwise stated, where obtained from public or commercial sources, e.g., American Tissue Culture Collection (ATCC, Rockville, Md.).

SYNTHESIS EXAMPLES

Example 1

Compound 25, a representative compound of the invention, may be prepared according to Reaction Scheme 1. Any number of compounds related to compound 25 could be produced using similar methodology. Starting compound 18 may be prepared according to the procedures outlined in U.S. Pat. No. 6,046,185.

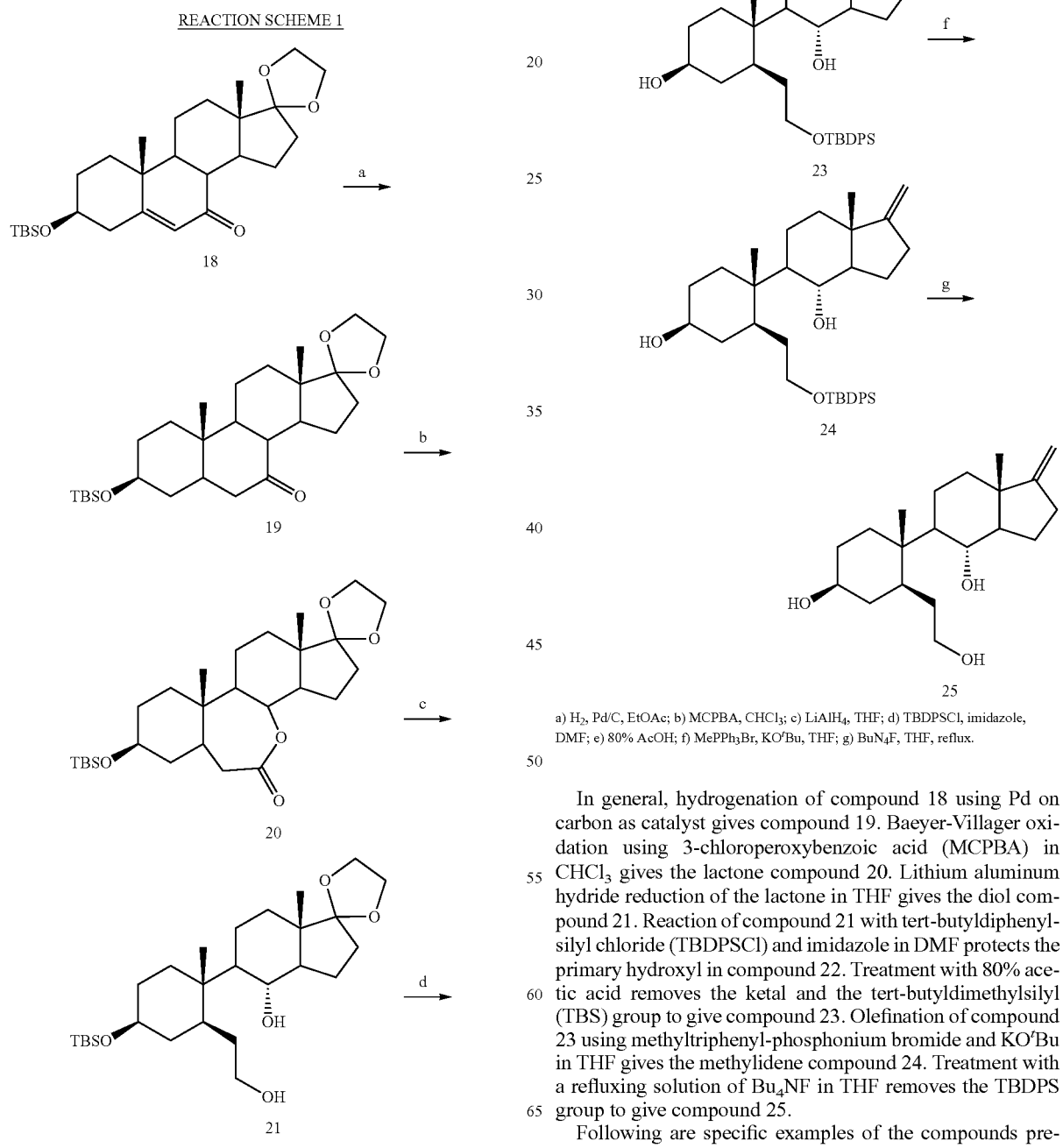

a) $H_2$, Pd/C, EtOAc; b) MCPBA, CHCl$_3$; c) LiAlH$_4$, THF; d) TBDPSCl, imidazole, DMF; e) 80% AcOH; f) MePPh$_3$Br, KO$^t$Bu, THF; g) Bu$_4$NF, THF, reflux.

In general, hydrogenation of compound 18 using Pd on carbon as catalyst gives compound 19. Baeyer-Villager oxidation using 3-chloroperoxybenzoic acid (MCPBA) in CHCl$_3$ gives the lactone compound 20. Lithium aluminum hydride reduction of the lactone in THF gives the diol compound 21. Reaction of compound 21 with tert-butyldiphenylsilyl chloride (TBDPSCl) and imidazole in DMF protects the primary hydroxyl in compound 22. Treatment with 80% acetic acid removes the ketal and the tert-butyldimethylsilyl (TBS) group to give compound 23. Olefination of compound 23 using methyltriphenyl-phosphonium bromide and KO$^t$Bu in THF gives the methylidene compound 24. Treatment with a refluxing solution of Bu$_4$NF in THF removes the TBDPS group to give compound 25.

Following are specific examples of the compounds prepared above.

Synthesis of Compound 19

A solution of compound 18 (2.03 g, 4.41 mmol) in EtOAc (135 mL) was treated overnight with hydrogen (balloon pressure) in the presence of a catalytic amount of Pd on carbon. The catalyst was removed by filtration and the solution was concentrated to dryness. The residue was purified by chromatography on silica gel (hexanes/EtOAc/CH$_2$Cl$_2$, 8:1:1) to give compound 19 (1.79 g, 88%) as a white solid.

Synthesis of Compound 20

A mixture of compound 19 (2.38 g, 5.14 mmol) and MCPBA (3.11 g, 10.3 mmol) in chloroform (26 mL) was refluxed for 4 hours. After cooling to ambient temperature, the reaction mixture was diluted with EtOAc (25 mL), washed with saturated Na$_2$SO$_3$ (2×20 mL), saturated NaHCO$_3$ (2×20 mL) and brine (2×20 mL) then dried over anhydrous MgSO$_4$, and concentrated to dryness. The crude compound 20 (2.43 g, white solid) was used for the next reaction without further purification.

Synthesis of Compound 21

To a solution of compound 20 (1.00 g, 2.09 mmol) in THF at 0° C. was added LiAlH$_4$ (21 mL of a 1 M solution in THF, 2.09 mmol). The reaction mixture was stirred at ambient temperature for one hour then brine (5 mL) was slowly added. The solution was extracted with CH$_2$Cl$_2$ (2×15 mL) then was dried over MgSO$_4$, filtered and concentrated. The residue was purified by chromatography on silica gel (EtOAc) to afford compound 21 (0.786 g, 78%) as a white solid.

Synthesis of Compound 22

A solution of compound 21 (0.93 g, 1.93 mmol), TBDPSCl (1.1 mL, 4.4 mmol) and imidazole (0.57 g, 8.5 mmol) in dry DMF (10 mL) was stirred overnight. The reaction mixture was diluted with EtOAc (50 mL) and washed with brine (2×20 mL) then was dried over MgSO$_4$, filtered and concentrated. The residue was purified by chromatography on silica gel (hexanes/EtOAc, 3:1) to afford compound 22 (1.22 g, 66%) as a white solid.

Synthesis of Compound 23

A mixture of compound 22 (1.00 g, 1.39 mmol) and 80% acetic acid (20 mL)) was stirred at 50° C. for 2 hours then was diluted with toluene (30 mL) and concentrated. The crude compound 23 was used for the next reaction without further purification.

Synthesis of Compound 24

A mixture of KO$^t$Bu (0.487 g, 4.12 mmol) and MePPh$_3$Br (1.47 g, 4.12 mmol) in THF (6 mL) was stirred at ambient temperature for 1 hour under argon then compound 23 (0.773 g, 1.37 mmol) in THF (6 mL) was added. The reaction mixture was stirred at ambient temperature overnight then was diluted with EtOAc (40 mL) and washed with brine (2×30 mL) then was dried over MgSO$_4$, filtered and concentrated. The residue was purified by chromatography on silica gel (hexanes/EtOAc, 1:1) to afford compound 24 (0.606 g, 79%) as a white solid.

Synthesis of Compound 25

A solution of compound 24 (0.15 g, 0.267 mmol) and Bu$_4$NF (0.4 mL of a 1.0 M solution in THF) in THF (5 mL) was refluxed under argon for 2 hours. The solvent was evaporated under reduced pressure and the residue was purified by chromatography on silica gel (MeOH/EtOAc, 2:98) to give compound 25 (0.073 g, 82%) as a white solid: LC/MS (direct infusion, electrospray +ve, 10 mM NH$_4$OAc in 3:7 water and MeCN) 287.10; C$_{20}$H$_{31}$O.

Example 2

Compound 29, a representative compound of the invention, may be prepared according to the following Reaction Scheme 2. Any number of compounds related to compound 29 could be produced using similar methodology. Starting compound 20 may be prepared according to procedures set forth in Example 1 above.

REACTION SCHEME 2

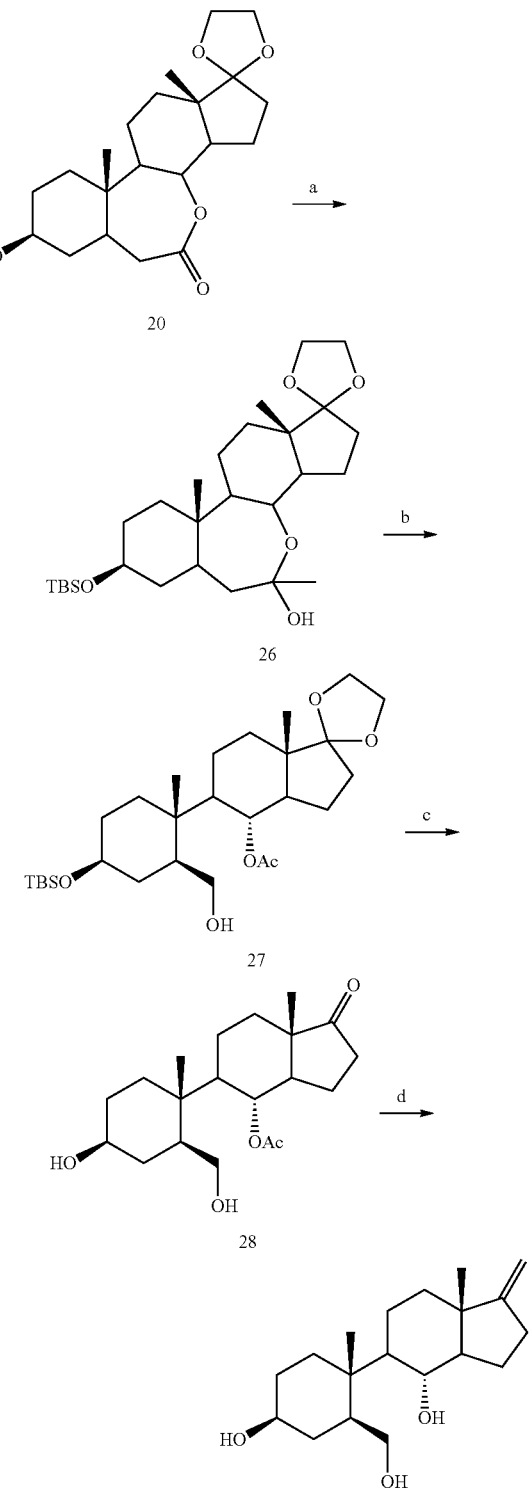

a) MeLi, THF; b) MCPBA, CHCl$_3$; c) 80% AcOH; d) MePPh$_3$Br, KO$^t$Bu, THF, reflux.

In general, treatment of lactone compound 20 with MeLi in THF gives the lactol compound 26. Baeyer-Villager oxidation using MCPBA in CHCl₃ gives compound 27. Treatment with 80% acetic acid removes the ketal and the TBS group to give compound 28. Reaction of compound 28 with methyltriphenyl-phosphonium bromide and KO$^t$Bu in THF introduces the methylidene group and removes the acyl group to give compound 29.

Following are specific examples of the compounds prepared above.

Synthesis of Compound 26

To a 0° C. solution of compound 20 (2.0 g, 4.18 mmol) in dry THF (12 mL) was added dropwise MeLi (8.95 mL of a 1.4 M solution in ether). The reaction mixture was stirred for 2 hours then was poured over ice and extracted with EtOAc (3×100 mL). The combined organic layer was washed with brine (2×50 mL) then was dried over Na₂SO₄, filtered and concentrated. The residue was purified by chromatography on silica gel (hexane/EtOAc, 8:2) to yield compound 26 (1.49 g, 72%) as a white solid.

Synthesis of Compound 27

To a solution of compound 26 (1.49 g, 3.00 mmol) in chloroform was added MCPBA (1.8 g, 6.00 mmol). The reaction mixture was stirred at ambient temperature for 20 hours then was diluted with EtOAc (200 mL). The solution was washed successively with 5% NaHSO₃ solution (2×100 mL), saturated K₂CO₃ solution (2×50 mL) and brine (2×50 mL) then was dried over Na₂SO₄, filtered and concentrated. The residue was purified by chromatography on silica gel (hexane/EtOAc, 9:1) to afford compound 27 (1.3 g, 85%) as a white solid.

Synthesis of Compound 28

A mixture of compound 27 (400 mg, 0.783 mmol) and 80% acetic acid (5 mL) was stirred at 50° C. for 5 hours then was diluted with toluene (50 mL) and concentrated. The residue was purified by chromatography on silica gel (hexanes/acetone, 1:1) to yield compound 28 (322 mg, 86%) as a white solid.

Synthesis of Compound 29

A mixture of KO$^t$Bu (286 mg, 2.55 mmol) and MePPh₃Br (911 mg, 2.55 mmol) in THF (2 mL) was stirred at ambient temperature for 1 hour under argon, then compound 28 (300 mg, 0.85 mmol) in THF (2 mL) was added. The reaction mixture was refluxed for 4 hours then was cooled to ambient temperature and diluted with water (5 mL). The solution was extracted with EtOAc (3×50 mL) and washed with brine (2×20 mL) then was dried over Na₂SO₄, filtered and concentrated. The residue was purified by chromatography on silica gel (hexanes/EtOAc, 2:8) to afford compound 29 (144 mg, 55%) as a white solid: LC/MS (direct infusion, electrospray +ve, 10 mM NH₄OAc in 3:7 water and MeCN) 273.01; C₁₉H₂₉O.

Example 3

Compound 38, a representative compound of the invention, may be prepared according to the following Reaction Scheme 3. Any number of compounds related to compound 38 could be produced using similar methodology. Starting compound 30 may be prepared according to the procedures outlined in U.S. Pat. No. 6,046,185.

REACTION SCHEME 3

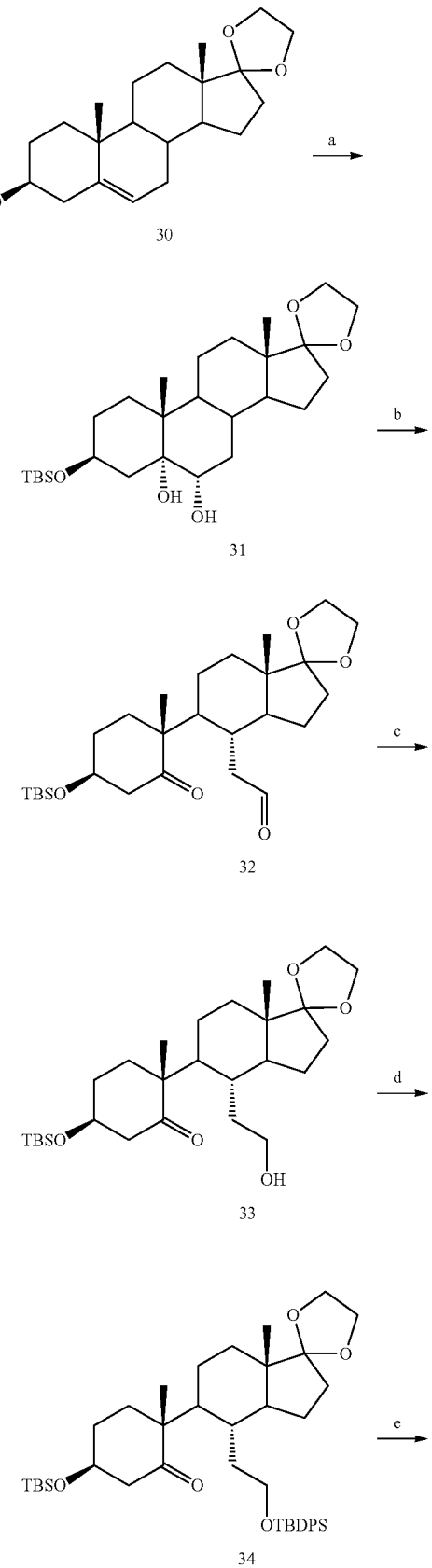

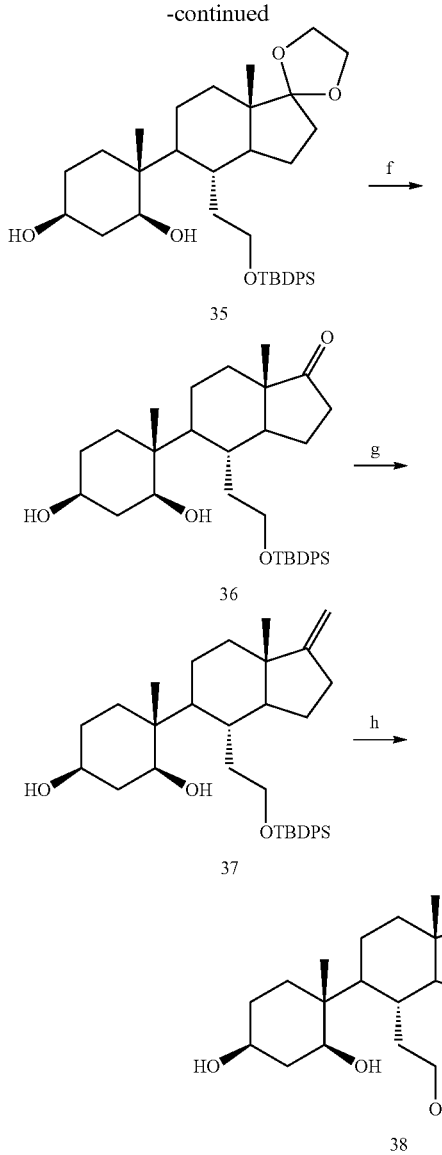

a) OsO$_4$, pyridine; b) Pb(OAc)$_4$, CH$_2$Cl$_2$; c) LiEt$_3$BH, THF; d) TBDPSCl, imidazole, DMF; e) LiAlH$_4$, THF; f) 80% HOAc; g) CH$_3$PPh$_3$Br, KO$^t$Bu, THF; h) Bu$_4$NF, THF, reflux.

In general, dihydroxylation of compound 30 using osmium tetraoxide in pyridine gives compound 31. Oxidative cleavage of the diol using lead tetraacetate in CH$_2$Cl$_2$ gives compound 32. Selective reduction of the aldehyde group using LiBEt$_3$H in THF gives compound 33. Reaction of compound 33 with TBDPSCl and imidazole in DMF protected the free hydroxyl to give compound 34. Lithium aluminum hydride reduction of the ketone group gives compound 35. Treatment with 80% acetic acid removes the ketal to give compound 36. Olefination using methyltriphenylphosphonium bromide and KO$^t$Bu in THF gives the methylidene compound 37. Treatment with a refluxing solution of Bu$_4$NF in THF removes the TBDPS group to give compound 38.

Following are specific examples of the compounds prepared above.

Synthesis of Compound 31

To a solution of compound 30 (0.45 g, 0.89 mmol) in pyridine (2.5 mL) was added OsO$_4$ (0.25 g, 0.98 mmol). The reaction mixture was stirred at 90° C. overnight then a solution of Na$_2$S$_2$O$_3$ (0.5 g) in a mixture of water (8 mL) and pyridine was added. The reaction mixture was stirred for 20 minutes then extracted with CH$_2$Cl$_2$ (2×20 mL) and washed with brine (30 mL), then dried over MgSO$_4$, filtered and concentrated. The residue was purified by chromatography on silica gel (hexanes/EtOAc, 4:1) to afford compound 31 (0.249 g, 58%) as a white solid.

Synthesis of Compound 32

To a solution of compound 31 (0.52 g, 1.08 mmol) in CH$_2$Cl$_2$ was added Pb(OAc)$_4$ (0.527 g, 1.19 mmol). The reaction mixture was stirred at ambient temperature for 10 minutes under argon. A precipitate was removed by filtration and the solvent was evaporated under reduced pressure. The residue was filtered through a silica gel plug (hexanes/EtOAc, 1:1) to afford compound 32 (0.482 g, 58%) as a white solid.

Synthesis of Compound 33

To a solution of compound 32 (0.562 g, 1.17 mmol) in THF at 0° C. was added LiBEt$_3$H (1.29 mL of a 1M solution in THF). The reaction mixture was stirred at ambient temperature for 40 minutes under argon then was cooled in an ice bath and NaOH (1.29 mL, 1M) and H$_2$O$_2$ (0.2 mL, 30%) were slowly added. The resulting solution was stirred at 0° C. for an additional 5 minutes. The solution was extracted with CH$_2$Cl$_2$ (2×15 mL) and the extracts were dried over MgSO$_4$, filtered concentrated. The residue was purified by chromatography on silica gel (hexanes/EtOAc, 75:25 to 40:60) to afford compound 33 (256 mg, 46%) as a white solid.

Synthesis of Compound 34

A solution of compound 33 (0.185 g, 0.385 mmol), TBDPSCl (0.175 mL, 0.673 mmol) and imidazole (0.09 g, 1.161 mmol) in dry DMF (4 mL) was stirred overnight. The reaction mixture was diluted with toluene (30 mL) and washed with brine (2×15 mL) then was dried over MgSO$_4$, filtered and concentrated. The crude compound 34 was used for the next reaction without further purification.

Synthesis of Compound 35

To a solution of compound 34 (crude, 0.104 mmol) in THF at 0° C. was added LiAlH$_4$ (0.1 mL of a 1M solution in THF) under argon. The reaction mixture was stirred at 0° C. for 1 hour, then brine (5 mL) was slowly added. The solution was extracted with CH$_2$Cl$_2$ (2×15 mL) and the extracts were dried over MgSO$_4$, filtered concentrated. The residue was purified by chromatography on silica gel (hexanes/EtOAc, 2:3) to afford compound 35 (39 mg, 51% over two steps) as a white solid.

Synthesis of Compound 36

A mixture of compound 35 (120 mg, 0.197 mmol) and 80% acetic acid (1.5 mL) was stirred at ambient temperature overnight then was diluted with toluene (10 mL) and concentrated. The crude compound 36 was used for the next reaction without further purification.

Synthesis of Compound 37

A mixture of KO$^t$Bu (60 mg, 0.54 mmol) and MePPh$_3$Br (194 mg, 0.54 mmol) in THF (0.9 mL) was stirred at ambient temperature for 1 hour under argon then compound 36 (97 mg, 0.17 mmol) was added. The reaction mixture was stirred at ambient temperature for 3 hours then was diluted with EtOAc (80 mL) and washed with brine (2×30 mL) then was dried over MgSO$_4$, filtered and concentrated. The residue was purified by chromatography on silica gel (hexanes/EtOAc, 2:3) to afford compound 37 (63 mg, 65%) as a white solid.

Synthesis of Compound 38

A solution of compound 37 (59 mg, 0.105 mmol) and n-Bu$_4$NF (0.16 mL of a 1.0 M solution in THF) in THF (0.35 mL) was refluxed under argon for 2 hours. The solvent was evaporated under reduced pressure and the residue was purified by chromatography on silica gel (MeOH/EtOAc, 2:98) to afford compound 38 (38 mg) as a white solid: LC/MS (direct infusion, electrospray +ve, 10 mM NH₄OAc in 3:7 water and MeCN) 286.93; $C_{20}H_{31}O$.

Example 4

Compound 45, a representative compound of the invention, may be prepared according to the following Reaction Scheme 4. Any number of compounds related to compound 45 could be produced using similar methodology. Starting compound 18 may be prepared according to procedures outlined in U.S. Pat. No. 6,046,185.

REACTION SCHEME 4

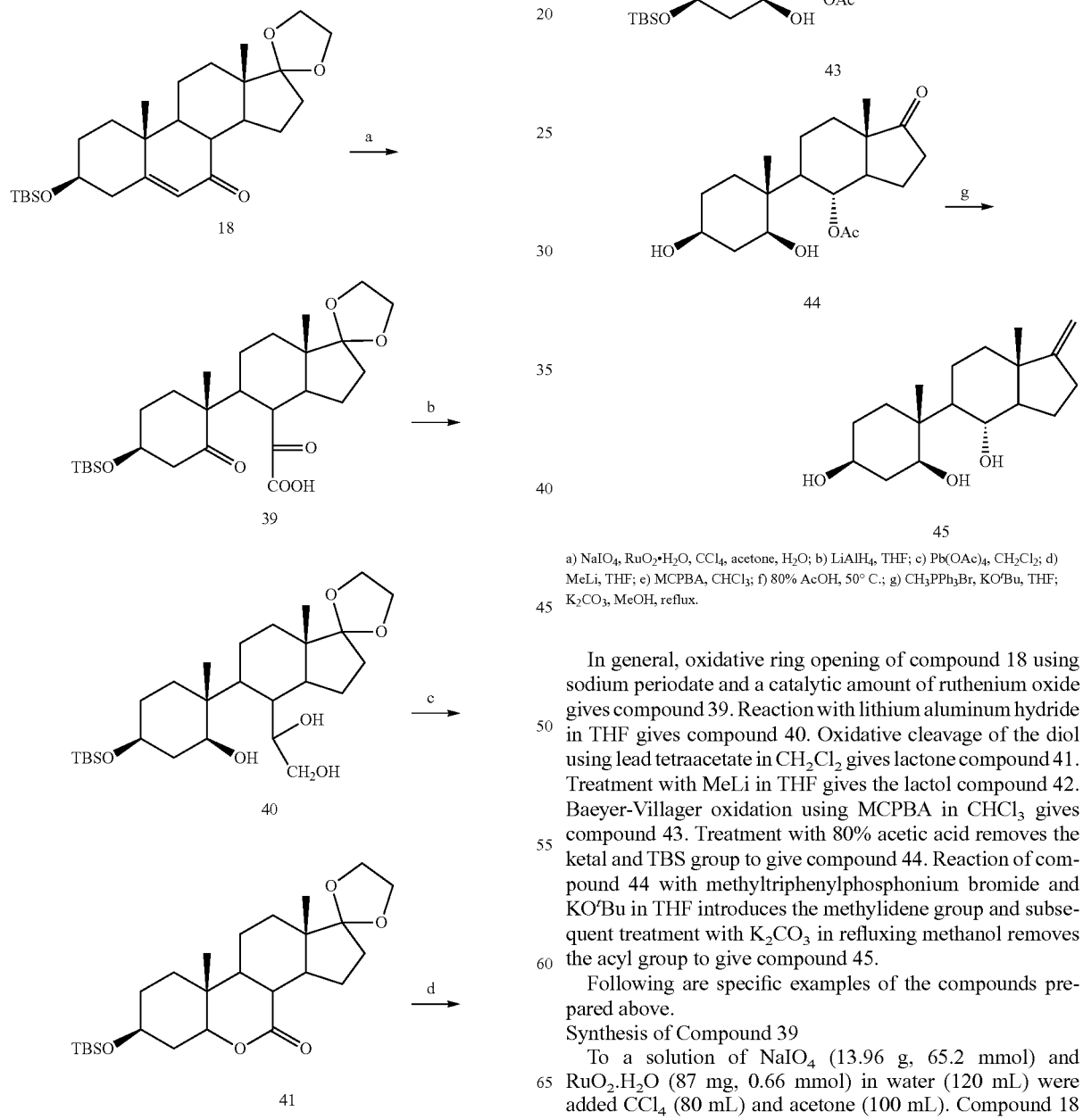

a) NaIO₄, RuO₂·H₂O, CCl₄, acetone, H₂O; b) LiAlH₄, THF; c) Pb(OAc)₄, CH₂Cl₂; d) MeLi, THF; e) MCPBA, CHCl₃; f) 80% AcOH, 50° C.; g) CH₃PPh₃Br, KO^tBu, THF; K₂CO₃, MeOH, reflux.

In general, oxidative ring opening of compound 18 using sodium periodate and a catalytic amount of ruthenium oxide gives compound 39. Reaction with lithium aluminum hydride in THF gives compound 40. Oxidative cleavage of the diol using lead tetraacetate in CH₂Cl₂ gives lactone compound 41. Treatment with MeLi in THF gives the lactol compound 42. Baeyer-Villager oxidation using MCPBA in CHCl₃ gives compound 43. Treatment with 80% acetic acid removes the ketal and TBS group to give compound 44. Reaction of compound 44 with methyltriphenylphosphonium bromide and KO^tBu in THF introduces the methylidene group and subsequent treatment with K₂CO₃ in refluxing methanol removes the acyl group to give compound 45.

Following are specific examples of the compounds prepared above.

Synthesis of Compound 39

To a solution of NaIO₄ (13.96 g, 65.2 mmol) and RuO₂·H₂O (87 mg, 0.66 mmol) in water (120 mL) were added CCl₄ (80 mL) and acetone (100 mL). Compound 18 (crude, 0.81 mmol), in a mixture of CCl₄ (40 mL) and acetone (60 mL) was then slowly added. The reaction mixture was stirred at ambient temperature for 3 hours. The solution was extracted with CH$_2$Cl$_2$ (2×200 mL) and the combined organic layer was washed with brine (200 mL) then was dried over MgSO$_4$, filtered and concentrated. The residue was purified by chromatography on silica gel (hexanes/EtOAc/MeOH, 70:25:5) to afford compound 39 (3.41 g, 37%) as a white solid.

Synthesis of Compound 40

To a solution of compound 39 (0.509 g, 1.00 mmol) in THF was slowly added LiAlH$_4$ (3 mL of a 1 M solution in THF). The reaction mixture was stirred for 2 hours then saturated NaHCO$_3$ (5 mL) was slowly added. The solution was extracted with CH$_2$Cl$_2$ (2×20 mL) and the extracts were dried over MgSO$_4$, filtered and concentrated. The residue was purified by chromatography on silica gel (MeOH/EtOAc, 5:95) to afford compound 40 (0.16 g, 32%) as a white glassy solid.

Synthesis of Compound 41

To a solution of compound 40 (0.16 g, 0.32 mmol) in CH$_2$Cl$_2$ was added Pb(OAc)$_4$ (0.156 g, 0.35 mmol). The reaction mixture was stirred at ambient temperature for 10 minutes under argon. A precipitate was removed by filtration and solvent was evaporated under reduced pressure. The residue was purified by chromatography on silica gel (hexanes/EtOAc, 9:1) to afford compound 41 (0.113 g, 87%) as a white glassy solid.

Synthesis of Compound 42

To a solution of compound 41 (0.20 g, 0.43 mmol) in THF (3 mL) at 0° C. was added MeLi (1.5 mL of a 1.4 M solution in diethyl ether) under argon. The reaction mixture was stirred at ambient temperature for 2 hours then was quenched with saturated NH$_4$Cl (15 mL) and extracted with EtOAc (2×15 mL) then was dried over MgSO$_4$, filtered and concentrated. The crude compound 42 was used for the next reaction without further purification.

Synthesis of Compound 43

A mixture of compound 42 (crude, 0.43 mmol) and MCPBA (0.26 g, 57-86%, 1.51 mmol) in chloroform (3 mL) was stirred at ambient temperature for 1 day. The reaction mixture was diluted with EtOAc (15 mL) and washed successively with saturated Na$_2$SO$_3$ (20 mL), saturated NaHCO$_3$ (20 mL) and brine (20 mL), then was dried over MgSO$_4$, filtered and concentrated. The residue was purified by chromatography on silica gel (hexanes/EtOAc, 4:1) to afford compound 43 (66 mg, 31% over two steps) as a white solid.

Synthesis of Compound 44

A mixture of compound 43 (0.40 g, 0.81 mmol) and 80% acetic acid (5 mL) was stirred at 50° C. for 2 hours, then was diluted with toluene (20 mL) and concentrated. The crude compound 44 was used for the next reaction without further purification.

Synthesis of Compound 45

A mixture of KO$^t$Bu (0.45 g, 4.05 mmol) and MePPh$_3$Br (1.45 g, 4.05 mmol) in THF (10 mL) was stirred at ambient temperature for 1 hour under argon then compound 44 (crude, 0.81 mmol) in THF (5 mL) was added. The reaction mixture was stirred at ambient temperature overnight then was diluted with CH$_2$Cl$_2$ (50 mL) and washed with brine (2×30 mL), then dried over MgSO$_4$, filtered and concentrated. The crude product was refluxed with K$_2$CO$_3$ (0.34 g, 2.42 mmol) in THF (5 mL) for 3 hours. The solvent was removed and the residue was purified by chromatography on silica gel (hexane/EtOAc/MeOH, 5:5:0.5) to afford compound 45 (0.13 g, 55% over two steps) as a white solid: LC/MS (direct infusion, electrospray +ve, 10 mM NH$_4$OAc in 3:7 water and MeCN) 317.00; C$_{18}$H$_{30}$NaO$_3$.

Example 5

Compound 51, a representative compound of the invention, may be prepared according to the following Reaction Scheme 5. Starting compound 46 may be prepared according to the procedures outlined in U.S. Pat. No. 6,046,185. Any number of compounds related to compound 51 could be produced using similar methodology.

REACTION SCHEME 5

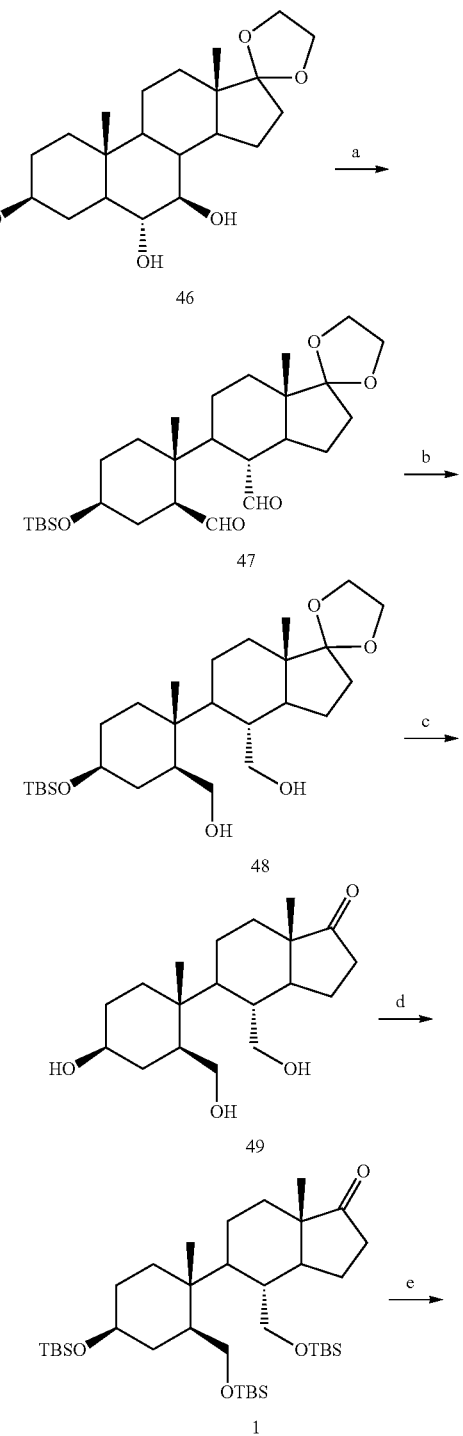

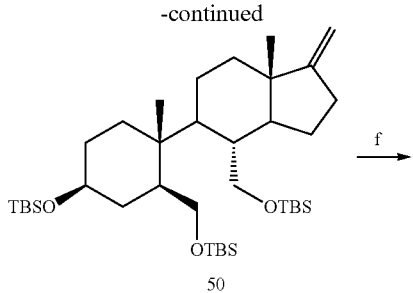

50

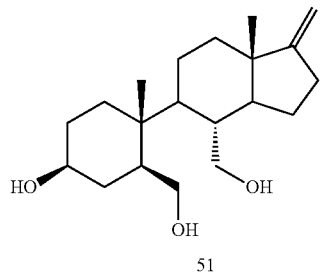

51 a) NaIO$_4$, THF; b) NaBH$_4$, MeOH, CH$_2$Cl$_2$; c) 80% AcOH; d) TBSCl, imidazole, DMF; e) CH$_3$PPh$_3$Br, KO$^t$Bu, THF; f) 80% AcOH; Bu$_4$NF, THF.

In general, reaction of compound 46 with sodium periodate in THF oxidatively cleaves the diol to give compound 47. Sodium borohydride reduction of the aldehyde groups gives compound 48. Treatment with 80% acetic acid removes the ketal and TBS group to give compound 49. Reaction with TBSCl and imidazole in DMF protected the hydroxyls to give compound 1. Olefination using methyltriphenylphosphonium bromide and KO$^t$Bu in THF gives compound 50. Treatment with 80% acetic acid followed by a refluxing solution of Bu$_4$NF in THF removes the TBS groups to give compound 51.

Following are specific examples of the compounds prepared above.

Synthesis of Compound 47

A solution of compound 46 (450 mg, 0.94 mmol), NaIO$_4$ (240 mg, 1.12 mmol), water (2 mL) and THF (4 mL) was stirred overnight at ambient temperature. The reaction mixture was diluted with EtOAc and washed with brine then was dried over Na$_2$SO$_4$, filtered and concentrated. The residue was purified by column chromatography on silica gel (EtOAc/hexanes, 15:85) to afford compound 47 (140 mg, 31%) as a white solid.

Synthesis of Compound 48

A solution of compound 47 (1.32 g, 2.76 mmol), NaBH$_4$ (229 mg, 6.06 mmol), MeOH (17 mL) and CH$_2$Cl$_2$ (3 mL) was stirred at 0° C. for 4 hours, then at ambient temperature overnight. The solvents were evaporated under reduced pressure and the residue was diluted with EtOAc and washed with brine. The EtOAc layer was dried over Na$_2$SO$_4$, filtered and concentrated. The residue was purified by column chromatography on silica gel (EtOAc/hexanes, 2:3) to afford compound 48 (0.35 g, 26%) as a white solid.

Synthesis of Compound 49

A mixture of compound 48 (350 mg, 0.72 mmol) and 80% acetic acid (20 mL) was stirred overnight at ambient temperature. The solvents were evaporated under reduced pressure and the residual solvent was removed by co-distillation with toluene to afford compound 49 (250 mg, 100%) as a yellow solid.

Synthesis of Compound 1

A solution of compound 49 (impure, 0.72 mmol), TBSCI (382 mg, 2.54 mmol), imidazole (346 mg, 5.08 mmol) in dry DMF (15 mL) was stirred at ambient temperature overnight. The reaction mixture was diluted with EtOAc (100 mL), washed with water, then was dried over Na$_2$SO$_4$, filtered and concentrated. The residue was purified by chromatography on silica gel (EtOAc/hexanes, 5:95) to afford compound 1 (374 mg, 78%).

Synthesis of Compound 50

A mixture of KO$^t$Bu (191 mg, 1.7 mmol) and MePPh$_3$Br (600 mg, 1.7 mmol) in THF (1.5 mL) was stirred at ambient temperature for 1 hour under argon, then compound 1 (374 mg, 0.56 mmol) in THF (1.5 mL) was added. The reaction mixture was heated at reflux for 3 hours then was diluted with water (3 mL) and extracted with EtOAc (30 mL). The EtOAc layer was washed with water (10 mL) and brine (10 mL) then was dried over Na$_2$SO$_4$, filtered and concentrated. The residue was eluted through silica gel (EtOAc/hexanes, 1:99) to afford compound 50 (354 mg, 95%) as a yellow oil.

Synthesis of Compound 51

A mixture of compound 50 (350 mg, 0.53 mmol) and 80% acetic acid (10 mL) was heated at 50° C. for 6 hours. The solvents were evaporated under reduced pressure and residual solvent was removed by co-distillation with toluene. The residue still contained some TBS protected material, therefore the residue was taken up in THF (1 mL) and Bu$_4$NF (2.5 mL of a 1.0 M solution in THF) and the resulting solution was heated at reflux for 3.5 hours. The reaction mixture was diluted with EtOAc and washed with water and brine then was dried over Na$_2$SO$_4$, filtered and concentrated. The residue was purified by column chromatography on silica gel (EtOAc) to afford compound 51 (119 mg, 70%) as a pale yellow solid: LC/MS (direct infusion, electrospray +ve, 10 mM NH$_4$OAc in 3:7 water and MeCN) 305.16; C$_{20}$H$_{32}$O$_2$, 287.19; C$_{20}$H$_{30}$O.

Example 6

Compound 59, a representative compound of the invention may be prepared according to the following Reaction Scheme 6. Any number of compounds related to compound 59 could be produced using similar methodology. Starting compound 27 may be prepared according to procedures described above in Example 2.

REACTION SCHEME 6

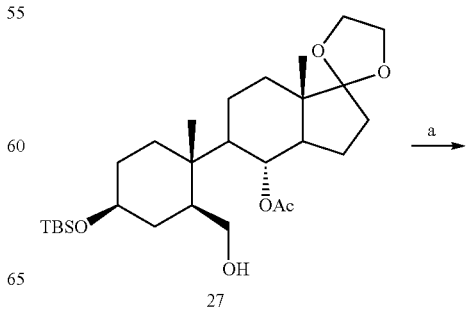

27

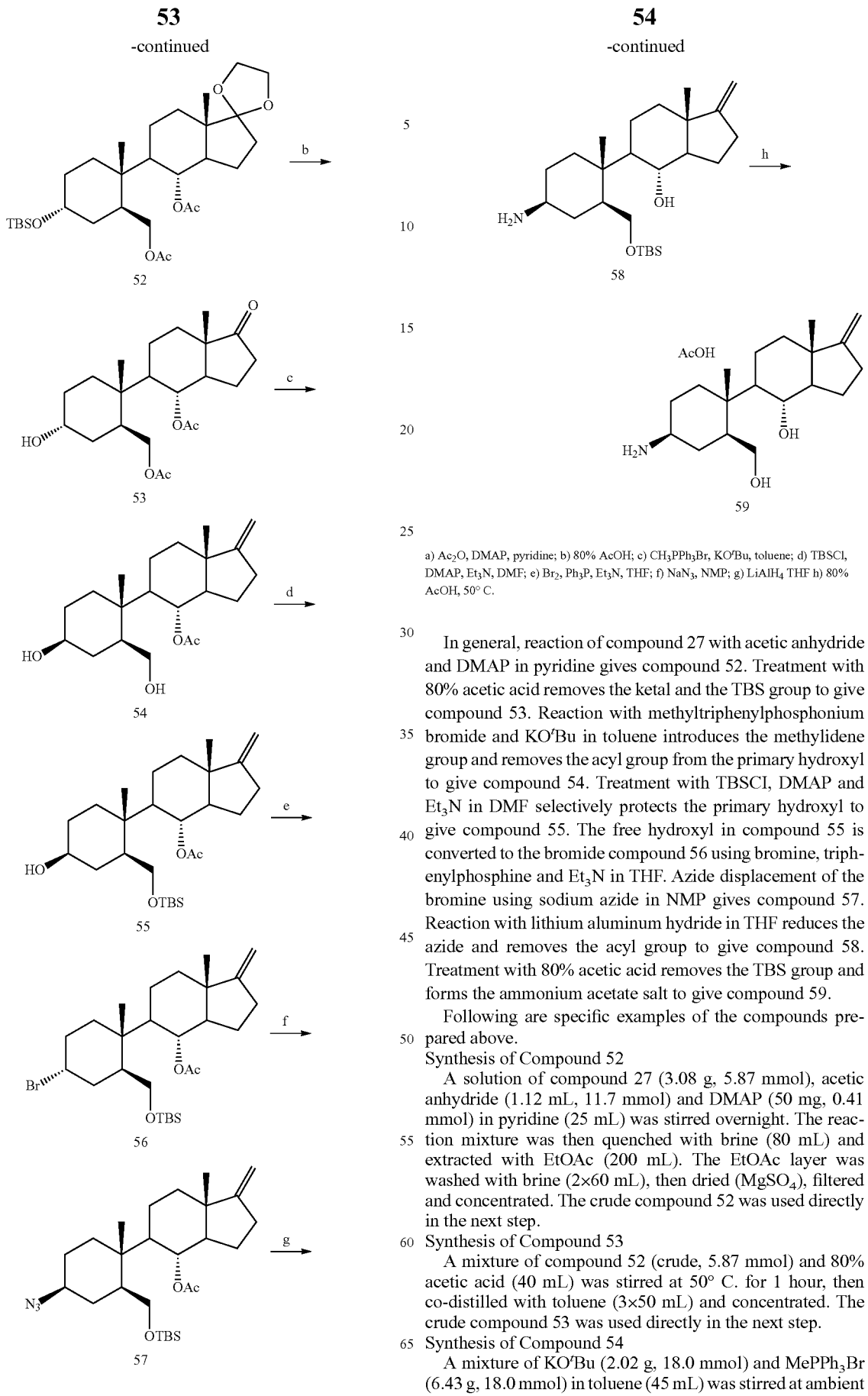

a) Ac₂O, DMAP, pyridine; b) 80% AcOH; c) CH₃PPh₃Br, KO'Bu, toluene; d) TBSCl, DMAP, Et₃N, DMF; e) Br₂, Ph₃P, Et₃N, THF; f) NaN₃, NMP; g) LiAlH₄ THF h) 80% AcOH, 50° C.

In general, reaction of compound 27 with acetic anhydride and DMAP in pyridine gives compound 52. Treatment with 80% acetic acid removes the ketal and the TBS group to give compound 53. Reaction with methyltriphenylphosphonium bromide and KO'Bu in toluene introduces the methylidene group and removes the acyl group from the primary hydroxyl to give compound 54. Treatment with TBSCl, DMAP and Et₃N in DMF selectively protects the primary hydroxyl to give compound 55. The free hydroxyl in compound 55 is converted to the bromide compound 56 using bromine, triphenylphosphine and Et₃N in THF. Azide displacement of the bromine using sodium azide in NMP gives compound 57. Reaction with lithium aluminum hydride in THF reduces the azide and removes the acyl group to give compound 58. Treatment with 80% acetic acid removes the TBS group and forms the ammonium acetate salt to give compound 59.

Following are specific examples of the compounds prepared above.

Synthesis of Compound 52

A solution of compound 27 (3.08 g, 5.87 mmol), acetic anhydride (1.12 mL, 11.7 mmol) and DMAP (50 mg, 0.41 mmol) in pyridine (25 mL) was stirred overnight. The reaction mixture was then quenched with brine (80 mL) and extracted with EtOAc (200 mL). The EtOAc layer was washed with brine (2×60 mL), then dried (MgSO₄), filtered and concentrated. The crude compound 52 was used directly in the next step.

Synthesis of Compound 53

A mixture of compound 52 (crude, 5.87 mmol) and 80% acetic acid (40 mL) was stirred at 50° C. for 1 hour, then co-distilled with toluene (3×50 mL) and concentrated. The crude compound 53 was used directly in the next step.

Synthesis of Compound 54

A mixture of KO'Bu (2.02 g, 18.0 mmol) and MePPh₃Br (6.43 g, 18.0 mmol) in toluene (45 mL) was stirred at ambient temperature for 1 hour under argon, then compound 53 (crude, 5.87 mmol) in toluene (10 mL) was added. The reaction mixture was stirred at ambient temperature overnight, then diluted with saturated NH₄Cl solution (100 mL) and extracted with EtOAc (100 mL). The EtOAc layer was washed with brine (80 mL), then dried (MgSO₄), filtered and concentrated. The residue was eluted through silica gel (hexanes/acetone, 7:3) to afford impure compound 54.

Synthesis of Compound 55

A solution of compound 54 (impure, 2.85 mmol), TBSCI (490 mg, 3.25 mmol), DMAP (58 mg, 0.47 mmol) and Et₃N (600 μL, 4.3 mmol) in dry DMF (6 mL) was stirred for 5 hours. The reaction mixture was diluted with toluene (80 mL), washed with saturated NaHCO₃ solution and brine, then dried (MgSO₄), filtered and concentrated. The residue was purified by chromatography on silica gel to afford compound 55 (480 mg, 45%).

Synthesis of Compound 56

Bromine (80 μL, 1.6 mmol) was added to a solution of Ph₃P (407 mg, 1.6 mmol) in THF (5 mL) at ambient temperature. After 5 minutes Et₃N (290 μL, 2.1 mmol) was added followed by a solution of compound 55 (480 mg, 1.03 mmol) in THF (5 mL). After 1.5 hours the reaction mixture was diluted with EtOAc (100 mL) and washed with water and brine, then dried over MgSO₄, filtered and concentrated. The residue was purified by column chromatography (hexanes/EtOAc, 95:5) to afford compound 56 (510 mg, 94%).

Synthesis of Compound 57

A solution of compound 56 (510 mg, 0.97 mmol), NaN₃ (200 mg, 3.1 mmol) and NMP (8 mL) was heated at 55° C. for 4 hours. The reaction mixture was diluted with toluene (100 mL) and EtOAc (30 mL) and washed with water and brine, dried over MgSO₄, filtered and concentrated. The residue was purified by column chromatography (hexanes/EtOAc, 98:2) to afford compound 57 (197 mg, 41%).

Synthesis of Compound 58

To a solution of compound 57 (197 mg, 0.40 mmol) in THF at ambient temperature was added LiAlH₄ (1 mL of a 1.0 M solution in ether). The reaction mixture was stirred at ambient temperature for 2.5 hours then Na₂SO₄.10H₂O was added. The solution was filtered and the solid was washed with MeOH and CH₂Cl₂. The filtrate was concentrated and the residue was purified by chromatography on silica gel (CHCl₃/MeOH/Et₃N, 90:8:2) to afford compound 58 (144 mg, 78%).

Synthesis of Compound 59

A mixture of compound 58 (114 mg, 0.27 mmol) and 80% acetic acid (7 mL) was stirred overnight at ambient temperature. The solution was diluted with toluene (3×50 mL) and concentrated to afford compound 59 (58 mg, 59%) as a yellow solid: LC/MS (direct infusion, electrospray +ve, 10 mM NH₄OAc in 3:7 water and MeCN) 307.92; $C_{19}H_{34}NO_2$.

Example 7

Compounds 67 and 68, representative compounds of the invention, may be prepared according to the following Reaction Scheme 7. Any number of compounds related to compounds 67 and 68 could be produced using similar methodology. Starting compound 21 may be prepared according to procedures described above in Example 1.

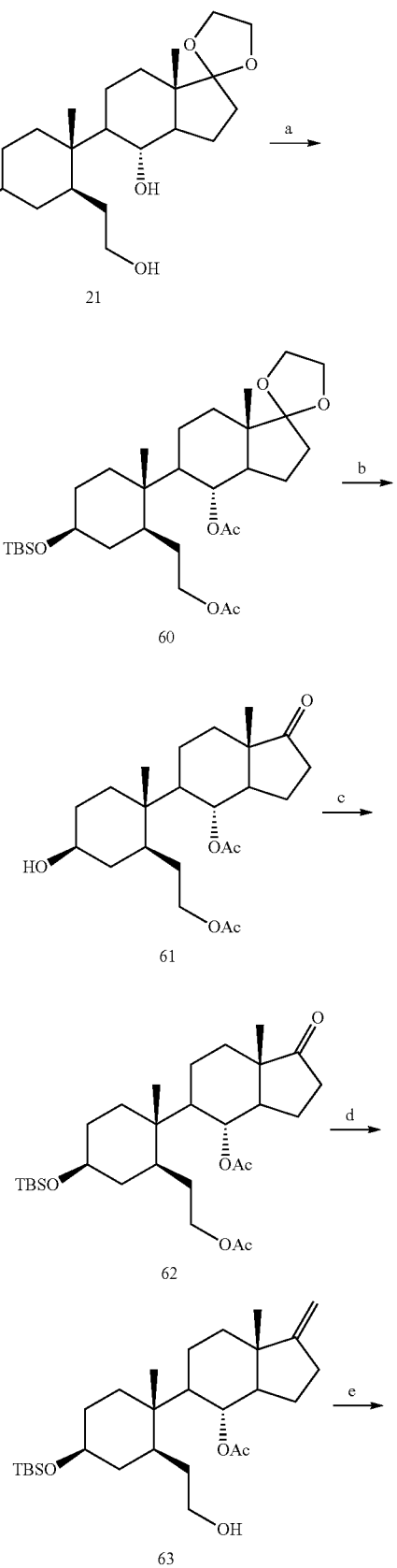

REACTION SCHEME 7

-continued

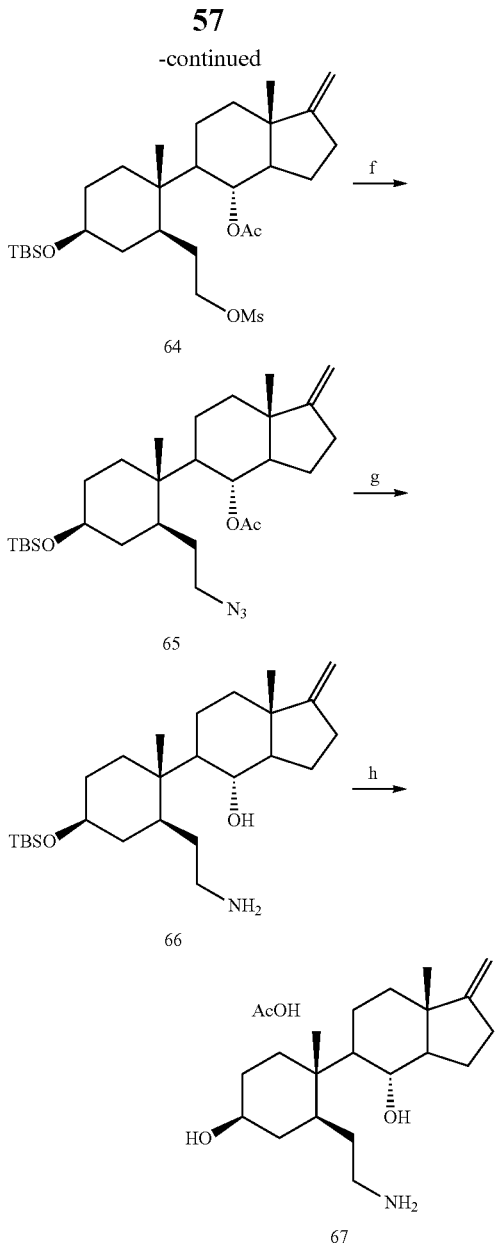

a) Ac₂O, DMAP, pyridine; b) 80% AcOH, 50° C.; c) TBSCl, imidazole, DMF; d) MePPh₃Br, KO'Bu, toluene; K₂CO₃, MeOH, reflux; e) MsCl, pyridine; f) NaN₃, DMF, 60° C.; g) LiAlH₄, THF; h) 80% AcOH, 50° C.

In general, treatment of compound 21 with acetic anhydride in pyridine (to protects the free hydroxyls) gives compound 60. Treatment with 80% acetic acid removes the ketal and the TBS groups to give compound 61. Treatment with TBSCl and imidazole in DMF protects the free hydroxyl in compound 62. Olefination of compound 62 with methyltriphenylphosphonium bromide and KO'Bu in toluene introduces the methylidene group. In some instances the olefination conditions result in removal of the acetate from the primary hydroxyl giving a compound such as 63. The primary acetate may be selectively hydrolyzed by reaction with K₂CO₃ in refluxing methanol. The free hydroxyl in compound 63 is converted to the mesylate compound 64 using MsCl and pyridine. Azidation using sodium azide in DMF gives the azido compound 65. Lithium aluminum hydride reduction of the azide in THF gives the amine compound 66. Treatment with 80% acetic acid removes the TBS group and forms the ammonium acetate salt to give compound 67.

Following are specific examples of the compounds prepared above.

Synthesis of Compound 60

To a solution of compound 21 (0.686 g, 1.42 mmol) in pyridine (5 mL) was added acetic anhydride (0.94 mL, 9.94 mmol) and the reaction mixture was stirred at 50° C. overnight. The solution was diluted with EtOAc (25 mL) and washed with brine (2×20 mL), then dried over MgSO₄, filtered and concentrated. The crude compound 60 was used for the next reaction without further purification.

Synthesis of Compound 61

A mixture of compound 60 (crude, 1.42 mmol) and 80% acetic acid (15 mL) was stirred at 50° C. for 2 hours, then diluted with toluene (2×20 mL) and concentrated. The residue was purified by chromatography on silica gel (hexanes/EtOAc, 1:2) to afford compound 61 (0.479 g, 87%) as a white solid.

Synthesis of Compound 62

A solution of compound 61 (0.971 g, 2.38 mmol), TBSCl (0.716 g, 4.75 mmol) and imidazole (0.647 g, 9.51 mmol) in dry DMF (10 mL) was stirred for 3 hours. The reaction mixture was diluted with toluene (50 mL) and washed with brine (2×20 mL), then dried over MgSO₄, filtered and concentrated. The residue was purified by chromatography on silica gel (hexanes/EtOAc, 4:1) to afford compound 62 (1.218 g, 98%) as a viscous pale yellow oil.

Synthesis of Compound 63

A mixture of KO'Bu (5.00 g, 42.3 mmol) and MePPh₃Br (15.1 g, 42.3 mmol) in toluene (100 mL) was stirred at ambient temperature for 1 hour under argon, then a solution of compound 62 (crude, 14.1 mmol) in 100 mL of toluene was added. The reaction mixture was stirred overnight at ambient temperature, then quenched with saturated NaHCO₃ solution (75 mL) and water (75 mL). The solution was further diluted with 100 mL of water and was extracted with EtOAc (4×100 mL). The combined extracts solution was washed with brine (2×100 mL), then dried over MgSO₄, filtered and concentrated. The residue was purified by chromatography on silica gel (hexanes/EtOAc, 100:0, then 9:1, then 4:1) to afford the diacetate compound (4.5 g, 62%) as a yellow oil and compound 63 (1.8 g, 27%) as a yellow oil. A solution of the diacetate compound (4.5 g, 8.6 mmol), K₂CO₃ (4.78 g, 34.6 mmol) and methanol (100 mL) was heated at reflux under argon. After 75 minutes the reaction mixture was cooled to ambient temperature and filtered through celite eluting with CH₂Cl₂. The filtrate was concentrated and dissolved in EtOAc (250 mL), then washed with water and dried over MgSO₄, filtered and concentrated. The residue was purified by chromatography on silica gel (hexanes/EtOAc, 100:0, then 19:1, then 9:1) to afford compound 63 (3.2 g, 47%) as a yellow foam.

Synthesis of Compound 64

To a solution of compound 63 (3.17 g, 6.62 mmol) in pyridine (50 mL) and CH₂Cl₂ (0.5 mL) was added methanesulfonyl chloride (1.02 mL, 13.2 mmol) and the reaction mixture was stirred under argon at ambient temperature for 3 hours. The reaction was quenched with saturated NaHCO₃ solution (60 mL) and extracted with EtOAc (3×80 mL). The combined extracts solution was washed with water and brine, then dried over MgSO₄, filtered and concentrated. The residue was concentrated from toluene to afford crude compound 64 that was used for the next reaction without further purification.

Synthesis of Compound 65

A solution of compound 64 (crude, 6.62 mmol) and NaN₃ (646 mg, 9.93 mmol) in DMF (40 mL) was heated under argon at 60° C. overnight. After cooling, the reaction mixture was diluted with water (100 mL) and was extracted with diethyl ether (4×100 mL). The combined extracts solution was washed with water and brine, then dried over MgSO₄, filtered and concentrated. The residue was purified by chromatography on silica gel (hexanes/EtOAc, 100:0, then 98:2, then 95:5) to afford compound 65 (2.56 g, 77% for 2 steps) as a yellow oil.

Synthesis of Compound 66

A solution of LiAlH₄ (3.85 mL of a 1.0 M solution in THF) was added to a solution of compound 65 (647 mg, 1.28 mmol) in THF (15 mL) under argon. After 3 hours the reaction mixture was quenched with Na₂SO₄.10H₂O and diluted with THF (10 mL). After 30 minutes the solution was filtered and concentrated. The residue was purified by chromatography on silica gel (CH₂Cl₂/MeOH/Et₃N, 100:0:0, then 95:5:0, then 90:10:0, then 95:5:2) to afford compound 66 (324 mg, 58%) as a colourless oil.

Synthesis of Compound 67

A solution of compound 66 (320 mg, 0.734 mmol) and 80% acetic acid (25 mL) was heated at 50° C. for 3 hours. The residue was purified by chromatography on reverse-phase silica gel (H₂O, then H₂O/MeOH/AcOH 50:50:2). Concentration from MeOH/MeCN gave compound 67 (244 mg, 87%) as a white solid: LC/MS (direct infusion, electrospray +ve, 10 mM NH₄OAc in 3:7 water and MeCN) 322.12; $C_{20}H_{36}NO_2$.

Synthesis of Compound 68

Using the procedures described for the synthesis of compound 67, with the exception of olefination by EtPPh₃Br, compound 68 (75 mg) was prepared as a white solid in 22% yield starting from compound 62. LC/MS (direct infusion, electrospray +ve, 10 mM NH₄OAc in 3:7 water and MeCN) 336.16; $C_{21}H_{38}NO_2$.

Example 8

Compounds 77-81, representative compounds of the invention, may be prepared according to the following Reaction Scheme 8. Starting compounds such as 69 may be prepared according to the procedures outlined in U.S. Pat. No. 6,046,185. Any number of compounds related to compounds 77-81 could be produced using similar methodology.

REACTION SCHEME 8

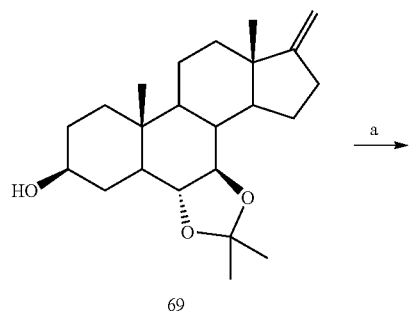

69

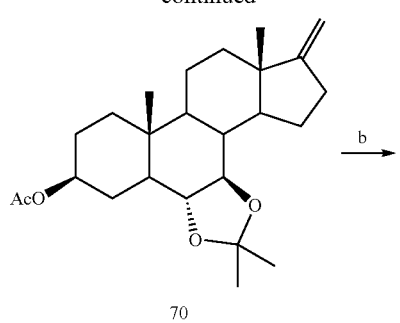

70

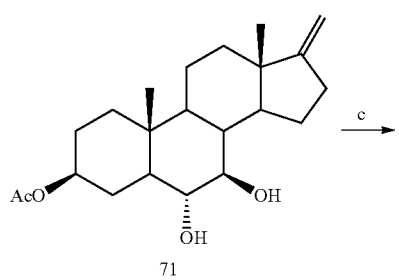

71

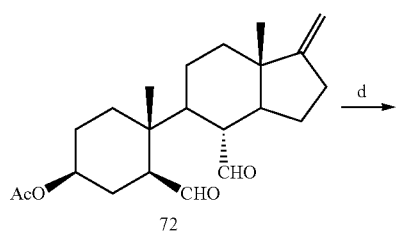

72

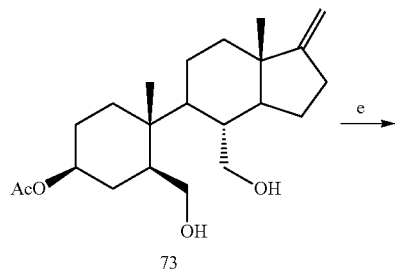

73

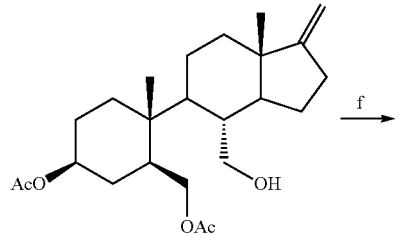

74

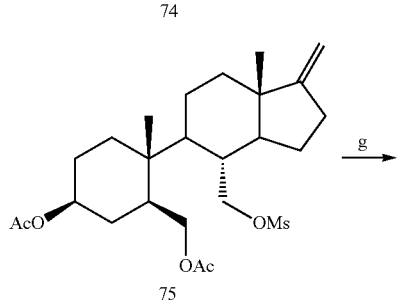

75

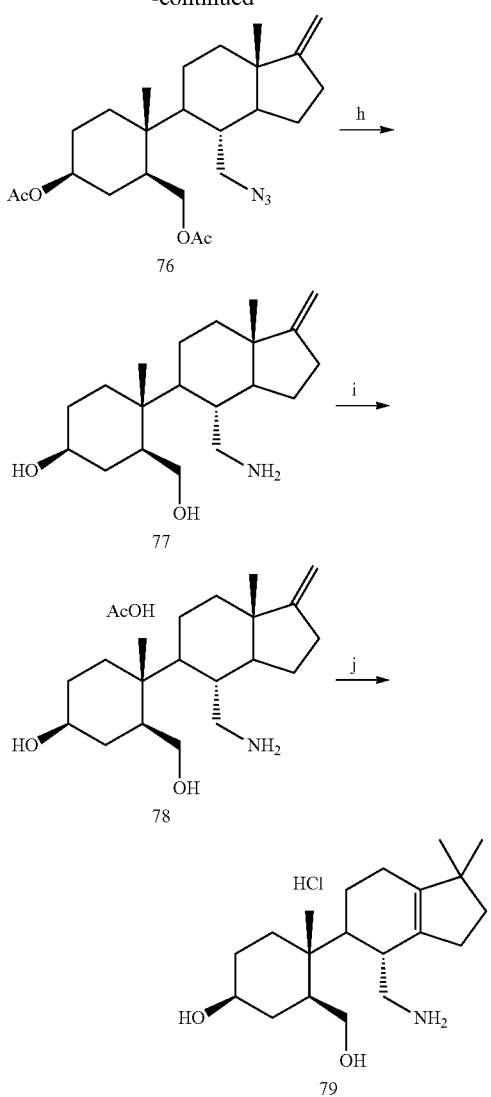

a) Ac₂O, DMAP, pyridine; b) 80% AcOH; c) NaIO₄, THF; d) NaBH₄, MeOH, THF; e) Ac₂O, DMAP, pyridine; f) MsCl, pyridine; g) NaN₃, DMF; h) LiAlH₄, THF; i) 80% AcOH; j) HCl, water, MeOH, 65° C.

In general, reaction of compound 69 with acetic anhydride and DMAP in pyridine gives compound 70. Treatment with 80% acetic acid removes the acetonide group to give compound 71. Reaction with sodium periodate in THF oxidatively cleaves the diol to give compound 72. Sodium borohydride reduction of the aldehyde groups gives compound 73. Reaction with acetic anhydride and DMAP in pyridine selectively protects the one primary hydroxyl to give compound 74. The free hydroxyl is converted to the mesylate compound 75 using MsCl and pyridine. Reaction with sodium azide in DMF gives the azido compound 76. Reaction with lithium aluminum hydride in THF reduces the azide and removes the acyl groups to give compound 77. Treatment with 80% acetic acid forms compound 78 as the ammonium acetate salt. Reaction of a compound such as 78 with HCl in water and MeOH facilitates migration of the 18-methyl group to C17 to give a compound such as 79. Careful treatment of compound 77 with HCl in MeCN and water forms the ammonium chloride salt of compound 77 (i.e., compound 80).

Following are specific examples of the compounds prepared above.

Synthesis of Compound 70

A solution of compound 69 (6.9 g, 19.1 mmol), acetic anhydride (3.62 mL, 38.3 mmol) and DMAP (0.23 g, 1.9 mmol) in pyridine (50 mL) was stirred for 4.5 hours. The reaction mixture was diluted cold water (150 mL) and extracted with EtOAc (600 mL) and washed with brine (2×200 mL), then dried over MgSO₄, filtered and concentrated. The crude compound 70 was used directly in the next step.

Synthesis of Compound 71

A mixture of compound 70 (crude, 19.1 mmol) and 80% acetic acid (50 mL) was stirred at 40° C. for 2 hours. The solution was concentrated to afford crude compound 71 that was used in the next step without further purification.

Synthesis of Compound 72

A solution of compound 71 (crude, 19.1 mmol), NaIO₄ (8.19 g, 38.3 mmol), water (53 mL) and THF (106 mL) was stirred at ambient temperature for 3.5 hours. The reaction mixture was diluted with CH₂Cl₂ and was washed with brine, then dried over MgSO₄, filtered and concentrated to afford crude compound 72 that was used in the next step without further purification.

Synthesis of Compound 73

A solution of compound 72 (crude, 19.1 mmol), NaBH₄ (1.45 g, 38.3 mmol), THF (120 mL) and MeOH (40 mL) was stirred at 0° C. for 10 minutes, then at ambient temperature for 1 hour. The mixture was cooled in ice and 80% acetic acid (62 mL) was slowly added. The solution was stirred at ambient temperature for 10 minutes, then diluted with EtOAc (400 mL) and then washed with brine. The EtOAc layer was dried over MgSO₄, filtered and concentrated to afford crude compound 73 which was used in the next step without further purification.

Synthesis of Compound 74

A solution of compound 73 (crude, 19.1 mmol), acetic anhydride (2.1 mL, 22.0 mmol) and DMAP (230 mg, 1.9 mmol) in pyridine (65 mL) was stirred at ambient temperature for 1.5 hours. The reaction mixture was diluted with EtOAc (400 mL) and washed with brine, then dried over MgSO₄, filtered and concentrated. The residue was purified by chromatography on silica gel (hexanes/EtOAc, 5:1 then 4:1 then 7:3) to afford compound 74 (4.9 g, 63%).

Synthesis of Compound 75

To a solution of compound 74 (4.9 g, 12.1 mmol) in pyridine (40 mL) was added methanesulfonyl chloride (1.68 mL, 21.7 mmol) and the reaction mixture was stirred at ambient temperature for 2 hours. The solution was diluted with EtOAc (400 mL) and washed with brine, then dried over MgSO₄, filtered and concentrated to afford crude compound 75 that was used for the next reaction without further purification.

Synthesis of Compound 76

A mixture of compound 75 (crude, 12.1 mmol) and NaN₃ (1.57 g, 24.1 mmol) in DMF (100 mL) was heated under argon at 60° C. overnight. After cooling, the reaction mixture was diluted with toluene (400 mL) and was washed with brine, then dried over MgSO₄, filtered and concentrated. The residue was purified by chromatography on silica gel (hexanes/EtOAc, 8:2) to afford compound 76 (4.8 g, 92% for 2 steps).

Synthesis of Compound 77

A solution of LiAlH₄ (44.5 mL of a 1.0 M solution in Et₂O) was added to an ice cooled solution of compound 76 (4.8 g, 11.1 mmol) in THF (111 mL). After 10 minutes the solution was continued at ambient temperature for another 4 hours. The reaction mixture was cooled in ice and quenched with Na$_2$SO$_4$.10H$_2$O. After 15 minutes the solution was diluted with EtOAc (100 mL), stirred for an additional 20 minutes at ambient temperature, then filtered. The filtrate was washed with brine, then dried over MgSO$_4$, filtered and concentrated to afford compound 77 (3.8 g, quantitative) as a white solid.

Synthesis of Compound 78

A solution of compound 77 (1.00 g, 2.93 mmol) and 80% acetic acid (15 mL) was heated at 40° C. for 1 hour, then concentrated. Residual solvent was removed by codistillation with toluene. The residue was triturated in diethyl ether and filtered to give compound 78 (923 mg, 83%) as a white solid. LC/MS (direct infusion, electrospray +ve, 10 mM NH$_4$OAc in 3:7 water and MeCN) 321.95; C$_{20}$H$_{36}$NO$_2$.

Synthesis of Compound 79

A solution of compound 78 (600 mg, 1.57 mmol), concentrated HCl (5 drops), water (1 mL) and MeOH (9 mL) was heated at 65° C. for 5 days, then concentrated. The residue was triturated in MeCN and filtered to give compound 79 (504 mg, 90%) as a white solid. LC/MS (direct infusion, electrospray +ve, 10 mM NH$_4$OAc in 3:7 water and MeCN) 322.2; C$_{20}$H$_{36}$NO$_2$.

Synthesis of Compound 80

To a suspension of compound 77 (0.1 g, 0.3 mmol) in MeCN (2 mL) was added HCl (337 μL of a 1.0 M solution in Et$_2$O). After 15 minutes the solution was filtered to afford the ammonium chloride salt of compound 77, i.e., compound 80 (76 mg, 72%) as a white powder.

Synthesis of Compound 81

Using the procedures described for the synthesis of compound 80, compound 81 (0.646 g) was prepared as a white powder in 37% yield starting from the ethylidene compound analogous to compound 69. The salt formation step differed in that the compound was isolated by codistillation of the residual acid solution using MeOH: LC/MS (direct infusion, electrospray +ve, 10 mM NH$_4$OAc in 3:7 water and MeCN) 335.89; C$_{21}$H$_{38}$NO$_2$.

Example 9

Compounds 88 and 89, representative compounds of the invention, may be prepared according to the following Reaction Scheme 9. Any number of compounds related to compounds 88-89 could be produced using similar methodology. Starting compound 73 may be prepared according to the procedures described above in Example 8.

REACTION SCHEME 9

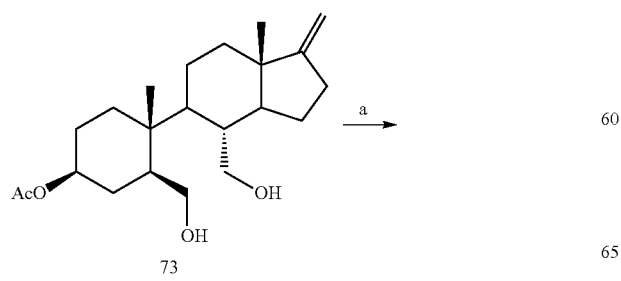

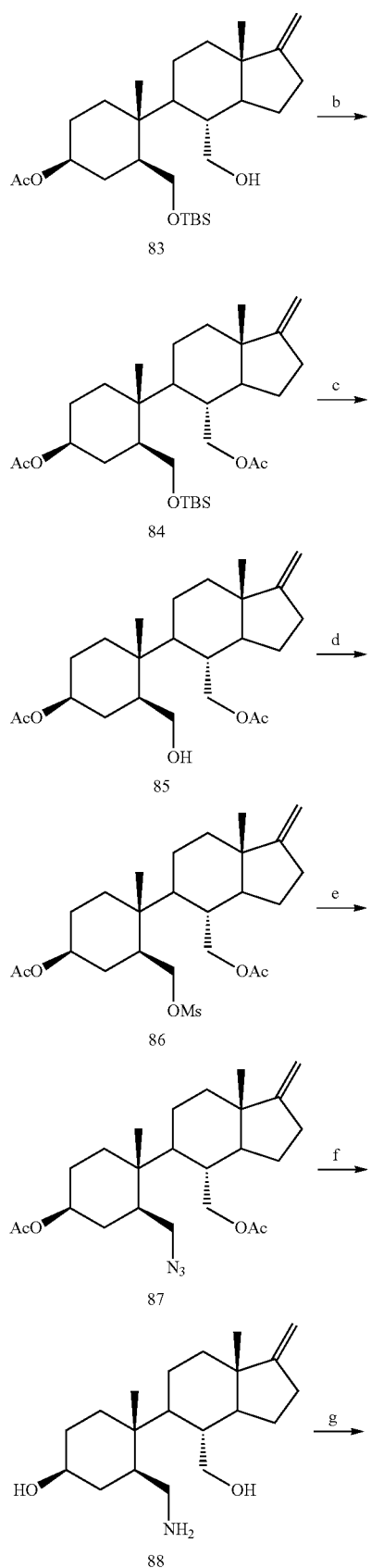

-continued

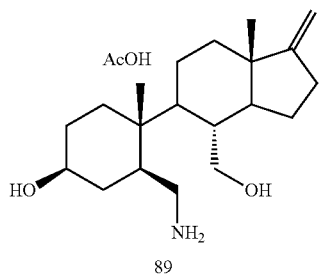

89 a) TBSCl, imidazole, DMF; b) Ac₂O, DMAP, pyridine; c) Bu4NF, THF; d) MsCl, pyridine; e) NaN₃, DMF; f) LiAlH₄, THF; g) 80% AcOH.

In general, reaction of compound 73 with TBSCI and imidazole in DMF gives compound 83. Reaction with acetic anhydride and DMAP in pyridine protects the remaining free hydroxyl to give compound 84. Reaction with tetrabutylammonium fluoride removes the TBS group to give compound 85. The free hydroxyl is converted to the mesylate compound 86 using MsCl and pyridine. Reaction with sodium azide in DMF gives the azido compound 87. Reaction with lithium aluminum hydride in THF reduces the azide and removes the acyl groups to give compound 88. Treatment with 80% acetic acid forms the ammonium acetate salt to give compound 89.

Following are specific examples of the compounds prepared above.

Synthesis of Compound 83

A solution of compound 73 (2.9 g, 7.92 mmol), TBSCI (1.32 g, 8.76 mmol), imidazole (813 mg, 11.9 mmol) and DMF (20 mL) was stirred at ambient temperature for 1.5 hours. The solution was diluted with water (50 mL) and was extracted with toluene (100 mL). The toluene layer was washed with brine (40 mL), then dried over MgSO₄, filtered and concentrated to give crude compound 83 that was used in the next step without further purification.

Synthesis of Compound 84

A solution of compound 83 (crude, 7.96 mmol), acetic anhydride (2.25 mL, 23.9 mmol) and DMAP (100 mg, 0.82 mmol) in pyridine (25 mL) was stirred at ambient temperature for 1 hour. The reaction mixture was diluted with EtOAc and washed with brine, then dried over MgSO₄, filtered and concentrated. The crude compound 84 was used in the next step without further purification.

Synthesis of Compound 85

A solution of compound 84 (crude g, 7.96 mmol), Bu₄NF (12 mL of a 1.0 M solution in THF) and THF was stirred at ambient temperature for 2 hours and at 40° C. for 30 minutes. The reaction mixture was filtered through silica gel and concentrated. The residue was purified by chromatography on silica gel (EtOAc/hexanes 3:7) to afford compound 85 (2.06 g, 64%).

Synthesis of Compound 86

To a solution of compound 85 (1.06 g, 2.61 mmol) in pyridine (12 mL) was added methanesulfonyl chloride (400 µL, 5.16 mmol) and the reaction mixture was stirred at ambient temperature for 2 hours. The reaction was quenched with water and was extracted with EtOAc. The solution washed with brine, then dried over MgSO₄, filtered and concentrated to afford crude compound 86 which was used for the next reaction without further purification.

Synthesis of Compound 87

A mixture of compound 86 (crude, 2.61 mmol) and NaN₃ (1.0 g, 15 mmol) in DMF (15 mL) was heated under argon at 95° C. overnight. After cooling, the reaction mixture was diluted with toluene and was washed with brine, then dried over MgSO₄, filtered and concentrated. The residue was purified by chromatography on silica gel to afford compound 87 (575 mg, 89%).

Synthesis of Compound 88

A solution of LiAlH₄ (3.2 mL of a 1.0 M solution in THF) was added to an ice cooled solution of compound 87 (274 mg, 0.635 mmol) in THF (3 mL). After 10 minutes the solution was continued at ambient temperature for another 3 hours. The reaction mixture was cooled in ice and quenched with Na₂SO₄.10H₂O. After 15 minutes the solution was filtered and the filtrate was washed with brine, then dried over MgSO₄, filtered and concentrated. Purification by chromatography on silica gel (EtOAc/MeOH/H₂O/NH₄OH 7:2:1: 0.15, then 7:2:1:0.2, then 7:2:1:0.3) afforded compound 88 (135 mg, 66%).

Synthesis of Compound 89

A solution of compound 88 (135 mg, 0.42 mmol) and 80% acetic acid (3 mL) was heated at 40° C. for 30 minutes, then concentrated. Residual solvent was removed by codistillation with methanol to give compound 89 (158 mg, 99%) as a pale yellow foam. LC/MS (direct infusion, electrospray +ve, 10 mM NH₄OAc in 3:7 water and MeCN) 322.11; C₂₀H₃₆NO₂.

Example 10

Compounds 100 and 101, a representative compound of the invention, may be prepared according to the following Reaction Scheme 10. Any number of compounds related to compounds 100 and 101 could be produced using similar methodology. Starting compound 60 may be prepared according to procedures described above in Example 7.

REACTION SCHEME 10

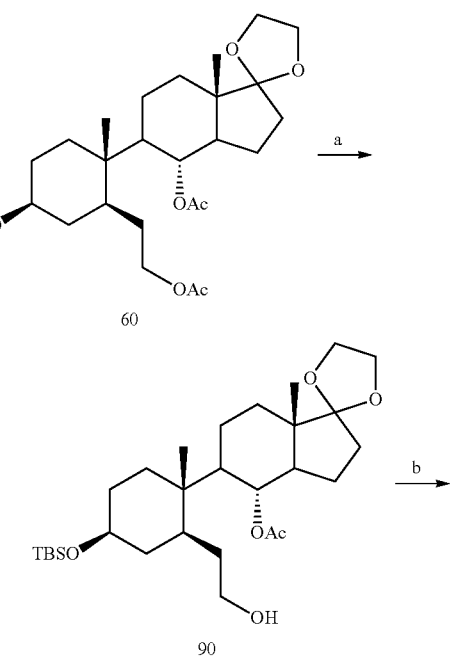

67
-continued
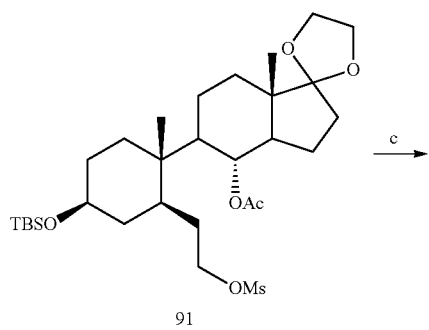
91
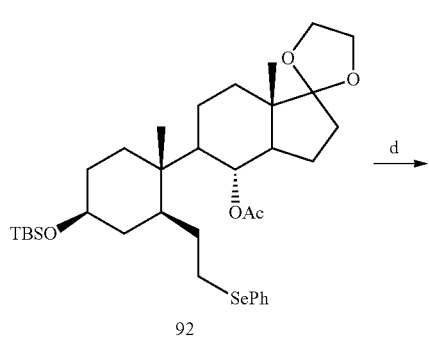
92
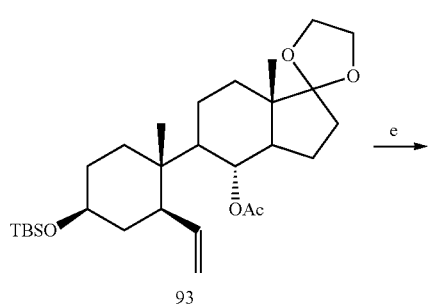
93
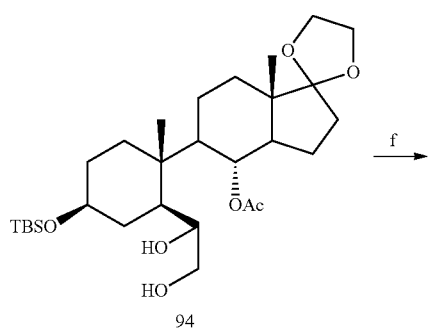
94
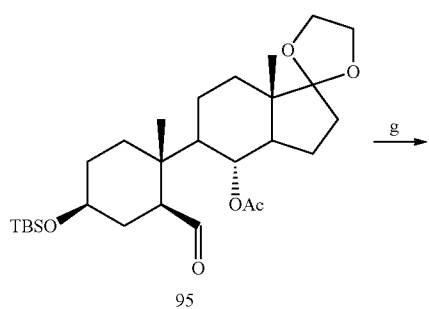
95
68
-continued
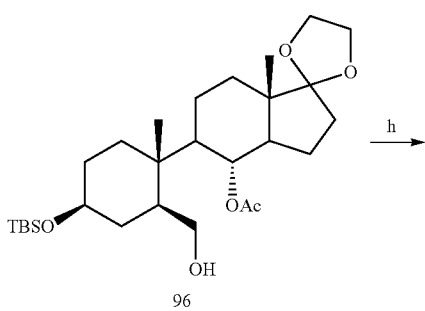
96
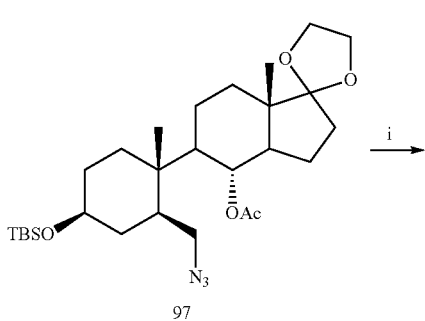
97
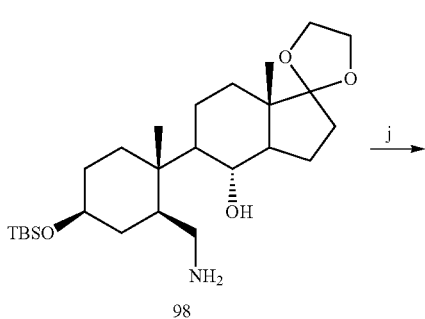
98
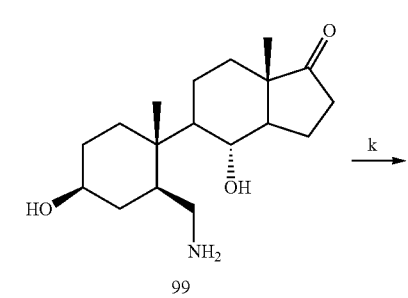
99
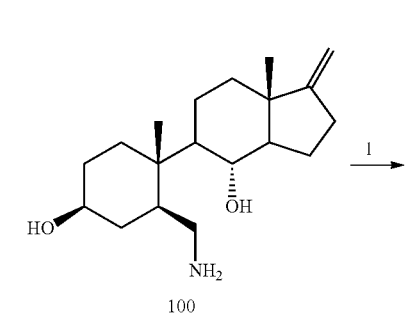
100

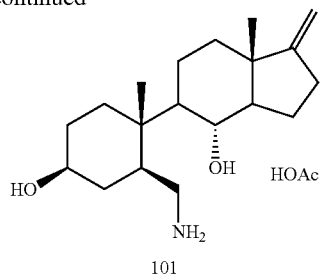

101 a) K$_2$CO$_3$, H$_2$O, MeOH, 55° C.; b) MsCl, pyridine; c) (SePh)$_2$, NaBH$_4$, EtOH, 50° C.; d) 30% H$_2$O$_2$, THF, 65° C.; e) NMo, OsO$_4$, H$_2$O, $^t$BuOH, THF; f) Pb(OAc)$_4$, CH$_2$Cl$_2$; g) NaBH$_4$, MeOH/THF; h) DIAD, DPPA, Ph$_3$P THF; i) LAH, THF; j) 2N HCl, THF; k) Ph$_3$PMeBr, KO$^t$Bu, THF; l) HOAc In general, selective hydrolysis of the primary acetate in compound 60 using K$_2$CO$_3$ gives compound 90. The free hydroxyl is reacted to give the mesylate compound 91 using MsCl and pyridine. Mesylate displacement by phenylselenide gives compound 92. Oxidative elimination using hydrogen peroxide gives the olefin compound 93. Osmolation gives dihydroxylated compound 94, which is then oxidatively cleaved by lead tetraacetate to give compound 95. Sodium borohydride reduction gives alcohol compound 96. Azidation using diisopropyl azodicarboxylate (DIAD), diphenylphosphoryl azide (DPPA) and PPh$_3$ in THF gives the azido compound 97. Reaction with lithium aluminum hydride in THF reduces the azide and removes the acyl group to give compound 98. Treatment with HCl removes both the TBS group and the cyclic ketal to give compound 99. Olefination using methyltriphenylphosphonium bromide and KO$^t$Bu in THF gives compound 100. Treatment with acetic acid forms the ammonium acetate salt to give compound 101.

Following are specific examples of the compounds prepared above.

Synthesis of Compound 90

A mixture of compound 60 (12.7 g, 22.4 mmol), K$_2$CO$_3$, (9.38 g, 67.2 mmol), MeOH (250 mL) and water (94 mL) was stirred 55° C. for 2 hours, cooled to ambient temperature then concentrated. The residue was dissolved in EtOAc, washed twice with saturated NaHCO$_3$ solution then twice with brine, dried over anhydrous MgSO$_4$ and concentrated. The residue was purified by chromatography on silica gel (hexanes/EtOAc) to afford compound 90 (10.16 g, 86%) as a white foam.

Synthesis of Compound 91

To a solution of compound 90 (10.14 g, 19.3 mmol) in pyridine (50 mL) at 0° C. was added methanesulfonyl chloride (2.69 mL, 34.8 mmol). The mixture was stirred at 0° C. for 10 minutes, then at ambient temperature for 2 hours. The mixture was diluted with EtOAc (200 mL) and washed with water (2×50 mL). The combined aqueous portions were back-extracted with EtOAc (50 mL). The combined organics were washed with brine (2×50 mL), dried over anhydrous MgSO$_4$ and concentrated. The residue was dissolved in toluene and concentrated to give compound 91 (11.3 g, 97%) as a white foam which was used for the next reaction without further purification.

Synthesis of Compound 92

To a stirred mixture of diphenyl diselenide (7.04 g, 22.1 mmol) and EtOH (100 mL) at 0° C., NaBH$_4$ (1.69 g, 44.2 mmol) was added portionwise over 7 minutes, then after 5 minutes the mixture was allowed to warm to ambient temperature and stirred for an additional hour. The resulting solution was added via cannula to a slurry of compound 91 in EtOH (175 mL), rinsing with EtOH (25 mL). The mixture was stirred at 50° C. for 35 minutes. The mixture was cooled, water (70 mL) was added and the mixture was concentrated. The residue was dissolved in EtOAc (400 mL) and washed with water (100 mL), then brine (100 mL). The combined aqueous washes were back-extracted with EtOAc (3×75 mL). The combined organics were washed with brine (2×100 mL), dried over anhydrous MgSO$_4$ and concentrated. The residue was purified by chromatography on silica gel (hexanes/EtOAc) to afford compound 92 (10.6 g, 87%) as a yellow foam.

Synthesis of Compound 93

A mixture of compound 92 (10.2 g, 15.4 mmol) and 30% H$_2$O$_2$ solution in THF (4500 mL) was stirred at ambient temperature for 50 minutes then at 65° C. for 40 minutes. After cooling, the mixture was diluted with EtOAc (500 mL) and washed with brine (200 mL), then saturated NaHCO$_3$ solution (200 mL). The combined aqueous portions were back-extracted with EtOAc (2×100 mL). The combined organic portions were washed with brine (2×200 mL), dried over anhydrous MgSO$_4$ and concentrated. The residue was purified by chromatography on silica gel (hexanes/EtOAc, 3:1; EtOAc) to afford compound 93 (5.86 g, 75%) as a white foam.

Synthesis of Compound 94

To a solution of compound 93 (4.81 g, 9.49 mmol) in THF (90 mL), $^t$BuOH (30 mL) and water (9 mL) were added NMO (1.72 g, 14.2 mmol) and OsO$_4$ (3.0 mL of a 4% solution in water, 0.47 mmol). The reaction mixture was stirred at ambient temperature overnight, then a solution of Na$_2$S$_2$O$_3$.5H$_2$O (1.75 g) in water (30 mL) was added. The mixture was stirred for 30 minutes then diluted with brine (350 mL) and extracted with CH$_2$Cl$_2$ (200 mL, 2×125 mL, 75 mL). The combined organics were washed with brine (2×150 mL), dried over anhydrous MgSO$_4$ and concentrated to give compound 94 (5.70 g) as a light brown foam which was used for the next reaction without further purification.

Synthesis of Compound 95

To a solution of compound 94 (5.70 g) in CH$_2$Cl$_2$ (100 mL) was added Pb(OAc)$_4$ (4.43 g, 9.49 mmol). The reaction mixture was stirred at ambient temperature for 35 minutes, then filtered through a silica plug and concentrated. The residue was purified by chromatography on silica gel (hexanes/EtOAc, 9:1, 4:1) to afford compound 95 (4.21 g, 85% from INT1660) as a white foam.

Synthesis of Compound 96

To a stirred solution of compound 95 (300 mg, 0.59 mmol) in a mixture of MeOH/THF (2 mL/7 mL) at 0° C. was added NaBH$_4$ (45 mg, 1.2 mmol). After 5 min at 0° C., the mixture was stirred at ambient temperature and additional NaBH$_4$ (89 mg, 2.4 mmol) was added in portions over 4 hours. The mixture was cooled to 0° C. and the reaction was quenched by water (1 mL). The mixture was diluted with EtOAc (200 mL), washed twice with brine, dried and concentrated. The residue was purified by column chromatography (hexanes/EtOAc, 6:4) to afford compound 96 in 82% yield.

Synthesis of Compound 97

Using the methods described in the Method B procedure in Example 12 below for the synthesis of compound 116, compound 97 was prepared from compound 96. The crude compound 97 was subjected to column chromatography (hexanes/EtOAc, 8:2), and used in next step without further purification.

Synthesis of Compound 98

To a stirred solution of impure compound 97 (0.59 mmol) in THF (20 mL) at 0° C. was added 1M LAH in THF (5.8 mL, 5.8 mmol) dropwise. After 25 min at 0° C., the mixture was stirred at ambient temperature for 3 hours. The mixture was cooled to 0° C. again and solid $Na_2SO_4.10H_2O$ (1.86 g, 5.8 mmol) was added portionwise. The mixture was stirred at 0° C. for 5 min and then at ambient temperature for another 20 min before filtration through Celite. The filtrate was concentrated and the residue was purified by column chromatography (EtOAc/MeOH/Et$_3$N, 9:1:0.5) to afford compound 98 (150 mg, 59% from compound 96) as a clear gum.

Synthesis of Compound 99

A mixture of compound 98 (150 mg, 0.32 mmol) and 80% HOAc (5 mL) was stirred at 40° C. for 7 hours. The solvents were removed by rotary evaporation and dried in vacuum. The crude compound 99 was used in next step without purification.

Synthesis of Compound 100

A mixture of MePPh$_3$Br (1.26 g, 3.5 mmol) and KO$^t$Bu (395 mg, 3.5 mmol) in THF (15 mL) was stirred at ambient temperature for 2 hours and then added to a mixture of compound 99 obtained above in THF (5 mL) and DMF (1 mL). The reaction mixture was stirred at ambient temperature for 2 days and then quenched with saturated NH$_4$Cl (0.25 mL). The mixture was diluted with EtOAc (20 mL) and MeOH (5 mL) and filtered through Celite. The filtrate was concentrated and the residue was purified by column chromatography (EtOAc/MeOH/water/Et$_3$N, 6:3:0.5:0.5) to yield compound 100 (47 mg, 47% from compound 98).

Synthesis of Compound 101

A solution of compound 100 (47 mg, 0.15 mmol) in 80% HOAc was stirred at ambient temperature for a few minutes and then the solvents were removed by rotary evaporation. The residue was co-evaporated with MeOH several times. The residue was dissolved in a small amount of MeOH and treated with a small amount of acetonitrile. The product was precipitated out and the supernatant was removed with pipette. The solid obtained was dried in vacuum to afford compound 101 (35 mg, 62%) as a pale powder: LC/MS (direct infusion, electrospray +ve, 10 mM NH$_4$OAc in 3:7 water and MeCN) 308.06; $C_{19}H_{34}NO_2$.

Example 11

Compounds 107-108, representative compounds of the invention, may be prepared according to the following Reaction Scheme 11. Any number of compounds related to compounds 107-108 could be produced using similar methodology. Starting compound 33 may be prepared according to procedures described above in Example 3.

REACTION SCHEME 11

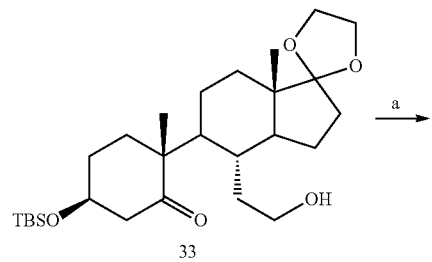

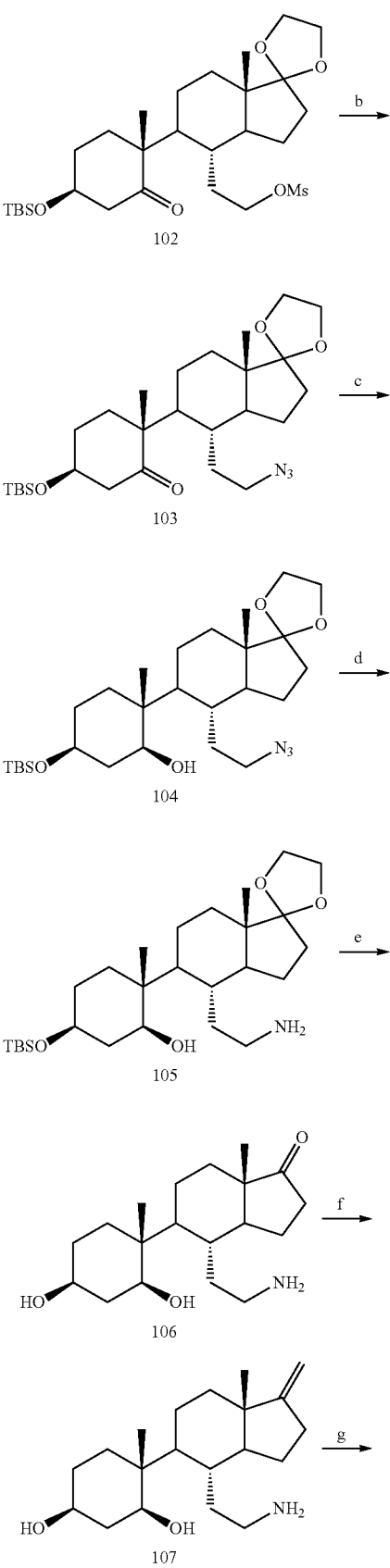

73

-continued

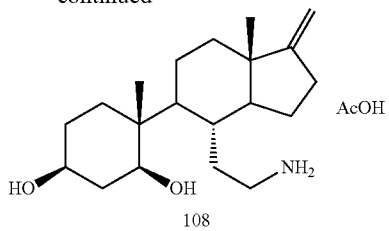

a) MsCl, pyridine; b) NaN₃, DMF, 40° C.; c) NaBH₄, MeOH, THF; d) PPh₃, H₂O, THF, 40° C.; e) 2N HCl, THF; f) MePPh₃Br, KO$^t$Bu, THF, DMF; g) 80% AcOH.

In general, the free hydroxyl is reacted to give the mesylate compound 102 using MsCl and pyridine. Azide displacement of the mesylate using sodium azide in DMF gives compound 103. Sodium borohydride selectively reduces the carbonyl to give compound 104. Reduction of the azide using PPh₃ and water in THF gives compound 105. Treatment with HCl removes the TBS group and the cyclic ketal to give compound 106. Olefination using MePPh₃Br and KO$^t$Bu in THF gives compound 107. Treatment with acetic acid forms the ammonium acetate salt to give compound 108.

Following are specific examples of the compounds prepared above.

Synthesis of Compound 102

To a solution of compound 33 (15.0 g, 31.2 mmol) in pyridine (100 mL) at 0° C. was added methanesulfonyl chloride (4.35 mL, 56.2 mmol). The reaction mixture was stirred at 0° C. for 10 minutes, then at ambient temperature for 4 hours. The mixture was diluted with EtOAc (400 mL), washed with water (2×100 mL) and then brine (2×100 mL), then dried over anhydrous MgSO₄ and concentrated. The residue was purified by chromatography on silica gel (hexanes/EtOAc, 3:1, 1:1) to give compound 102 (12.8 g, 78%) as a white foam.

Synthesis of Compound 103

A mixture of compound 102 (0.800 g, 1.43 mmol) and NaN₃ (0.190 g, 2.89 mmol) in dry DMF (15 mL) was stirred at 50° C. for 3 hours, then at 40° C. overnight. After cooling to ambient temperature, the mixture was diluted with water (80 mL) and extracted with Et₂O (3×30 mL). The organic portion was washed with brine (2×20 mL), dried over anhydrous MgSO₄ and concentrated. The residue was purified by chromatography on silica gel (hexanes; hexanes/EtOAc, 19:1, 9:1, 4:1) to give compound 103 (0.476 g, 66%) as a yellow oil.

Synthesis of Compound 104

To a stirred solution of compound 103 (0.473 g, 0.935 mmol) in THF (15 mL) and MeOH (5 mL) at 0° C. was added NaBH₄ (0.286 g, 7.48 mmol) in portions over 5 minutes. The resulting mixture was stirred at 0° C. for 10 minutes then at ambient temperature overnight. The reaction was quenched with water (50 mL), then extracted with EtOAc (30 mL, 2×20 mL). The organic extracts were washed with brine (2×20 mL), dried over anhydrous MgSO₄ and concentrated. The residue was purified by chromatography on silica gel (hexanes/EtOAc, 9:1, 4:1) to give compound 104 (0.349 g, 73%) as a white foam.

Synthesis of Compound 105

A mixture of compound 104 (0.346 g, 0.681 mmol), PPh₃ (0.542 g, 2.04 mmol), water (1 mL) and THF (20 mL) was stirred at 40° C. overnight and then concentrated. The residue was purified by chromatography on silica gel (CH₂Cl₂/MeOH, 19:1; CH₂Cl₂/MeOH/Et₃N, 9:1:0.2) to give compound 105 (0.336 g, quantitative) as a colourless glass.

Synthesis of Compound 106

A mixture of compound 105 (0.050 g, 0.10 mmol) and 2 N HCl (1 mL, 2 mmol) in THF (3 mL) was stirred at ambient temperature for 2 hours, then concentrated.

To a solution of the residue in CH₂Cl₂/MeOH (1:1, 8 mL) was added macroporous polystyrene-bound carbonate (0.105 g, 0.300 mmol) and the mixture was stirred at ambient temperature for 3 hours. The mixture was filtered, rinsing with CH₂Cl₂/MeOH (1:1, 3×5 mL) and the filtrate was concentrated to give compound 106 (0.032 g, 94%) as a colourless oil.

Synthesis of Compound 107

A mixture of KO$^t$Bu (0.339 g, 2.87 mmol) and MePPh₃Br (1.02 g, 2.87 mmol) in THF (12 mL) was stirred at ambient temperature for 2.5 hours, then a solution of compound 106 (0.116 g, 0.359 mmol) in THF (6 mL) and DMF (2 mL) was added. The reaction mixture was stirred at ambient temperature overnight, then quenched with saturated NH₄Cl solution (4 mL), diluted with MeOH (10 mL), filtered and the filtrate was concentrated. The residue was washed with EtOAc (3×10 mL) and MeOH (2×10 mL). The combined washes were concentrated. The residue was purified by chromatography on silica gel (EtOAc/MeOH; EtOAc/MeOH/H₂O/Et₃N) to afford compound 107 (0.024 g, 21%) as a colourless glass.

Synthesis of Compound 108

A mixture of compound 107 (0.035 g, 0.11 mmol) and 80% acetic acid (5 mL) was stirred at ambient temperature for 45 minutes, then concentrated. The residue was dissolved in MeOH and concentrated three times. Precipitation from ACN/MeOH gave compound 108 (0.036 g, 86%) as a yellow solid: LC/MS (direct infusion, electrospray +ve, 10 mM NH₄OAc in 3:7 water and MeCN) 322.24; C₂₀H₃₆NO₂.

Example 12

Compounds 119-120, representative compounds of the invention, may be prepared according to the following Reaction Scheme 12. Any number of compounds related to compounds 119-120 could be produced using similar methodology. Starting compound 102 may be prepared according to procedures described above in Example 11.

REACTION SCHEME 12

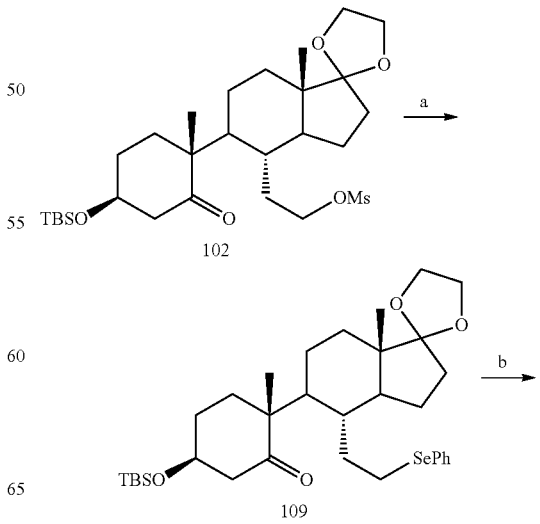

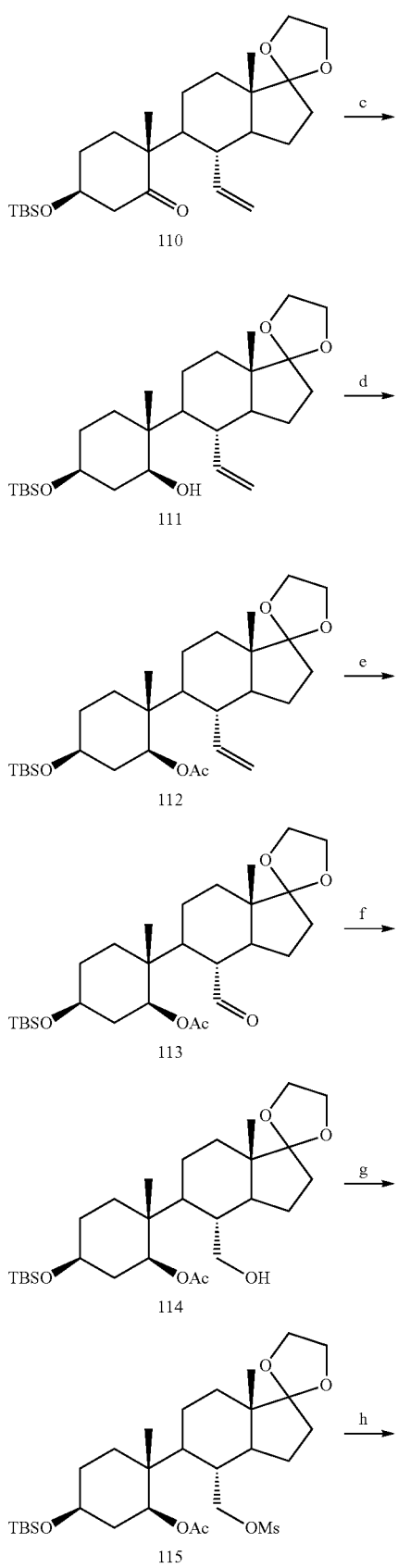

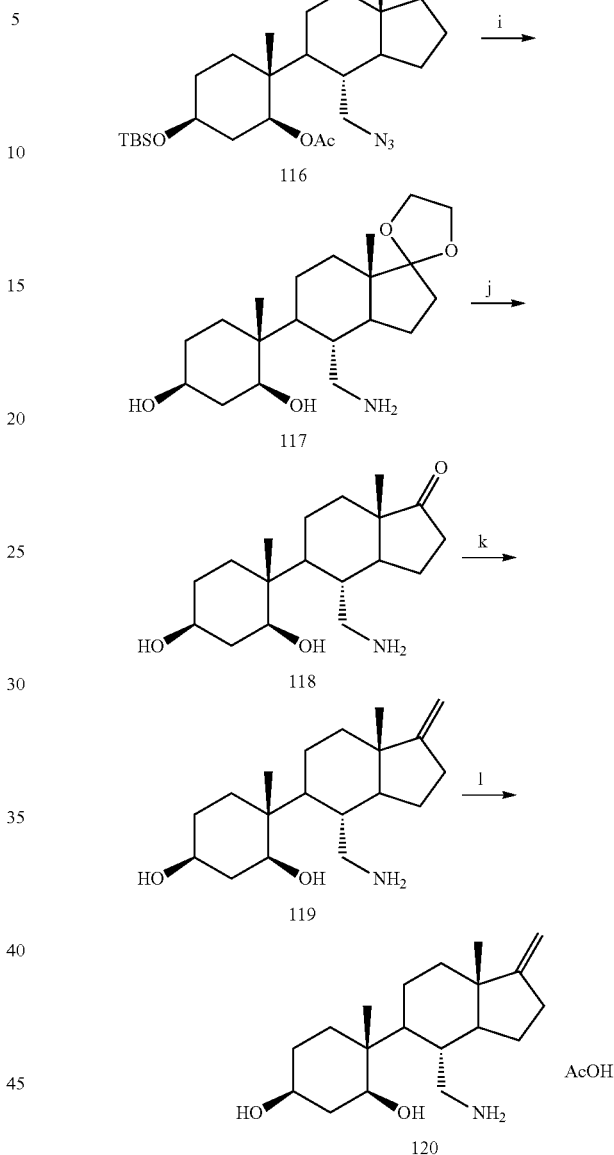

a) (SePh)$_2$, NaBH$_4$, EtOH, 50° C.; b) 30% H$_2$O$_2$, THF, 65° C.; c) NaBH$_4$, MeOH, THF; d) Ac$_2$O, DMAP, pyridine; e) O$_3$, MeOH, CH$_2$Cl$_2$, -78° C.; Me$_2$S; f) NaBH$_4$, MeOH/THF; g) MsCl, pyridine; h) NaN$_3$, DMF, 60° C.; i) LAH, THF; j) 2N HCl, THF; k) MePPh$_3$Br, KO$^t$Bu, THF; l) AcOH In general, mesylate displacement by phenylselenide gives compound 109. Oxidative elimination using hydrogen peroxide gives the olefin compound 110. Sodium borohydride reduction gives the alcohol compound III. Reaction with acetic anhydride and DMAP in pyridine gives compound 112. Ozonation gives the aldehyde compound 113. Sodium borohydride reduction gives compound 114. The free hydroxyl is reacted to give the mesylate compound 115 using MsCl and pyridine. Azide displacement of the mesylate using sodium azide in DMF gives compound 116. Reaction with lithium aluminum hydride in THF reduces the azide and removes both the acyl group and the TBS group to give compound 117. Treatment with HCl removed the cyclic ketal to give compound 118. Olefination using MePPh$_3$Br and KO$^t$Bu in THF gave compound 119. Treatment with acetic acid forms the ammonium acetate salt to give compound 120.

Following are specific examples of the compounds prepared above.

Synthesis of Compound 109

To a stirred mixture of diphenyl diselenide (7.25 g, 22.8 mmol) and EtOH (100 mL) at 0° C. $NaBH_4$ (1.74 g, 45.5 mmol) was added portionwise, after 5 minutes the mixture was allowed to warm to ambient temperature and stirred for an additional hour. The resulting solution was added via cannula to a slurry of compound 102 in EtOH (175 mL), rinsing with EtOH (25 mL). The mixture was stirred at ambient temperature for 30 minutes then at 50° C. for 45 minutes. The mixture was cooled, water (80 mL) was added and the mixture was concentrated. The residue was dissolved in EtOAc (500 mL) and washed with brine (2×100 mL). The combined aqueous washes were back-extracted with EtOAc (200 mL) and the EtOAc portion was washed with brine (2×50 mL). The combined organic extracts were dried over anhydrous $MgSO_4$ and concentrated. The residue was purified by chromatography on silica gel (hexanes/EtOAc, 9:1) to afford compound 109 (8.9 g, 75%) as a light yellow solid.

Synthesis of Compound 110

A mixture of compound 109 (0.907 g, 1.46 mmol) and 30% $H_2O_2$ solution in THF (60 mL) was stirred at ambient temperature for 1 hour then at 65° C. for 1 hour. After cooling, the mixture was diluted with EtOAc (60 mL) and washed with brine (30 mL), then saturated $NaHCO_3$ solution (40 mL). The combined aqueous portions were back-extracted with EtOAc (2×20 mL). The combined organic portions were washed with brine (2×40 mL), dried over anhydrous $MgSO_4$ and concentrated. The residue was purified by chromatography on silica gel (hexanes; hexanes/EtOAc, 7:1) to afford compound 110 (0.447 g, 66%) as a white solid.

Synthesis of Compound 111

To a stirred solution of compound 110 (3.82 g, 8.26 mmol) in THF (75 mL) and MeOH (25 mL) at 0° C. was added $NaBH_4$ (1.06 g, 27.7 mmol) in portions over 20 minutes. The resulting mixture was stirred at 0° C. for 10 minutes, then at ambient temperature overnight. The reaction was cooled to 0° C. and quenched with water (200 mL), then extracted with EtOAc (3×100 mL). The organic extracts were washed with brine (2×100 mL), dried over anhydrous $MgSO_4$ and concentrated to afford compound 111 (3.76 g, 98%) as a white foam.

Synthesis of Compound 112

To a solution of compound III (5.36 g, 11.5 mmol) and DMAP (0.282 g, 2.31 mmol) in pyridine (85 mL) was added acetic anhydride (10.9 mL, 115 mmol). The resulting mixture was stirred at 50° C. overnight, then cooled to ambient temperature, diluted with EtOAc (350 mL) and washed with water (120 mL). The aqueous portion was back-extracted with EtOAc (2×50 mL). The combined organics were washed with brine (2×125 mL), dried over anhydrous $MgSO_4$ and concentrated. The residue was purified by chromatography on silica gel (hexanes/EtOAc, 9:1) to afford compound 112 (5.37 g, 92%) as a white foam.

Synthesis of Compound 113

A solution of compound 112 (4.84 g, 9.55 mmol) in $CH_2Cl_2$ (75 mL) and MeOH (25 mL) was treated with ozone at −78° C. for 3.5 hours. Nitrogen was bubbled at −78° C. for 10 minutes, then dimethyl sulfide (12 mL, 164 mmol) was added and the mixture was stirred at −78° C. for 10 minutes, then at ambient temperature for 2 hours. The mixture was concentrated, then the residue was dissolved in EtOAc (200 mL), washed with water (2×50 mL) and then brine (2×50 mL), dried over anhydrous $MgSO_4$ and concentrated to afford compound 113 (4.59 g, 94%) as a white foam.

Synthesis of Compound 114

To a stirred solution of compound 113 (300 mg, 0.59 mmol) in a mixture of MeOH/THF (2 mL/7 mL) at 0° C. was added $NaBH_4$ (64 mg, 1.7 mmol). After 15 min at 0° C., the mixture was stirred at ambient temperature for 1 hour and then additional $NaBH_4$ (20 mg, 0.53 mmol) was added. The mixture was stirred for another 50 min before cooled to 0° C. and the reaction was quenched by water (5 mL). The mixture was diluted with EtOAc (200 mL), washed twice with brine, dried and concentrated to afford crude compound 114 (299 mg, 99%). The product was used in next step without purification.

Synthesis of Compound 115

To a stirred solution of compound 114 (103 mg, 0.2 mmol) in pyridine at 0° C. was added MsCl (0.1 mL, 0.9 mmol) dropwise. The resulting mixture was stirred at ambient temperature for 8 hours, then diluted with EtOAc (200 mL), washed with brine, dried and concentrated to give crude compound 115, which was used in next step without purification.

Synthesis of Compound 116

Method A

A mixture of compound 115 obtained above and $NaN_3$ (46 mg, 0.7 mmol) in DMF (1.6 mL) was stirred at 60° C. overnight. The reaction mixture was diluted with toluene (150 mL) and washed with brine. The aqueous washings were combined and extracted with toluene. The organic extracts were combined and washed with brine, dried and concentrated. The residue was purified by column chromatography on silica gel (hexanes/EtOAc, 9:1) to afford compound 116 (45 mg, 43% from INT1861) as a pale gum.

Method B

To a stirred solution of compound 114 (293 mg, 0.57 mmol) in THF (6 mL) at 0° C. were added $Ph_3P$ (329 mg, 1.25 mmol), DIAD (0.25 mL, 1.27 mmol), and DPPA (0.27 mL, 1.25 mmol). After 10 min at 0° C., the mixture was stirred at ambient temperature overnight. The reaction was quenched by water (20 mL), and extracted with EtOAc. The EtOAc extracts were combined and washed with saturated $NaHCO_3$, brine, dried and concentrated. The residue was purified by column chromatography (hexanes/EtOAc, 9:1) to yield compound 116 (275 mg, 89%) as a pale gum.

Synthesis of Compound 117

To a stirred solution of compound 116 (128 mg, 0.24 mmol) in THF (5 mL) at 0° C. was added 1M LAH in THF (0.95 mL, 0.95 mmol) dropwise. After 10 min at 0° C., the mixture was stirred at ambient temperature for 4.5 hours. The mixture was cooled to 0° C. again and solid $Na_2SO_4 \cdot 10H_2O$ (308 mg, 0.95 mmol) was added portionwise.

The mixture was stirred at 0° C. for 10 min and then at ambient temperature for another 20 min before filtration through Celite. The filtrate was diluted with EtOAc (200 mL), washed with brine, dried ($Na_2SO_4$) and concentrated. The residue was purified by column chromatography (EtOAc/MeOH/water/$Et_3N$, 7:2:0.5:0.5) to afford compound 117 (45 mg, 53%).

Synthesis of Compound 118

A mixture of compound 117 (45 mg, 0.13 mmol) and 2N HCl (1 mL) in THF (3 mL) was stirred at ambient temperature overnight. The solvents were removed by rotary evaporation and the residue was purified by column chromatography (EtOAc/MeOH/water/$Et_3N$, 7:2:0.5:0.5) to give compound 118 (50 mg, with traces of $Et_3N$).

Synthesis of Compound 119

A mixture of MePPh₃Br (457 mg, 1.28 mmol) and KO'Bu (144 mg, 1.28 mmol) in THF (6 mL) was stirred at ambient temperature for 1 hour 40 min and then added to a mixture of compound 118 (50 mg, 0.16 mmol) in THF (3 mL) and DMF (1 mL). The reaction mixture was stirred at ambient temperature overnight and then quenched with saturated NH₄Cl (2 mL). After being stirred for a few minutes, the mixture was concentrated by rotary evaporation. The residue paste was repeatedly extracted with EtOAc and filtered. The filtrates were combined and concentrated. The residue was purified by column chromatography (EtOAc/MeOH/water/Et₃N, 7:2:0.5:0.5) to yield compound 119 (24 mg, 63% from compound 117).

Synthesis of Compound 120

To a stirred solution of compound 119 (43 mg) in MeOH (~2 mL) was added 80% HOAc (0.5 mL) and then the mixture was concentrated to dryness. The residue was re-dissolved in a small amount of MeOH and treated with a small amount of acetonitrile. The mixture was concentrated again and the resulting precipitate was dried in vacuum to afford compound 120 (53 mg, 100%) as a pale powder: LC/MS (direct infusion, electrospray +ve, 10 mM NH₄OAc in 3:7 water and MeCN) 308.11; $C_{19}H_{34}NO_2$.

Example 13

Compounds 132-133, representative compounds of the invention, may be prepared according to the following Reaction Scheme 13. Any number of compounds related to compounds 132-133 could be produced using similar methodology. The starting compound 121 was prepared according to the procedures described in U.S. Pat. No. 6,046,185.

REACTION SCHEME 13

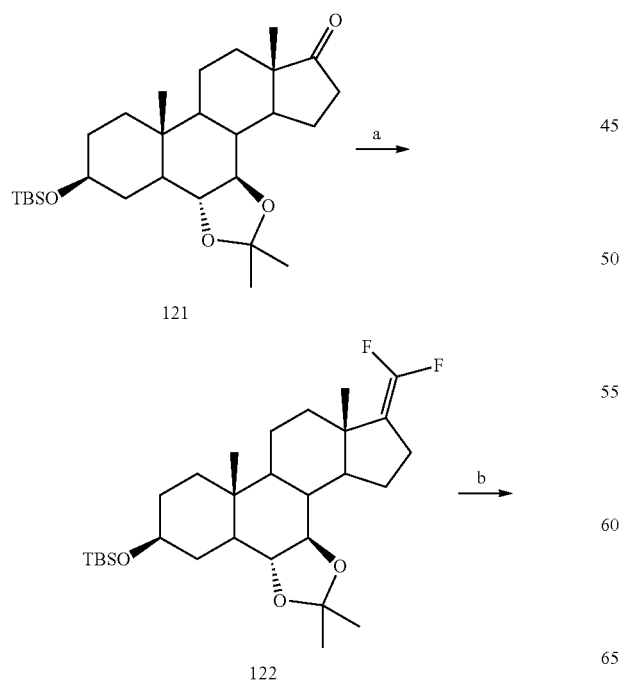

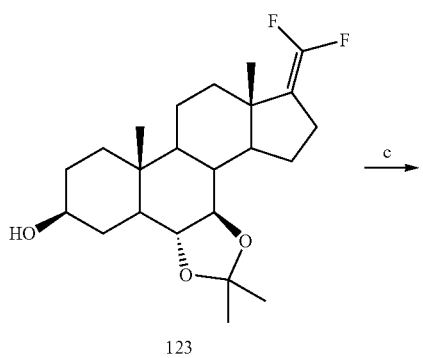

123

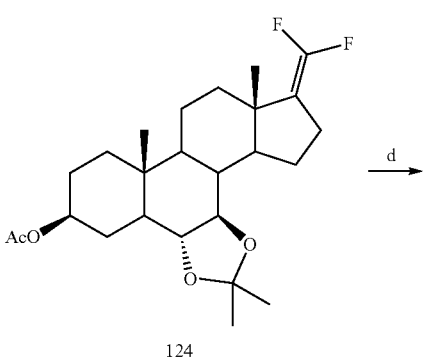

124

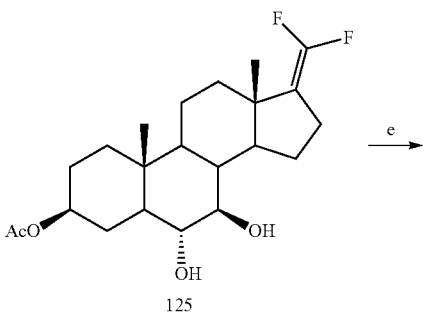

125

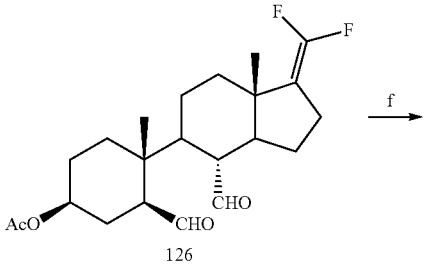

126

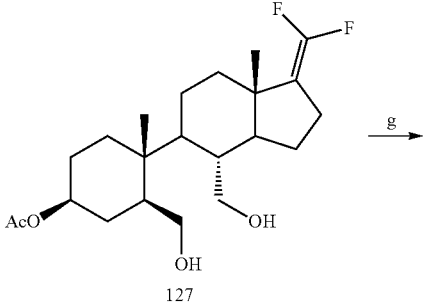

127

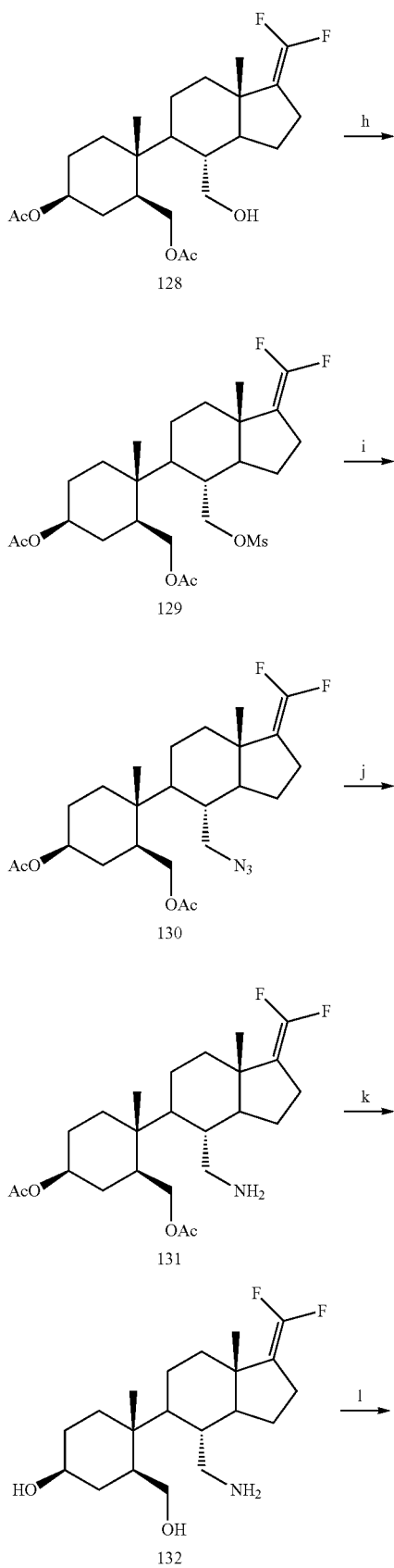

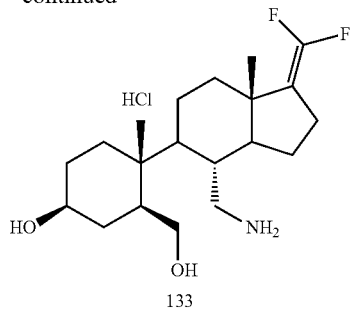

a) (EtO)$_2$P(O)CHF$_2$, LDA, THF; b) Bu$_4$NF, THF; c) Ac$_2$O, pyridine; d) 80% AcOH; e) NaIO$_4$, THF; f) NaBH$_4$, MeOH, THF; g) Ac$_2$O, pyridine; h) MsCl, pyridine; i) NaN$_3$, DMF; j) PPh$_3$, THF, H$_2$O; k) NaOMe, MeOH; l) HCl, MeCN, MeOH.

In general, olefination using (EtO)$_2$P(O)CHF$_2$ and lithium diisopropylamide (LDA) in THF gives compound 122. Tetrabutylammonium fluoride in THF removes the TBS group to give compound 123. Reaction with acetic anhydride in pyridine gives compound 124. Treatment with 80% acetic acid removes the acetonide group to give compound 125. NaIO$_4$ oxidation gives the dialdehyde compound 126. Sodium borohydride reduction gives compound 127. Reaction with acetic anhydride in pyridine gives compound 128. The free hydroxyl is reacted to give the mesylate compound 129 using MsCl and pyridine. Azide displacement of the mesylate using sodium azide in DMF gives compound 130. Reduction of the azide using PPh$_3$ and water in THF gives compound 131. Methanolysis of the acetates gives compound 132. Treatment with HCl forms the salt compound 133.

Following are specific examples of the compounds prepared above.

Synthesis of Compound 122

Freshly prepared LDA (3.4 mL, 2.4 mmol) was added to a −78° C. solution of F$_2$CHPO(OEt)$_2$ (0.40 mL, 2.5 mmol) in dry THF (3 mL) under argon. After 20 minutes, a solution of compound 121 (0.30 g, 0.63 mmol) in dry THF was added. The reaction was continued for 1 hour, then slowly warmed to ambient temperature over 2 hours and finally was heated at 60° C. for 3 hours. The reaction was cooled to ambient temperature, then quenched by 0.5 mL of water. The solution was diluted with EtOAc and was washed with brine, then dried over MgSO$_4$, filtered and concentrated. The residue was purified by column chromatography on silica gel (4% EtOAc/hexanes) to afford compound 122 (0.145 g, 45%) as a white solid.

Synthesis of Compound 123

A solution of compound 122 (0.65 g, 1.3 mmol), Bu$_4$NF (2.7 ml of a 1M solution in THF) and THF (10 ml) was heated at 50° C. for 3 hours. The reaction mixture was concentrated and the residue was purified by column chromatography on silica gel (30% EtOAc/hexanes) to afford compound 123 (0.54 g, quantitative).

Synthesis of Compound 124

A solution of compound 123 (0.54 g, 1.3 mmol), acetic anhydride (0.24 mL, 2.5 mmol) and pyridine (5 mL) was stirred at ambient temperature for 3 days. The solution was diluted with EtOAc, was washed with brine, then dried over MgSO$_4$, filtered and concentrated. The crude compound 124 was used in the next step without further purification.

Synthesis of Compound 125

A solution of compound 124 (crude, 1.3 mmol) and 80% acetic acid (10 mL) was heated at 50° C. for 2 hours. The reaction mixture was concentrated under reduced pressure and the residual solvents were removed by codistillation with toluene. The crude compound 125 was used in the next step without further purification.
Synthesis of Compound 126
A solution of NaIO$_4$ (0.54 g, 2.5 mmol) and water (4 mL) was added to a solution of compound 125 (crude, 1.3 mmol) and THF (10 mL). After 3 hours the solution was diluted with CH$_2$Cl$_2$ and washed with brine, then dried over MgSO$_4$, filtered and concentrated. The crude compound 126 was used in the next step without further purification.
Synthesis of Compound 127
Sodium borohydride (48 mg, 1.3 mmol) was added to a solution of compound 126 (crude, 1.3 mmol), THF (6 mL) and MeOH (2 mL). After 3 hours, the reaction was quenched by water (15 mL) and the solution was extracted using 2×15 mL of EtOAc. The combined extracts were dried over MgSO$_4$, filtered and concentrated. The residue was purified by column chromatography on silica gel (30% EtOAc/hexanes) to afford compound 127 (0.38 g, 75%) as a white solid.
Synthesis of Compound 128
A solution of compound 127 (0.38 g, 0.95 mmol), acetic anhydride (0.09 mL, 1 mmol) and pyridine (5 mL) was stirred overnight at ambient temperature. The reaction mixture was diluted with water and extracted with 2×15 mL of EtOAc. The combined extracts were dried over MgSO$_4$, filtered and concentrated. The residue was purified by column chromatography on silica gel to afford compound 128 (0.32 g, 76%) as a white solid.
Synthesis of Compound 129
A solution of compound 128 (0.32 g, 0.72 mmol), MsCl (0.11 mL, 1.4 mmol) and pyridine (5 mL) was stirred at ambient temperature for 3 hours. The reaction mixture was quenched with water and was extracted with EtOAc (2×25 mL). The combined extracts were washed with brine then were dried over MgSO$_4$, filtered and concentrated. The crude compound 129 was used in the next step without further purification.
Synthesis of Compound 130
A solution of compound 129 (crude, 0.72 mmol), NaN$_3$ (0.83 g, 3.6 mmol) and DMF (5 mL) was heated overnight at 55° C. The reaction mixture was cooled to ambient temperature and was diluted with water (10 mL), then extracted with toluene. The toluene solution was dried over MgSO$_4$, filtered and concentrated. The residue was purified by column chromatography on silica gel (20% EtOAc/hexanes) to afford compound 130 (0.30 g, 89%) as a white foam.
Synthesis of Compound 131
A solution of compound 130 (0.13 g, 0.28 mmol), PPh$_3$ (0.15 g, 0.56 mmol), THF (3 mL) and water (0.3 mL) was stirred under argon for 3 days. The reaction mixture was concentrated and the residue was purified by column chromatography on silica gel (EtOAc/MeOH/Et$_3$N 9:1:0.5) to afford compound 131 (98 mg, 79%) as a white solid.
Synthesis of Compound 132
A solution of compound 131 (0.28 g, 0.65 mmol), NaOMe (0.5 mL of a 25% solution in MeOH) and MeOH (5 mL) was stirred at ambient temperature for 3 hours. The reaction mixture was concentrated and the residue was purified by column chromatography (EtOAc/MeOH/NH$_4$OH 9:1:0.6) to afford compound 132 (0.21 g, 89%) as a white solid.
Synthesis of Compound 133
A solution of compound 132 (0.24 g, 0.68 mmol), HCl (1.36 mL of a 1M solution in Et$_2$O) and MeOH (3 mL) was stirred at ambient temperature for 30 minutes. The reaction mixture was concentrated and the residue was triturate in EtOAc (5 mL). The resulting white solid was filtered and dried overnight under high vacuum at 56° C. to afford compound 133 (0.21 g, 78%): LC/MS (direct infusion, electrospray +ve, 10 mM NH$_4$OAc in 3:7 water and MeCN) 358.14; C$_{20}$H$_{34}$F$_2$NO$_2$.

Example 14

Compound 143, a representative compound of the invention, may be prepared according to the following Reaction Scheme 14. Any number of compounds related to compound 143 could be produced using similar methodology. Starting compound 121 may be prepared by the procedures described in U.S. Pat. No. 6,046,185.

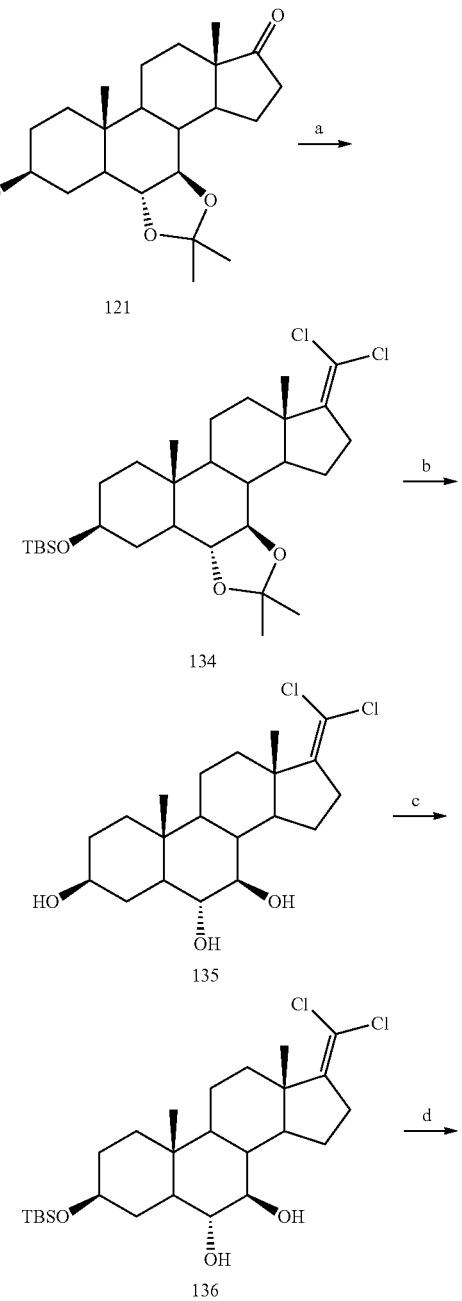

REACTION SCHEME 14

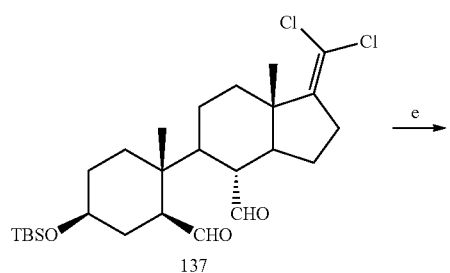

137

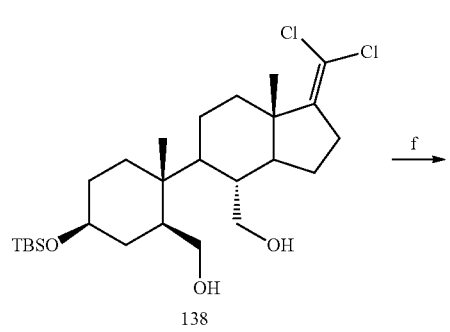

138

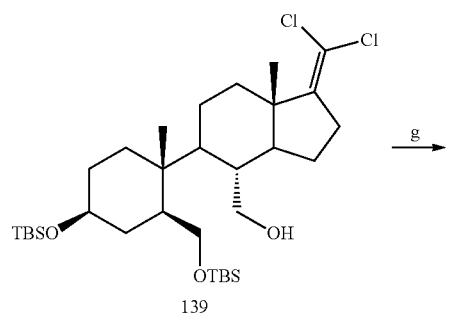

139

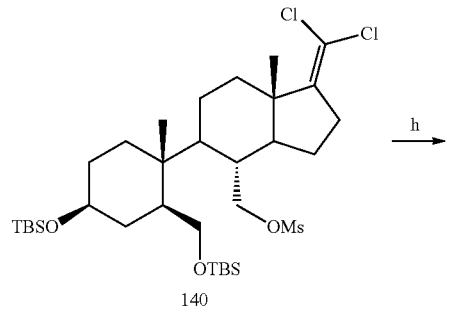

140

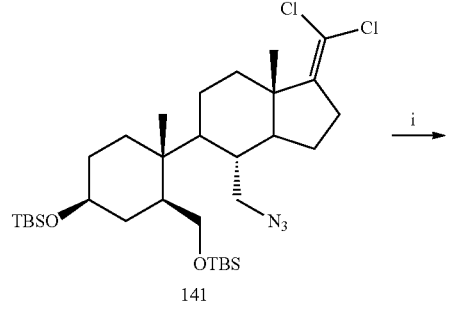

141

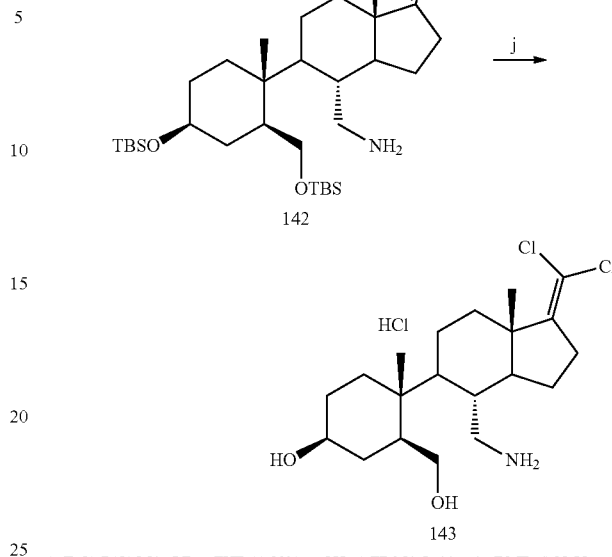

142

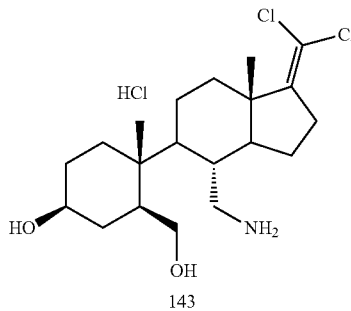

143 a) (EtO)₂P(O)CCl₃, LDA, THF; b) 80% AcOH; c) TBSCl, Imidazole, DMF; d) NaIO₄, THF; e) NaBH₄, MeOH, THF; f) TBSCl, Imidazole, DMF; g) MsCl, pyridine; h) NaN₃, DMF; i) PPh₃, THF, H₂O; j) HCl, THF, H₂O.

In general, olefination using $(EtO)_2P(O)CCl_3$ and LDA in THF gives compound 134. Treatment with 80% acetic acid removes both the TBS group and the acetonide group to give compound 135. Treatment with TBSCl and imidazole in DMF selectively protects one hydroxyl to give compound 136. NaIO₄ oxidation gives the dialdehyde compound 137. Sodium borohydride reduction gives compound 138. Treatment with TBSCl and imidazole in DMF selectively protects one hydroxyl to give compound 139. The free hydroxyl is reacted to give the mesylate compound 140 using MsCl and pyridine. Azide displacement of the mesylate using sodium azide in DMF gives compound 141. Reduction of the azide using PPh₃ and water in THF gives compound 142. Treatment with HCl removes the TBS groups and forms the salt compound 143.

Following are specific examples of the compounds prepared above.

Synthesis of Compound 134

CCl₃P(O)(OEt)₂ (1.12 ml, 6 mmol) was added to a −78° C. solution of freshly prepared LDA (6 mmol) in dry THF (20 mL) under argon. After 5 minutes a compound 121 (954 mg, 2 mmol) was added. The reaction was continued for 1 hour, then slowly warmed to ambient temperature over 2 hours and finally was stirred at ambient temperature for overnight. The reaction quenched by 0.5 mL of water. The solution was diluted with EtOAc and was washed with water, then dried over MgSO₄, filtered and concentrated. The residue was purified by column chromatography on silica gel (3% EtOAc/hexanes) to afford compound 134 (109 mg, 10%) as a pale yellow foam.

Synthesis of Compound 135

A solution of compound 134 (288 mg, 0.53 mmol) in 2 ml THF and 80% acetic acid (8 mL) was heated at 50° C. for 2 hours. The reaction mixture was concentrated under reduced pressure and the residual solvents were removed by codistillation with toluene. The crude compound 135 was used in the next step without further purification.

Synthesis of Compound 136

A solution of compound 135 (crude, 0.53 mmol) in DMF (3 mL), imidazole (108 mg, 1.6 mmol) and TBSCI (160 mg, 1.1 mmol) was stirred at ambient temperature for 2 hours. The reaction mixture was diluted with 50 ml water and extracted with 100 mL of EtOAc. The extracts were dried over $MgSO_4$, filtered and concentrated. The residue was purified by column chromatography on silica gel to afford compound 136 (243 mg, 91%) as a pale yellow foam.

Synthesis of Compound 137

A solution of $NaIO_4$ (205 mg, 0.96 mmol) and water (2 mL) was added to a solution of compound 136 (243 mg, 0.48 mmol) and THF (6 mL). After 3 hours the solution was diluted with $CH_2Cl_2$ and washed with brine, then dried over $MgSO_4$, filtered and concentrated. The crude compound 137 was used in the next step without further purification.

Synthesis of Compound 138

Sodium borohydride (36 mg, 0.96 mmol) was added to a solution of compound 137 (crude, 0.48 mmol), THF (3 mL) and MeOH (1 mL). After 3 hours, the reaction was quenched by water (30 mL) and the solution was extracted using 2×50 mL of EtOAc. The combined extracts were dried over $MgSO_4$, filtered and concentrated. The residue was purified by column chromatography on silica gel (30% EtOAc/hexanes) to afford compound 138 (201 mg, 83%) as pale yellow oil.

Synthesis of Compound 139

A solution of compound 138 (201 mg, 0.4 mmol), imidazole (136 mg, 2 mmol), TBSCI (110 mg, 0.73 mmol) and DMF (3 mL) was stirred for 1 hour at ambient temperature. The reaction mixture was diluted with 30 mL water and extracted with 2×40 mL of EtOAc. The combined extracts were dried over $MgSO_4$, filtered and concentrated. The residue was purified by column chromatography on silica gel to afford compound 139 (230 mg, 93%) as pale yellow oil.

Synthesis of Compound 140

A solution of compound 139 (216 mg, 0.35 mmol), MsCl (0.14 mL, 1.8 mmol) and pyridine (3.5 mL) was stirred at ambient temperature for 2 hours. The reaction mixture was quenched with 30 mL water and was extracted with EtOAc (2×40 mL). The combined extracts were washed with brine then were dried over $MgSO_4$, filtered and concentrated. The crude compound 140 was used in the next step without further purification.

Synthesis of Compound 141

A solution of compound 140 (crude, 0.35 mmol), $NaN_3$ (178 mg, 2.7 mmol) and DMF (3 mL) was heated overnight at 55° C. The reaction mixture was cooled to ambient temperature and was diluted with water (30 mL), then extracted with toluene. The toluene solution was dried over $MgSO_4$, filtered and concentrated. The residue was purified by column chromatography on silica gel (5% EtOAc/hexanes) to afford compound 141 (202 mg, 89%) as pale yellow oil.

Synthesis of Compound 142

A solution of compound 141 (202 mg, 0.31 mmol), $PPh_3$ (320 mg, 1.2 mmol), THF (4 mL) and water (0.3 mL) was stirred under argon overnight, then heated at 50° C. for 4 hours. The reaction mixture was concentrated and the residue was purified by 2 g SCX ion-exchange (6 volume MeOH, 3 volume 5% ammonia/MeOH) to afford compound 142 as a pale yellow foam (TBS group lost partially during this process).

Synthesis of Compound 143

A solution of compound 142 (crude, 0.31 mmol), HCl (1 mL of a 1M solution in $Et_2O$), THF (3 mL) and water (0.5 mL) was stirred at ambient temperature for 2 hours. The reaction mixture was kept at 4° C. for 1 hour. The resulting white solid was filtered and washed with EtOAc, then dried overnight under high vacuum at 56° C. to afford compound 143 (122 mg, 92%): LC/MS (direct infusion, electrospray +ve, 10 mM $NH_4OAc$ in 3:7 water and MeCN) 390.06; $C_{20}H_{34}Cl_2NO_2$.

Example 15

Compounds 157-158, representative compounds of the invention, may be prepared according to the following Reaction Scheme 15. Starting compound 144 may be prepared according to the procedures outlined in U.S. Pat. No. 6,046,185. Any number of compounds related to compounds 157-158 could be produced using similar methodology.

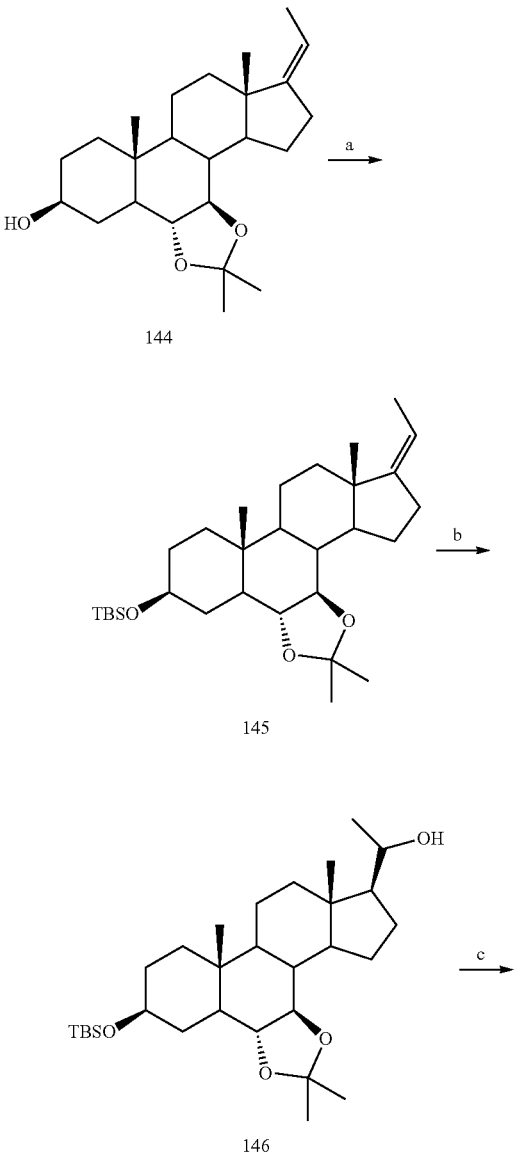

REACTION SCHEME 15

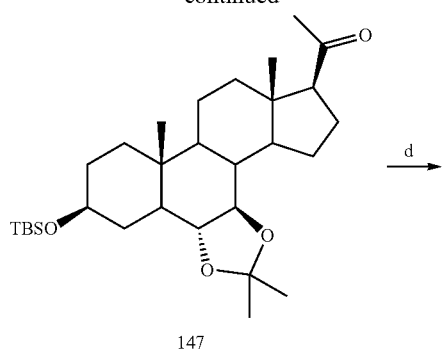
147
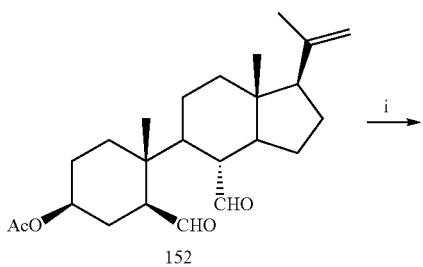
152
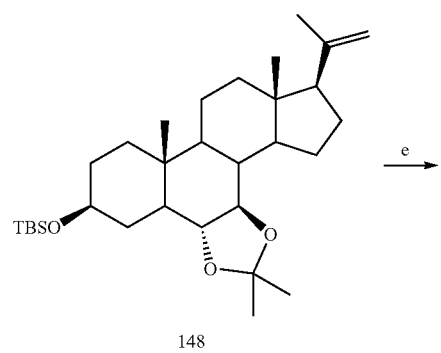
148
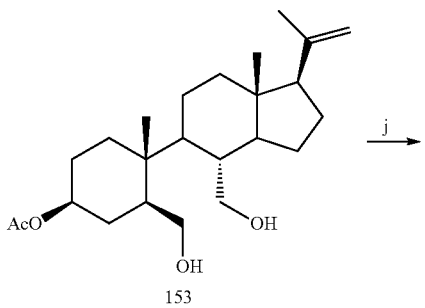
153
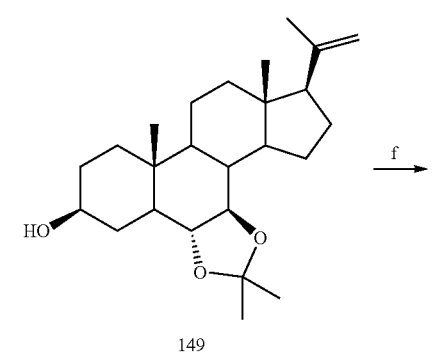
149
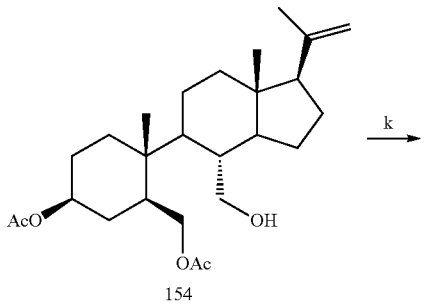
154
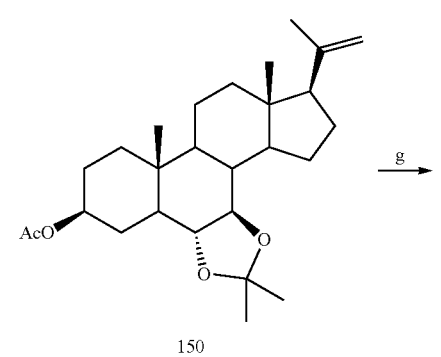
150
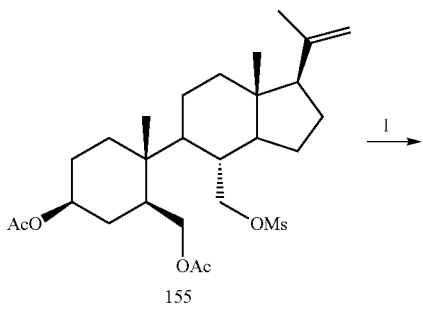
155
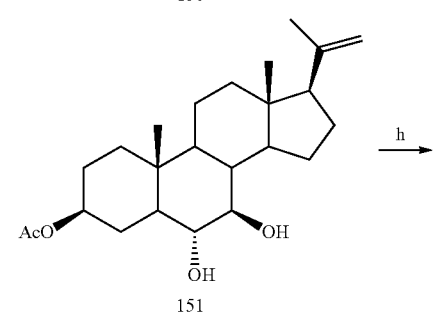
151
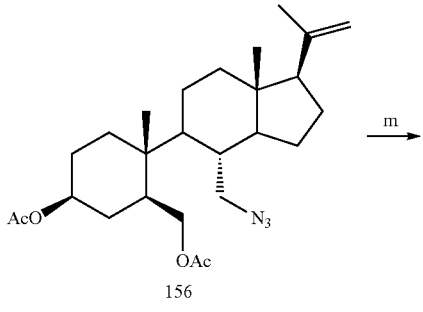
156

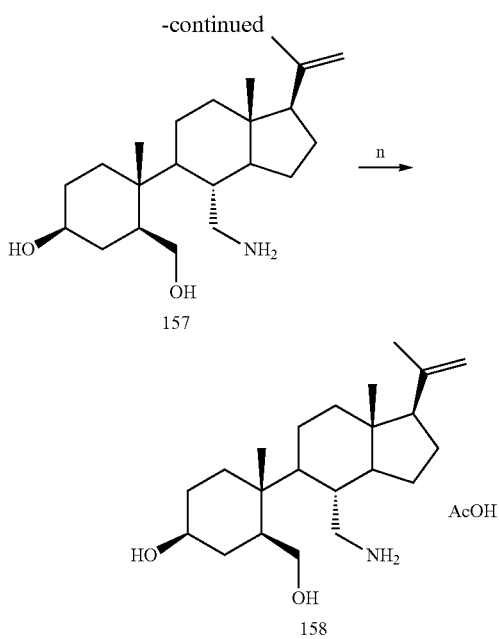

a) TBSCl, imidazole, DMF; b) BH$_3$•THF, H$_2$O$_2$, THF; c) n-Pr$_4$N(RuO$_4$), NMO, 4Å molecular sieves, CH$_2$Cl$_2$; d) MePPh$_3$Br, KO$^t$Bu, THF; e) n-Bu$_4$NF, THF; f) Ac$_2$O, DMAP, pyridine; g) 80% AcOH; h) NaIO$_4$, THF, H$_2$O; i) NaBH$_4$, MeOH, THF; j) Ac$_2$O, DMAP, pyridine; k) MsCl, pyridine; l) NaN$_3$, DMF; m) LiAlH$_4$, THF; n) 80% AcOH.

In general, reaction of compound 144 with TBSCl and imidazole in DMF gives compound 145. Hydroboration with borane-tetrahydrofuran complex in THF, followed by oxidative workup with NaOH and H$_2$O$_2$ converts compound 145 to the secondary alcohol compound 146. Oxidation with a catalytic amount of tetra-n-propylammonium perruthenate (TPAP) and NMO in CH$_2$Cl$_2$ gives compound 147. Olefination with MePPh$_3$Br and KO$^t$Bu in THF gives alkene 148. Tetrabutylammonium fluoride removes the TBS group to give compound 149. Reaction with acetic anhydride in pyridine gives compound 150. Treatment with 80% acetic acid removes the acetonide group to give compound 151. NaIO$_4$ oxidation gives the dialdehyde compound 152. Sodium borohydride reduction gives compound 153. Reaction with acetic anhydride in pyridine selectively protects one hydroxyl to give compound 154. The free hydroxyl is reacted to give the mesylate compound 155 using MsCl and pyridine. Azide displacement of the mesylate using sodium azide in DMF gives compound 156. Reaction with lithium aluminum hydride in THF reduces the azide and removes the acetates to give compound 157. Treatment with 80% acetic acid forms the ammonium acetate salt compound 158.

Synthesis of Compound 145

A solution of compound 144 (10.0 g, 26.7 mol), TBSCI (6.22 g, 40.1 mmol), and imidazole (3.67 g, 53.4 mmol) in dry DMF (178 mL) was stirred at ambient temperature for 2.5 hours. The reaction mixture was diluted with water (250 mL) and extracted with toluene (3×250 mL). The combined toluene extracts were washed with brine (250 mL), dried over MgSO$_4$, filtered, and concentrated. The crude compound 145 (12.5 g, 96%) was used in the next reaction without further purification.

Synthesis of Compound 146

To a solution of compound 145 (12.5 g, 25.6 mmol) in dry THF (150 mL) was added borane-tetrahydrofuran complex (46 mL of 1.0 M solution in THF) and the reaction mixture was stirred at ambient temperature for 1 hour. 10% aqueous NaOH (180 mL) was slowly added. The mixture was cooled in ice and 30% aqueous solution of H$_2$O$_2$ (120 mL) was slowly added. The mixture was stirred at ambient temperature for hour and then extracted with EtOAc (3×250 mL). The combined EtOAc extracts were washed with 10% aqueous Na$_2$S$_2$O$_3$ (200 mL), brine (200 mL), dried over MgSO$_4$, filtered, and concentrated. The residue was purified by chromatography on silica gel (CH$_2$Cl$_2$/EtOAc, 95:5 then 85:15 and hexanes/EtOAc, 90:10 then 85:15) to afford compound 146 (10.7 g, 83%) as a white solid.

Synthesis of Compound 147

To a mixture of compound 146 (8.50 g, 16.8 mmol), NMO (2.23 g, 18.5 mmol), 4 Å molecular sieves (5.3 g) in CH$_2$Cl$_2$ (85 mL) was added TPAP (152 mg, 0.42 mmol). The reaction mixture was stirred at ambient temperature for 1 hour, then filtered through silica gel packed in a sintered glass funnel (eluted with hexanes/EtOAc, 1:1), and concentrated to dryness. The crude product 147 was used in the next reaction without further purification.

Synthesis of Compound 148

A mixture of KO$^t$Bu (5.69 g, 48.1 mmol) and MePPh$_3$Br (17.2 g, 48.1 mmol) in THF (160 mL) was stirred at ambient temperature for one hour under argon then compound 147 (8.10 g, 16.1 mmol) was added. The reaction mixture was stirred at ambient temperature for 4 hours, diluted with brine (150 mL), extracted with EtOAc (3×200 mL). The combined EtOAc extracts were washed with brine (200 mL), dried over MgSO$_4$, filtered, and concentrated. The residue was purified by chromatography on silica gel (hexanes/EtOAc, 96:4 then 10:1 then 4:1) to afford compound 148 (6.3 g, 79%) as a white foam.

Synthesis of Compound 149

A solution of compound 148 (6.3 g, 12.5 mmol) and n-Bu$_4$NF (18.8 mL of a 1.0 M solution in THF) in THF (125 mL) was refluxed under argon for 1 hour. Solvent was evaporated under reduced pressure and the residue was purified by chromatography on silica gel (hexanes/EtOAc, 2:1 then 1:1) to afford compound 149 (4.8 g, 99%) as a white solid.

Synthesis of Compound 150

A solution of compound 149 (4.8 g, 12.4 mmol), acetic anhydride (2.3 mL, 24.7 mmol) and DMAP (151 mg, 1.24 mmol) in pyridine (60 mL) was stirred at ambient temperature overnight. The reaction mixture was diluted with EtOAc (300 mL) and washed with brine (2×100 mL). The EtOAc layer was dried over MgSO$_4$, filtered, and concentrated. The crude compound 150 was used directly in the next step.

Synthesis of Compound 151

A mixture of compound 150 (crude, 12.4 mmol) and 80% acetic acid (90 mL) was stirred at 40° C. for 1 hour. The solution was concentrated to afford compound 151 that was used in the next step without further purification.

Synthesis of Compound 152

A solution of compound 151 (2.20 g, 5.63 mmol), NaIO$_4$ (2.43 g, 11.3 mmol), water (23 mL) and THF (46 mL) was stirred at ambient temperature for 3 hours. The reaction mixture was diluted with CH$_2$Cl$_2$ (200 mL) and washed with brine (3×75 mL). The CH$_2$Cl$_2$ layer was dried over MgSO$_4$, filtered, and concentrated to afford compound 152 that was used in the next step without further purification.

Synthesis of Compound 153

A solution of compound 152 (crude, 5.63 mmol), NaBH$_4$ (538 mg, 14.1 mmol), THF (36 mL) and MeOH (12 mL) was stirred at 0° C. for 10 minutes then at ambient temperature for 2 hours. The mixture was cooled in ice and 80% acetic acid (23 mL) was slowly added. The solution was stirred at ambient temperature for 10 minutes, then diluted with EtOAc (200 mL) and washed with brine (3×75 mL). The EtOAc layer was dried over MgSO$_4$, filtered, and concentrated to afford crude compound 153 that was used in the next step without further purification.

Synthesis of Compound 154

A solution of compound 153 (crude, 5.63 mmol), acetic anhydride (0.58 mL, 6.20 mmol) and DMAP (69 mg, 0.56 mmol) in pyridine (22 mL) was stirred at ambient temperature for 1.5 hours. The reaction mixture was diluted with EtOAc (200 mL) and washed with brine (3×75 mL). The EtOAc layer was dried over MgSO$_4$, filtered, and concentrated. The residue was purified by chromatography on silica gel (hexanes/EtOAc, 5:1 then 4:1 then 7:3) to afford compound 154 (1.6 g, 65% for 5 steps).

Synthesis of Compound 155

To a solution of compound 154 (1.60 g, 3.68 mmol) in pyridine (15 mL) was added methanesulfonyl chloride (0.600 mL, 7.37 mmol) and the reaction mixture was stirred at ambient temperature for 4 hours. The solution was diluted with EtOAc (200 mL) and washed with brine (3×70 mL), then dried over MgSO$_4$, filtered, and concentrated to afford crude compound 155 that was used for the next reaction without further purification.

Synthesis of Compound 156

A mixture of compound 155 (crude, 3.68 mmol) and NaN$_3$ (479 mg, 7.36 mmol) in DMF (25 mL) was heated under argon at 60° C. overnight. After cooling, the reaction mixture was diluted with toluene (300 mL) and was washed with brine (3×75 mL), then dried over MgSO$_4$, filtered, and concentrated. The residue was purified by chromatography on silica gel (hexanes/EtOAc, 9:1 then 8:2) to afford compound 156 (1.6 g, 95% for 2 steps) as a white foam.

Synthesis of Compound 157

A solution of LiAlH$_4$ (13.9 mL of a 1.0 M solution in THF) was added to an ice cooled solution of compound 156 (1.60 g, 13.9 mmol) in THF (35 mL) and stirred for 15 minutes. The stirring was continued at ambient temperature for 3 hours. The reaction mixture was cooled in ice, quenched with Na$_2$SO$_4$.10H$_2$O and stirred for 10 minutes. The mixture was then stirred for an additional 30 minutes at ambient temperature, diluted with EtOAc, and then filtered. The filtrate was washed with brine, dried over MgSO$_4$, filtered, and concentrated. The residue was purified by chromatography on silica gel (EtOAc/MeOH/H$_2$O/Et$_3$N, 70:20:10:0 then 70:20:10:3) to afford compound 157 (0.8 g, 66%) as a white solid.

Synthesis of Compound 158

A solution of compound 157 (0.800 g, 2.29 mmol) and 80% acetic acid (20 mL) was heated at 40° C. for 1 hour and, then concentrated. Residual solvent was removed by codistillation with acetonitrile. The residue was triturated in diethyl ether and filtered to give compound 158 (700 mg, 75%) as a white solid. LC/MS (direct infusion, electrospray +ve, 10 mM NH$_4$OAc in 3:7 water and MeCN) 350.12; C$_{22}$H$_{40}$NO$_2$.

Example 16

Compound 163, a representative compound of the invention, may be prepared according to the following Reaction Scheme 16. Any number of compounds related to compound 163 could be produced using similar methodology. Starting compound 21 may be prepared according to the procedures described above in Example 1.

REACTION SCHEME 16

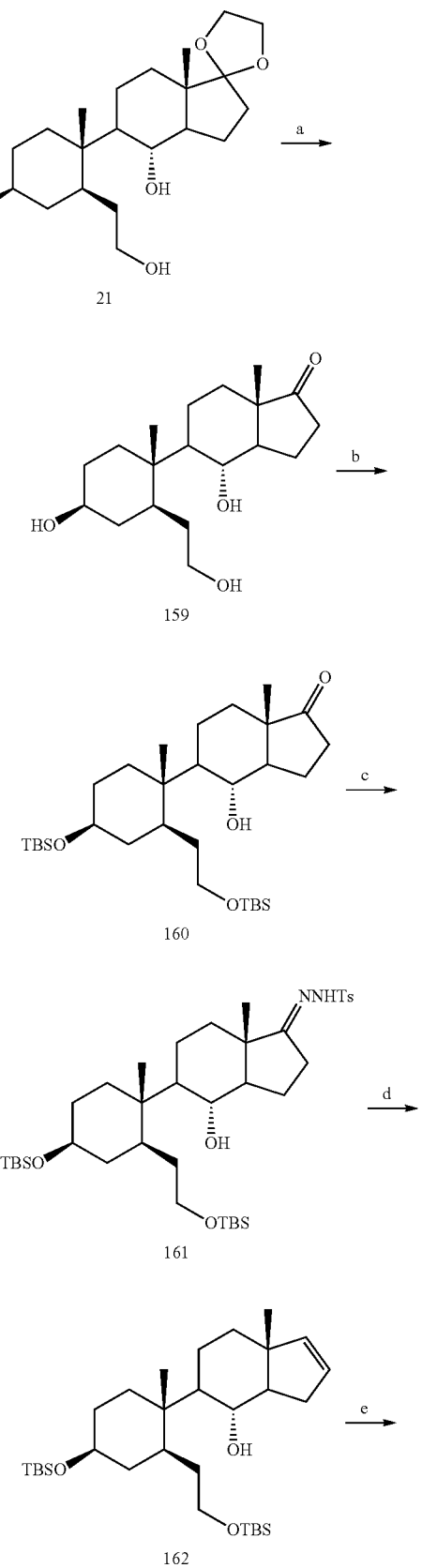

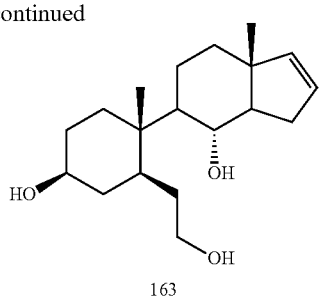

a) 80% AcOH, 55° C.; b) TBSCl, imidazole, DMF; c) TsNHNH$_2$, toluene, reflux; d) LDA, THF; e) 80% AcOH In general, treatment with 80% acetic acid removes the TBS group to give compound 159. Reaction with TBSCl and imidazole in DMF gives compound 160. Reaction with tosylhydrazine in toluene gives compound 161. Reaction with LDA gives the elimination product compound 162. Treatment with 80% acetic acid removes the TBS groups to give compound 163.

Synthesis of Compound 159

A mixture of compound 21 (1.19 g, 2.46 mmol) and 80% acetic acid (20 mL) was stirred at 55° C. for 3 hours then concentrated. The residue was dissolved in toluene and concentrated three times. The residue was purified by chromatography on silica gel (EtOAc/MeOH, 49:1) to give compound 159 (0.747 g, 93%) as a white foam.

Synthesis of Compound 160

A mixture of compound 159 (0.747 g, 2.30 mmol), TBSCl (2.08 g, 13.8 mmol) and imidazole (1.88 g, 27.6 mmol) in dry DMF (12 mL) was stirred at ambient temperature for 3 hours then diluted with water (50 mL) and extracted with EtOAc (3×50 mL). The combined organics were washed with brine (2×30 mL), dried over anhydrous Na$_2$SO$_4$ and concentrated. The residue was purified by chromatography on silica gel (hexanes/EtOAc, 7:3) to give compound 160 (1.11 g, 93%) as a white foam.

Synthesis of Compound 161

A mixture of compound 160 (0.500 g, 0.904 mmol) and TsNHNH$_2$ (0.236 g, 1.27 mmol) in toluene (20 mL) was heated at reflux for 1 hour, then stirred at ambient temperature overnight, then heated at reflux for another hour. After cooling, the mixture was concentrated. To the residue was added CH$_2$Cl$_2$ and the mixture was cooled in ice. The precipitate was filtered out, washing with cold CH$_2$Cl$_2$, then dried to afford compound 161 (0.588 g, 90%) as a white solid.

Synthesis of Compound 162

LDA solution was prepared by adding "BuLi (2 mL of a 2.5 M solution in hexanes, 5.0 mmol) to a solution of $^i$Pr$_2$NH (0.77 mL, 5.5 mmol) in THF (4.23 mL) at 0° C., then stirring the solution at 0° C. for 30 minutes. To a solution of compound 161 (0.550 g, 0.763 mmol) in THF (4 mL) at ambient temperature was added LDA solution (6.4 mL of a 0.71 M solution, 4.6 mmol). The reaction mixture was stirred at ambient temperature overnight. The mixture was diluted with brine (50 mL) and extracted with EtOAc (3×50 mL). The combined organics were washed with brine (2×30 mL), dried over anhydrous Na$_2$SO$_4$ and concentrated. The residue was purified by chromatography on silica gel (hexanes/EtOAc, 19:1, 9:1) to give compound 162 (0.062 g, 15%) as a yellow gel.

Synthesis of Compound 163

A mixture of compound 162 (0.062 g, 0.11 mmol) and 80% acetic acid (2 mL) was stirred at ambient temperature for 3 hours and then concentrated. The residue was dissolved in toluene and concentrated. The residue was purified by chromatography on silica gel (EtOAc/MeOH, 19:1) to give compound 163 (0.022 g, 65%) as a light yellow solid.

Example 17

Compound 178, a representative compound of the invention, may be prepared according to the following Reaction Scheme 17. Any number of compounds related to compound 178 could be produced using similar methodology. Starting compound 164 may be prepared according to the procedures outlined in U.S. Pat. No. 6,046,185.

REACTION SCHEME 17

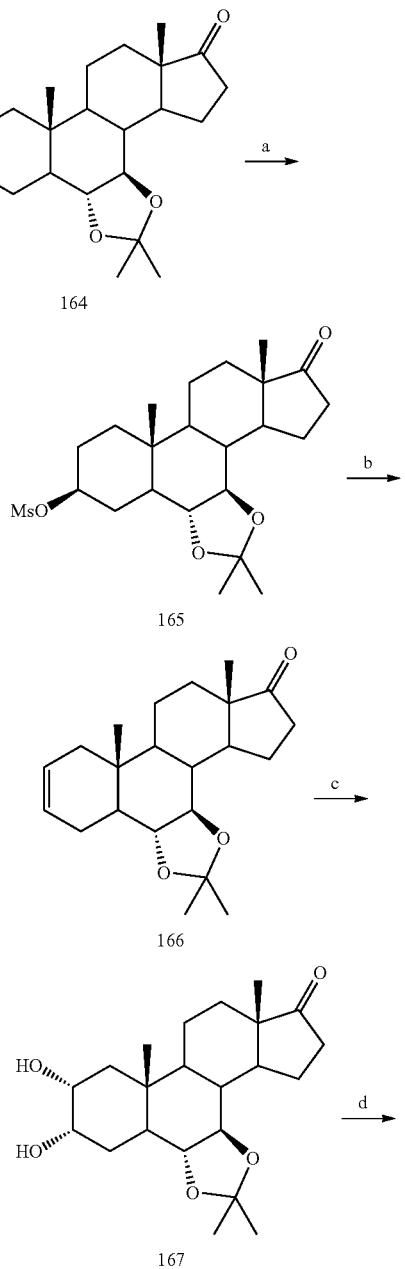

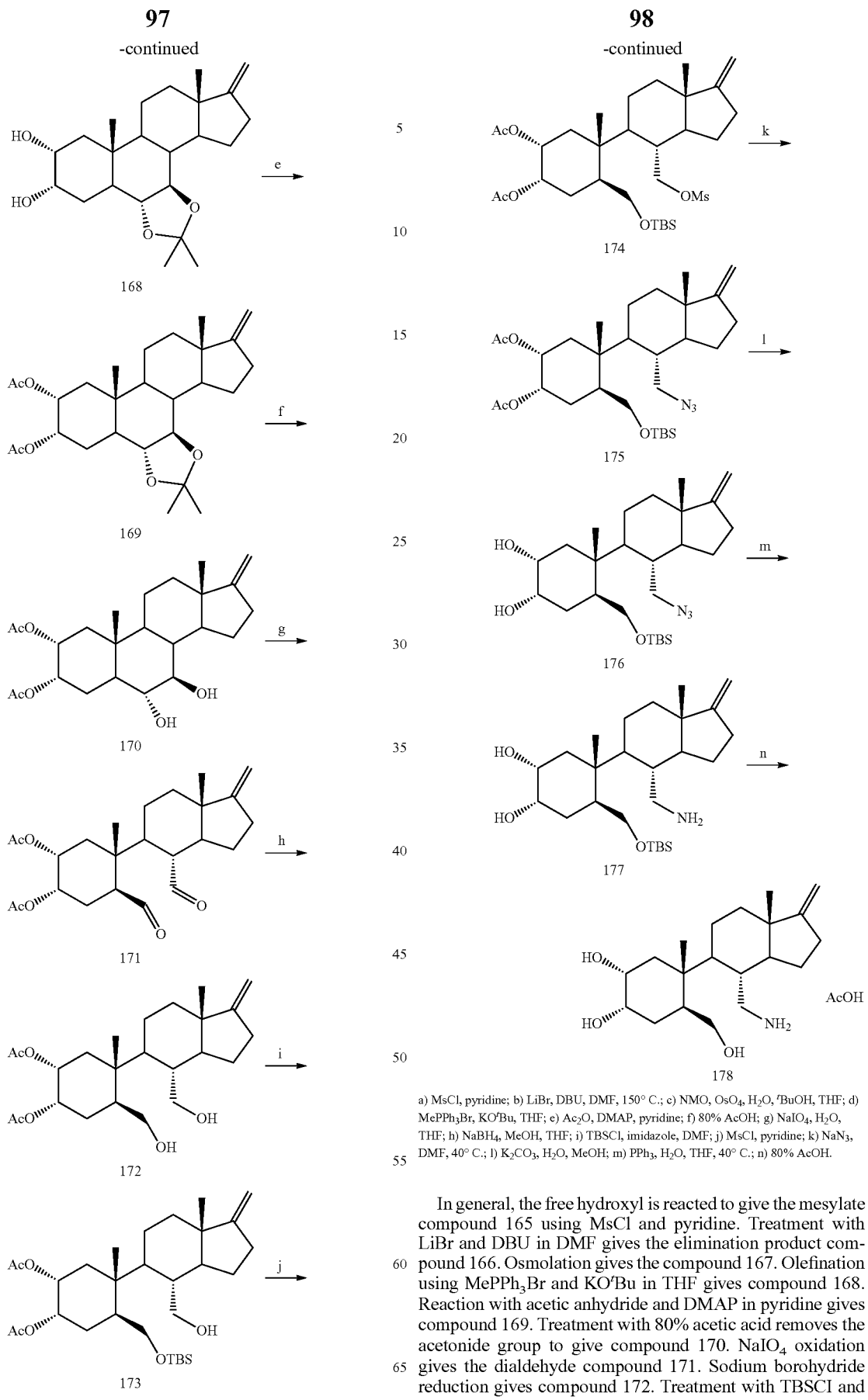

a) MsCl, pyridine; b) LiBr, DBU, DMF, 150° C.; c) NMO, OsO$_4$, H$_2$O, $^t$BuOH, THF; d) MePPh$_3$Br, KO$^t$Bu, THF; e) Ac$_2$O, DMAP, pyridine; f) 80% AcOH; g) NaIO$_4$, H$_2$O, THF; h) NaBH$_4$, MeOH, THF; i) TBSCl, imidazole, DMF; j) MsCl, pyridine; k) NaN$_3$, DMF, 40° C.; l) K$_2$CO$_3$, H$_2$O, MeOH; m) PPh$_3$, H$_2$O, THF, 40° C.; n) 80% AcOH.

In general, the free hydroxyl is reacted to give the mesylate compound 165 using MsCl and pyridine. Treatment with LiBr and DBU in DMF gives the elimination product compound 166. Osmolation gives the compound 167. Olefination using MePPh$_3$Br and KO$^t$Bu in THF gives compound 168. Reaction with acetic anhydride and DMAP in pyridine gives compound 169. Treatment with 80% acetic acid removes the acetonide group to give compound 170. NaIO$_4$ oxidation gives the dialdehyde compound 171. Sodium borohydride reduction gives compound 172. Treatment with TBSCl and imidazole in DMF selectively protects one hydroxyl to give compound 173. The free hydroxyl is reacted to give the mesylate compound 174 using MsCl and pyridine. Azide displacement of the mesylate using sodium azide in DMF gives compound 175. Base hydrolysis of the acetates gives compound 176. Reduction of the azide using $PPh_3$ and water in THF gives compound 177. Treatment with 80% acetic acid removes the TBS group and forms the salt compound 178.

Following are specific examples of the compounds prepared above.

Synthesis of Compound 165

To a solution of compound 164 (4.00 g, 11.03 mmol) in pyridine (20 mL) was added MsCl (1.28 mL, 16.55 mmol). The reaction mixture was stirred at ambient temperature for one hour under argon, then diluted with EtOAc (100 mL), washed with brine (2×50 mL), dried over anhydrous $MgSO_4$, and concentrated to dryness. The crude product compound 165 used for the next reaction without further purification.

Synthesis of Compound 166

A mixture of crude compound 165 (2.00 g, 4.54 mmol), lithium bromide (0.59 g, 6.81 mmol) and DBU (2 mL, 13.62 mmol) in dry DMF (50 mL) was heated at 150° C. for 1.5 hours. After cooling, toluene (120 mL) and water (60 mL) were added to the reaction mixture. The layers were separated and the aqueous phase was extracted with toluene (80 mL). The combined toluene solution was washed with brine (100 mL), dried over anhydrous $MgSO_4$, and concentrated to dryness. The residue was purified by chromatography on silica gel (hexanes/EtOAc, 9/1) to afford impure compound 166 (1.09 g, 70%) as a white solid.

Synthesis of Compound 167

To a solution of compound 166 (1.00 g, 2.90 mmol) in a mixture of THF (15 mL) and t-BuOH (5 mL) was added water (2.5 mL), followed by NMO (0.60 mL, 50% in $H_2O$) and $OsO_4$ (0.89 mL, 4% in $H_2O$). The reaction mixture was stirred at ambient temperature for 3 hours then a solution of $Na_2S_2O_3$ (0.5 g) in water (15 mL) was added. The reaction mixture was stirred for 20 minutes then extracted with $CH_2Cl_2$ (2×30 mL), washed with brine (50 mL), dried over anhydrous $MgSO_4$, and concentrated to dryness. The residue was purified by chromatography on silica gel (hexanes/EtOAc, 1:1) to afford compound 167 (0.65 g, 60%) as a white solid.

Synthesis of Compound 168

A mixture of KO$^t$Bu (2.88 g, 32.9 mmol) and MePPh$_3$Br (11.8 g, 32.9 mmol) in THF (40 mL) was stirred at ambient temperature for 1 hour then compound 167 (4.15 g, 11.0 mmol) in THF (10 mL) was added and the mixture was stirred at ambient temperature overnight. Saturated $NaHCO_3$ solution (50 mL) was added and the mixture was stirred for 15 minutes, then diluted with water (50 mL) and extracted with EtOAc (4×50 mL). The combined organics were washed with brine (2×60 mL), dried over anhydrous $MgSO_4$ and concentrated. The residue was purified by chromatography on silica gel (hexanes/EtOAc/MeOH, 1:1:0.02) to give a mixture containing compound 168 (6.29 g) as a light brown foam.

Synthesis of Compound 169

To a solution of the mixture containing compound 168 (6.29 g, 11.0 mmol) and DMAP (0.128 g, 1.05 mmol) in pyridine (40 mL) was added acetic anhydride (4.15 mL, 44.0 mmol). The mixture was stirred at ambient temperature overnight, then diluted with EtOAc (100 mL), washed with saturated $NaHCO_3$ solution (50 mL), water (50 mL) and brine (2×50 mL), dried over anhydrous $MgSO_4$ and concentrated. The residue was purified by chromatography on silica gel (hexanes/EtOAc, 1:3) to give compound 169 (4.12 g, 81% from INT395) as a white foam.

Synthesis of Compound 170

A mixture of compound 169 (1.97 g, 4.28 mmol) and 80% acetic acid (15 mL) was stirred at ambient temperature for 3 hours and then concentrated. The residue was purified by chromatography on silica gel to give compound 170 (1.35 g, 75%) as a yellow foam.

Synthesis of Compound 171

A mixture of compound 170 (1.29 g, 3.07 mmol) and $NaIO_4$ (1.32 g, 6.13 mmol) in THF (20 mL) and water (10 mL) was stirred at ambient temperature. After 1.5 hours, 0.20 g (0.92 mmol) more $NaIO_4$ was added. After 3 hours total reaction time the mixture was diluted with water (20 mL) and extracted with $CH_2Cl_2$ (60 mL). The organic portion was washed with brine (30 mL), dried over anhydrous $MgSO_4$ and concentrated to give crude compound 171 that was used for the next reaction without further purification.

Synthesis of Compound 172

To a solution of crude compound 171 (3.07 mmol) in THF (15 mL) and MeOH (5 mL) at 0° C. was added $NaBH_4$ (0.232 g, 6.14 mmol). The mixture was stirred at 0° C. for 15 minutes then at ambient temperature for 1.5 hours. The mixture was cooled to 0° C. and 80% acetic acid (10 mL) was slowly added. The mixture was stirred at ambient temperature for 10 minutes then diluted with EtOAc (80 mL) and washed with brine (2×30 mL). The organic portion was dried over anhydrous $MgSO_4$ and concentrated to give compound 172 (1.23 g, 95% from compound 170) as a light yellow foam.

Synthesis of Compound 173

A mixture of compound 172 (1.23 g, 2.91 mmol), imidazole (0.600 g, 8.73 mmol) and TBSCl (0.585 g, 3.76 mmol) in DMF (15 mL) was stirred at ambient temperature for 35 minutes, then diluted with water (140 mL) and extracted with $Et_2O$ (4×50 mL). The combined organics were washed with brine (2×50 mL), dried over anhydrous $MgSO_4$ and concentrated. The residue was purified by chromatography on silica gel (hexanes; hexanes/EtOAc, 9:1, 4:1, 3:1) to give compound 173 (0.992 g, 64%) as a white foam.

Synthesis of Compound 174

To a solution of compound 173 (0.990 g, 1.84 mmol) in pyridine (10 mL) was added methanesulfonyl chloride (0.257 mL, 3.32 mmol). The reaction mixture was stirred at ambient temperature for 1.5 hours, then diluted with EtOAc (50 mL), washed with water (20 mL) then brine (20 mL), dried over anhydrous $MgSO_4$ and concentrated to afford crude compound 174 (1.17 g, white foam) that was used for the next reaction without further purification.

Synthesis of Compound 175

A mixture of crude compound 174 (1.84 mmol) and $NaN_3$ (0.242 g, 3.68 mmol) in dry DMF (15 mL) was stirred at 40° C. overnight. After cooling to ambient temperature, the mixture was diluted with water (150 mL) and extracted with $Et_2O$ (4×50 mL). The combined organics were washed with brine (2×50 mL), dried over anhydrous $MgSO_4$ and concentrated. The residue was purified by chromatography on silica gel (hexanes; hexanes/EtOAc, 9:1, 4:1) to give compound 175 (0.708 g, 69% from compound 173) as a white foam.

Synthesis of Compound 176

A mixture of compound 175 (0.397 g, 0.645 mmol), $K_2CO_3$ (0.446 g, 3.23 mmol), water (5 mL) and MeOH (15 mL) was stirred at ambient temperature for 4 hours, then diluted with water (100 mL) and extracted with $CH_2Cl_2$ (3×50 mL). The combined organics were washed with brine (2×50 mL), dried over anhydrous MgSO₄ and concentrated to afford compound 176 (0.284 g, 92%) as a white solid that was used for the next reaction without further purification.

Synthesis of Compound 177

A mixture of compound 176 (0.284 g, 0.594 mmol), triphenylphosphine (0.472 g, 1.78 mmol), water (1 mL) and THF (15 mL) was stirred at 40° C. overnight and then concentrated. The residue was purified by chromatography on silica gel (CH₂Cl₂; CH₂Cl₂/MeOH, 19:1, 12:1; CH₂Cl₂/MeOH/Et₃N, 9:1:0.3) to give compound 177 (0.241 g, 90%) as a white solid.

Synthesis of Compound 178

A mixture of compound 177 (0.234 g, 0.518 mmol) and 80% acetic acid (20 mL) was stirred at ambient temperature overnight and then concentrated. The residue was dissolved in MeOH three times and concentrated. Precipitation from ACN/MeOH (20 mL) gave compound 178 (0.223 g, quantitative) as a white solid. LC/MS (direct infusion, electrospray +ve, 10 mM NH₄OAc in 3:7 water and MeCN) 338.26; $C_{20}H_{36}NO_3$.

Example 18

Compounds 182-185, representative compounds of the invention, may be prepared according to the following Reaction Scheme 18. Any number of compounds related to compounds 182-185 could be produced using similar methodology. Starting compound 95 may be prepared according to the procedures describe above in Example 10.

REACTION SCHEME 18

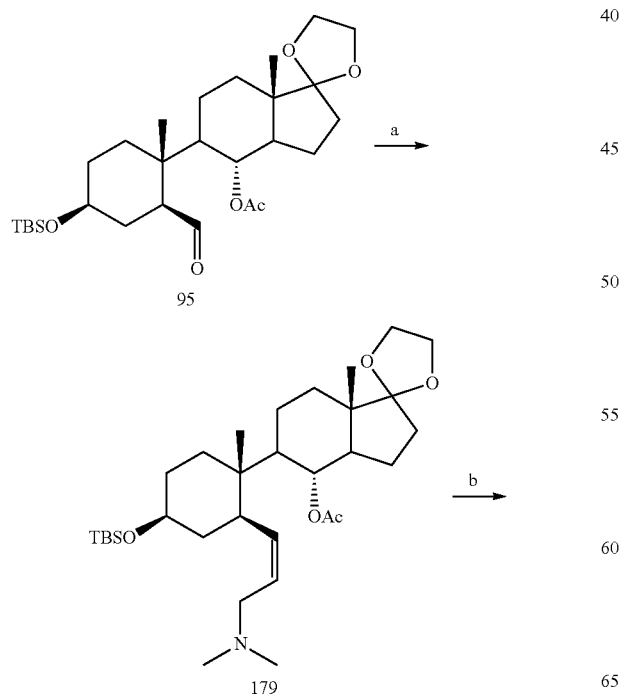

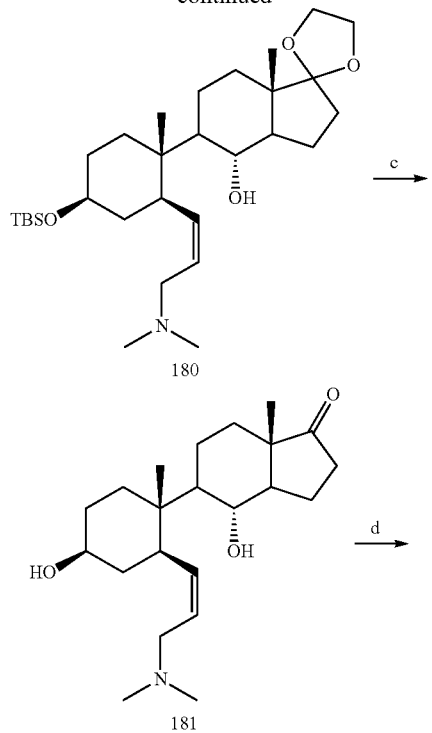

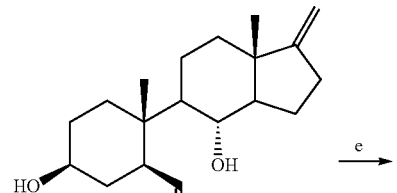

a) KO^tBu, Me₂NCH₂CH₂PPh₃Br, THF; b) LAH, THF; c) 80% AcOH; d) MePPh₃Br, KO^tBu, THF; e) 80% AcOH

In general, olefination using Me₂NCH₂CH₂PPh₃Br and KO^tBu in THF gives compound 179. Lithium aluminum hydride reduction removes the acyl group to give compound 180. Treatment with 80% acetic acid removes the cyclic ketal group to give compound 181. Olefination using MePPh₃Br and KO^tBu in THF gives compound 182. Treatment with 80% acetic acid forms the salt compound 183.

Following are specific examples of the compounds prepared above.

Synthesis of Compound 179

A mixture of KO$^t$Bu (101 mg, 0.9 mmol) and (2-dimethylaminoethyl) triphenylphosphonium bromide (373 mg, 0.9 mmol) in THF (10 mL) was stirred at ambient temperature for 1 hour 20 min. A solution of compound 95 (154 mg, 0.3 mmol) in THF (5 mL) was added and the mixture was stirred at ambient temperature overnight. Saturated NH$_4$Cl (1 mL) was added and the mixture was diluted with EtOAc (100 mL), washed with saturated NaHCO$_3$, brine, dried and concentrated. The crude product was purified by column chromatography (EtOAc/MeOH, 9:1) to give compound 179 (118 mg, 69%).

Synthesis of Compound 180

To a stirred solution of compound 179 (118 mg, 0.21 mmol) in THF (10.5 mL) at 0° C. was added 1M LAH in THF (0.63 mL, 0.63 mmol) dropwise. After 30 min at 0° C., the mixture was stirred at ambient temperature for 3 hours. The mixture was cooled to 0° C. again and solid Na$_2$SO$_4$.10H$_2$O (203 mg, 0.63 mmol) was added portionwise. After 5 min at 0° C., the mixture was stirred at ambient temperature for 45 min and then filtered through Celite and washed with EtOAc. The filtrate was concentrated, and the crude compound 180 thus obtained was used in next step without purification.

Synthesis of Compound 181

A solution of crude compound 180 obtained above in 80% HOAc (5 mL) was stirred at 40° C. for 7 hours 20 min. The solvents were removed by rotary evaporation and the residue was purified by column chromatography (EtOAc/MeOH/water/Et$_3$N, 7:2:0.5:0.5) to give compound 181 (73 mg, 96% from compound 179).

Synthesis of Compound 182

A mixture of Ph$_3$PMeBr (357 mg, 1.0 mmol) and KO$^t$Bu (112 mg, 1.0 mmol) in THF (5 mL) was stirred at ambient temperature for 1 hour 20 min. A solution of compound 181 (73 mg, 0.2 mmol) in THF (3 mL) was added, and the mixture was stirred at ambient temperature overnight. The reaction was quenched with saturated NH$_4$Cl (0.5 mL) and the mixture was diluted with EtOAc (150 mL), washed with saturated NaHCO$_3$, brine, dried and concentrated. The residue was purified by column chromatography (EtOAc/MeOH/water/Et$_3$N, 7:2:0.5:0.5, then EtOAc/MeOH/Et$_3$N, 7.5:2:0.5) to afford compound 182 (57 mg, 79%).

Synthesis of Compound 183

A solution of compound 182 (57 mg, 0.16 mmol) in 80% HOAc (1 mL) was stirred at 40° C. for a few minutes and then the solvents were removed by rotary evaporation and the residue was dried under vacuum. The product was dissolved in a small amount of MeOH and treated with a small amount of ether. The salt precipitated out and dried under vacuum to give compound 183 (68 mg, quant.) as a pale powder. LC/MS (direct infusion, electrospray +ve, 10 mM NH$_4$OAc in 3:7 water and MeCN) 362.09; C$_{23}$H$_{40}$NO$_2$.

Synthesis of Compound 184

Using the procedures described for the synthesis of compound 183, with the exception of olefination by (4-chlorobenzyl)triphenyl-phosphonium chloride, compound 184 (34 mg) was prepared in 51% yield starting from compound 95. Other notable exceptions were the use of HCl in MeOH to affect the desilylation/deketalization step (to prepare the intermediate analogous to compound 181) and the inclusion of the following double bond hydrogenation step. The intermediate analogous to compound 181 was treated with a catalytic amount of 10% Pd on carbon in THF and MeOH while under H$_2$ atmosphere. The catalyst was filtered off and the filtrate was concentrated. The crude intermediate was treated with 80% HOAc to form the acetate salt of compound 184: LC/MS (direct infusion, electrospray +ve, 10 mM NH$_4$OAc in 3:7 water and MeCN) 434.68; C$_{26}$H$_{41}$ClNO$_2$.

Synthesis of Compound 185

Step 1: Synthesis of (3-pyridylmethyl)triphenylphosphonium chloride

To a stirred solution of 3-(chloromethyl)pyridine hydrochloride (5.17 g, 31.5 mmol) in water (8 mL) was added K$_2$CO$_3$ (4.34 g, 31.5 mmol) portionwise. The resulting mixture was extracted three times with diethyl ether. The extracts were combined and washed twice with brine, dried and concentrated. The residue (3.25 g, 25.5 mmol) was dissolved in xylene (30 mL) and Ph$_3$P (6.70 g, 25.5 mmol) was added. The mixture was heated at 133-134° C. overnight and then cooled to ambient temperature. The solid product was filtered, washed with toluene, and dried under vacuum to give (3-pyridylmethyl)triphenylphosphonium chloride (5.86 g, 48%) as a pinkish solid.

Step 2: Synthesis of Compound 185

Using the procedures described above for the synthesis of compound 184, with the exception of substitution by (3-pyridylmethyl)triphenylphosphonium chloride, compound 185 (19 mg) was prepared in 20% yield starting from compound 95. LC/MS (direct infusion, electrospray +ve, 10 mM NH$_4$OAc in 3:7 water and MeCN) 384.15; C$_{25}$H$_{38}$NO$_2$.

Example 19

Compound 189, a representative compound of the invention, may be prepared according to the following Reaction Scheme 19. Any number of compounds related to compound 189 could be produced using similar methodology. Starting compound 93 may be prepared according to the procedures described above in Example 10.

REACTION SCHEME 19

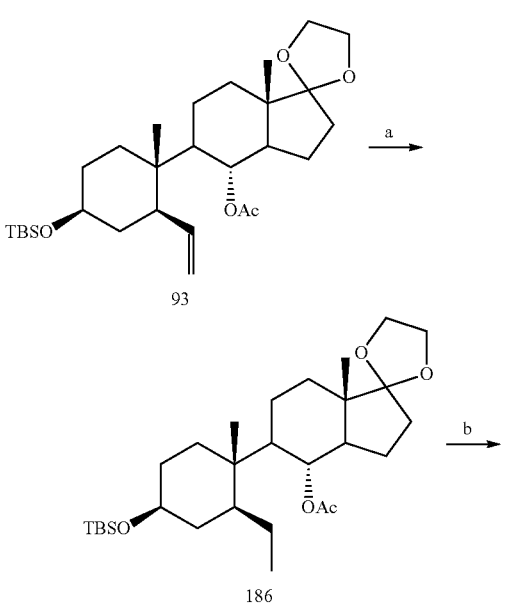

105
-continued

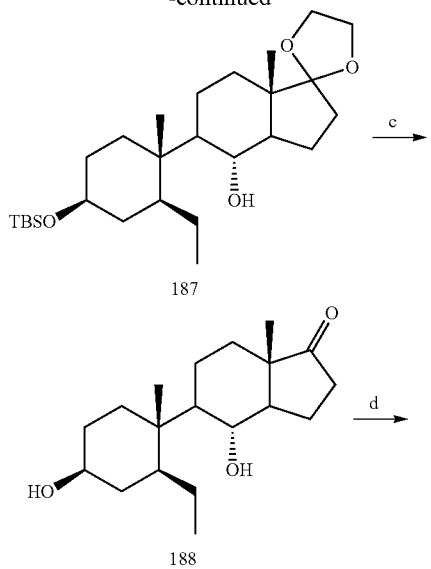

a) H₂, 10% Pd/C; b) LAH, THF; c) 80% AcOH; d) MePPh₃Br, KO'Bu, THF

In general, catalytic hydrogenation of the double bond gives compound 186. Lithium aluminum hydride reduction removes the acyl group to give compound 187. Treatment with 80% acetic acid removes both the TBS group and the cyclic ketal group to give compound 188. Olefination using MePPh₃Br and KO'Bu in THF gives compound 189.

Following are specific examples of the compounds prepared above.

Synthesis of Compound 186

A mixture of compound 93 (98 mg, 0.19 mmol), 10% Pd/C (10 mg) in EtOH (4 mL) was stirred under H₂ (1 atm) overnight. The catalyst was removed by filtration and the filtrate was concentrated. The crude compound 186 (98 mg) was used in next step without purification.

Synthesis of Compound 187

To a stirred solution of compound 186 (98 mg, 0.19 mmol) in THF (9 mL) at 0° C. was added 1M LAH in THF (0.86 mL, 0.86 mmol) dropwise. After 5 min at 0° C., the mixture was stirred at ambient temperature for 6 hours. The mixture was cooled to 0° C. again and solid Na₂SO₄.10H₂O (275 mg, 0.86 mmol) was added portionwise. After 5 min at 0° C., the mixture was stirred at ambient temperature for 1 hour and then filtered through Celite. The filtrate was concentrated, and the crude product was purified by column chromatography (hexanes/EtOAc, 1:1) to give compound 187.

Synthesis of Compound 188

A solution of compound 187 obtained above in 80% HOAc (5 mL) was stirred at 40° C. for 7.5 hours. The solvents were removed by rotary evaporation and the residue was purified by column chromatography (EtOAc/hexanes, 8:2 then 9:1) to give compound 188 (35 mg, 59% from compound 186).

106

Synthesis of Compound 189

A mixture of Ph₃PMeBr (196 mg, 0.55 mmol) and KO'Bu (62 mg, 0.54 mmol) in THF (5 mL) was stirred at ambient temperature for 1.5 hours. A solution of compound 188 (35 mg, 0.11 mmol) in THF (2 mL) was added, and the mixture was stirred at ambient temperature overnight. The reaction was quenched with saturated NH₄Cl (1 mL) and the mixture was diluted with EtOAc (150 mL), washed with brine, dried and concentrated. The residue was purified by column chromatography (EtOAc/hexanes, 7:3) to yield compound 189 (37 mg, quant.). LC/MS (direct infusion, electrospray +ve, 10 mM NH₄OAc in 3:7 water and MeCN) 324.74; $C_{20}H_{38}NO_2$.

Example 20

Compound 192, a representative compound of the invention, may be prepared according to the following Reaction Scheme 20. Any number of compounds related to compound 192 could be produced using similar methodology.

REACTION SCHEME 20

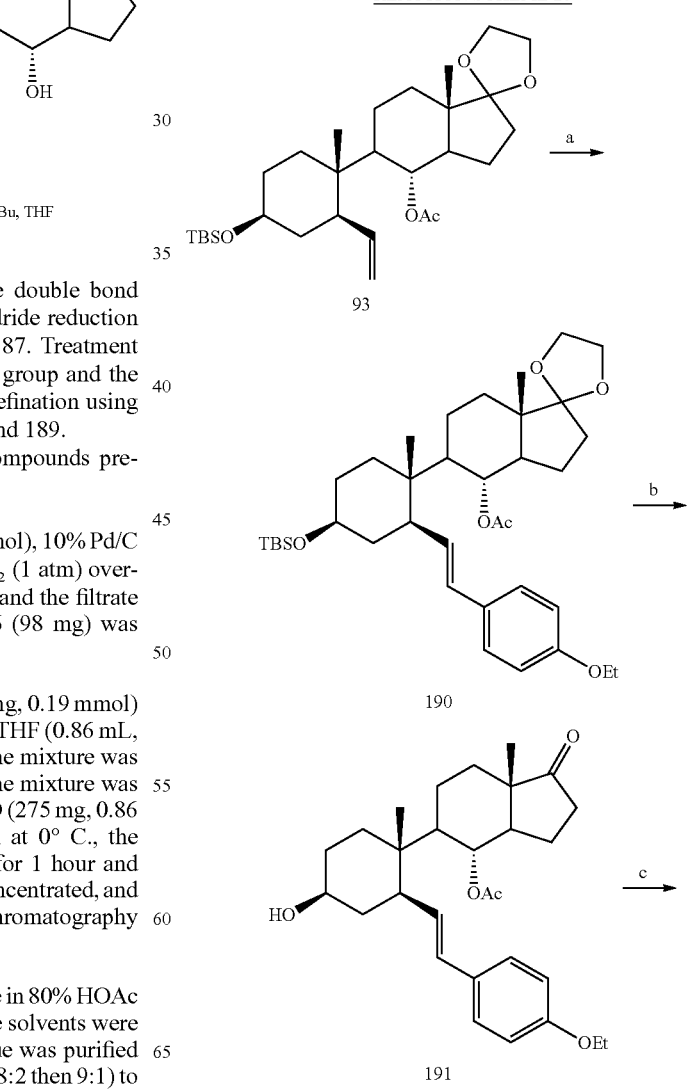

107
-continued

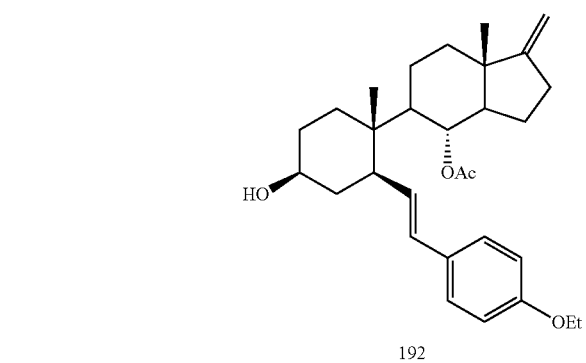

192 a) 4-BrC$_6$H$_4$OEt, P(o-tol)$_3$, Pd(OAc)$_2$, Et$_3$N; b) 80% AcOH; c) Ph$_3$PMeBr, KO$^t$Bu, THF In general, palladium catalyzed coupling of the olefin 93 with the aryl halide 4-BrC$_6$H$_4$OEt gives compound 190. Treatment with 80% acetic acid removes the TBS group and the cyclic ketal to give compound 191. Olefination using MePPh$_3$Br and KO$^t$Bu in THF gives compound 192.

Following are specific examples of the compounds prepared above.

Synthesis of Compound 190

A mixture of compound 93 (100 mg, 0.2 mmol), 4-bromophenetole (0.04 mL, 0.28 mmol), tri(orthotolyl)phosphine (12 mg, 0.04 mmol), Pd(OAc)$_2$ (2.3 mg, 0.01 mmol), Et$_3$N (0.06 mL) in acetonitrile (2 mL) was heated at 80° C. overnight. The solvents were removed and the residue was purified by column chromatography (hexanes/EtOAc, 9:1 then 85:15) to yield compound 190 (61 mg, 49%).

Synthesis of Compound 191

A solution of compound 190 in 80% HOAc (5 mL) was stirred at 40° C. for 7.5 hours. The solvents were removed by rotary evaporation and the residue was purified by column chromatography (EtOAc/hexanes, 8:2) to give compound 191 (27 mg, 60%).

Synthesis of Compound 192

A mixture of Ph$_3$PMeBr (114 mg, 0.32 mmol) and KO$^t$Bu (36 mg, 0.32 mmol) in THF (3 mL) was stirred at ambient temperature for 1.5 hours. A solution of compound 191 (27 mg, 0.064 mmol) in THF (1 mL) was added, and the mixture was stirred at ambient temperature overnight. The reaction was quenched with saturated NH$_4$Cl (1 mL) and the mixture was diluted with EtOAc (150 mL), washed with brine, dried and concentrated. The residue was purified by column chromatography (EtOAc/hexanes, 1:1) to yield compound 192 (13 mg, 43%). LC/MS (direct infusion, electrospray +ve, 10 mM NH$_4$OAc in 3:7 water and MeCN) 484.69; C$_{30}$H$_{46}$NO$_4$.

Example 21

Compounds 195-201, representative compounds of the invention, may be prepared according to the following Reaction Scheme 21. Any number of compounds related to compounds 195-201 could be produced using similar methodology. Starting compound 85 may be prepared according to procedures described above in Example 9.

108

REACTION SCHEME 21

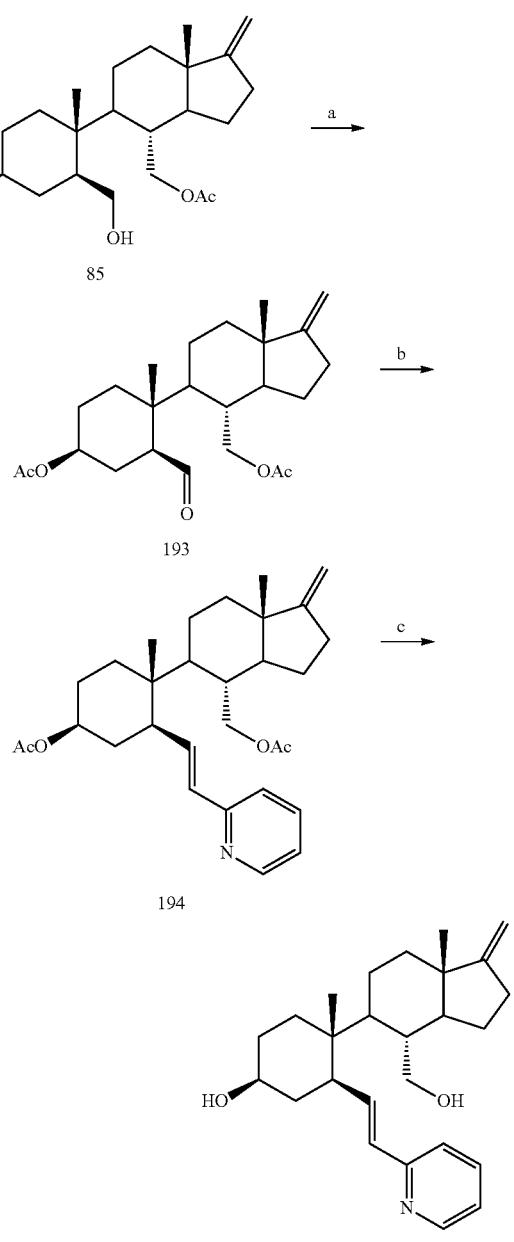

a) TPAP, NMO, CH$_2$Cl$_2$; b) KO$^t$Bu, (2-pyridylmethyl)triphenylphosphonium chloride, THF; c) LAH, THF.

In general, TPAP catalyzed oxidation of the free alcohol gives compound 193. Olefination using (2-pyridylmethyl)triphenylphosphonium chloride and KO$^t$Bu in THF gives compound 194. Lithium aluminum hydride reduction removes the acyl groups to give compound 195.

Following are specific examples of the compounds prepared above.

Synthesis of Compound 193

To a solution of compound 85 (11.6 g, 28.4 mmol) in CH$_2$Cl$_2$ (100 mL) at 0° C. were added TPAP (1.50 g, 4.26 mmol) and NMO (9.98 g, 85.2 mmol). The mixture was stirred at 0° C. for 10 minutes then at ambient temperature for 3 hours. The mixture was concentrated to dryness and the residue was purified by chromatography on silica gel (hexanes/EtOAc, 3:2, 1:1; EtOAc) to give compound 193 (8.61 g, 75%) as a white solid.

Synthesis of Compound 194

Step 1: Synthesis of (2-pyridylmethyl)triphenylphosphonium chloride)

To a stirred solution of 2-(chloromethyl)pyridine hydrochloride (8.0 g, 48.8 mmol) in water (20 mL) was added $K_2CO_3$ (6.74 g, 48.7 mmol) portionwise. The resulting mixture was extracted four times with diethyl ether. The extracts were combined and washed twice with brine, dried and concentrated. The residue (5.78 g, 45.3 mmol) was dissolved in 1,4-dioxane (19 mL) and $Ph_3P$ (11.89 g, 45.3 mmol) was added. The mixture was heated at 110° C. overnight and then cooled to ambient temperature. The solid product was filtered, washed with ether, and dried under vacuum to give (2-pyridylmethyl)triphenylphosphonium chloride (15.78 g, 83%) as a pale solid.

Step 2: Synthesis of Compound 194

A mixture of $KO^tBu$ (132 mg, 1.2 mmol) and (2-pyridylmethyl) triphenylphosphonium chloride (460 mg, 1.2 mmol) in THF (15 mL) was stirred at ambient temperature for 1.5 hours. A solution of compound 193 (195 mg, 0.48 mmol) in THF (5 mL) was added and the mixture was stirred at ambient temperature overnight. Saturated $NH_4Cl$ (1 mL) was added and the mixture was diluted with EtOAc (150 mL), washed with brine, dried and concentrated. The crude product was purified by column chromatography (EtOAc/hexanes, 1:1) to give compound 194 (207 mg, 90%).

Synthesis of Compound 195

To a stirred solution of compound 194 (207 mg, 0.43 mmol) in THF (15 mL) at 0° C. was added 1M LAH in THF (1.9 mL, 1.9 mmol) dropwise. After 5 min at 0° C., the mixture was stirred at ambient temperature for 6 hours. The reaction was cooled to 0° C. again and solid $Na_2SO_4 \cdot 10H_2O$ (623 mg, 1.9 mmol) was added portionwise. After 5 min at 0° C., the mixture was stirred at ambient temperature for 1 hour and then filtered through Celite and washed with EtOAc. The filtrate and washings were combined and concentrated. The residue was purified by column chromatography (EtOAc/MeOH, 95:5) to yield compound 195 (135 mg, 79%): LC/MS (direct infusion, electrospray +ve, 10 mM $NH_4OAc$ in 3:7 water and MeCN) 396.43; $C_{26}H_{38}NO_2$.

Synthesis of Compound 196

Using the procedures described for the synthesis of compound 195, with the exception of olefination by (3-pyridylmethyl)triphenylphosphonium chloride, compound 196 (90 mg) was prepared in 61% yield starting from compound 193: LC/MS (direct infusion, electrospray +ve, 10 mM $NH_4OAc$ in 3:7 water and MeCN) 396.17; $C_{26}H_{38}NO_2$.

Synthesis of Compound 197

Using the procedures described for the synthesis of compound 195, with the exception of olefination by hexyltriphenylphosphonium bromide, compound 197 (Z-isomer, 124 mg) was prepared in 85% yield starting from compound 193: LC/MS (direct infusion, electrospray +ve, 10 mM $NH_4OAc$ in 3:7 water and MeCN) 405.86; $C_{26}H_{48}NO_2$.

Synthesis of Compounds 198 and 201

Using the procedures described for the synthesis of compound 195, with the exception of olefination by (3-benzyloxypropyl)triphenylphosphonium bromide, compound 198 (Z-isomer, 114 mg, 68%) and compound 201, product of debenzylation, (Z-isomer, 10 mg, 7%) were prepared starting from compound 193. Compound 198: LC/MS (direct infusion, electrospray +ve, 10 mM $NH_4OAc$ in 3:7 water and MeCN) 452.57; $C_{30}H_{44}O_3$. Compound 201: LC/MS (direct infusion, electrospray +ve, 10 mM $NH_4OAc$ in 3:7 water and MeCN) 363.15; $C_{23}H_{39}O_3$.

Synthesis of Compound 199

Using the procedures described for the synthesis of compound 195, with the exceptions of olefination by (2-dimethylaminoethyl)triphenylphosphonium bromide, and salt formation with acetic acid, compound 199 (Z-isomer, 93 mg) was prepared in 57% yield starting from compound 193: LC/MS (direct infusion, electrospray +ve, 10 mM $NH_4OAc$ in 3:7 water and MeCN) 376.06; $C_{24}H_{42}NO_2$.

Synthesis of Compound 200

Using the procedures described for the synthesis of compound 195, with the exceptions of olefination by (4-chlorobenzyl)triphenylphosphonium chloride, compound 200 (118 mg) was prepared in 74% yield starting from compound 193.

Example 22

Compound 203, a representative compound of the invention, may be prepared according to the following Reaction Scheme 22. Any number of compounds related to compound 203 could be produced using similar methodology. Starting compound 193 may be prepared according to procedures described above in Example 21.

REACTION SCHEME 22

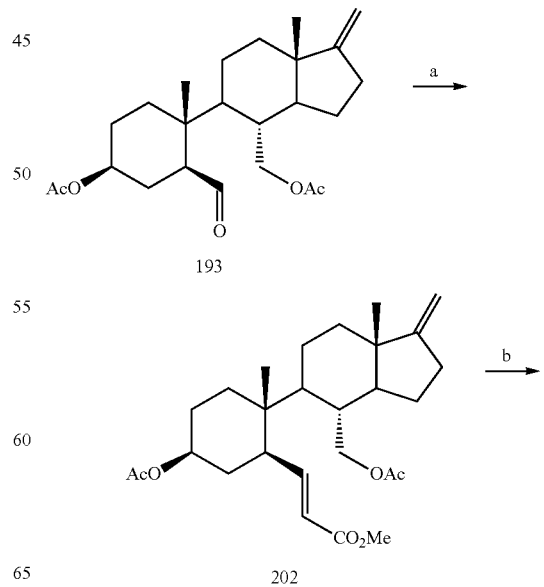

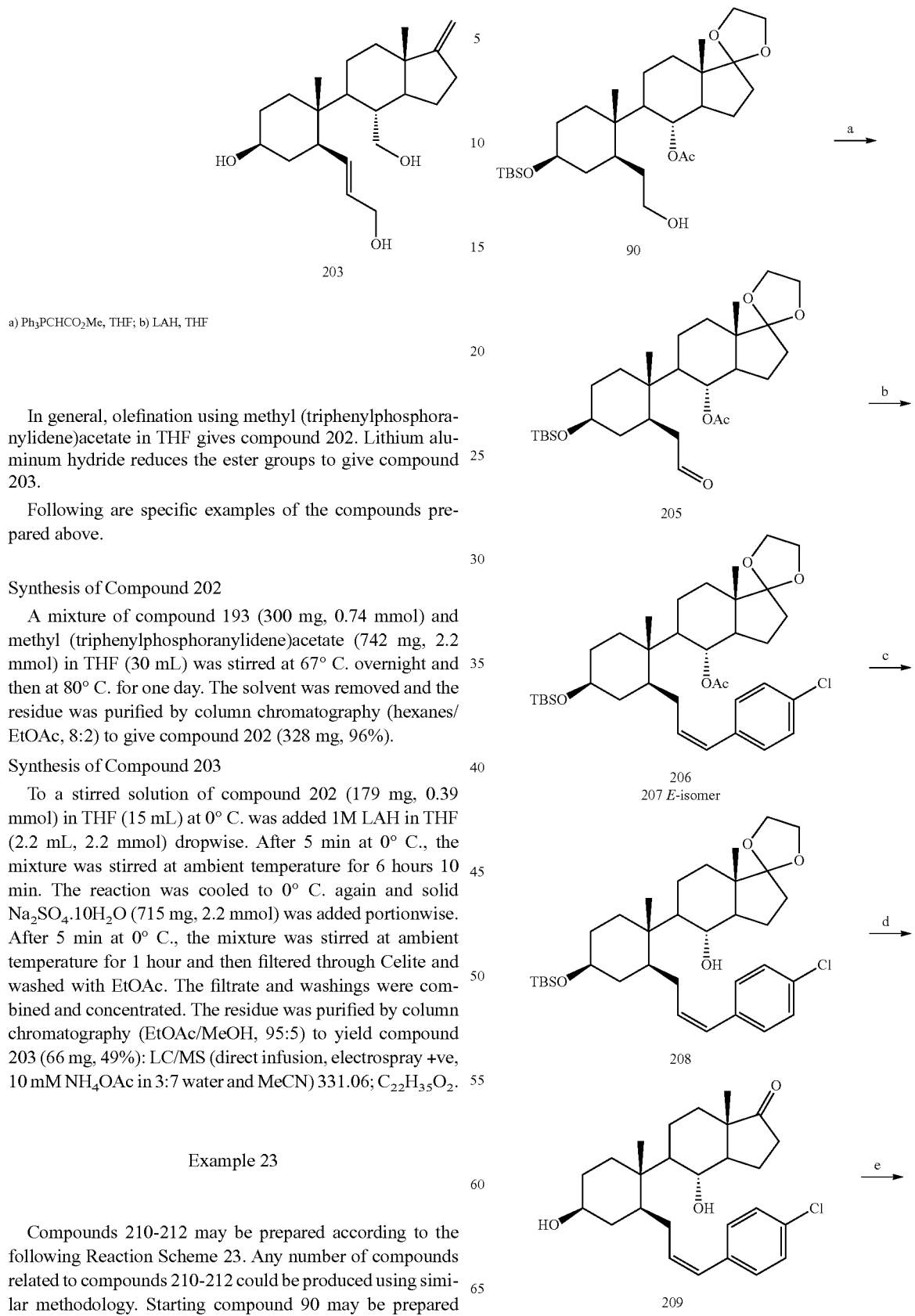

REACTION SCHEME 23 a) Ph₃PCHCO₂Me, THF; b) LAH, THF

In general, olefination using methyl (triphenylphosphoranylidene)acetate in THF gives compound 202. Lithium aluminum hydride reduces the ester groups to give compound 203.

Following are specific examples of the compounds prepared above.

Synthesis of Compound 202

A mixture of compound 193 (300 mg, 0.74 mmol) and methyl (triphenylphosphoranylidene)acetate (742 mg, 2.2 mmol) in THF (30 mL) was stirred at 67° C. overnight and then at 80° C. for one day. The solvent was removed and the residue was purified by column chromatography (hexanes/EtOAc, 8:2) to give compound 202 (328 mg, 96%).

Synthesis of Compound 203

To a stirred solution of compound 202 (179 mg, 0.39 mmol) in THF (15 mL) at 0° C. was added 1M LAH in THF (2.2 mL, 2.2 mmol) dropwise. After 5 min at 0° C., the mixture was stirred at ambient temperature for 6 hours 10 min. The reaction was cooled to 0° C. again and solid Na₂SO₄·10H₂O (715 mg, 2.2 mmol) was added portionwise. After 5 min at 0° C., the mixture was stirred at ambient temperature for 1 hour and then filtered through Celite and washed with EtOAc. The filtrate and washings were combined and concentrated. The residue was purified by column chromatography (EtOAc/MeOH, 95:5) to yield compound 203 (66 mg, 49%): LC/MS (direct infusion, electrospray +ve, 10 mM NH₄OAc in 3:7 water and MeCN) 331.06; $C_{22}H_{35}O_2$.

Example 23

Compounds 210-212 may be prepared according to the following Reaction Scheme 23. Any number of compounds related to compounds 210-212 could be produced using similar methodology. Starting compound 90 may be prepared according to procedures described above in Example 10.

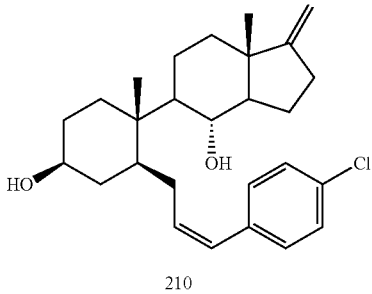

210 a) NMO, TPAP, CH$_2$Cl$_2$; b) (4-chlorobenzyl)triphenylphosphonium chloride, KO$^t$Bu, THF; c) LiAlH$_4$, THF; d) 80% AcOH, MeOH, THF, 40° C.; e) MePPh$_3$Br, KO$^t$Bu, THF.

In general, TPAP catalyzed oxidation of the free alcohol gives compound 205. Olefination using (4-chlorobenzyl)triphenylphosphonium chloride and KO$^t$Bu in THF gives compound 206 and the E-isomer compound 207. Lithium aluminum hydride reduction removes the acyl group to give compound 208. Treatment with 80% acetic acid removes the TBS group and the cyclic ketal group to give compound 209. Olefination using MePPh$_3$Br and KO$^t$Bu in THF gives compound 210.

Following are specific examples of the compounds prepared above.

Synthesis of Compound 205

To a solution of compound 204 (8.60 g, 16.4 mmol) in CH$_2$Cl$_2$ (100 mL) at 0° C. were added TPAP (0.86 g, 2.5 mmol) and NMO (5.76 g, 49.2 mmol). The mixture was stirred at 0° C. for 5 minutes then at ambient temperature. After 3 hours, more TPAP (0.29 g, 0.83 mmol) and NMO (1.92 g, 16.4 mmol) were added and stirring continued. After 5.5 hours total reaction time the mixture was concentrated to dryness. The residue was purified by chromatography on silica gel (hexanes/EtOAc, 49:1, 19:1, 9:1, 4:1) to give compound 205 (5.13 g, 60%) as a white solid.

Synthesis of Compounds 206 and 207

A mixture of KO$^t$Bu (0.136, 1.15 mmol) and (4-chlorobenzyl)triphenylphosphonium chloride (0.496 g, 1.15 mmol) in THF (10 mL) was stirred at ambient temperature for 1 hour, then a solution of compound 205 (0.20 g, 0.38 mmol) in THF (5 mL) was added. The reaction mixture was stirred at ambient temperature overnight, then quenched with saturated NH$_4$Cl solution (1 mL), diluted with EtOAc (150 mL), washed with brine (2×25 mL), dried over anhydrous MgSO$_4$ and concentrated. The residue was purified by chromatography on silica gel (hexanes/EtOAc) to give compound 206 (0.093, 39%) as a colourless glass and compound 207 (0.126 g, 53%) as a colourless glass.

Synthesis of Compound 208

To a solution of compound 206 (0.15 mmol) in THF (10 mL) was added LiAlH$_4$ (0.59 mL of a 1 M solution in THF, 0.59 mmol). The mixture was stirred at ambient temperature overnight, then quenched with Na$_2$SO$_4$.10H$_2$O and stirred for 30 minutes. The mixture was filtered, rinsing with EtOAc, and concentrated to dryness to give crude compound 208 (0.089 g, colourless glass) that was used in the next reaction without further purification.

Synthesis of Compound 209

Crude compound 208 (0.15 mmol) was dissolved in 80% acetic acid (10 mL) with THF (1 mL) and MeOH (1 mL) and stirred at 40° C. for 4.5 hours, then at ambient temperature overnight. The mixture was concentrated to give crude compound 209 (0.074 g) as a colourless glass that was used in the next reaction without further purification.

Synthesis of Compound 210

A mixture of KO$^t$Bu (0.122, 1.03 mmol) and MePPh$_3$Br (0.368 g, 1.03 mmol) in THF (5 mL) was stirred at ambient temperature for 1 hour, then a solution of compound 209 (0.074 g, 0.17 mmol) in THF (5 mL) was added. The reaction mixture was stirred at ambient temperature overnight, then quenched with saturated NH$_4$Cl solution (1 mL), diluted with EtOAc (100 mL), washed with brine (2×20 mL), dried over anhydrous MgSO$_4$ and concentrated. The residue was purified by chromatography on silica gel (hexanes/EtOAc, 3:1, 1:1) to afford compound 210 (0.035 g, 21% from compound 205) as a white solid after concentration from CH$_2$Cl$_2$. LC/MS (direct infusion, electrospray +ve, 10 mM NH$_4$OAc in 3:7 water and MeCN) 411.14; C$_{27}$H$_{36}$C10.

Synthesis of Compound 211

Using the procedure described for the synthesis of compound 208, compound 207 (0.126 g, 0.200 mmol) was reacted with LiAlH$_4$ (0.80 mL of a 1 M solution in THF, 0.80 mmol) to give the alcohol intermediate (0.121 g, colourless glass). Using the procedure described for the synthesis of compound 209, the alcohol intermediate (0.20 mmol) was converted to ketone intermediate (0.104 g, colourless glass). Using the procedure described for the synthesis of compound 210, with the exception that a different solvent system was used for chromatography on silica gel (hexanes/EtOAc, 4:1, 7:3, 3:2, 1:1), the ketone intermediate (0.20 mmol) was converted to the alkene. Concentration from CH$_2$Cl$_2$ gave compound 211 (0.058 g, 36% from compound 205) as a light yellow solid: LC/MS (direct infusion, electrospray +ve, 10 mM NH$_4$OAc in 3:7 water and MeCN) 411.09; C$_{27}$H$_{36}$ClO.

Synthesis of Compound 212

Using the procedure described for the synthesis of compound 206, with the exception that a different solvent system was used for chromatography on silica gel (EtOAc/MeOH, 9:1; EtOAc/MeOH/Et$_3$N, 9:0.75:0.25), compound 205 (0.20 g, 0.38 mmol) was reacted with (2-dimethylaminoethyl)triphenylphosphonium bromide (0.485 g, 1.15 mmol) to give the amine intermediate (0.204 g, 93%, yellow oil). Using the procedure described for the synthesis of compound 208, with the exceptions that 0.76 mL more LiAlH$_4$ solution (1 M in THF, 0.76 mmol) were added after 2.5 hours and total reaction time was 5.5 hours, the amine intermediate (0.35 mmol) was reacted with LiAlH$_4$ (0.76 mL of a 1 M solution in THF, 0.76 mmol) to give the alcohol intermediate (0.203 g, colourless glass). Using the procedure described for the synthesis of compound 209, with the exceptions that THF and MeOH were not added and the reaction mixture was not heated, the alcohol intermediate (0.35 mmol) was converted to ketone intermediate as the acetic acid salt (0.189 g, colourless glass). Using the procedure described for the synthesis of compound 210, with the exceptions that 0.331 g (2.80 mmol) KO$^t$Bu, 1.00 g (2.80 mmol) MePPh$_3$Br and 15 mL THF were used, and after quenching the reaction mixture was concentrated, then purified by chromatography on silica gel (EtOAc/MeOH, 9:1; EtOAc/MeOH/Et$_3$N, 9:0.9:0.1, 9:0.75:0.25), the ketone intermediate (0.35 mmol) was converted to the alkene. A mixture of the alkene, 80% AcOH (1 mL) and MeOH (5 mL) was concentrated by rotary evaporation. Precipitation from Et$_2$O afforded compound 212 (0.072 g, 43% from compound 205) as a white solid: LC/MS (direct infusion, electrospray +ve, 10 mM NH$_4$OAc in 3:7 water and MeCN) 375.98; C$_{24}$H$_{42}$NO$_2$.

Example 24

Compounds 219-222, representative compounds of the invention, may be prepared according to the following Reaction Scheme 24. Any number of compounds related to compounds 219-222 could be produced using similar methodology. Starting compound 35 may be prepared according to procedures described above in Example 3.

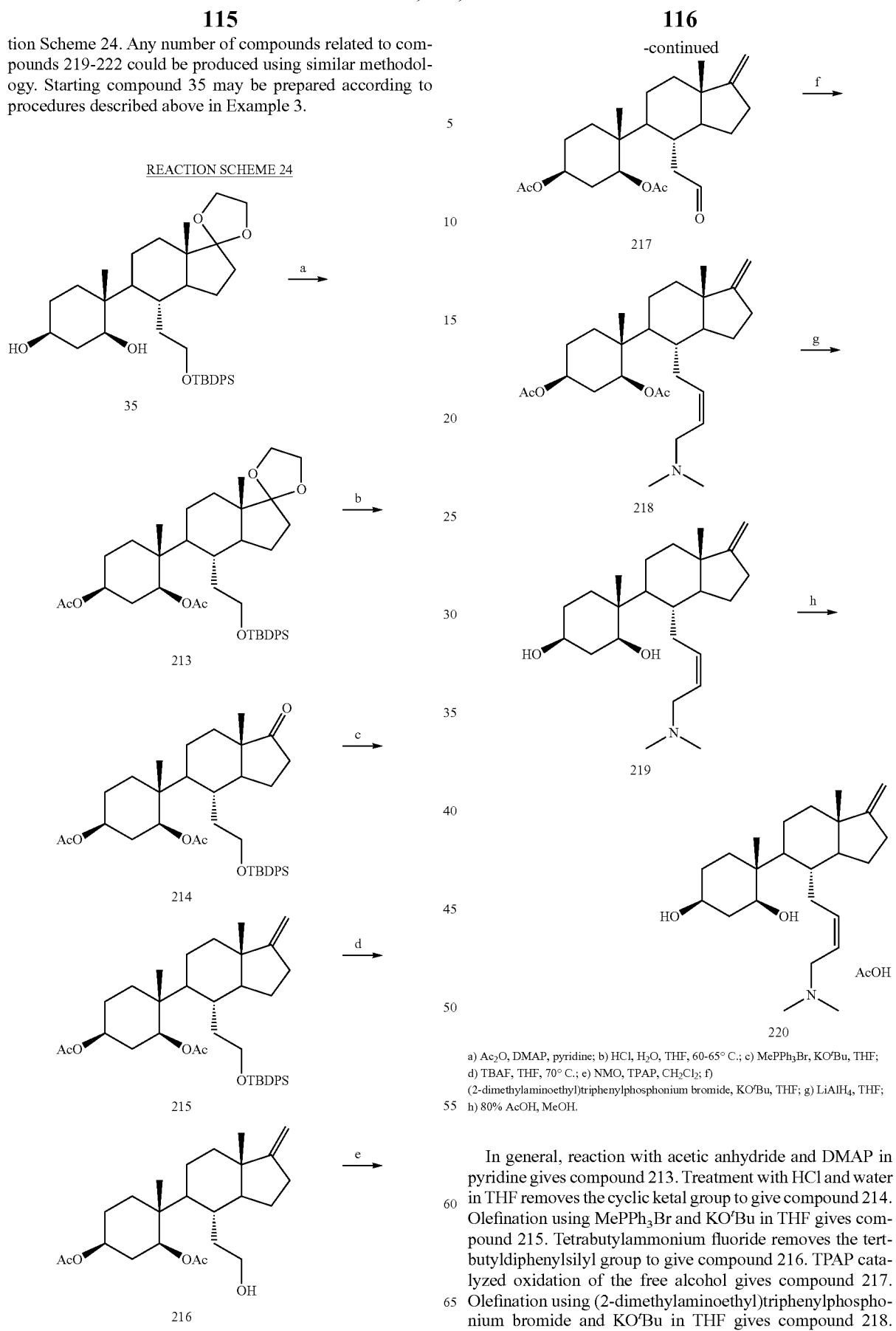

a) Ac₂O, DMAP, pyridine; b) HCl, H₂O, THF, 60-65° C.; c) MePPh₃Br, KO'Bu, THF; d) TBAF, THF, 70° C.; e) NMO, TPAP, CH₂Cl₂; f) (2-dimethylaminoethyl)triphenylphosphonium bromide, KO'Bu, THF; g) LiAlH₄, THF; h) 80% AcOH, MeOH.

In general, reaction with acetic anhydride and DMAP in pyridine gives compound 213. Treatment with HCl and water in THF removes the cyclic ketal group to give compound 214. Olefination using MePPh₃Br and KO'Bu in THF gives compound 215. Tetrabutylammonium fluoride removes the tert-butyldiphenylsilyl group to give compound 216. TPAP catalyzed oxidation of the free alcohol gives compound 217. Olefination using (2-dimethylaminoethyl)triphenylphosphonium bromide and KO'Bu in THF gives compound 218. Lithium aluminum hydride reduction removes the acyl groups to give compound 219. Treatment with 80% acetic acid forms the salt compound 220.

Following are specific examples of the compounds prepared above.

Synthesis of Compound 213

To a solution of compound 35 (67 mmol) in pyridine (150 mL) at 0° C. were added DMAP (1.0 g, 8.2 mmol) and acetic anhydride (12.7 mL, 134 mmol). The reaction mixture was stirred at ambient temperature for 2 hours. The reaction was quenched with water and diluted with EtOAc, then concentrated to dryness to give crude compound 213 that was used for the next reaction without further purification.

Synthesis of Compound 214

A mixture of compound 213 (67 mmol), HCl (20 mL), water (50 mL) and THF (150 mL) was stirred at 60-65° C. for 2 hours, then cooled to ambient temperature. With $K_2CO_3$ the mixture was adjusted to pH=7.0-8.0, then water and $CH_2Cl_2$ were added. The mixture was dried over anhydrous $MgSO_4$ and concentrated. Precipitation from EtOAc gave a crude mixture that contained compound 214 (white solid) and was used in the next reaction without further purification.

Synthesis of Compound 215

A mixture of KO$^t$Bu (9.43 g, 83.9 mmol) and MePPh$_3$Br (30.0 g, 83.9 mmol) in THF (200 mL) was stirred at ambient temperature, then crude compound 214 (67 mmol) was added and the mixture was stirred at ambient temperature for 2 hours. The reaction was quenched with cold water and extracted with EtOAc. The organic portion was concentrated to dryness, then the residue was treated with hexanes/EtOAc (4:1), filtered and the filtrate was concentrated to dryness. The residue was dissolved in pyridine and acetic anhydride was added. The mixture was stirred at ambient temperature for 2 hours, then quenched with water and extracted with EtOAc. The organic portion was concentrated to dryness to give crude compound 215 that was used in the next reaction without further purification.

Synthesis of Compound 216

A mixture of crude compound 215 (67 mmol) and TBAF (30 mL of a 1 M solution in THF, 30 mmol) in THF (80 mL) was stirred at ambient temperature for 2 hours then at 70° C. for 1 hour. The mixture was concentrated and the residue was purified by chromatography on silica gel to give compound 216 (6.12 g, 22% from compound 35) as a white solid.

Synthesis of Compound 217

To a solution of compound 216 (6.0 g, 15 mmol) in $CH_2Cl_2$ (50 mL) were added TPAP (0.052 g, 0.15 mmol) and NMO (4.4 g, 38 mmol). The mixture was stirred at ambient temperature. After 2 hours, more TPAP (0.052 g, 0.15 mmol) was added and stirring continued. After 3 hours total reaction time, the mixture was concentrated. The residue was purified by chromatography on silica gel (hexanes/EtOAc, 9:1) to give compound 217 (2.9 g, 48%) as a white solid.

Synthesis of Compound 218

A mixture of KO$^t$Bu (0.157, 1.33 mmol) and (2-dimethylaminoethyl)triphenylphosphonium bromide (0.563 g, 1.33 mmol) in THF (10 mL) was stirred at ambient temperature for 1 hour, then a solution of compound 217 (0.20 g, 0.49 mmol) in THF (5 mL) was added. The reaction mixture was stirred at ambient temperature overnight, then quenched with saturated NH$_4$Cl solution (1 mL), diluted with EtOAc (150 mL), washed with brine (2×25 mL), dried over anhydrous MgSO$_4$ and concentrated. The residue was purified by chromatography on silica gel (EtOAc/MeOH, 9:1; EtOAc/MeOH/Et$_3$N, 9:0.75:0.25) to give compound 218 (0.197, 88%) as a white foam.

Synthesis of Compound 219

To a solution of compound 218 (0.197 g, 0.428 mmol) in THF (10 mL) was added LiAlH$_4$ (0.98 mL of a 1 M solution in THF, 0.98 mmol). The mixture was stirred at ambient temperature for 4 hours, then quenched with Na$_2$SO$_4$.10H$_2$O and stirred for 30 minutes. The mixture was filtered, rinsing with EtOAc, and concentrated to dryness. The residue was purified by chromatography on silica gel (EtOAc/MeOH, 9:1; EtOAc/MeOH/Et$_3$N, 9:0.75:0.25, 9:0.5:0.5) to give compound 219 as a white solid that was used for the next reaction.

Synthesis of Compound 220

A mixture of compound 219, 80% AcOH (1 mL) and MeOH (5 mL) was concentrated by rotary evaporation. Concentration from CH$_2$Cl$_2$ afforded compound 220 (0.154 g, 72% from compound 217) as a white foam: LC/MS (direct infusion, electrospray +ve, 10 mM NH$_4$OAc in 3:7 water and MeCN) 375.96; C$_{24}$H$_{42}$NO$_2$.

Synthesis of Compounds 221 and 222

Using the procedure described for the synthesis of compound 218, with the exception that a different solvent system was used for chromatography on silica gel (hexanes/EtOAc, 3:1, 3:2), compound 217 (0.20 g, 0.49 mmol) was reacted with (3-pyridylmethyl)triphenylphosphonium chloride (0.519 g, 1.33 mmol) to give a mixture of alkene intermediates (0.195 g, colourless glass). Using the procedure described for the synthesis of compound 219, with the exceptions that reaction time was 3 hours and different solvent systems were used for chromatography on silica gel (EtOAc/MeOH and CH$_2$Cl$_2$/acetone), the alkene intermediate mixture (0.41 mmol) was reacted with LiAlH$_4$ (0.81 mL of a 1 M solution in THF, 0.81 mmol) to give compound 221 (Z-isomer) (0.037 g, 19% from compound 217) as a white foam after concentration from CH$_2$Cl$_2$ and compound 222 (E-isomer) (0.047 g, 24% from compound 217) as a white solid after precipitation from Et$_2$O. Compound 221: LC/MS (direct infusion, electrospray +ve, 10 mM NH$_4$OAc in 3:7 water and MeCN) 395.98; C$_{26}$H$_{38}$NO$_2$. Compound 222: LC/MS (direct infusion, electrospray +ve, 10 mM NH$_4$OAc in 3:7 water and MeCN) 395.96; C$_{26}$H$_{38}$NO$_2$.

Example 25

Compound 225, a representative compound of the invention, may be prepared according to the following Reaction Scheme 25. Any number of compounds related to compound 225 could be produced using similar methodology. Starting compound 76 may be prepared according to procedures described above in Reaction Scheme 8.

REACTION SCHEME 25

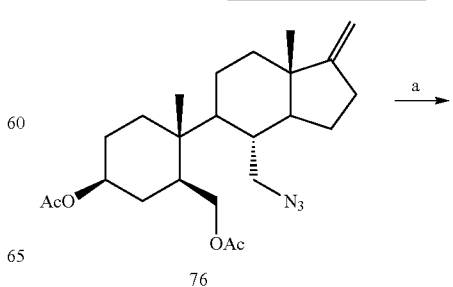

76

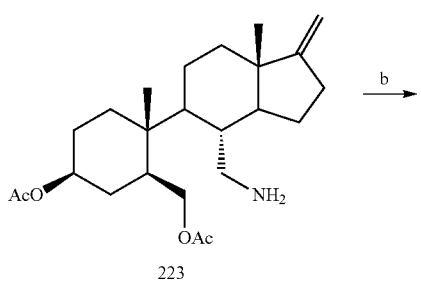

223

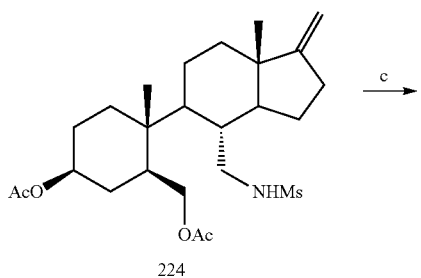

224

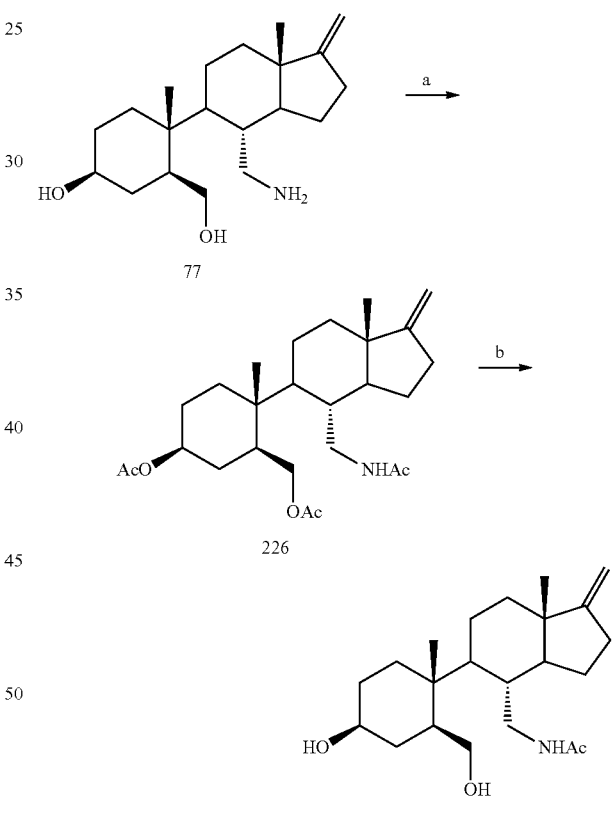

225 a) PPh₃, THF, H₂O; b) MsCl, Et₃N, CH₂Cl₂; c) K₂CO₃, MeOH, H₂O.

In general, reaction of compound 76 with triphenylphosphine and water in THF reduces the azide group to give compound 223. The amine group is converted to the sulfonamide compound 224 using MsCl and triethylamine in CH₂Cl₂. Treatment with potassium carbonate in methanol and water gives compound 225.

Following are specific examples of the compounds prepared above.

Synthesis of Compound 223

A solution of compound 76 (6.00 g, 13.9 mmol), PPh₃ (5.85 g, 22.3 mmol), water (3.72 mL, 206 mmol) and THF (100 mL) was heated overnight at 40° C. The reaction mixture was concentrated and the residue was purified by chromatography on silica gel (EtOAc/MeOH/Et₃N 90:10 then 90:10:3) to afford compound 223 (4.59 g, 81%) as a white foam.

Synthesis of Compound 224

A solution of compound 223 (250 mg, 0.616 mmol), MsCl (72 μL, 0.92 mmol), Et₃N (258 μL, 1.84 mmol) and CH₂Cl₂ was stirred at ambient temperature under argon for 1.5 hours. The reaction was quenched with saturated NaHCO₃ solution (3 mL) and water (2 mL). The solution was further diluted with water (5 mL) and was extracted with 100 mL of EtOAc. The EtOAc solution was washed with water and brine, then dried over MgSO₄, filtered and concentrated. The residue was purified by chromatography on silica gel (hexanes/EtOAc 3:1, then 1:1) to afford compound 224 (310 mg, quantitative) as a white foam.

Synthesis of Compound 225

A solution of compound 224 (223 mg, 0.46 mmol), K₂CO₃ (255 mg, 1.84 mmol), water (3 mL) and methanol (6 mL) was heated at reflux for 2 hours. The reaction mixture was concentrated, then dissolved in water and CH₂Cl₂ and was extracted with CH₂Cl₂ (240 mL). The CH₂Cl₂ solution was washed with water and brine, then dried over MgSO₄, filtered and concentrated. The residue was purified by chromatography on silica gel (CH₂Cl₂/MeOH 100:0, then 19:1, then 9:1). The residue from the pure fractions was concentrated from a minimum of MeOH and acetonitrile (5 mL) to afford compound 225 (132 mg, 72%) as a white powder: LC/MS (direct infusion, electrospray +ve, 10 mM NH₄OAc in 3:7 water and MeCN) 381.90; C₂₁H₃₅NO₃S, 363.85; C₂₁H₃₃NO₂S.

Example 26

Compound 227, a representative compound of the invention, may be prepared according to the following Reaction Scheme 26. Any number of compounds related to compound 227 could be produced using similar methodology. Starting compound 77 may be prepared according to procedures described above in Example 8.

REACTION SCHEME 26 a) Ac₂O, DMAP, pyridine; b) LiAlH₄, THF.

In general, reaction of compound 77 with acetic anhydride and DMAP in pyridine acylates the hydroxyl and amino groups to give compound 226. Selective lithium aluminum hydride reduction of the acetates gives compound 227.

Following are specific examples of the compounds prepared above.

Synthesis of Compound 226

A solution of compound 77 (208 mg, 0.647 mmol), acetic anhydride (214 μL, 2.27 mmol), DMAP (17 mg) and pyridine (5 mL) was stirred overnight at ambient temperature. The reaction was quenched with brine and was extracted with EtOAc. The EtOAc solution was washed with brine, then dried over MgSO$_4$, filtered and concentrated. The residual solvent was removed by codistillation with toluene. The residue was purified by chromatography on silica gel (EtOAc) to afford compound 226 (235 mg, 81%).

Synthesis of Compound 227

A solution of LiAlH$_4$ (1.57 mL of a 1.0 M solution in THF) was added to an ice cooled solution of compound 226 (235 mg, 0.525 mmol) in THF (10 mL). After 10 minutes the solution was continued at ambient temperature for another 2 hours. The reaction was quenched with Na$_2$SO$_4$.10H$_2$O. After 1 hour MgSO$_4$ was added and the solution was filtered and concentrated. The resulting crystalline solid was triturated successively with Et$_2$O, CH$_2$Cl$_2$, EtOAc and MeOH to afford compound 227 (128 mg, 67%) as a white powder. LC/MS (direct infusion, electrospray +ve, 10 mM NH$_4$OAc in 3:7 water and MeCN) 386.48; C$_{22}$H$_{37}$NNaO$_3$.

Example 27

Compounds 229 and 231-233, representative compounds of the invention, may be prepared according to the following Reaction Scheme 27. Any number of compounds related to compounds 229 and 231-233 could be produced using similar methodology. Starting compound 223 may be prepared according to procedures described above in Example 25.

REACTION SCHEME 27

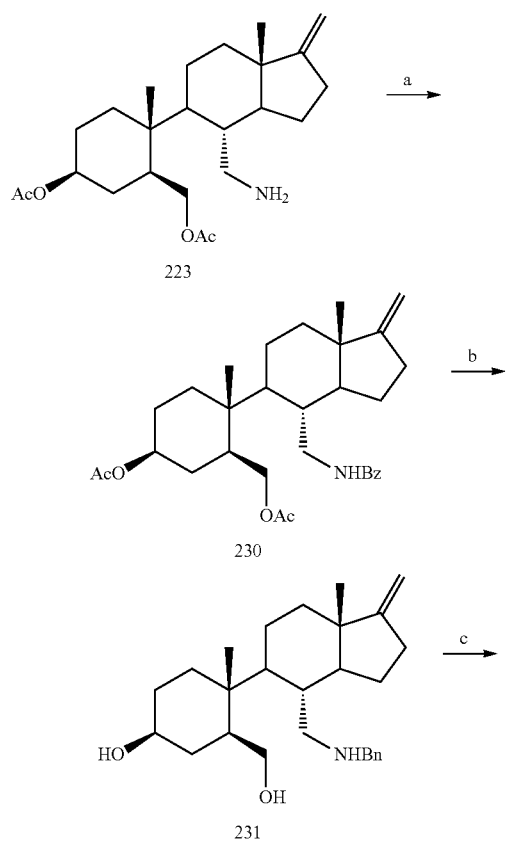

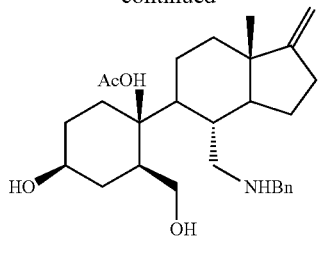

a) BzCl, DMAP, pyridine, CH$_2$Cl$_2$, pyridine; b) LiAlH$_4$, THF; c) 80% AcOH.

In general, reaction of an amino compound such as compound 223 with benzoyl chloride gives the amide compound 230. Lithium aluminum hydride reduces the amide and the acetates to give compound 231. Treatment with 80% acetic acid forms the salt compound 232.

Following are specific examples of the compounds prepared above.

Synthesis of Compound 230

A solution of compound 223 (405 mg, 1.00 mmol), benzoyl chloride (0.17 mL, 1.46 mmol), DMAP (15 mg), pyridine (4 mL) and CH$_2$Cl$_2$ (6 mL) was stirred for 2 hours at ambient temperature. The reaction was diluted with EtOAc (250 mL) and was washed with saturated NaHCO$_3$ solution and brine, then dried over NaSO$_4$, filtered and concentrated. The residue was purified by chromatography on silica gel (EtOAc/hexanes 45:55) to afford compound 230 (490 mg, 96%) as a colourless syrup.

Synthesis of Compound 231

A solution of LiAlH$_4$ (6×4.8 mL of a 1.0 M solution in THF) was added over 3 days to a solution of compound 230 (490 mg, 0.96 mmol) in THF (20 mL) at reflux under argon. The reaction was cooled in ice and was quenched with Na$_2$SO$_4$.10H$_2$O. After 20 minutes the solution was filtered and concentrated. The residue was purified by chromatography (EtOAc/MeOH 95:5) to afford compound 231 (395 mg, 39%) as a crystalline solid.

Synthesis of Compound 232

A solution of compound 231 (150 mg, 0.36 mmol) and 80% AcOH was heated at 40° C. for 10 minutes. The solution was concentrated to give compound 232 (162 mg, 94%) as a white foam. LC/MS (direct infusion, electrospray +ve, 10 mM NH$_4$OAc in 3:7 water and MeCN) 412.16; C$_{27}$H$_{42}$NO$_2$.

Synthesis of Compound 233

Using the procedures described for the synthesis of compound 232, with the exception of substitution by cyclopropane carbonyl chloride, compound 233 (231 mg) was prepared as a white solid in 67% yield starting from compound 223: LC/MS (direct infusion, electrospray +ve, 10 mM NH$_4$OAc in 3:7 water and MeCN) 376.35; C$_{24}$H$_{42}$NO$_2$.

Synthesis of Compound 229

Using the procedures described for the synthesis of compound 232, compound 229 (549 mg) was prepared as a glass-like solid in 36% yield starting from compound 226. LC/MS (direct infusion, electrospray +ve, 10 mM NH$_4$OAc in 3:7 water and MeCN) 350.63; C$_{22}$H$_{40}$NO$_2$.

Example 28

Compounds 235-236, representative compounds of the invention, may be prepared according to the following Reaction Scheme 28. Any number of compounds related to compounds 235-236 could be produced using similar methodology. Starting compound 223 may be prepared according to procedures described above in Example 25.

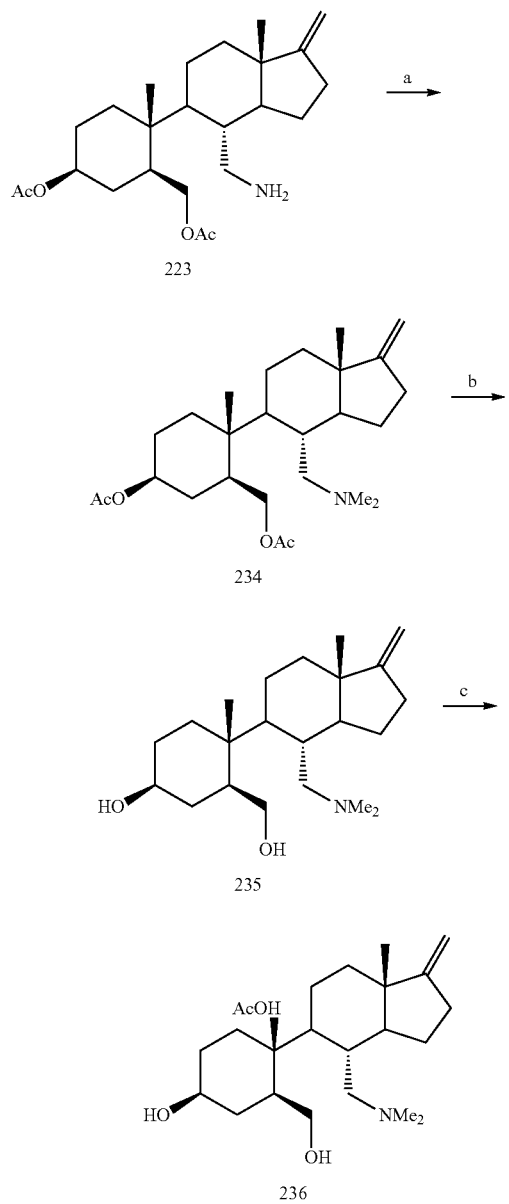

a) CH$_2$O, NaBH$_3$CN, MeCN; b) LiAlH$_4$, THF; c) 80% AcOH.

In general, reaction of an amino compound such as compound 223 with an aldehyde such as formaldehyde and a reducing agent such as NaBH$_3$CN gives a tertiary amino compound such as compound 234. A reducing agent such as lithium aluminum hydride is used to reduce the ester-protected hydroxyls to give compound 235. Treatment with 80% acetic acid forms the ammonium acetate salt compound 236.

Following are specific examples of the compounds prepared above.

Synthesis of Compound 234

NaBH$_3$CN (2×25 mg, 0.8 mmol) was added over 25 minutes to a ambient temperature solution of compound 223 (99 mg, 0.24 mmol), 37% CH$_2$O in water (0.1 mL) and acetonitrile (2 mL). After 15 minutes the pH of the solution was adjusted to pH 7 by the dropwise addition of 80% acetic acid. After 1 hour the reaction mixture was diluted with EtOAc (150 mL) and was washed with saturated NaHCO$_3$ solution and brine, then dried over MgSO$_4$, filtered and concentrated. The residue was purified by chromatography on silica gel (EtOAc/MeOH 95:5) to afford compound 234 (104 mg, 98%).

Synthesis of Compound 235

A solution of LiAlH$_4$ (5.5 mL of a 1.0 M solution in THF) was added to an ice cooled solution of compound 234 (492 mg, 1.1 mmol) in THF (15 mL) under argon. After 25 minutes the cold bath was removed and the reaction was continued for 4 hours at ambient temperature. The reaction was cooled in ice and was quenched with Na$_2$SO$_4$.10H$_2$O. After 10 minutes at ambient temperature, the solution was filtered, rinsing with EtOAc and the filtrate was washed with brine, then dried over MgSO$_4$, filtered and concentrated. The residue was purified by chromatography on silica gel (EtOAc/MeOH/H$_2$O 16:3:1) to afford compound 235 (294 mg, 74%) as a crystalline solid.

Synthesis of Compound 236

A solution of compound 235 (287 mg, 0.82 mmol) and 80% AcOH (10 mL) was stirred at 40° C. for 10 minutes, then concentrated. Repeated concentration from a minimum of methanol in acetonitrile gave compound 236 (287 mg, 85%) as a white solid: LC/MS (direct infusion, electrospray +ve, 10 mM NH$_4$OAc in 3:7 water and MeCN) 350.69; C$_{22}$H$_{40}$NO$_2$.

Example 29

Compounds 240-241, representative compounds of the invention, may be prepared according to the following Reaction Scheme 29. Any number of compounds related to compounds 240-241 could be produced using similar methodology. Starting compound 223 may be prepared according to procedures described above in Example 25.

REACTION SCHEME 29

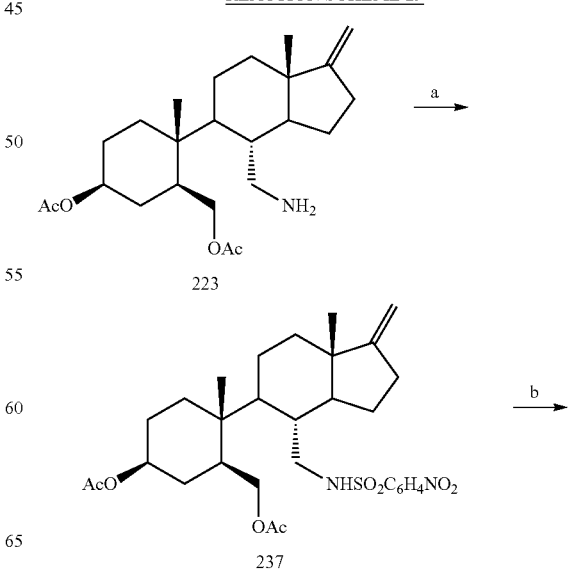

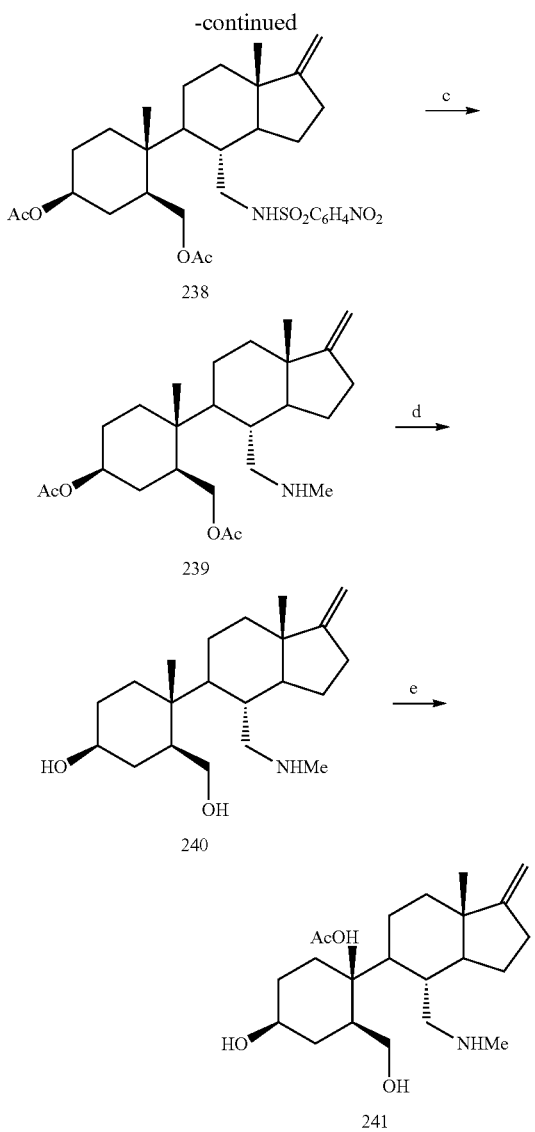

a) 2-nitrobenzenesulfonyl chloride, Et₃N, CH₂Cl₂; b) MeI, K₂CO₃, DMF; c) PhSH, Cs₂CO₃, MeCN; d) KOH, H₂O, MeOH; e) 80% AcOH.

In general, an amino compound may be converted to a sulfonamide such as the reaction of compound 223 with a sulfonyl chloride such as 2-nitrobenzenesulfonyl chloride to give compound 237. The sulfonamide nitrogen in a compound such as 237 may then be alkylated with an electrophile such as methyl iodide to give an amine compound such as 238. The sulfonamide may be cleaved by reaction with a nucleophile such as the thiophenolate anion to give compound 239. The acetates may be removed by base hydrolysis to give compound 240. Treatment with 80% acetic acid forms the ammonium acetate salt compound 241.

Following are specific examples of the compounds prepared above.

Synthesis of Compound 237

2-Nitrobenzenesulfonyl chloride (194 mg, 0.88 mmol) was added to an ice cooled solution of compound 223 (296 mg, 0.73 mmol), Et₃N (180 μL, 1.3 mmol) and CH₂Cl₂ (5 mL) under argon. After 30 minutes the cold bath was removed and the reaction was continued for 1 hour at ambient temperature. The reaction mixture was diluted with EtOAc and was washed with saturate NaHCO₃ solution and brine, then dried over MgSO₄, filtered and concentrated to afford compound 237 (433 mg, 100%) as a pale yellow solid.

Synthesis of Compound 238

MeI (60 μL and 2×30 μL, 1.9 mmol) was added over 7 hours to a solution of compound 237 (431 mg, 0.73 mmol), K₂CO₃ (232 mg, 1.7 mmol) and DMF (3 mL) under argon. After stirring overnight at ambient temperature, the reaction mixture was diluted with EtOAc and was washed with brine, then dried over MgSO₄, filtered and concentrated to give crude compound 238 that was used in the next step without further purification.

Synthesis of Compound 239

A solution of compound 238 (crude, 0.73 mmol), PhSH (225 μL, 2.19 mmol), CsCO₃ (714 mg, 2.19 mmol) and acetonitrile (6 mL) was heated at 55° C. under argon for 1.5 hours. The ambient temperature reaction mixture was diluted with EtOAc and was washed with brine, then dried with MgSO₄, filtered and concentrated. The residue was purified by chromatography on silica gel (EtOAc/hexanes 1:1, then EtOAc/MeOH/Et₃N 90:10:2) to afford compound 239 (268 mg, 88%) as a pale yellow oil.

Synthesis of Compound 240

A solution of compound 239 (268 mg, 0.639 mmol), 10% KOH in water (1 mL) and MeOH (5 mL) was heated at 55° C. for 4 hours. The ambient temperature reaction mixture was diluted with EtOAc (80 mL) and was washed with brine, then dried over MgSO₄, filtered and concentrated. The residue was purified by chromatography on silica gel (EtOAc/MeOH/H₂O/NH₄OH 80:15:5:1.5, then 70:20:10:2) to afford compound 240 (182 mg, 85%) as a white foam.

Synthesis of Compound 241

A solution of compound 240 (182 mg, 0.542 mmol) and 80% AcOH was heated at 40° C. for 15 minutes, then concentrated. Residual solvent was removed by codistillation with methanol to afford compound 241 (210 mg, 98%) as a pale yellow foam. LC/MS (direct infusion, electrospray +ve, 10 mM NH₄OAc in 3:7 water and MeCN) 336.08; C₂₁H₃₈NO₂.

Example 30

Compound 242, a representative compound of the invention, may be prepared according to the following Reaction Scheme 30. Any number of compounds related to compound 242 could be produced using similar methodology. Starting compound 77 may be prepared according to procedures described above in Example 8.

REACTION SCHEME 30

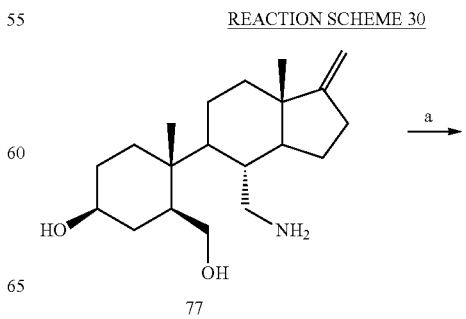

-continued

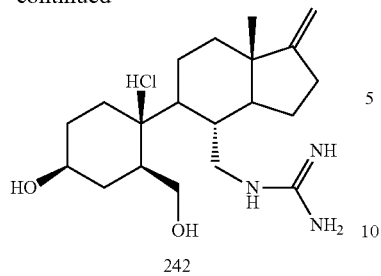

242 a) pyrazole-1-carboxamidine hydrochloride, DIEA, MeOH.

In general, reaction of an amino compound such as 77 with pyrazole-1-carboxamidine hydrochloride and diisopropylethylamine (DIEA) in methanol gives compound 242.

Following are specific examples of the compounds prepared above.

Synthesis of Compound 242

A solution of compound 77 (106 mg, 0.33 mmol), pyrazole-1-carboxamidine hydrochloride (51 mg, 0.35 mmol), DIEA (61 μl, 0.35 mmol) and MeOH (165 μl) was stirred at ambient temperature under argon for 3 days. The slurry was triturated in $Et_2O$, decanting off the solvent to give a white powder. The solid was then recrystallized from 3 ml of EtOAc/MeOH/$Et_2O$ to afford compound 242 (64 mg, 48%) as a white solid: LC/MS (direct infusion, electrospray +ve, 10 mM $NH_4OAc$ in 3:7 water and MeCN) 364.06; $C_{21}H_{38}N_3O_2$.

Example 31

Compounds 243-250, representative compounds of the invention, may be prepared according to the following Reaction Scheme 31. Any number of compounds related to compounds 243-250 could be produced using similar methodology. Starting compound 77 may be prepared according to procedures described above in Example 8.

REACTION SCHEME 31

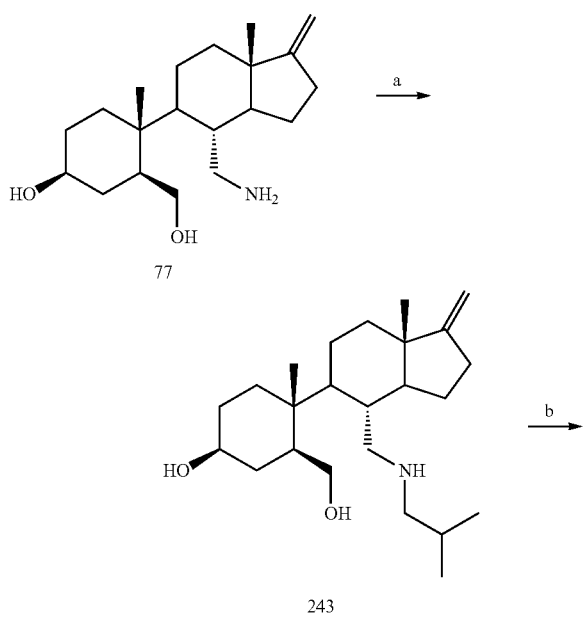

-continued

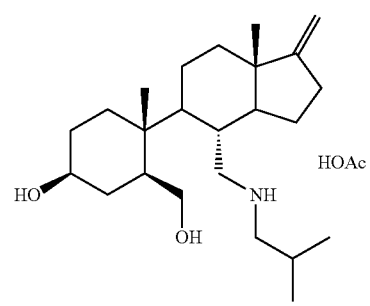

244 a) $Me_2CHCHO$, $NaB(OAc)_3H$, 4A molecular sieves, 1,2-dichloroethane; b) 80% AcOH In general, reductive amination of an amino compound such as compound 77 with a ketone or aldehyde such as isobutyraldehyde gives an amine such as compound 243. Treatment with 80% acetic acid gives the salt compound 244.

Following are specific examples of the compounds prepared above.

Synthesis of Compound 243

To a stirred mixture of compound 77 (100 mg, 0.31 mmol) in 1,2-dichloroethane (5 mL) and EtOH (1 mL) were added isobutyraldehyde (0.14 mL, 1.5 mmol), 4 Å molecular sieves (100 mg), and $NaB(OAc)_3H$ (197 mg, 0.93 mmol). The mixture was stirred at ambient temperature for three days and then filtered through Celite and washed with EtOAc. The filtrate and washings were combined and concentrated. The residue was purified by column chromatography (EtOAc/MeOH, 9:1 then 8:2) to yield compound 243 (79 mg, 67%).

Synthesis of Compound 244

A solution of compound 243 (79 mg) in 80% HOAc (2 mL) was stirred at 40° C. for a few minutes and then concentrated by rotary evaporation. The residue was codistilled with MeOH several times and dried under vacuum. The product was dissolved in a small amount of MeOH and treated with a small amount of acetonitrile. The solvents were removed and the product was dried under vacuum to give compound 244 (91 mg, 99%): LC/MS (direct infusion, electrospray +ve, 10 mM $NH_4OAc$ in 3:7 water and MeCN) 378.21; $C_{24}H_{44}NO_2$.

Synthesis of Compound 245

Using the procedures described for the synthesis of compound 244, with the exception of substitution by 1-methyl-4-piperidone, compound 245 (183 mg) was prepared in quantitative yield starting from compound 77: LC/MS (direct infusion, electrospray +ve, 10 mM $NH_4OAc$ in 3:7 water and MeCN) 419.21; $C_{26}H_{47}N_2O_2$.

Synthesis of Compound 246

Using the procedures described for the synthesis of compound 244, with the exception of substitution by 3-nitrobenzaldehyde, compound 246 (58 mg) was prepared in 35% yield starting from compound 77: LC/MS (direct infusion, electrospray +ve, 10 mM $NH_4OAc$ in 3:7 water and MeCN) 457.22; $C_{27}H_{41}N_2O_4$.

Synthesis of Compound 247

Using the procedures described for the synthesis of compound 244, with the exception of substitution by piperonal, compound 247 (161 mg) was prepared in 99% yield starting from compound 77: LC/MS (direct infusion, electrospray +ve, 10 mM NH$_4$OAc in 3:7 water and MeCN) 456.12; C$_{28}$H$_{42}$NO$_4$.

Synthesis of Compound 248

Using the procedures described for the synthesis of compound 244, with the exception of substitution by pyrrole-2-carboxaldehyde, compound 248 (131 mg) was prepared in 91% yield starting from compound 77: LC/MS (direct infusion, electrospray +ve, 10 mM NH$_4$OAc in 3:7 water and MeCN) 401.15; C$_{25}$H$_{41}$N$_2$O$_2$.

Synthesis of Compound 249

Using the procedures described for the synthesis of compound 244, with the exception of substitution by 2-furaldehyde, compound 249 (88 mg) was prepared in 61% yield starting from compound 77: LC/MS (direct infusion, electrospray +ve, 10 mM NH$_4$OAc in 3:7 water and MeCN) 402.23; C$_{25}$H$_{40}$NO$_3$.

Synthesis of Compound 250

Using the procedures described for the synthesis of compound 244, with the exception of substitution by 3-pyridinecarboxaldehyde, compound 250 (59 mg) was prepared in 40% yield starting from compound 77: LC/MS (direct infusion, electrospray +ve, 10 mM NH$_4$OAc in 3:7 water and MeCN) 413.22; C$_{26}$H$_{41}$N$_2$O$_2$.

Example 32

Compounds 252-261, representative compounds of the invention, may be prepared according to the following Reaction Scheme 32. Any number of compounds related to compounds 252-261 could be produced using similar methodology. Starting compound 193 may be prepared according to procedures described above in Example 9.

REACTION SCHEME 32

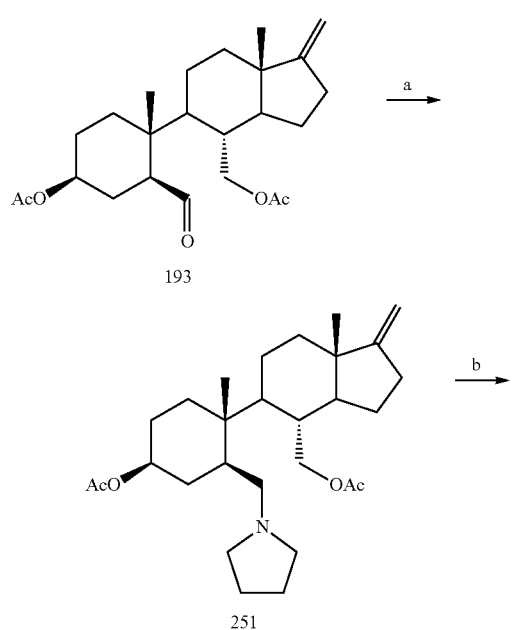

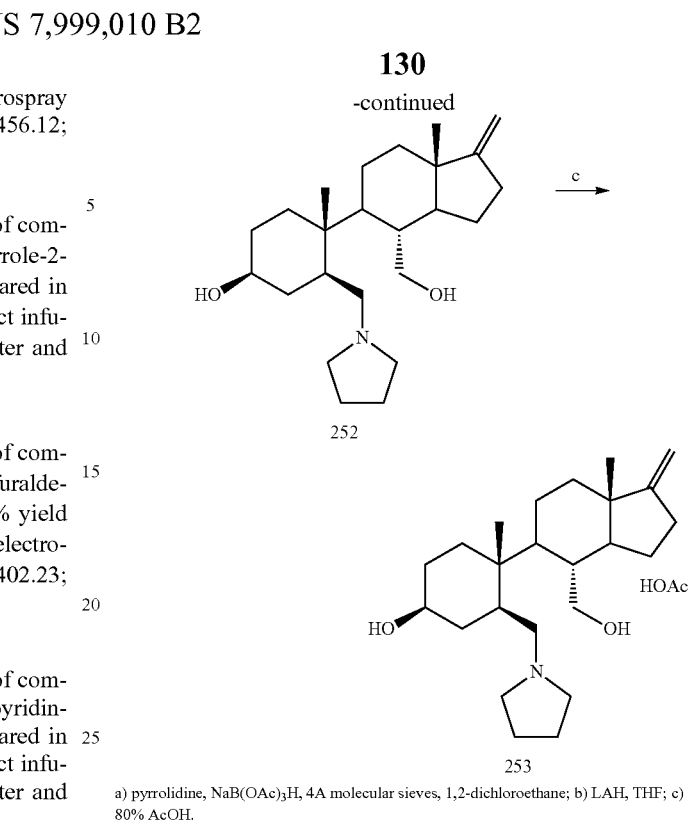

a) pyrrolidine, NaB(OAc)$_3$H, 4A molecular sieves, 1,2-dichloroethane; b) LAH, THF; c) 80% AcOH.

In general, reductive amination of a ketone or aldehyde compound such as compound 193 with an amine such as pyrrolidine gives an amine such as compound 251. Lithium aluminum hydride reduction removes the acyl groups to give compound 252. Treatment with 80% acetic acid gives the salt compound 253.

Following are specific examples of the compounds prepared above.

Synthesis of Compound 251

To a stirred solution of compound 193 (150 mg, 0.37 mmol) in 1,2-dichloroethane (7.5 mL) were added pyrrolidine (0.18 mL, 2.2 mmol), 4 Å molecular sieves (150 mg), and NaB(OAc)$_3$H (314 mg, 1.5 mmol). The mixture was stirred at ambient temperature for three days and then filtered through Celite and washed with EtOAc. The filtrate and washings were combined and concentrated. The residue was purified by column chromatography (EtOAc/MeOH/Et$_3$N, 8:2:0.5) to yield compound 251 (155 mg, 91%).

Synthesis of Compound 252

To a stirred solution of compound 251 (155 mg, 0.34 mmol) in THF (15 mL) at 0° C. was added 1M LAH in THF (1.7 mL, 1.7 mmol) dropwise. After 5 min at 0° C., the mixture was stirred at ambient temperature for 5 hours 40 min. The reaction was cooled to 0° C. again and solid Na$_2$SO$_4$.10H$_2$O (536 mg, 1.7 mmol) was added portionwise. After 5 min at 0° C., the mixture was stirred at ambient temperature for 1 hour and then filtered through Celite and washed with EtOAc. The filtrate and washings were combined and concentrated. The residue was purified by column chromatography (EtOAc/MeOH/water/Et$_3$N, 8:1:0.5:0.5) to yield compound 252 (121 mg, 92%).

Synthesis of Compound 253

A solution of compound 252 (121 mg) in 80% HOAc (2 mL) was stirred at 40° C. for a few minutes and then concentrated by rotary evaporation. The residue was codistilled with MeOH several times and dried under vacuum. The product was dissolved in a small amount of MeOH and treated with a small amount of acetonitrile. The solvents were removed and the product was dried under vacuum to give compound 253 (147 mg, quant.): LC/MS (direct infusion, electrospray +ve, 10 mM NH$_4$OAc in 3:7 water and MeCN) 376.24; C$_{24}$H$_{42}$NO$_2$.

Synthesis of Compound 254

Using the procedures described for the synthesis of compound 253, with the exception of substitution by ethanolamine, compound 254 (84 mg) was prepared in 51% yield starting from compound 193: LC/MS (direct infusion, electrospray +ve, 10 mM NH$_4$OAc in 3:7 water and MeCN) 366.13; C$_{22}$H$_{40}$NO$_3$.

Synthesis of Compound 255

Using the procedures described for the synthesis of compound 253, with the exception of substitution by N,N-dimethylethylenediamine, compound 255 (38 mg) was prepared in 20% yield starting from compound 193: LC/MS (direct infusion, electrospray +ve, 10 mM NH$_4$OAc in 3:7 water and MeCN) 393.11; C$_{26}$H$_{49}$N$_2$O$_4$.

Synthesis of Compound 256

Using the procedures described for the synthesis of compound 253, with the exception of substitution by cyclohexylamine, compound 256 (154 mg) was prepared in 87% yield starting from compound 193: LC/MS (direct infusion, electrospray +ve, 10 mM NH$_4$OAc in 3:7 water and MeCN) 404.28; C$_{26}$H$_{46}$NO$_2$.

Synthesis of Compound 257

Using the procedures described for the synthesis of compound 253, with the exception of substitution by 3-(aminomethyl)pyridine, compound 257 (122 mg) was prepared in 65% yield starting from compound 193: LC/MS (direct infusion, electrospray +ve, 10 mM NH$_4$OAc in 3:7 water and MeCN) 413.15; C$_{26}$H$_{41}$N$_2$O$_2$.

Synthesis of Compound 258

Using the procedures described for the synthesis of compound 253, with the exception of substitution by furfurylamine, compound 258 (83 mg) was prepared in 47% yield starting from compound 193: LC/MS (direct infusion, electrospray +ve, 10 mM NH$_4$OAc in 3:7 water and MeCN) 402.20; C$_{25}$H$_{40}$NO$_3$.

Synthesis of Compound 259

Using the procedures described for the synthesis of compound 253, with the exception of substitution by 3-fluoroaniline and no salt formation step, compound 259 (86 mg) was prepared in 57% yield starting from compound 193: LC/MS (direct infusion, electrospray +ve, 10 mM NH$_4$OAc in 3:7 water and MeCN) 416.08; C$_{26}$H$_{39}$FNO$_2$.

Synthesis of Compound 260

Using the procedures described for the synthesis of compound 259, with the exception of substitution by 3-aminopyridine, compound 260 (42 mg) was prepared in 28% yield starting from compound 193: LC/MS (direct infusion, electrospray +ve, 10 mM NH$_4$OAc in 3:7 water and MeCN) 399.20; C$_{25}$H$_{39}$N$_2$O$_2$.

Synthesis of Compound 261

Using the procedures described for the synthesis of compound 259, with the exception of substitution by m-toluidine, compound 261 (91 mg) was prepared in 60% yield starting from compound 193: LC/MS (direct infusion, electrospray +ve, 10 mM NH$_4$OAc in 3:7 water and MeCN) 412.20; C$_{27}$H$_{42}$NO$_2$.

Example 33

Compound 270, a representative compound of the invention, may be prepared according to the following Reaction Scheme 33. Any number of compounds related to compound 270 could be produced using similar methodology. Starting compound 262 may be prepared according to procedures described in U.S. Pat. No. 6,046,185.

REACTION SCHEME 33

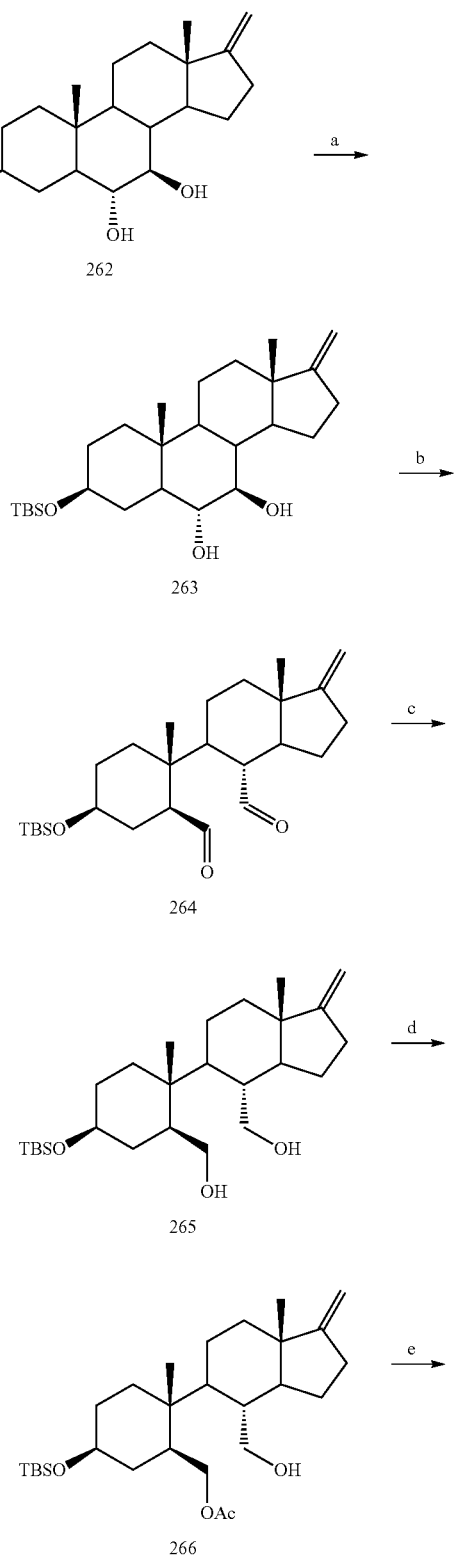

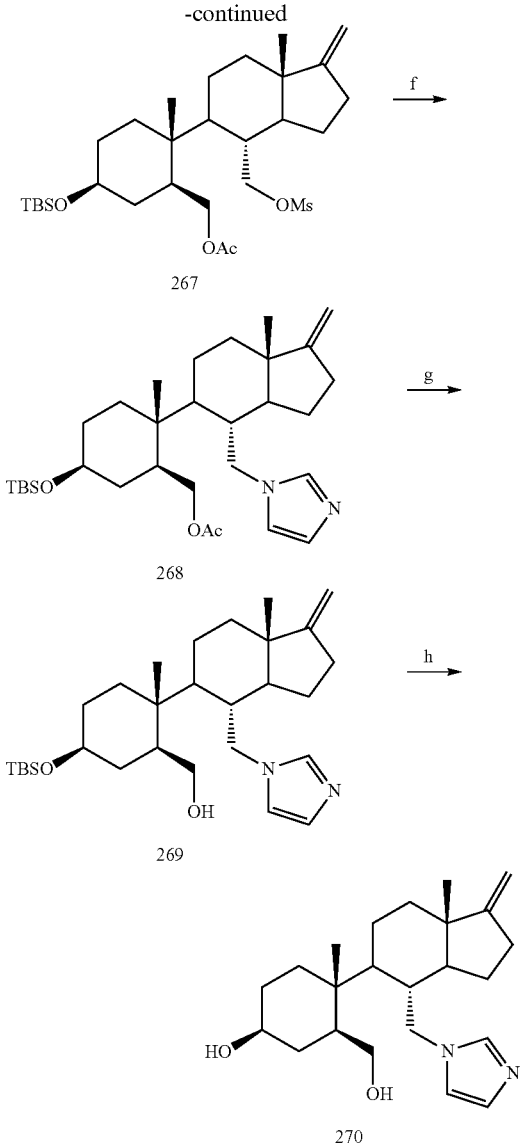

a) TBSCl, imidazole, DMAP, DMF, THF; b) NaIO₄, H₂O, THF; c) NaBH₄, MeOH, THF; d) Ac₂O, DMAP, pyridine; e) MsCl, pyridine; f) NaH, imidazole, DMF; g) LAH, THF; h) HOAc.

In general, treatment with TBSCl and imidazole in DMF selectively protects one hydroxyl to give compound 263. NaIO₄ oxidation gives the dialdehyde compound 264. Sodium borohydride reduction gives compound 265. Reaction with acetic anhydride and DMAP in pyridine selectively protects one hydroxyl to give compound 266. The free hydroxyl is reacted to give the mesylate compound 267 using MsCl and pyridine. Displacement of the mesylate by the anion of imidazole in DMF gives compound 268. Lithium aluminum hydride removes the acyl group to give compound 269. Treatment with 80% acetic acid removes the TBS group to give compound 270.

Following are specific examples of the compounds prepared above.

Synthesis of Compound 263

To a solution of crude compound 262 (86.3 mmol) in DMF (90 mL) and THF (150 mL) that was cooled in a cold water bath were added DMAP (0.50 g, 4.1 mmol), imidazole (11.8 g, 173 mmol) and TBSCl (15.6 g, 104 mmol). The mixture was stirred at ambient temperature for 2.5 hours, then cooled in a cold water bath. Water (100 mL) and EtOAc (100 mL) were added. The layers were separated and the aqueous portion was back-extracted with EtOAc (50 mL). The combined organics were washed with brine (2×250 mL), dried over anhydrous MgSO₄ and concentrated to dryness to give compound 263 (38.0 g, quantitative) as a white foam.

Synthesis of Compound 264

To a solution of compound 263 (38.0 g, 86.3 mmol) in THF (250 mL) that was cooled in a cold water bath was added a slurry of NaIO₄ (36.9 g, 173 mmol) in water (120 mL). The reaction mixture was stirred at ambient temperature for 1.5 hours, then water (150 mL) and EtOAc (150 mL) were added. The layers were separated and the aqueous portion was back-extracted with EtOAc (100 mL). The combined organics were washed with brine (200 mL), dried over anhydrous MgSO₄ and concentrated to dryness to give crude compound 264 that was used in the next step without further purification.

Synthesis of Compound 265

To a solution of crude compound 264 (86.3 mmol) in THF (125 mL) and MeOH (125 mL) at 0° C. was added NaBH₄ (6.53 g, 173 mmol) in portions. The mixture was stirred at 0° C. for 15 minutes, then at ambient temperature for 1 hour. The mixture was cooled in a cold water bath and quenched with 80% acetic acid until pH=7.0. Water (100 mL) and EtOAc (150 mL) were added. The layers were separated and the aqueous portion was back-extracted with EtOAc (100 mL). The combined organics were washed with brine (200 mL), dried over anhydrous MgSO₄ and concentrated to dryness. The residue was stirred with hexanes (150 mL) for 2 hours, then the precipitate was filtered out, rinsing with hexanes (2×25 mL). The solid was dried to afford compound 265 (19.8 g, 52% from compound 263) as a white solid.

Synthesis of Compound 266

To a solution of compound 265 (17.0 g, 38.9 mmol) in CH₂Cl₂ (25 mL) and pyridine (50 mL) that was cooled in a cold water bath were added DMAP (0.50 g, 4.1 mmol), then acetic anhydride (4.0 mL, 43 mmol) dropwise. The mixture was stirred at ambient temperature for 1.5 hours. Brine (120 mL) and EtOAc (250 mL) were added. The layers were separated and the aqueous portion was back-extracted with EtOAc (100 mL). The combined organics were washed with brine (2×150 mL), dried over anhydrous MgSO₄ and concentrated. The residue was purified by chromatography on silica gel (hexanes/EtOAc, 49:1, 19:1, 9:1, 4:1) to give compound 266 (11.0 g, 59%) as a white solid.

Synthesis of Compound 267

To a stirred solution of compound 266 (2.4 g, 5.0 mmol) in pyridine (20 mL) was added MsCl (0.39 mL, 5.0 mmol) dropwise. The resulting mixture was stirred at ambient temperature for 5 hours. The mixture was diluted with EtOAc (300 mL), washed with brine, and the aqueous washings were combined and extracted with EtOAc. The organic extracts were combined and washed with brine, dried and concentrated to yield compound 267 (2.8 g, 100%) as a pale solid.

Synthesis of Compound 268

To a stirred solution of imidazole (66 mg, 0.97 mmol) in DMF (6 mL) at ambient temperature was added NaH (39 mg, 60% in mineral oil, 0.97 mmol). After stirring for 1 hour at ambient temperature, the mixture became clear and compound 267 (200 mg, 0.36 mmol) was added as solid. The mixture was stirred at 60° C. for 3 hours 45 min and then left at ambient temperature overnight. The mixture was diluted with toluene (200 mL), washed with brine, dried and concentrated. The crude compound 268 was used in next step without purification.

135

Synthesis of Compound 269

To a stirred solution of compound 268 (0.36 mmol) in THF (15 mL) at 0° C. was added 1M LAH in THF (0.57 mL, 0.57 mmol) dropwise. After 5 minutes at 0° C., the mixture was stirred at ambient temperature for 5 hours. The reaction was cooled to 0° C. again and solid $Na_2SO_4.10H_2O$ (184 mg, 0.57 mmol) was added portionwise. After 5 min at 0° C., the mixture was stirred at ambient temperature for 1 hour and then filtered through Celite and washed with EtOAc. The filtrate and washings were combined and concentrated. The crude compound 269 was used in next step without purification Synthesis of Compound 270

A solution of crude compound 269 (0.36 mmol) in 80% HOAc (4 mL) was stirred at 40° C. for 6.5 hours. The solvents were removed and the residue was purified with column chromatography (EtOAc/MeOH/$Et_3N$, 8:1.5:0.5) to afford compound 270 (110 mg, 82% from compound 267). LC/MS (direct infusion, electrospray +ve, 10 mM $NH_4OAc$ in 3:7 water and MeCN) 372.87; $C_{23}H_{37}N_2O_2$.

Example 34

Compounds 276-277, representative compounds of the invention, may be prepared according to the following Reaction Scheme 34. Any number of compounds related to compounds 276-277 could be produced using similar methodology. Starting compound 267 may be prepared according to procedures described above in Example 33.

REACTION SCHEME 34

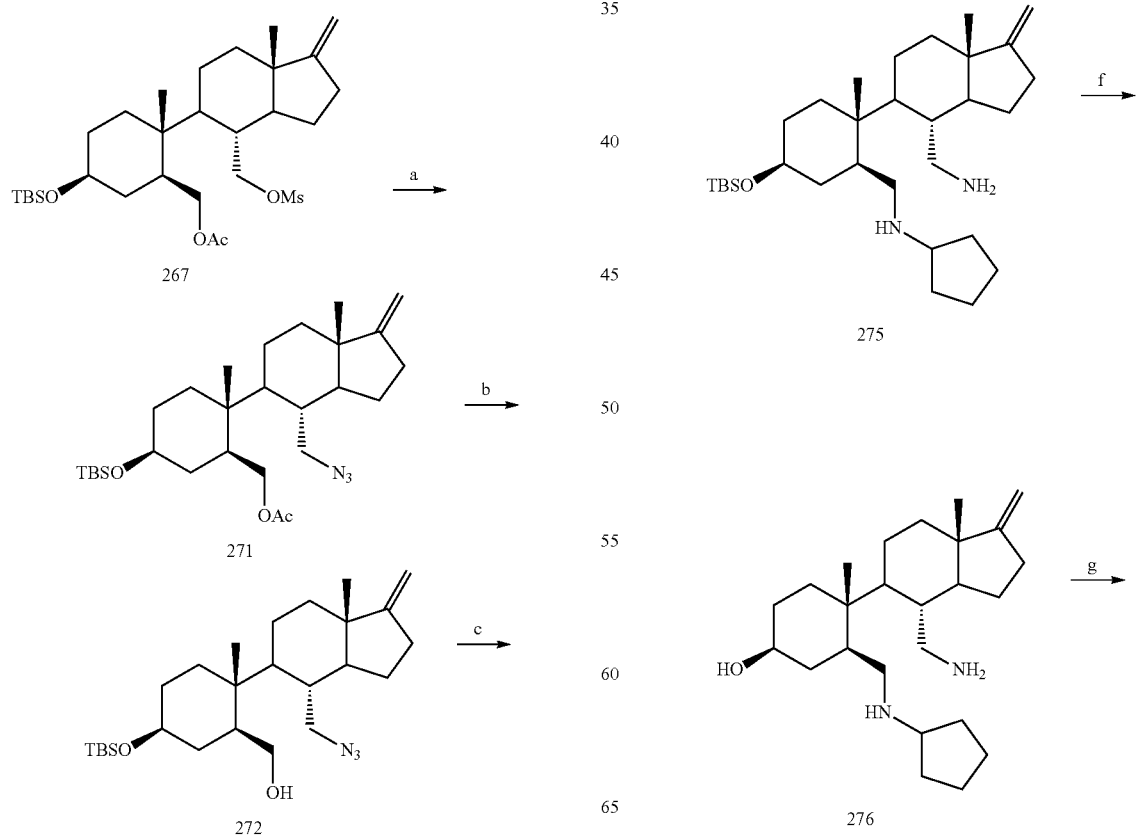

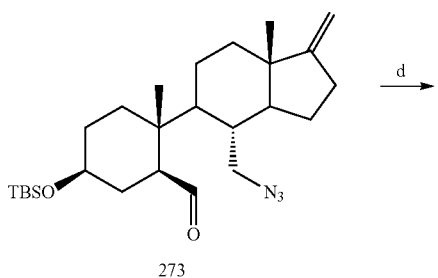

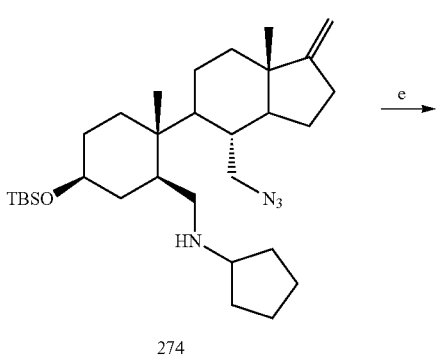

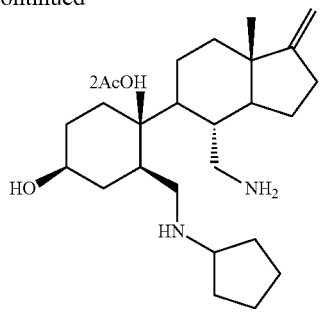

277 a) NaN₃, DMF; b) K₂CO₃, MeOH, H₂O; c) NMO, TPAP, CH₂Cl₂; d) cyclopentylamine, NaB(OAc)₃H, 4A molecular sieves, 1,2-dichloroethane; e) LAH, THF; f) 80% AcOH; g) 80% AcOH In general, azide displacement of the mesylate by NaN₃ in DMF gives compound 271. Base hydrolysis of the acetate gives compound 272. TPAP catalyzed oxidation of the hydroxyl group gives compound 273. Reductive amination with cyclopentylamine gives compound 274. Lithium aluminum hydride reduces the azide to give compound 275. Treatment with 80% acetic acid removes the TBS group to give compound 276. After column purification, further treatment with 80% acetic acid gives the salt compound 277.

Following are specific examples of the compounds prepared above.

Synthesis of Compound 271

A mixture of compound 267 (1.8 g, 3.2 mmol) and NaN₃ (420 mg, 6.5 mmol) in DMF (26 mL) was stirred at 60° C. overnight. The mixture was cooled to ambient temperature and diluted with toluene (300 mL), washed with brine, dried and concentrated to give compound 271 (1.56 g, 95%).

Synthesis of Compound 272

A mixture of compound 271 (1.35 g, 2.68 mmol), K₂CO₃ (2.9 g, 21 mmol) in MeOH/THF/water (50 mL/50 mL/39 mL) was stirred at ambient temperature overnight. Most of the solvents were removed by rotary evaporation and the residue was diluted with water (250 mL) and extracted with EtOAc. The EtOAc extracts were combined and washed with brine, dried and concentrated. The crude product was purified by column chromatography (hexanes/EtOAc, 85:15) to give compound 272 (856 mg) in 69% yield.

Synthesis of Compound 273

To a stirred solution of compound 272 (892 mg, 1.93 mmol) in CH₂Cl₂ (35 mL) was added NMO (333 mg, 2.84 mmol) and TPAP (57 mg, 0.16 mmol). The mixture was stirred at ambient temperature for 2 hours 15 min and then the solvent was removed by rotary evaporation. The residue was purified by column chromatography (hexanes/EtOAc, 9:1) to give compound 273 (769 mg) in 87% yield.

Synthesis of Compound 274

To a stirred solution of compound 273 (170 mg, 0.37 mmol) in 1,2-dichloroethane (8 mL) were added cyclopentylamine (0.18 mL, 1.8 mmol), 4 Å molecular sieves (170 mg), and NaB(OAc)₃H (331 mg, 1.56 mmol). The mixture was stirred at ambient temperature for 28 hours and then filtered through Celite and washed with EtOAc. The filtrate and washings were combined and concentrated. The residue was filtered through silica column with EtOAc/MeOH (9:1), and the crude compound 274 was used in next step without further purification.

Synthesis of Compound 275

To a stirred solution of compound 274 (0.37 mmol) in THF (15 mL) at 0° C. was added 1M LAH in THF (1.9 mL, 1.9 mmol) dropwise. After 5 min at 0° C., the mixture was stirred at ambient temperature for 5.5 hours. The reaction was cooled to 0° C. again and solid Na₂SO₄.10H₂O (596 mg, 1.9 mmol) was added portionwise. After 5 min at 0° C., the mixture was stirred at ambient temperature for 1 hour and then filtered through Celite and washed with EtOAc. The filtrate and washings were combined and concentrated. The crude compound 275 was used in next step without purification.

Synthesis of Compound 276

A solution of crude compound 275 (0.37 mmol) in 80% HOAc (5 mL) was stirred at 40° C. for 7.5 hours. The solvents were removed and the residue was purified by column chromatography (EtOAc/MeOH/water/Et₃N, 6.5:2.5:0.5:0.5) to afford compound 276 (74 mg, 52% from compound 273).

Synthesis of Compound 277

A solution of compound 276 (74 mg) in 80% HOAc (0.5 mL) was stirred at ambient temperature for a few minutes and then the solvents were removed by rotary evaporation. The residue was co-evaporated with MeOH several times and dried under vacuum. The product was dissolved in a small amount of MeOH and treated with a small amount of acetonitrile. The solvents were removed and the product was dried under vacuum to afford compound 277 (90 mg, 93%) as off-white powder: LC/MS (direct infusion, electrospray +ve, 10 mM NH₄OAc in 3:7 water and MeCN) 388.98; C₂₅H₄₅N₂O.

Example 35

Compounds 282-306, representative compounds of the invention, may be prepared according to the following Reaction Scheme 35. Any number of compounds related to compounds 282-306 could be produced using similar methodology. Starting compound 113 may be prepared according to procedures described above in Example 12.

REACTION SCHEME 35

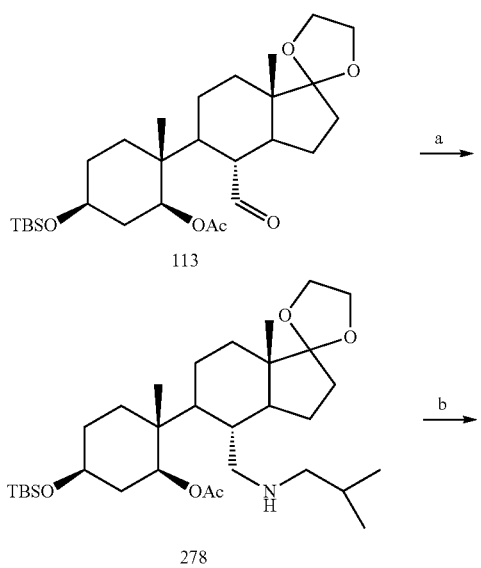

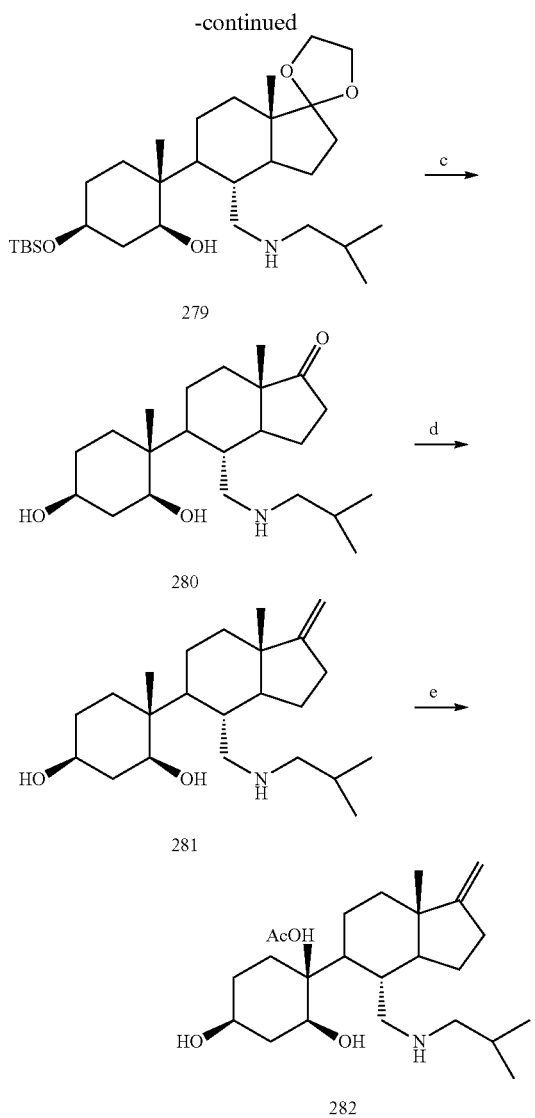

a) isobutylamine, NaB(OAc)₃H, 4 Å MS, DCE; b) LiAlH₄, THF; c) 80% AcOH, 40° C.; d) MePPh₃Br, KO$^t$Bu, THF; e) 80% AcOH.

In general, reductive amination of a ketone or aldehyde compound such as compound 113 with an amine such as isobutylamine gives an amine such as compound 278. Lithium aluminum hydride reduction removes the acyl group to give compound 279. Treatment with 80% acetic acid removes both the TBS group and the cyclic ketal to give compound 280. Olefination using MePPh₃Br and KO$^t$Bu in THF gives compound 281. Treatment with 80% acetic acid gives the salt compound 282.

Following are specific examples of the compounds prepared above.

Synthesis of Compound 278

A mixture of compound 113 (0.18 g, 0.35 mmol), isobutylamine (0.18 mL, 1.8 mmol) and 4 Å molecular sieves (0.15 g) in DCE (5 mL) was stirred at ambient temperature for 1 hour. NaB(OAc)₃H (0.395 g, 1.77 mmol) was added and the mixture was stirred at ambient temperature for 5 days. The reaction mixture was diluted with MeOH and filtered through a celite bed, rinsing with EtOAc. The filtrate was washed with saturated NaHCO₃ solution then brine twice, dried over anhydrous MgSO₄ and concentrated. The residue was purified by chromatography on silica gel to give a mixture of compound 278 and the imine of compound 278 (0.240 g) as a light yellow oil that was used in the next reaction without further purification.

Synthesis of Compound 279

To a solution of the mixture of compound 278 and its imine (0.33 mmol) in THF (10 mL) was added LiAlH₄ (0.99 mL of a 1 M solution in THF, 0.99 mmol). The mixture was stirred at ambient temperature overnight then quenched with Na₂SO₄·10H₂O and stirred for 30 minutes. The mixture was filtered, rinsing with EtOAc, and concentrated to dryness to give crude compound 279 (0.137 g) as a colourless glass that was used in the next reaction without further purification.

Synthesis of Compound 280

Crude compound 279 (0.33 mmol) was dissolved in 80% acetic acid (7 mL) and stirred at 40° C. overnight then concentrated. The residue was partially purified by chromatography on silica gel to give compound 280 (0.083 g) as a colourless glass.

Synthesis of Compound 281

A mixture of KO$^t$Bu (0.184 g, 1.56 mmol) and MePPh₃Br (0.557 g, 1.56 mmol) in THF (6 mL) was stirred at ambient temperature for 1.5 hours, then a solution of compound 281 (0.083 g, 0.20 mmol) in THF (4 mL) was added. The reaction mixture was stirred at ambient temperature overnight then quenched with saturated NH₄Cl solution and concentrated. The residue was partially purified by chromatography on silica gel to afford compound 281 that was used for the next reaction.

Synthesis of Compound 282

A mixture of compound 281 (0.2 mmol), 80% AcOH and MeOH was concentrated by rotary evaporation. The residue was dissolved in water and washed with CH₂Cl₂ (5×5 mL) then concentrated. Precipitation from hexanes afforded compound 282 (0.042 g, 28% from compound 113) as a white solid: LC/MS (direct infusion, electrospray +ve, 10 mM NH₄OAc in 3:7 water and MeCN) 364.22; C₂₃H₄₂NO₂.

Synthesis of Compound 283

Using the procedure described for the synthesis of compound 278, with the exceptions that 0.329 g (1.47 mmol) NaB(OAc)₃H were used and the reaction time was 4 days, compound 113 (0.25 g, 0.49 mmol) was reacted with (aminomethyl)pyridine (0.25 mL, 2.5 mmol) to give imine intermediate (0.225 g, 77%, white foam). Using the procedure described for the synthesis of compound 279, with the exception that reaction time was 5 hours, the imine intermediate (0.376 mmol) was reacted with LiAlH₄ (1.50 mL of a 1 M solution in Et₂O, 1.50 mmol) to give crude alcohol intermediate with TBS cleaved (0.162 g, yellow foam). Using the procedure described for the synthesis of compound 280, with the exceptions that 20 mL 80% AcOH were used and the reaction was performed at ambient temperature, the crude alcohol intermediate mixture (0.376 mmol) was converted to ketone intermediate (0.095 g, colourless glass). Using the procedure described for the synthesis of compound 281, with the exceptions that 0.163 g (1.38 mmol) KO$^t$Bu and 0.492 g (1.38 mmol) MePPh₃Br were used and after quenching the reaction mixture was filtered through celite, the ketone intermediate (0.23 mmol) was converted to the alkene. Precipitation from Et₂O afforded compound 283 (0.014 g, 7% from compound 113) as a white solid. LC/MS (direct infusion, electrospray +ve, 10 mM NH₄OAc in 3:7 water and MeCN) 397.75; C₂₅H₃₈N₂O₂.

Synthesis of Compound 284

Using the procedure described for the synthesis of compound 278, compound 113 (0.18 g, 0.35 mmol) was reacted with ethanolamine (0.11 mL, 1.8 mmol) to give amine intermediate (0.053 g, 27%, yellow oil). Using the procedure described for the synthesis of compound 279, the amine intermediate (0.096 mmol) was reacted with LiAlH$_4$ (0.19 mL of a 1 M solution in THF, 0.19 mmol) to give the alcohol intermediate with some TBS cleavage (0.040 g, colourless glass). Using the procedure described for the synthesis of compound 280, with the exceptions that 6 mL 80% acetic acid were used and the residue was not purified, the crude alcohol intermediate mixture was converted to ketone intermediate as the acetic acid salt (0.041 g, colourless glass). Using the procedure described for the synthesis of compound 281, the ketone intermediate (0.096 mmol) was converted to the crude alkene. Using the procedure described for the synthesis of compound 282, with the exception that the residue was not washed with CH$_2$Cl$_2$, the crude alkene was converted to the acetic acid salt. Precipitation from hexanes/CH$_2$Cl$_2$ afforded compound 284 (0.015 g, 10% from compound 113) as a yellow solid. LC/MS (direct infusion, electrospray +ve, 10 mM NH$_4$OAc in 3:7 water and MeCN) 352.12; C$_{21}$H$_{38}$NO$_3$.

Synthesis of Compound 285

Using the procedure described for the synthesis of compound 278, with the exceptions that 0.20 g 4 Å molecular sieves were used, the reaction began with 0.395 g (1.77 mmol) NaB(OAc)$_3$H, then 0.263 g (1.18 mmol) more NaB(OAc)$_3$H was added after 2 days and the total reaction time was 6 days, compound 113 (0.30 g, 0.59 mmol) was reacted with furfurylamine (0.27 mL, 3.0 mmol) to give a mixture of amine and imine intermediates (0.283 g, white foam). Using the procedure described for the synthesis of compound 279, with the exception that reaction time was 5 hours, the amine/imine intermediate mixture (0.48 mmol) was reacted with LiAlH$_4$ (1.44 mL of a 1 M solution in Et$_2$O, 1.44 mmol) to give crude alcohol intermediate with most TBS cleaved (0.248 g, yellow oil). Using the procedure described for the synthesis of compound 280, with the exceptions that 20 mL 80% AcOH were used, the reaction was performed at ambient temperature and the residue after purification was dissolved in THF (6 mL) and treated with 2 N HCl (2 mL) at ambient temperature overnight then concentrated, the crude alcohol intermediate mixture (0.481 mmol) was converted to ketone intermediate as the HCl salt (0.146 g, yellow oil). Using the procedure described for the synthesis of compound 281, with the exceptions that 0.236 g (2.00 mmol) KO$^t$Bu and 0.715 g (2.00 mmol) MePPh$_3$Br were used, DMF (0.5 mL) was added and after quenching the reaction mixture was filtered through celite, the ketone intermediate (0.33 mmol) was converted to the crude alkene. Using the procedure described for the synthesis of compound 282, the crude alkene was converted to the acetic acid salt. Precipitation from Et$_2$O afforded compound 285 (0.013 g, 14% from compound 113) as a light brown solid. LC/MS (direct infusion, electrospray +ve, 10 mM NH$_4$OAc in 3:7 water and MeCN) 388.16; C$_{24}$H$_{38}$NO$_3$.

Synthesis of Compound 286

Using the procedure described for the synthesis of compound 278, with the exception that the residue was not purified, compound 113 (0.18 g, 0.35 mmol) was reacted with N,N-dimethylethylenediamine (0.20 mL, 1.8 mmol) to give a mixture of amine and imine intermediates (0.192 g, colourless oil). Using the procedure described for the synthesis of compound 279, the amine/imine intermediate mixture (0.33 mmol) was reacted with LiAlH$_4$ (0.99 mL of a 1 M solution in THF, 0.99 mmol) to give crude alcohol intermediate (0.137 g, colourless glass). Using the procedure described for the synthesis of compound 280, with the exception that the residue was not purified, the crude alcohol intermediate was converted to ketone intermediate as the acetic acid salt (0.147 g, colourless glass). Using the procedure described for the synthesis of compound 281, the ketone intermediate (0.33 mmol) was converted to the crude alkene. Using the procedure described for the synthesis of compound 282, with the exception that the residue was not washed with CH$_2$Cl$_2$, the crude alkene was converted to the acetic acid salt. Concentration from CH$_2$Cl$_2$ afforded compound 286 (0.072 g, 47% from compound 113) as a light yellow solid: LC/MS (direct infusion, electrospray +ve, 10 mM NH$_4$OAc in 3:7 water and MeCN) 379.03; C$_{23}$H$_{43}$N$_2$O$_2$.

Synthesis of Compound 287

Using the procedure described for the synthesis of compound 278, compound 113 (0.18 g, 0.35 mmol) was reacted with 2-(1-cyclohexenyl)ethylamine (0.25 mL, 1.8 mmol) to give amine intermediate (0.165 g, 77%, yellow oil). Using the procedure described for the synthesis of compound 279, the amine intermediate (0.27 mmol) was reacted with LiAlH$_4$ (0.53 mL of a 1 M solution in THF, 0.53 mmol) to give crude alcohol intermediate (0.132 g, colourless glass). Using the procedure described for the synthesis of compound 280, with the exception that 8 mL 80% acetic acid were used, the crude alcohol intermediate was converted to ketone intermediate as the acetic acid salt (0.108 g, colourless glass). Using the procedure described for the synthesis of compound 281, the ketone intermediate (0.23 mmol) was converted to the crude alkene. Using the procedure described for the synthesis of compound 282, with the exception that the residue was washed with Et$_2$O (4×5 mL) instead of CH$_2$Cl$_2$, the crude alkene was converted to the acetic acid salt. Precipitation from hexanes/CH$_2$Cl$_2$ afforded compound 287 (0.051 g, 31% from compound 113) as a white solid: LC/MS (direct infusion, electrospray +ve, 10 mM NH$_4$OAc in 3:7 water and MeCN) 416.26; C$_{27}$H$_{46}$NO$_2$.

Synthesis of Compound 288

Using the procedure described for the synthesis of compound 278, with the exception that the residue was not purified, compound 113 (0.18 g, 0.35 mmol) was reacted with 4-(2-aminoethyl)morpholine (0.23 mL, 1.8 mmol) to give the amine intermediate (0.205 g, 94%, colourless oil). Using the procedure described for the synthesis of compound 279, the amine intermediate (0.33 mmol) was reacted with LiAlH$_4$ (0.66 mL of a 1 M solution in THF, 0.66 mmol) to give crude alcohol intermediate (0.150 g, colourless glass). Using the procedure described for the synthesis of compound 280, with the exceptions that 8 mL 80% acetic acid were used and the residue was not purified, the crude alcohol intermediate was converted to ketone intermediate as the acetic acid salt (0.203 g, brown oil). Using the procedure described for the synthesis of compound 281, the ketone intermediate (0.33 mmol) was converted to the crude alkene. Using the procedure described for the synthesis of compound 282, with the exception that the residue was purified by chromatography on silica gel after washing, the crude alkene was converted to the acetic acid salt. Precipitation from Et$_2$O afforded compound 288 (0.108 g, 64% from compound 113) as an off-white solid. LC/MS (direct infusion, electrospray +ve, 10 mM NH$_4$OAc in 3:7 water and MeCN) 421.16; C$_{25}$H$_{45}$N$_2$O$_3$.

Synthesis of Compound 289

Using the procedure described for the synthesis of compound 278, with the exceptions that 0.125 g 4 Å molecular sieves were used, the reaction began with 0.329 g (1.47 mmol) NaB(OAc)$_3$H, then 0.219 g (0.982 mmol) more NaB(OAc)$_3$H was added after 2 days and the total reaction time was 6 days, compound 113 (0.25 g, 0.49 mmol) was reacted with m-toluidine (0.27 mL, 2.5 mmol) to give amine intermediate (0.240 g, yellow oil). Using the procedure described for the synthesis of compound 279, with the exception that reaction time was 5 hours, the amine intermediate (0.400 mmol) was reacted with LiAlH$_4$ (0.80 mL of a 1 M solution in Et$_2$O, 0.80 mmol) to give crude alcohol intermediate with most TBS cleaved (0.224 g, yellow oil). Using the procedure described for the synthesis of compound 280, with the exceptions that 20 mL 80% AcOH were used and the reaction was performed at ambient temperature, the crude alcohol intermediate mixture (0.400 mmol) was converted to ketone intermediate (0.135 g, light brown solid). Using the procedure described for the synthesis of compound 281, with the exceptions that 0.238 g (2.01 mmol) KO$^t$Bu and 0.719 g (2.01 mmol) MePPh$_3$Br were used and after quenching the reaction mixture was filtered through celite, the ketone intermediate (0.34 mmol) was converted to the alkene. Concentration from CH$_2$Cl$_2$ gave compound 289 (0.095 g, 49% from compound 113) as a yellow foam.

Synthesis of Compound 290

Using the procedure described for the synthesis of compound 278, with the exceptions that 0.10 g 4 Å molecular sieves and 6 mL DCE were used, the reaction began with 0.165 g (0.740 mmol) NaB(OAc)$_3$H, then 0.083 g (0.37 mmol) more NaB(OAc)$_3$H was added after 8 hours and the total reaction time was 2 days, compound 113 (0.197 g, 0.387 mmol) was reacted with benzylamine (0.21 mL, 1.9 mmol) to give amine intermediate (0.171 g, 73%, colourless gum). Using the procedure described for the synthesis of compound 279, with the exceptions that 6 mL THF were used and reaction time was 5 hours, the amine intermediate (0.28 mmol) was reacted with LiAlH$_4$ (0.56 mL of a 1 M solution in THF, 0.56 mmol) to give crude alcohol intermediate with TBS cleaved (0.132 g, colourless gum). Using the procedure described for the synthesis of compound 280, with the exceptions that the alcohol was treated with 2 N HCl (2 mL) in THF (6 mL) instead of 80% acetic acid and the reaction was performed at ambient temperature, the crude alcohol intermediate mixture (0.28 mmol) was converted to ketone intermediate (0.095 g, colourless glass). Using the procedure described for the synthesis of compound 281, with the exceptions that 0.162 g (1.44 mmol) KO$^t$Bu, 0.514 g (1.44 mmol) MePPh$_3$Br and 13 mL THF were used and after quenching the reaction mixture was diluted with EtOAc (20 mL) and MeOH (10 mL) then filtered through celite, the ketone intermediate (0.24 mmol) was converted to the alkene. Precipitation from ACN gave compound 290 (0.063 g, 41% from compound 113) as a white solid. LC/MS (direct infusion, electrospray +ve, 10 mM NH$_4$OAc in 3:7 water and MeCN) 382.06; C$_{26}$H$_{36}$NO$_2$.

Synthesis of Compound 291

Using the procedures described for the synthesis of compound 282, with the exception of substitution by 3-fluorobenzylamine, compound 291 (0.039 g) was prepared as a yellow solid in 23% yield starting from compound 95: LC/MS (direct infusion, electrospray +ve, 10 mM NH$_4$OAc in 3:7 water and MeCN) 416.21; C$_{26}$H$_{39}$FNO$_2$.

Synthesis of Compound 292

Using the procedures described for the synthesis of compound 282, with the exception of substitution by morpholine, compound 292 (0.089 g) was prepared as a light pink solid in 58% yield starting from compound 95. LC/MS (direct infusion, electrospray +ve, 10 mM NH$_4$OAc in 3:7 water and MeCN) 378.12; C$_{23}$H$_{40}$NO$_3$.

Synthesis of Compound 293

Using the procedures described for the synthesis of compound 282, with the exception of substitution by 3,4-(methylenedioxy)aniline, compound 293 (0.068 g) was prepared as a white solid in 45% yield starting from compound 95. LC/MS (direct infusion, electrospray +ve, 10 mM NH$_4$OAc in 3:7 water and MeCN) 428.37; C$_{26}$H$_{38}$NO$_4$.

Synthesis of Compound 294

Using the procedures described for the synthesis of compound 282, with the exception of substitution by isobutylamine, compound 294 (0.111 g) was prepared as a orange solid in 75% yield starting from compound 95. LC/MS (direct infusion, electrospray +ve, 10 mM NH$_4$OAc in 3:7 water and MeCN) 364.12; C$_{23}$H$_{42}$NO$_2$.

Synthesis of Compound 295

Using the procedures described for the synthesis of compound 282, with the exception of substitution by cyclohexylamine, compound 295 (0.029 g) was prepared as a orange solid in 18% yield starting from compound 95. LC/MS (direct infusion, electrospray +ve, 10 mM NH$_4$OAc in 3:7 water and MeCN) 390.12; C$_{25}$H$_{42}$NO$_2$.

Synthesis of Compound 296

Using the procedures described for the synthesis of compound 282, with the exception of substitution by N-methylaniline, compound 296 (0.040 g) was prepared as a orange solid in 28% yield starting from compound 95. LC/MS (direct infusion, electrospray +ve, 10 mM NH$_4$OAc in 3:7 water and MeCN) 397.86; C$_{26}$H$_{40}$NO$_2$.

Synthesis of Compound 297

Using the procedure described for the synthesis of compound 278, with the exceptions that 0.20 g of 4 Å molecular sieves and 7 mL DCE were used, the mixture was stirred for 1 hour before NaB(OAc)$_3$H was added, reaction time was 3 days and the residue was purified by chromatography on silica gel (hexanes/EtOAc, 1:1; EtOAc/MeOH, 9:1), compound 95 (0.25 g, 0.49 mmol) was reacted with 3-(aminomethyl)pyridine (0.25 mL, 2.5 mmol) to give amine intermediate (0.266 g, 90%, colourless glass). Using the procedure described for the synthesis of compound 279, with the exception that reaction time was overnight, the amine intermediate (0.44 mmol) was reacted with LiAlH$_4$ (0.98 mL of a 1 M solution in Et$_2$O, 0.98 mmol) to give alcohol intermediate (0.255 g, yellow foam). Using the procedure described for the synthesis of compound 280, with the exceptions that 20 mL 80% AcOH were used, the reaction was run at ambient temperature for 4 days and the product was residue was purified by chromatography on silica gel (EtOAc/MeOH/H$_2$O/Et$_3$N, 9:1:0.25:0.25), the alcohol intermediate (0.46 mmol) was converted to ketone intermediate as the free amine (0.039 g, light brown solid). Using the procedure described for the synthesis of compound 281, with the exceptions that 0.069 g (0.58 mmol) KO$^t$Bu, 0.209 g, (0.585 mmol) MePPH$_3$Br and 7 mL THF were used, the reaction was stirred for 1 hour before the ketone intermediate solution was added and reaction time was 2 days, the ketone intermediate (0.097 mmol) was converted to the crude alkene. Using the procedure described for the synthesis of compound 282, with the exception that the residue was not purified by chromatography, the crude alkene was converted to compound 297 (0.011 g, 5% from INT1703) as a yellow glass. LC/MS (direct infusion, electrospray +ve, 10 mM NH$_4$OAc in 3:7 water and MeCN) 399.16; C$_{25}$H$_{39}$N$_2$O$_2$.

Synthesis of Compound 298

Using the procedure described for the synthesis of compound 278, with the exceptions that 0.20 g of 4 Å molecular sieves and 7 mL DCE were used, the mixture was stirred for 1 hour before NaB(OAc)$_3$H was added, reaction time was 3 days and the residue was purified by chromatography on silica gel (hexanes/EtOAc, 3:2, 1:1), compound 95 (0.25 g, 0.49 mmol) was reacted with furfurylamine (0.23 mL, 2.5 mmol) to give amine intermediate (0.269 g, 93%, yellow foam). Using the procedure described for the synthesis of compound 279, the amine intermediate (0.46 mmol) was reacted with LiAlH$_4$ (0.98 mL of a 1 M solution in Et$_2$O, 0.98 mmol) overnight then 1.96 mL more LiAlH$_4$ solution (1 M in Et$_2$O, 1.96 mmol) were added before further reaction overnight to give alcohol intermediate (0.228 g, white foam). Using the procedure described for the synthesis of compound 280, with the exceptions that 20 mL 80% AcOH were used and the reaction was run at ambient temperature for 3 days, the alcohol intermediate (0.42 mmol) was converted to ketone intermediate as the acetic acid salt (0.229 g, yellow glass). Using the procedure described for the synthesis of compound 281, with the exception that 0.2 mL DMF were added, the ketone intermediate (0.42 mmol) was converted to the crude alkene. Using the procedure described for the synthesis of compound 282, the crude alkene was converted to the acetic acid salt. Precipitation from Et$_2$O afforded compound 298 (0.088 g, 40% from compound 95) as an orange solid. LC/MS (direct infusion, electrospray +ve, 10 mM NH$_4$OAc in 3:7 water and MeCN) 388.05; C$_{24}$H$_{38}$NO$_3$.

Synthesis of Compound 299

Using the procedure described for the synthesis of compound 278, with the exceptions that 0.20 g of 4 Å molecular sieves and 7 mL DCE were used, the mixture was stirred for 1 hour before NaB(OAc)$_3$H was added, reaction time was 3 days and the residue was purified by chromatography on silica gel (EtOAc; EtOAc/MeOH/Et$_3$N, 9:1:0.3), compound 95 (0.25 g, 0.49 mmol) was reacted with ethanolamine (0.15 mL, 2.5 mmol) to give amine intermediate (0.274 g, quantitative, yellow foam). Using the procedure described for the synthesis of compound 279, the amine intermediate (0.49 mmol) was reacted with LiAlH$_4$ (0.98 mL of a 1 M solution in Et$_2$O, 0.98 mmol) overnight then 0.98 mL more LiAlH$_4$ solution (1 M in Et$_2$O, 0.98 mmol) were added before further reaction overnight to give alcohol intermediate (0.224 g, colourless glass). Using the procedure described for the synthesis of compound 280, with the exceptions that 20 mL 80% AcOH were used and the reaction was run at ambient temperature for 3 days, the alcohol intermediate (0.44 mmol) was converted to ketone intermediate as the acetic acid salt (0.216 g, colourless glass). Using the procedure described for the synthesis of compound 281, with the exception that 0.5 mL DMF were added, the ketone intermediate (0.44 mmol) was converted to the crude alkene. Using the procedure described for the synthesis of compound 282, with the exception that the residue was not purified by chromatography, the crude alkene was converted to the acetic acid salt. Concentration from CH$_2$Cl$_2$ afforded compound 299 (0.041 g, 20% from compound 95) as a yellow solid. LC/MS (direct infusion, electrospray +ve, 10 mM NH$_4$OAc in 3:7 water and MeCN) 352.06; C$_{21}$H$_{38}$NO$_3$.

Synthesis of Compound 300

Using the procedure described for the synthesis of compound 278, with the exceptions that 0.10 g of 4 Å molecular sieves were used, reaction time was 2.5 days and the residue was purified by chromatography on silica gel (hexanes/EtOAc, 8:2), compound 95 (0.10 g, 0.20 mmol) was reacted with m-toluidine (0.10 mL, 0.93 mmol) to give amine intermediate (0.091 g, 77%, yellowish gum). Using the procedure described for the synthesis of compound 279, with the exceptions that 8 mL THF were used, LiAlH$_4$ solution was added at 0° C. and the mixture was stirred at 0° C. for 20 minutes before stirring at ambient temperature, and reaction time was 3.5 hours, the amine intermediate (0.15 mmol) was reacted with LiAlH$_4$ (0.45 mL of a 1 M solution in THF, 0.45 mmol) to give crude alcohol intermediate. Using the procedure described for the synthesis of compound 280, with the exceptions that 4 mL 80% AcOH were used and reaction time was 5 hours, the crude alcohol intermediate (0.15 mmol) was converted to crude ketone intermediate. Using the procedure described for the synthesis of compound 281, with the exceptions that 7 mL THF and 0.5 mL DMF were used and after quenching the mixture was diluted with EtOAc (20 mL) and MeOH (5 mL) then filtered through celite, the ketone intermediate (0.15 mmol) was converted to alkene (0.021 g, pale gum). Using the procedure described for the synthesis of compound 282, with the exception that the residue was not purified by chromatography, the alkene was converted to the acetic acid salt. Precipitation from ACN/MeOH afforded compound 300 (0.020 g, 21% from compound 95) as a yellow foam.

Synthesis of Compound 301

Using the procedure described for the synthesis of compound 278, with the exceptions that 0.10 g of 4 Å molecular sieves were used, reaction time was 2.5 days and the residue was purified by chromatography on silica gel (EtOAc/MeOH, 9:1), compound 95 (0.10 g, 0.20 mmol) was reacted with pyrrolidine (0.10 mL, 1.2 mmol) to give amine intermediate (0.090 g, 82%, clear gum). Using the procedure described for the synthesis of compound 279, with the exceptions that 8 mL THF were used, LiAlH$_4$ solution was added at 0° C. and the mixture was stirred at 0° C. for 20 minutes before stirring at ambient temperature, and reaction time was 3.5 hours, the amine intermediate (0.16 mmol) was reacted with LiAlH$_4$ (0.45 mL of a 1 M solution in THF, 0.45 mmol) to give crude alcohol intermediate. Using the procedure described for the synthesis of compound 280, with the exceptions that 4 mL 80% AcOH were used and reaction time was 5 hours, the crude alcohol intermediate (0.16 mmol) was converted to crude ketone intermediate. Using the procedure described for the synthesis of compound 281, with the exceptions that 7 mL THF and 0.5 mL DMF were used and after quenching the mixture was diluted with EtOAc (20 mL) and MeOH (5 mL), then filtered through celite, the ketone intermediate (0.16 mmol) was converted to alkene (0.029 g, gum). Using the procedure described for the synthesis of compound 282, with the exception that the residue was not purified by chromatography, the alkene was converted to the acetic acid salt. Precipitation from ACN/MeOH afforded compound 301 (0.038 g, 42% from INT1703) as an off-white foam. LC/MS (direct infusion, electrospray +ve, 10 mM NH$_4$Ac in 3:7 water and MeCN) 362.18; C$_{23}$H$_{40}$NO$_2$.

Synthesis of Compound 302

Using the procedures described for the synthesis of compound 282, with the exception of substitution by N,N-dimethylethylenediamine, compound 302 (0.067 g) was prepared as a orange solid in 39% yield starting from compound 205: LC/MS (direct infusion, electrospray +ve, 10 mM NH$_4$OAc in 3:7 water and MeCN) 393.03; C$_{24}$H$_{45}$N$_2$O$_2$.

Synthesis of Compound 303

Using the procedures described for the synthesis of compound 282, with the exception of substitution by 3,4-(methylenedioxy)aniline, compound 303 (0.055 g) was prepared as a orange solid in 33% yield starting from compound 205: LC/MS (direct infusion, electrospray +ve, 10 mM NH$_4$OAc in 3:7 water and MeCN) 441.95; C$_{27}$H$_{40}$NO$_4$.

Synthesis of Compound 304

Using the procedures described for the synthesis of compound 282, with the exception of substitution by cyclohexylamine, compound 304 (0.022 g) was prepared as a light yellow solid in 12% yield starting from compound 205:

LC/MS (direct infusion, electrospray +ve, 10 mM NH$_4$OAc in 3:7 water and MeCN) 404.05; C$_{26}$H$_{46}$NO$_2$.

Synthesis of Compound 305

Using the procedures described for the synthesis of compound 282, with the exception of substitution by 3-trifluoromethylaniline, compound 305 (0.096 g) was prepared as a white solid in 54% yield starting from compound 205: LC/MS (direct infusion, electrospray +ve, 10 mM NH$_4$OAc in 3:7 water and MeCN) 465.45; C$_{27}$H$_{38}$F$_3$NO$_2$.

Synthesis of Compound 306

Using the procedures described for the synthesis of compound 282, with the exception of substitution by isobutylamine, compound 306 (0.035 g) was prepared as a white solid in 21% yield starting from compound 205: LC/MS (direct infusion, electrospray +ve, 10 mM NH$_4$OAc in 3:7 water and MeCN) 378.08; C$_{24}$H$_{44}$NO$_2$.

Example 36

Compounds 308-310, representative compounds of the invention, may be prepared according to the following Reaction Scheme 36. Any number of compounds related to compounds 308-310 could be produced using similar methodology. Starting compound 217 may be prepared according to the procedure described above in Example 24.

REACTION SCHEME 36

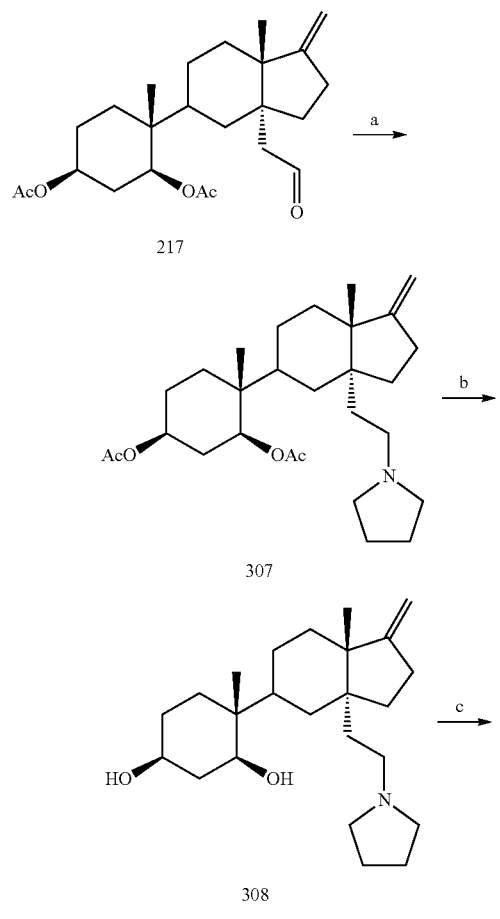

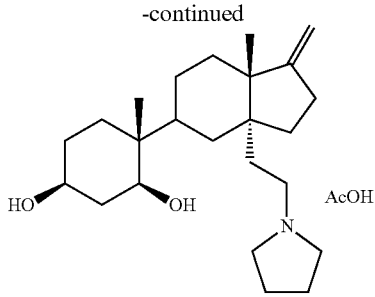

309 a) pyrrolidine, NaB(OAc)$_3$H, 4 Å MS, DCE; b) LiAlH$_4$, THF; c) 80% AcOH, MeOH.

In general, reductive amination of compound 217 gives compound 307. A reducing agent, such as lithium aluminum hydride, is used to reduce the ester-protected hydroxyls to give compound 305. Treatment with 80% acetic acid form the ammonium acetate salt of compound 309.

Synthesis of Compound 307

A mixture of compound 217 (0.20 g, 0.49 mmol), pyrrolidine (0.18 mL, 2.2 mmol) and 4 Å molecular sieves (0.20 g) in DCE (5 mL) was stirred at ambient temperature for 30 minutes. NaB(OAc)$_3$H (0.297 g, 1.33 mmol) was added, rinsing with DCE (2 mL), and the mixture was stirred at ambient temperature overnight. The reaction mixture was diluted with MeOH (3 mL) and filtered through a celite bed, rinsing with EtOAc (25 mL). The filtrate was washed with saturated NaHCO$_3$ solution (10 mL), then brine (2×5 mL), dried over anhydrous MgSO$_4$ and concentrated to give compound 307 (0.235 g, quantitative) as a colourless glass that was used in the next reaction without further purification.

Synthesis of Compound 308

To a solution of compound 307 (0.49 mmol) in THF (10 mL) was added LiAlH$_4$ (0.88 mL of a 1 M solution in THF, 0.88 mmol). The mixture was stirred at ambient temperature overnight, then quenched with Na$_2$SO$_4$.10H$_2$O and stirred for 1 hour. The mixture was filtered, rinsing with EtOAc, and concentrated to dryness. The residue was purified by chromatography on silica gel (EtOAc/MeOH, 9:1; EtOAc/MeOH/Et$_3$N, 9:0.75:0.25) to give compound 308 as a white solid that was used for the next reaction.

Synthesis of Compound 309

A mixture of compound 308, 80% AcOH (1 mL) and MeOH (5 mL) was concentrated by rotary evaporation. Concentration from CH$_2$Cl$_2$ afforded compound 309 (0.168 g, 79% from INT5) as a white foam: LC/MS (direct infusion, electrospray +ve, 10 mM NH$_4$OAc in 3:7 water and MeCN) 375.95; C$_{24}$H$_{42}$NO$_2$.

Synthesis of Compound 310

Using the procedures described for the synthesis of compound 309, with the exception of substitution by m-toluidine, compound 310 (0.20 g) was prepared as a yellow foam in 69% yield starting from compound 217. LC/MS (direct infusion, electrospray +ve, 10 mM NH$_4$OAc in 3:7 water and MeCN) 412.01; C$_{27}$H$_{42}$NO$_2$.

The following compounds of the invention were prepared according to the foregoing Examples:

Compound 25; 5-(1β-methyl-4β-hydroxy-2β-(2-hydroxyethyl)cyclohexyl)-4α-hydroxy-7αβ-methyl-1-methyleneoctahydroindene;

Compound 29; 5-(1β-methyl-4β-hydroxy-2β-hydroxymethylcyclohexyl)-4α-hydroxy-7αβ-methyl-1-methyleneoctahydroindene, Compound 38; 5-(1β-methyl-2β,4β-dihydroxycyclohexyl)-4α-(2-hydroxyethyl)-7αβ-methyl-1-methyleneoctahydroindene;

Compound 45; 5-(1β-methyl-2β,4β-dihydroxycyclohexyl)-4α-hydroxy-7αβ-methyl-1-methyleneoctahydroindene;

Compound 51; 5-(1β-methyl-4β-hydroxy-2β-hydroxymethylcyclohexyl)-4α-hydroxymethyl-7αβ-methyl-1-methyleneoctahydroindene;

Compound 59; 5-(1β-methyl-4β-amino-2β-hydroxymethylcyclohexyl)-4α-hydroxy-7αβ-methyl-1-methyleneoctahydroindene, ammonium acetate salt;

Compound 67; 5-(1β-methyl-4β-hydroxy-2β-(2-aminoethyl)cyclohexyl)-4α-hydroxy-7αβ-methyl-1-methyleneoctahydroindene, ammonium acetate salt;

Compound 68; 5-(1β-methyl-4β-hydroxy-2β-(2-aminoethyl)cyclohexyl)-4α-hydroxy-7αβ-methyl-1-ethylideneoctahydroindene, ammonium acetate salt;

Compound 77; 5-(1β-methyl-4β-hydroxy-2β-hydroxymethylcyclohexyl)-4α-aminomethyl-7αβ-methyl-1-methyleneoctahydroindene;

Compound 78; 5-(1β-methyl-4β-hydroxy-2β-hydroxymethylcyclohexyl)-4α-aminomethyl-7αβ-methyl-1-methyleneoctahydroindene, ammonium acetate salt;

Compound 79; 5-(1β-methyl-4β-hydroxy-2β-hydroxymethylcyclohexyl)-4α-aminomethyl-1,1-dimethyl-2,3,4,5,6,7-hexahydro-1H-indene, ammonium chloride salt;

Compound 80; 5-(1β-methyl-4β-hydroxy-2β-hydroxymethylcyclohexyl)-4α-aminomethyl-7αβ-methyl-1-methyleneoctahydroindene, ammonium chloride salt;

Compound 81; 5-(1β-methyl-4β-hydroxy-2β-hydroxymethylcyclohexyl)-4α-aminomethyl-7αβ-methyl-1-ethylideneoctahydroindene, ammonium chloride salt;

Compound 88; 5-(1β-methyl-4β-hydroxy-2β-aminomethylcyclohexyl)-4α-hydroxymethyl-7αβ-methyl-1-methyleneoctahydroindene;

Compound 89; 5-(1β-methyl-4β-hydroxy-2β-aminomethylcyclohexyl)-4α-hydroxymethyl-7αβ-methyl-1-methyleneoctahydroindene, ammonium acetate salt;

Compound 100; 5-(1β-methyl-4β-hydroxy-2β-aminomethylcyclohexyl)-4α-hydroxy-7αβ-methyl-1-methyleneoctahydroindene;

Compound 101; 5-(1β-methyl-4β-hydroxy-2β-aminomethylcyclohexyl)-4α-hydroxy-7αβ-methyl-1-methyleneoctahydroindene, ammonium acetate salt;

Compound 107; 5-(1β-methyl-2β,4β-dihydroxycyclohexyl)-4α-(2-aminoethyl)-7αβ-methyl-1-methyleneoctahydroindene;

Compound 108; 5-(1β-methyl-2β,4β-dihydroxycyclohexyl)-4α-(2-aminoethyl)-7αβ-methyl-1-methyleneoctahydroindene, ammonium acetate salt;

Compound 119; 5-1β-methyl-2β,4β-dihydroxycyclohexyl)-4α-aminomethyl-7αβ-methyl-1-methyleneoctahydroindene;

Compound 120; 5-(1β-methyl-2β,4β-dihydroxycyclohexyl)-4α-aminomethyl-7αβ-methyl-1-methyleneoctahydroindene, ammonium acetate salt;

Compound 132; 5-(1β-methyl-4β-hydroxy-2β-hydroxymethylcyclohexyl)-4α-aminomethyl-7αβ-methyl-1-difluoromethyleneoctahydroindene;

Compound 133; 5-(1β-methyl-4β-hydroxy-2β-hydroxymethylcyclohexyl)-4α-aminomethyl-7αβ-methyl-1-difluoromethyleneoctahydroindene, ammonium chloride salt;

Compound 143; 5-(1β-methyl-4β-hydroxy-2β-hydroxymethylcyclohexyl)-4α-aminomethyl-7αβ-methyl-1-dichloromethyleneoctahydroindene, ammonium chloride salt;

Compound 157; 5-(1β-methyl-4β-hydroxy-2β-hydroxymethylcyclohexyl)-4α-aminomethyl-7αβ-methyl-1β-(propen-2-yl)octahydroindene;

Compound 158; 5-(1β-methyl-4β-hydroxy-2β-hydroxymethylcyclohexyl)-4α-aminomethyl-7αβ-methyl-1β-(propen-2-yl)octahydroindene, ammonium acetate salt;

Compound 163; 5-(1β-methyl-4β-hydroxy-2β-(2-hydroxyethyl)cyclohexyl)-4α-hydroxy-7αβ-methyl-3a,4,5,6,7,7a-hexahydro-3H-indene;

Compound 178; 5-(1β-methyl-4α,5α-dihydroxy-2β-hydroxymethylcyclohexyl)-4α-aminomethyl-7αβ-methyl-1-methyleneoctahydroindene, ammonium acetate salt;

Compound 182; 5-(1β-methyl-4β-hydroxy-2β-(3-dimethylaminoprop-1-enyl)cyclohexyl)-4α-hydroxy-7αβ-methyl-1-methyleneoctahydroindene;

Compound 183; 5-(1β-methyl-4β-hydroxy-2β-(3-dimethylaminoprop-1-enyl)cyclohexyl)-4α-hydroxy-7αβ-methyl-1-methyleneoctahydroindene, ammonium acetate salt;

Compound 184; 5-(1β-methyl-4β-hydroxy-2β-(2-(4-chlorophenyl)ethyl)cyclohexyl)-4α-hydroxy-7αβ-methyl-1-methyleneoctahydroindene, ammonium acetate salt;

Compound 185; 5-(1β-methyl-4β-hydroxy-2β-(2-pyridin-3-ylethyl)cyclohexyl)-4α-hydroxy-7αβ-methyl-1-methyleneoctahydroindene, ammonium acetate salt;

Compound 189; 5-(1β-methyl-4β-hydroxy-2β-ethylcyclohexyl)-4α-hydroxy-7αβ-methyl-1-methyleneoctahydroindene;

Compound 192; 5-(1β-methyl-4β-hydroxy-2β-(2-(4-ethoxyphenyl)eth-1-en-1-yl)cyclohexyl)-4α-acetoxy-7αβ-methyl-1-methyleneoctahydroindene;

Compound 195; 5-(1β-methyl-4β-hydroxy-2β-(2-(pyridin-2-yl)eth-1-en-1-yl)cyclohexyl)-4α-hydroxymethyl-7αβ-methyl-1-methyleneoctahydroindene;

Compound 196; 5-(1β-methyl-4β-hydroxy-2β-(2-(pyridin-3-yl)eth-1-en-1-yl)cyclohexyl)-4α-hydroxymethyl-7αβ-methyl-1-methyleneoctahydroindene, Compound 197; 5-(1β-methyl-4β-hydroxy-2β-(hept-1-en-1-yl)cyclohexyl)-4α-hydroxymethyl-7αβ-methyl-1-methyleneoctahydroindene, Compound 198; 5-(1β-methyl-4β-hydroxy-2β-(4-benzyloxybut-1-en-1-yl)cyclohexyl)-4α-hydroxymethyl-7αβ-methyl-1-methyleneoctahydroindene;

Compound 199; 5-(1β-methyl-4β-hydroxy-2β-(3-dimethylaminoprop-1-en-1-yl)cyclohexyl)-4α-hydroxymethyl-7αβ-methyl-1-methyleneoctahydroindene, ammonium acetate salt;

Compound 200; 5-(1β-methyl-4β-hydroxy-2β-(2-(4-chlorophenyl)ethenyl)cyclohexyl)-4α-hydroxymethyl-7αβ-methyl-1-methyleneoctahydroindene;

Compound 201; 5-(1β-methyl-4β-hydroxy-2β-(4-hydroxybut-1-en-1-yl)cyclohexyl)-4α-hydroxymethyl-7αβ-methyl-1-methyleneoctahydroindene;

Compound 203; 5-(1β-methyl-4β-hydroxy-2β-(3-hydroxyprop-1-en-1-yl)cyclohexyl)-4α-hydroxymethyl-7αβ-methyl-1-methyleneoctahydroindene;

Compound 210; 5-(1β-methyl-4β-hydroxy-2β-(3-(4-chlorophenyl)prop-2Z-en-1-yl)cyclohexyl)-4α-hydroxy-7αβ-methyl-1-methyleneoctahydroindene;

Compound 211; 5-(1β-methyl-4β-hydroxy-2β-(3-(4-chlorophenyl)prop-2E-en-1-yl)cyclohexyl)-4α-hydroxy-7αβ-methyl-1-methyleneoctahydroindene;

Compound 212; 5-(1β-methyl-4β-hydroxy-2β-(4-dimethylamino/but-1-en-1-yl)cyclohexyl)-4α-hydroxy-7αβ-methyl-1-methyleneoctahydroindene;

Compound 219; 5-(1β-methyl-2β,4β-dihydroxycyclohexyl)-4α-(4-dimethylaminobut-2Z-en-1-yl)-7αβ-methyl-1-methyleneoctahydroindene;

Compound 220; 5-(1β-methyl-2β,4β-dihydroxycyclohexyl)-4α-(4-dimethylaminobut-2Z-en-1-yl)-7αβ-methyl-1-methyleneoctahydroindene, ammonium acetate salt;

Compound 221; 5-(1β-methyl-2β,4β-dihydroxycyclohexyl)-4α-(3-pyridin-3-ylprop-2Z-en-1-yl)-7αβ-methyl-1-methyleneoctahydroindene;

Compound 222; 5-(1β-methyl-2β,4β-dihydroxycyclohexyl)-4α-(3-pyridin-3-ylprop-2E-en-1-yl)-7αβ-methyl-1-methyleneoctahydroindene;

Compound 225; 5-(1β-methyl-4β-hydroxy-2β-hydroxymethylcyclohexyl)-4α-(methylsulfonyl)aminomethyl-7αβ-methyl-1-methyleneoctahydroindene, Compound 227; 5-(1β-methyl-4β-hydroxy-2β-hydroxymethylcyclohexyl)-4α-(acetyl)aminomethyl-7αβ-methyl-1-methyleneoctahydroindene, Compound 229; 5-(1β-methyl-4β-hydroxy-2β-hydroxymethylcyclohexyl)-4α-(ethyl)aminomethyl-7αβ-methyl-1-methyleneoctahydroindene, ammonium acetate salt;

Compound 231; 5-(1β-methyl-4β-hydroxy-2β-hydroxymethylcyclohexyl)-4α-(benzyl)aminomethyl-7αβ-methyl-1-methyleneoctahydroindene;

Compound 232; 5-(1β-methyl-4β-hydroxy-2β-hydroxymethylcyclohexyl)-4α-(benzyl)aminomethyl-7αβ-methyl-1-methyleneoctahydroindene, ammonium acetate salt;

Compound 233; 5-(1β-methyl-4β-hydroxy-2β-hydroxymethylcyclohexyl)-4α-(cyclopropylmethyl)aminomethyl-7αβ-methyl-1-methyleneoctahydroindene, ammonium acetate salt;

Compound 235; 5-(1β-methyl-4β-hydroxy-2β-hydroxymethylcyclohexyl)-4α-(dimethyl)aminomethyl-7αβ-methyl-1-methyleneoctahydroindene;

Compound 236; 5-(1β-methyl-4β-hydroxy-2β-hydroxymethylcyclohexyl)-4α-(dimethyl)aminomethyl-7αβ-methyl-1-methyleneoctahydroindene, ammonium acetate salt;

Compound 240; 5-(1β-methyl-4β-hydroxy-2β-hydroxymethylcyclohexyl)-4α-(methyl)aminomethyl-7αβ-methyl-1-methyleneoctahydroindene;

Compound 241; 5-(1β-methyl-4β-hydroxy-2β-hydroxymethylcyclohexyl)-4α-(methyl)aminomethyl-7αβ-methyl-1-methyleneoctahydroindene, ammonium acetate salt;

Compound 242; 5-(1β-methyl-4β-hydroxy-2β-hydroxymethylcyclohexyl)-4α-(guanidino)methyl-7αβ-methyl-1-methyleneoctahydroindene, ammonium chloride salt;

Compound 243; 5-(1β-methyl-4β-hydroxy-2β-hydroxymethylcyclohexyl)-4α-(2-methylpropyl)aminomethyl-7αβ-methyl-1-methyleneoctahydroindene, Compound 244; 5-(1β-methyl-4β-hydroxy-2β-hydroxymethylcyclohexyl)-4α-(2-methylpropyl)aminomethyl-7αβ-methyl-1-methyleneoctahydroindene, ammonium acetate salt;

Compound 245; 5-(1β-methyl-4β-hydroxy-2β-hydroxymethylcyclohexyl)-4α-(1-methylpiperidin-4-yl)aminomethyl-7αβ-methyl-1-methyleneoctahydroindene, ammonium diacetate salt;

Compound 246; 5-(1β-methyl-4β-hydroxy-2β-hydroxymethylcyclohexyl)-4α-(3-nitrobenzyl)aminomethyl-7αβ-methyl-1-methyleneoctahydroindene, ammonium acetate salt;

Compound 247; 5-(1β-methyl-4β-hydroxy-2β-hydroxymethylcyclohexyl)-4α-(piperonyl)aminomethyl-7αβ-methyl-1-methyleneoctahydroindene, ammonium acetate salt;

Compound 248; 5-(1β-methyl-4β-hydroxy-2β-hydroxymethylcyclohexyl)-4α-(pyrrol-2-ylmethyl)aminomethyl-7αβ-methyl-1-methyleneoctahydroindene, ammonium acetate salt;

Compound 249; 5-(1β-methyl-4β-hydroxy-2β-hydroxymethylcyclohexyl)-4α-(furfuryl)aminomethyl-7αβ-methyl-1-methyleneoctahydroindene, ammonium acetate salt;

Compound 250; 5-(1β-methyl-4β-hydroxy-2β-hydroxymethylcyclohexyl)-4α-(pyridin-3-ylmethyl)aminomethyl-7αβ-methyl-1-methyleneoctahydroindene, ammonium acetate salt;

Compound 252; 5-(1β-methyl-4β-hydroxy-2β-(pyrrolidin-1-yl)methylcyclohexyl)-4α-hydroxymethyl-7αβ-methyl-1-methyleneoctahydroindene;

Compound 253; 5-(1β-methyl-4β-hydroxy-2β-(pyrrolidin-1-yl)methylcyclohexyl)-4α-hydroxymethyl-7αβ-methyl-1-methyleneoctahydroindene, ammonium acetate salt;

Compound 254; 5-(1β-methyl-4β-hydroxy-2β-(2-hydroxyethyl)aminomethylcyclohexyl)-4α-hydroxymethyl-7αβ-methyl-1-methyleneoctahydroindene, ammonium acetate salt;

Compound 255; 5-(1β-methyl-4β-hydroxy-2β-(2-dimethylaminoethyl)aminomethylcyclohexyl)-4α-hydroxymethyl-7αβ-methyl-1-methyleneoctahydroindene, ammonium acetate salt;

Compound 256; 5-(1β-methyl-4β-hydroxy-2β-(cyclohexyl)aminomethylcyclohexyl)-4α-hydroxymethyl-7αβ-methyl-1-methyleneoctahydroindene, ammonium acetate salt;

Compound 257; 5-(1β-methyl-4β-hydroxy-2β-(pyridin-3-ylmethyl)aminomethylcyclohexyl)-4α-hydroxymethyl-7αβ-methyl-1-methyleneoctahydroindene, ammonium acetate salt;

Compound 258; 5-(1β-methyl-4β-hydroxy-2β-(furfuryl)aminomethylcyclohexyl)-4α-hydroxymethyl-7αβ-methyl-1-methyleneoctahydroindene, ammonium acetate salt;

Compound 259; 5-(1β-methyl-4β-hydroxy-2β-(3-fluorophenyl)aminomethylcyclohexyl)-4α-hydroxymethyl-7αβ-methyl-1-methyleneoctahydroindene;

Compound 260; 5-(1β-methyl-4β-hydroxy-2β-(pyridin-3-yl)aminomethylcyclohexyl)-4α-hydroxymethyl-7αβ-methyl-1-methyleneoctahydroindene, Compound 261; 5-(1β-methyl-4β-hydroxy-2β-(3-methylphenyl)aminomethylcyclohexyl)-4α-hydroxymethyl-7αβ-methyl-1-methyleneoctahydroindene;

Compound 270; 5-(1β-methyl-4β-hydroxy-2β-hydroxymethylcyclohexyl)-4α-(imidazol-1-yl)methyl-7αβ-methyl-1-methyleneoctahydroindene;

Compound 276; 5-(1β-methyl-4β-hydroxy-2β-(cyclopentyl)aminomethylcyclohexyl)-4α-aminomethyl-7αβ-methyl-1-methyleneoctahydroindene;

Compound 277; 5-(1β-methyl-4β-hydroxy-2β-(cyclopentyl)aminomethylcyclohexyl)-4α-aminomethyl-7αβ-methyl-1-methyleneoctahydroindene, ammonium diacetate salt;

Compound 282; 5-(1β-methyl-2β,4β-dihydroxycyclohexyl)-4α-(2-methylpropyl)aminomethyl-7αβ-methyl-1-methyleneoctahydroindene, ammonium acetate salt;

Compound 283; 5-(1β-methyl-2β,4β-dihydroxycyclohexyl)-4α-(pyridin-3-ylmethyl)aminomethyl-7αβ-methyl-1-methyleneoctahydroindene;

Compound 284; 5-(1β-methyl-2β,4β-dihydroxycyclohexyl)-4α-(2-hydroxyethyl)aminomethyl-7αβ-methyl-1-methyleneoctahydroindene, ammonium acetate salt;

Compound 285; 5-(1β-methyl-2β,4β-dihydroxycyclohexyl)-4α-(furfuryl)aminomethyl-7αβ-methyl-1-methyleneoctahydroindene, ammonium acetate salt;

Compound 286; 5-(1β-methyl-2β,4β-dihydroxycyclohexyl)-4α-(2-dimethylaminoethyl)aminomethyl-7αβ-methyl-1-methyleneoctahydroindene, ammonium acetate salt;

Compound 287; 5-(1β-methyl-2β,4β-dihydroxycyclohexyl)-4α-(2-cyclohex-1-en-1-ylethyl)aminomethyl-7αβ-methyl-1-methyleneoctahydroindene, ammonium acetate salt;

Compound 288; 5-(1β-methyl-2β,4β-dihydroxycyclohexyl)-4α-(2-morpholin-4-ylethyl)aminomethyl-7αβ-methyl-1-methyleneoctahydroindene, ammonium acetate salt;

Compound 289; 5-(1β-methyl-2β,4β-dihydroxycyclohexyl)-4α-(3-methylphenyl)aminomethyl-7αβ-methyl-1-methyleneoctahydroindene;

Compound 290; 5-(1β-methyl-2β,4β-dihydroxycyclohexyl)-4α-(benzyl)aminomethyl-7αβ-methyl-1-methyleneoctahydroindene;

Compound 291; 5-(1β-methyl-4β-hydroxy-2β-(3-fluorobenzyl)aminomethylcyclohexyl)-4α-hydroxy-7αβ-methyl-1-methyleneoctahydroindene, ammonium acetate salt;

Compound 292; 5-(1β-methyl-4β-hydroxy-2β-(morpholin-4-yl)methylcyclohexyl)-4α-hydroxy-7αβ-methyl-1-methyleneoctahydroindene, ammonium acetate salt;

Compound 293; 5-(1β-methyl-4β-hydroxy-2β-(1,3-benzodioxol-5-yl)aminomethylcyclohexyl)-4α-hydroxy-7αβ-methyl-1-methyleneoctahydroindene;

Compound 294; 5-(1β-methyl-4β-hydroxy-2β-(2-methylpropyl)aminomethylcyclohexyl)-4α-hydroxy-7αβ-methyl-1-methyleneoctahydroindene, ammonium acetate salt;

Compound 295; 5-(1β-methyl-4β-hydroxy-2β-(cyclohexyl)aminomethylcyclohexyl)-4α-hydroxy-7αβ-methyl-1-methyleneoctahydroindene, ammonium acetate salt;

Compound 296; 5-(1β-methyl-4β-hydroxy-2β-(N-phenyl-N-methylamino)methylcyclohexyl)-4α-hydroxy-7αβ-methyl-1-methyleneoctahydroindene;

Compound 297; 5-(1β-methyl-4β-hydroxy-2β-(pyridin-3-ylmethyl)aminomethylcyclohexyl)-4α-hydroxy-7αβ-methyl-1-methyleneoctahydroindene, ammonium acetate salt;

Compound 298; 5-(1β-methyl-4β-hydroxy-2β-(furfuryl)aminomethylcyclohexyl)-4α-hydroxy-7αβ-methyl-1-methyleneoctahydroindene, ammonium acetate salt;

Compound 299; 5-(1β-methyl-4β-hydroxy-2β-(2-hydroxyethyl)aminomethylcyclohexyl)-4α-hydroxy-7αβ-methyl-1-methyleneoctahydroindene, ammonium acetate salt;

Compound 300; 5-(1β-methyl-4β-hydroxy-2β-(3-methylphenyl)aminomethylcyclohexyl)-4α-hydroxy-7αβ-methyl-1-methyleneoctahydroindene, ammonium acetate salt;

Compound 301; 5-(1β-methyl-4β-hydroxy-2β-(pyrrolidin-1-yl)methylcyclohexyl)-4α-hydroxy-7αβ-methyl-1-methyleneoctahydroindene, ammonium acetate salt;

Compound 302; 5-(1β-methyl-4β-hydroxy-2β-(2-(2-dimethylaminoethyl)aminoethyl)cyclohexyl)-4α-hydroxy-7αβ-methyl-1-methyleneoctahydroindene, ammonium acetate salt;

Compound 303; 5-(1β-methyl-4β-hydroxy-2β-(2-(1,3-benzodioxol-5-yl)aminoethyl)cyclohexyl)-4α-hydroxy-7αβ-methyl-1-methyleneoctahydroindene;

Compound 304; 5-(1β-methyl-4β-hydroxy-2β-(2-(cyclohexyl)aminoethyl)cyclohexyl)-4α-hydroxy-7αβ-methyl-1-methyleneoctahydroindene, ammonium acetate salt;

Compound 305; 5-(1β-methyl-4β-hydroxy-2β-(2-(3-trifluoromethylphenyl)aminoethyl)cyclohexyl)-4α-hydroxy-7αβ-methyl-1-methyleneoctahydroindene;

Compound 306; 5-(1β-methyl-4β-hydroxy-2β-(2-(2-methylpropyl)aminoethyl)cyclohexyl)-4α-hydroxy-7αβ-methyl-1-methyleneoctahydroindene, ammonium acetate salt;

Compound 308; 5-(1β-methyl-2β,4β-dihydroxycyclohexyl)-4α-(2-pyrrolidin-1-ylethyl)-7αβ-methyl-1-methyleneoctahydroindene;

Compound 309; 5-(1β-methyl-2β,4β-dihydroxycyclohexyl)-4α-(2-pyrrolidin-1-ylethyl)-7αβ-methyl-1-methyleneoctahydroindene, ammonium acetate salt;

Compound 310; 5-(1β-methyl-2β,4β-dihydroxycyclohexyl)-4α-(2-(3-methylphenyl)aminoethyl)-7αβ-methyl-1-methyleneoctahydroindene.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

UTILITY EXAMPLES

Example A

Effect of Compounds on Ear Edema in a TH1 Mouse Model of Chemical Hapten Delayed Type Hypersensitivity Delayed type hypersensitivity models are T cell dependent responses. The type of chemical hapten used can bias the T cell response towards a predominantly TH1 or TH2 polarization. Oxazolone and di-nitro-chloro-benzene (DNCB) induce a TH1 dominant immune response.

Mice are sensitized on day 0 by epicutaneous application of 100 μL 3% oxazolone solution in 95% ethanol on the shaved abdomen. This procedure is repeated on day 1. Six days after sensitization (i.e., on day 5), mice are challenged by topically painting 25 μL 0.8% oxazolone dissolved in 95% ethanol on both sides of the right ears and 25 μL of 95% ethanol on the left ears. On day 6 (24 hours after challenge), mice are sacrificed, both ears are removed and a standard disc of tissue is harvested immediately from each ear using a cork borer. Care is taken to sample the tissues from the same ear area. The weight of the ear disc tissues is immediately measured. Test compounds are administered orally at a dose of 5 mg/kg once daily for 7 days (from day 0 to day 6) with the last dose 2 hours prior to sacrifice.

Alternatively, mice are sensitized on day 0 by epicutaneous application of 50 μL 1% di-nitrochlorobenzene (DNCB) solution in 4: ratio of acetone:olive oil on the shaved abdomen. This procedure is repeated on day 5. Starting eleven days after the initial sensitization, mice are challenged 3 times (on days 10, 11, and 12) by topically painting 25 μL 0.5% DNCB dissolved in a 4:1 ratio of acetone:olive oil on both sides of the right ears and 25 μL of vehicle on the left ears. Twenty-four hours after challenge, mice are sacrificed as described above. Test compounds are administered orally at a dose of 10 mg/kg once daily for 5 days (from day 8 to day 12) with the last dose 2 hours prior to challenge.

Ear edema is expressed as increase in ear weight, and calculated by subtracting the left ear weight (challenged with vehicle) from that of right ear (challenged with chemical hapten). The percentage inhibition of the ear edema by drugs is calculated using following equation: 100−((drug edema/mean control edema)*100).

Compounds of the invention may be tested in this assay to show their ability to inhibit oxazolone and DNCB induced dermal inflammation.

Example B

Effect of Compounds on Ear Edema in a TH2 Mouse Model of Delayed Type Hypersensitivity to Fluorescein Isothiocyanate Mice are sensitized on day 0 by epicutaneous application of 50 μL 0.5% fluorescein isothiocyanate (FITC) solution in 1:1 acetone and dibutyl phthalate on the shaved abdomen. This procedure is repeated on day 7. Fourteen days after sensitization (i.e., on day 13), mice are challenged by topically painting 25 μL 0.5% FITC dissolved in 1:1 acetone and dibutyl phthalate on both sides of the right ears and 25 μL 1:1 acetone and dibutyl phthalate solution on the left ears. On day 14 (24 hours after challenge), mice are sacrificed, both ears are removed and a standard disc of tissue is harvested immediately from each ear using a cork borer. Care is taken to sample the tissues from the same ear area. The weight of the ear disc tissues is immediately measured. Test compounds (5-10 mg/kg) or vehicle is administered orally once daily for 3 days (from day 11 to day 13) 2 hours prior to challenge.

Ear edema is expressed as increase in ear weight, and calculated by subtracting the left ear weight (challenged with vehicle) from that of right ear (challenged with FITC). The percentage inhibition of the ear edema by drugs is calculated using the following equation: 100-((drug edema/mean control edema)*100).

Compounds of the invention, when tested in this assay, were shown to inhibit FITC induced dermal inflammation at doses of less than 20 mg/kg.

Example C

Effect of Compounds on LPS-Induced Peritonitis in Mouse

Mice are administered drug (5 mg/kg) or vehicle orally q.d. for four days with the last dose 2 hours prior to challenge. On day 4, mice are challenged with either saline or lipopolysaccharide (LPS) dissolved in saline (4 mg/kg) via intra-peritoneal injection. At 24 h or 48 h post challenge, animals are anesthetized, and euthanized by trans-thoracic cardiac exsanguination. The peritoneal cavity is lavaged with ice-cold EDTA containing phosphate buffered saline (PBS). The peritoneal lavage fluid is centrifuged and the supernatant removed. The pellet is resuspended in PBS at 4° C. Cytospins are prepared and stained for manual differentiation and enumeration of cell types. In addition, the resuspended lavage fluid is analyzed for absolute cell numbers and cell differentials by the CellDyn 3700SC hematology analyzer (Abbott Laboratories Inc.).

Compounds of the invention, when tested in this assay, were shown to inhibit LPS induced peritoneal inflammation at doses of less than 20 mg/kg.

Example D

Effect of Compounds on Cartilage Degradation in Mice

This model is used to investigate the effect of novel compounds on cartilage degradation induced by the natural inflammatory response created by implantation of a foreign body. Activity in this model may be indicative of activity in arthritis.

Zyphoid sternum cartilage is excised from $CO_2$ terminated rats, washed in Hibitane, and rinsed in sterile, phosphate buffered saline. A 4 cm diameter disc is removed from the sternum with a #4 stainless steel leather hole punch, and cut in half. Each half is weighed and wrapped in pre-weighed, moist, sterile cotton before implantation. A piece of cotton wrapped cartilage is implanted subcutaneously into each dorsolateral surface of anaesthetized female CD/1 mice (aged 6-8 weeks) via a 1 cm incision along the dorsal midline (Day 0). Mice are administered test articles by oral administration on days 3 to 17. On day 18, mice are sacrificed, the cotton and cartilage removed, and the cartilage separated from the cotton. Both the cartilage and the cotton are weighed, and differences between pre and post implant weights are calculated. The cotton is rinsed in 1 mL of buffer, and cytospins are prepared and stained for differentiation and enumeration of cell types. In addition, the resuspended lavage fluid is analyzed for absolute cell numbers and cell differentials by the CellDyn 3700SC hematology analyzer (Abbott Laboratories Inc.).

The cartilage is digested overnight in a papain and cysteine hydrochloric acid solution at 65° C. and glucosaminoglycan content remaining in the cartilage is assayed by spectrophotometrically and calculated as % GAG/mg of cartilage degraded (normalized to pre implant cartilage weight).

Compounds of the invention may be tested in this assay to show their ability to inhibit cartilage degradation.

Example E

Effect of Compounds on Irritant-Induced Mouse Ear Edema

A number of mice are uniquely identified by placing a mark with an indelible marker on their tail. Mice are dosed orally with 15 mg/kg test compound in 100 μL of 45% β-cyclodextrin in saline. Mice are briefly anaesthesized with 2% halothane, and 2 μg of phorbol 12-myristate 13-acetate (PMA) in 25 μl of acetone is applied to the inner and outer sides of the left ear of the mouse. Acetone is applied to the right ear of the mouse in the same manner to serve as a vehicle control. Control animals receive the same treatment but without any test compound. After 3 hours, mice are sacrificed by cervical dislocation, and a standard sized biopsy is excised from the ears and weighed to the nearest 1/10 of a mg. Data are analyzed by taking the difference of each left ear from the right ear, and then calculating the % inhibition of edema by (((mean Rx/mean irritant))×100)−100.

Compounds of the invention may be tested in this assay to show their ability to inhibit PMA induced dermal edema.

Example F

Effect of Compounds on Cytokine-Induced Transendothelial Migration of Leukocytes The Flow Chamber assay allows for an in vitro analysis of the effects of test compounds on leukocyte adhesion to human endothelium. Using a parallel plate flow chamber, human blood is perfused at physiological rates across an inflamed HUVEC monolayer.

HUVEC monolayers are prepared at passage 3 in 35 mm tissue culture dishes coated with 2% gelatin and 5 μg/mL fibronectin. Following 3 days, confluent monolayers are treated with 25 μg/mL of TNF-α for 4 hours. Test compound is added as required for appropriate incubation times (10 min or 4 hr). Blood is collected from healthy human adults, drawn into Vacutainers with sodium heparin, and maintained at 37° C. Blood is treated with various concentrations of test compound for 10 min at 37° C. The whole blood is then perfused through the flow chamber for 2 min at a shear force of 10 dynes/cm$^2$. Monolayers are then washed with HBSS at 37° C. for approximately 6 min at 10 dynes/cm$^2$. Monolayers are video taped at the start of the wash period. During the last 5 min of the wash period, rolling, adherent, and transmigrated leukocytes are manually counted at 20× objective within two fields of view every minute. Adherent leukocytes are defined as being stationary for a minimum of 10 seconds. Data from each minute is averaged and defined as a percent inhibition against the vehicle treated, TNF-α stimulated, sample. Efficacy of drug articles is compared to a gold standard control sample prepared by treating a HUVEC monolayer with an anti-human E-selectin antibody (10 μg/mL) and the blood with a rat anti-human CD18 antibody (20 μg/mL), both for 10 min at 37° C.

Compounds of the invention, when tested in this assay, were shown to inhibit TNF-α induced transendothelial migration at concentrations of less than 20 μM.

Example G

Effect of Compounds on Allergen-Induced Lung Inflammation in the Rat

The ability of a compound to inhibit the allergen-induced accumulation of inflammatory cells such as eosinophils and neutrophils in the lavage fluid obtained from sensitized animals is indicative of that compound's anti-asthma activity. In particular, this model system is useful in the evaluation of the effects of a test compound in the treatment of the late phase response of asthma, when lung inflammation and the second phase of bronchoconstriction is apparent, and in allergy, especially where it affects the respiratory system. The test is conducted as follows.

Male Brown Norway rats are sensitized to ovalbumin by single intraperitoneal injection of 1 mg ovalbumin adsorbed to 100 mg Al(OH)$_3$ (alum) in 1 mL sterile saline (saline control rats receive only sterile saline) on day 1, and allowed to sensitize until day 21. Test compounds are given orally q.d. for three days prior to challenge (days 19, 20, 21), and one day post challenge (day 22), with the third dose given 2 hours before challenge, and the fourth day dose given 24 hours after challenge (volume=300 μl/dose). Rats are challenged with 5% ovalbumin in saline generated using a Devillbis nebulizer for 5 min on day 21.

Forty-eight hours after challenge, animals are sacrificed with an overdose of intraperitoneally-delivered sodium pentobarbitol and the lungs are lavaged with cold 2×7 mL phosphate buffered saline. The recovered lavage fluid is placed on ice. The bronchoalveolar lavage fluid is centrifuged and the supernatant removed. The pellet is resuspended in phosphate buffered saline at 4° C. Cytospins are prepared and stained for differentiation and enumeration of cell types. Compounds of the invention were shown to inhibit allergen induced lung inflammation at doses of less than 20 mg/kg.

Compounds of the invention, when tested in this assay, were shown to inhibit allergen induced lung inflammation at doses of less than 20 mg/kg.

Example H

Effect of Compounds on Allergen-Induced Bronchoconstriction in the Mouse

The Buxco murine airway hyper-responsiveness (AHR) model has been well characterized by numerous investigators, and mimics the severe airway constriction in response to aerosol challenges that sensitized animals exhibit compared to unsensitized animals. The Buxco system uses a technique called whole body plethysmography, in which breathing-induced changes in chamber pressure are quantified using the correlation between increased airway resistance and increased expiratory time/breathing pause to calculate the degree of airway constriction (Penh). Following allergen sensitization and inhalation challenge of the airway, the Penh will increase compared to sham sensitized, sham challenged animals. Thus the effectiveness of a potential anti-inflammatory agent can be determined by examining its impact on ovalbumin induced AHR.

Female Balb/c mice are sensitized on day 1 and 14 by i.p. injection of 100 μL sterile saline containing 20 μg ovalbumin and 2.25 mg Al(OH)$_3$. Sham sensitized mice receive 100 μL sterile saline alone. Test compounds (5 mg/kg) are administered by oral gavage on five consecutive days, two days before challenge (days 26 and 27) and on the three days of ovalbumin challenge (days 28, 29 and 30, 2 hours before challenge). Mice are challenged with aerosolized ovalbumin (5% in saline) for 20 min on days 28, 29 and 30. On day 31, mice are placed in the whole body plethysmography chambers of the Buxco system and airway reactivity to aerosolized PBS and methacholine (MCh; 0.78, 1.56, 3.125, 6.25, 12.5, 25, 50 mg/mL) challenge is measured as Penh.

Compounds of the invention, when tested in this assay, were shown to inhibit allergen induced airway hyper-reactivity at doses of less than 20 mg/kg.

Example I

Effect of Compounds on LPS-Induced Acute Lung Inflammation in Rat

Rats are administered drug (1-20 mg/kg) or vehicle orally q.d. for four days prior to challenge. On day 4, rats are challenged with either saline or LPS dissolved in saline (2 mg/kg) via intra-tracheal installation. Animals are sacrificed via intra-peritoneal sodium pentobarbitol overdose 3 hours post challenge, and the lungs lavaged with 14 mL of phosphate buffered saline (PBS). The lung lavage fluid is centrifuged at 300 g for 3 min, and the supernatant removed. The pellet is resuspended in 1-3 mL of PBS at 4° C. depending on pellet size and numbers of total leukocytes. A volume of the final cell suspension, containing approximately 240,000 cells, is added to an appropriate volume of PBS at 4° C. to give a final volume of 220 μL and a final concentration of 1×10$^6$ cells/mL (final Cytospin suspension). A 100 μL sample (100,000 cells) is loaded onto a cytospin centrifuge and spun for 4 min at 55 g. Two slides are prepared per lavage sample, and are fixed and stained in DifQuik. In addition, the resuspended lavage fluid is analyzed for absolute cell numbers and cell differentials by the CellDyn 37005C hematology analyzer (Abbott Laboratories Inc.).

Compounds of the invention, when tested in this assay, were shown to inhibit LPS induced lung inflammation at doses of less than 20 mg/kg.

Example J

Effect of Compounds on LPS-Induced Acute Lung Inflammation in Mouse

Mice are administered drug (1-20 mg/kg) or vehicle orally q.d. for four days prior to challenge. On day 4, mice are challenged with either saline or LPS dissolved in saline (0.15 mg/kg) via intra-tracheal installation. Animals are sacrificed using an intra-peritoneal sodium pentobarbitol overdose 6 hours post challenge. After thoracotomy, lungs are lavaged with 3×0.75 mL of PBS. The bronchoalveolar lavage fluid is centrifuged and the supernatant removed. The pellet is resuspended in PBS at 4° C. Cytospins are prepared and stained for differentiation and enumeration of cell types. In addition, the resuspended lavage fluid is analyzed for absolute cell numbers and cell differentials by the CellDyn 3700SC hematology analyzer (Abbott Laboratories Inc.).

Compounds of the invention may be tested in this assay to show their ability to inhibit LPS induced lung inflammation.

Example K

Effect of Compounds on Prostaglandin E2 Synthesis

Prostaglandin E2 (PGE2) is a primary product of arachidonic acid (AA) metabolism. Like most eicosanoids, it does not exist preformed in cellular reservoirs. PGE2 synthesis is catalyzed by cyclooxygenase-2 (COX-2), an inducible enzyme up-regulated by inflammatory stimuli, cytokines and mitogens. COX-2 up-regulation results in increased PGE2 production. Elevated concentrations of PGE2 have been reported in chronic inflammatory conditions such as rheumatoid arthritis and asthma. Inhibition of COX-2 and PGE2 synthesis would be a major target for the future treatment of inflammatory arthropathies.

Human umbilical vein endothelial cells (HUVEC-C) are grown to confluency in gelatin coated plates in the presence of endothelial growth medium (EGM-2). EGM-2 is replaced with RPMI-1640 medium containing 2% fetal bovine serum (FBS) for the assay. HUVEC-Cs are incubated with the tested compounds for 1 hour before stimulation with IL-1β for 24 hours. Exogenous AA is added for 15 minutes and PGE2 concentration in cell culture supernatants is determined by a competitive enzyme immunoassay (EIA).

The compounds are dissolved at a concentration of 20 mM in DMSO, and tested in the assay at 5 and 1 μM with final DMSO concentration of 0.05%. Samples are tested in triplicates. Controls included in each experiment are: untreated cells, IL-1β treated cells, NS-398/IL-1β treated cells and a standard curve of known concentrations of PGE2. NS-398 is a selective inhibitor of COX-2 activity. PGE2 concentration is calculated by log-logit curve fit software and plotted versus PGE2 concentration in a standard curve.

Percent inhibition is calculated as: % I=100−[PGE2]$_c$/[PGE2]$_{Co}$×100, where [PGE2]$_c$ is the concentration of PGE2 in compound/IL-1β treated samples and

[PGE2]$_{Co}$ is the concentration of PGE2 in IL-1β treated sample.

Compounds of the invention were shown to inhibit PGE2 synthesis at concentrations of less than 10 μM.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of formula (Ia):

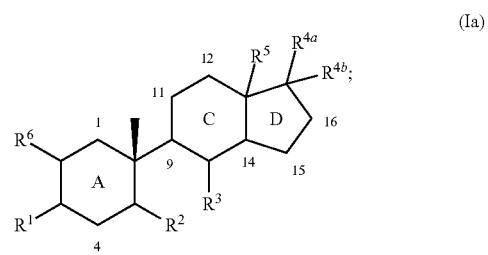

wherein:
the A, C and D rings are each fully saturated;
C1, C4, C11, C12, C15 and C16 are each substituted with two hydrogens;
C9 and C14 are each substituted with one hydrogen;
$R^1$ is —OH;
$R^2$ is —CH$_2$OH;
$R^3$ is —CH$_2$NH$_2$;
$R^{4a}$ and $R^{4b}$ together form methylene;
$R^5$ is methyl; and
$R^6$ is hydrogen;
as a single stereoisomer, a mixture of stereoisomers, or as a racemic mixture of stereoisomers;
or a pharmaceutically acceptable salt thereof.

2. The compound of claim 1 as a single stereoisomer.

3. The compound of claim 1 as a mixture of stereoisomers.

4. The compound of claim 1 as a racemic mixture of stereoisomers.

5. The compound of claim 1 as a free base.

6. The compound of claim 1 as a pharmaceutically acceptable salt.

7. The compound of claim 6 wherein the pharmaceutically acceptable salt is a pharmaceutically acceptable acid addition salt formed from an inorganic or organic acid.

8. The compound of claim 7 wherein the inorganic or organic acid is selected from:

hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid or undecylenic acid.

9. The compound of claim 8 wherein the inorganic or organic acid is selected from hydrochloric acid, acetic acid, tartaric acid, citric acid, succinic acid or ascorbic acid.

10. The compound of claim 1 which is 5-(1β-methyl-4β-hydroxy-2β-hydroxymethylcyclohexyl)-4α-aminomethyl-7aβ-methyl-1-methyleneoctahydroindene, or a pharmaceutically acceptable salt thereof.

11. The compound of claim 10 which is 5-(1β-methyl-4β-hydroxy-2β-hydroxymethylcyclohexyl)-4α-aminomethyl-7a β-methyl-1-methyleneoctahydroindene.

12. The compound of claim 10 wherein the pharmaceutically acceptable salt is a pharmaceutically acceptable acid addition salt formed from an inorganic or organic acid.

13. The compound of claim 12 wherein the inorganic or organic acid is selected from:

hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid or undecylenic acid.

14. The compound of claim 12 wherein the inorganic or organic acid is selected from hydrochloric acid, acetic acid, tartaric acid, citric acid, succinic acid or ascorbic acid.

15. The compound of claim 14 which is 5-(1β-methyl-4β-hydroxy-2β-hydroxymethylcyclohexyl)-4α-aminomethyl-7a β-methyl-1-methyleneoctahydroindene, ammonium acetate salt.

16. The compound of claim 14 which is 5-(1β-methyl-4β-hydroxy-2β-hydroxymethylcyclohexyl)-4α-aminomethyl-7a β-methyl-1-methyleneoctahydroindene, ammonium chloride salt.

17. The compound of claim 14 which is 5-(1β-methyl-4β-hydroxy-2β-hydroxymethylcyclohexyl)-4α-aminomethyl-7a β-methyl-1-methyleneoctahydroindene, ammonium tartrate salt.

18. The compound of claim 14 which is 5-(1β-methyl-4β-hydroxy-2β-hydroxymethylcyclohexyl)-4α-aminomethyl-7a β-methyl-1-methyleneoctahydroindene, ammonium succinate salt.

19. The compound of claim 14 which is 5-(1β-methyl-4β-hydroxy-2β-hydroxymethylcyclohexyl)-4α-aminomethyl-7a β-methyl-1-methyleneoctahydroindene, ammonium citrate salt.

20. The compound of claim 14 which is 5-(1β-methyl-4β-hydroxy-2β-hydroxymethylcyclohexyl)-4α-aminomethyl-7a β-methyl-1-methyleneoctahydroindene, ammonium ascorbate salt.

21. A pharmaceutical composition comprising a pharmaceutically acceptable excipient and a compound of claim 1, as a single stereoisomer, a mixture of stereoisomers, or as a racemic mixture of stereoisomers; or as a pharmaceutically acceptable salt thereof.

22. A method of causing regression of an inflammatory condition or disease selected from atopic dermatitis, peritonitis, asthma and rheumatoid arthritis in a mammal in need thereof, comprising administering to the mammal a therapeutically effective amount of a compound of claim 1, as a single stereoisomer, a mixture of stereoisomers, or as a racemic mixture of stereoisomers; or as a pharmaceutically acceptable salt thereof.

* * * * *